US007872014B2

(12) United States Patent
Anand et al.

(10) Patent No.: US 7,872,014 B2
(45) Date of Patent: Jan. 18, 2011

(54) ANAPLASTIC LYMPHOMA KINASE MODULATORS AND METHODS OF USE

(75) Inventors: Neel Kumar Anand, Burlingame, CA (US); Charles M. Blazey, San Francisco, CA (US); Owen Joseph Bowles, Pacifica, CA (US); Joerg Bussenius, Foster City, CA (US); Simona Costanzo, Los Altos, CA (US); Jeffry Kimo Curtis, San Anselmo, CA (US); Larisa Dubenko, San Francisco, CA (US); Abigail R. Kennedy, Oakland, CA (US); Richard G. Khoury, Redwood City, CA (US); Angie I. Kim, San Mateo, CA (US); Jean-Claire L. Manalo, Daly City, CA (US); Csaba J. Peto, Alameda, CA (US); Kenneth D. Rice, San Rafael, CA (US); Tsze H. Tsang, El Cerrito, CA (US)

(73) Assignee: Exelixis, Inc., South San Francisco, CA (US)

( * ) Notice: Subject to any disclaimer, the term of this patent is extended or adjusted under 35 U.S.C. 154(b) by 986 days.

(21) Appl. No.: 10/565,657

(22) PCT Filed: Jul. 23, 2004

(86) PCT No.: PCT/US2004/023762

§ 371 (c)(1),
(2), (4) Date: Oct. 5, 2006

(87) PCT Pub. No.: WO2005/009389

PCT Pub. Date: Feb. 3, 2005

(65) Prior Publication Data

US 2007/0032515 A1    Feb. 8, 2007

Related U.S. Application Data

(60) Provisional application No. 60/489,658, filed on Jul. 23, 2003.

(51) Int. Cl.
C07D 471/02    (2006.01)
A61K 31/4745    (2006.01)
(52) U.S. Cl. .......................... 514/291; 514/292; 546/82
(58) Field of Classification Search ....................... None
See application file for complete search history.

(56) References Cited

U.S. PATENT DOCUMENTS

| 2002/0000217 A1 | 1/2002 | Takahashi et al. |
| 2003/0028018 A1 | 2/2003 | Renhowe et al. |
| 2003/0187014 A1 | 10/2003 | Uchikawa et al. |

FOREIGN PATENT DOCUMENTS

| EP | 0 574 174 A2 | 12/1993 |
| EP | 574 174 A2 | 12/1993 |
| JP | 06-199855 A2 | 7/1994 |
| JP | 06199855 A2 | 7/1994 |
| JP | 06-247966 A2 | 9/1994 |
| JP | 06247966 A2 | 9/1994 |
| WO | 01/02369 A | 1/2001 |
| WO | 01/44244 A1 | 6/2001 |
| WO | 01/72749 A1 | 10/2001 |
| WO | 01/77101 A1 | 10/2001 |
| WO | WO 01/72749 A1 | 10/2001 |
| WO | WO 02/22598 | 3/2002 |
| WO | 02/076439 A1 | 10/2002 |
| WO | WO 03/087095 | 10/2003 |

OTHER PUBLICATIONS

Tikk et al, Journal of Chemical Research, Synopses (1987),(4), 95.*
Tikk et al, Acta Chimica Hungarica (1988), 125(2),289-93.*
Bogza, S. L. et al., "Convenient One Pot Synthesis of 5-Unsubstituted Pyrazolo[3,4-c]isoquinolines", J. Heterocyclic Chem., vol. 38, 2001, 523-525.
Bogza, S. L. et al., "Intramolecular Cyclization of N-(4-Aryl-5-Pyrazolyl)-Formamidines", Chemistry of Heterocyclic Compounds, 30(9), 1994, p. 1120.
Bogza, S. D. et al., "Cyclodesamination of N-Azolylformamidines. Synthesis of Polyazaheterocycles with Isoquinoline and Indolo[2,3-C]-Pyridine Structural Fragments", Chemistry of Heterocyclic Compounds, 33(1), 1997, 69-73.
Almansa, C. et al., "Synthesis and SAR of a New Series of COX-2-Selective Inhibitors: Pyrazolo[1,5-a]pyrimidines", J. Med. Chem., vol. 44, 2001, 350-361.
Pawlas, J. et al., "First Nucleophilic Aromatic Substitution of Annelated Pyrazole", J. Org. Chem., vol. 67, 2002, 585-586.
Nikolyukin, Y. A. et al., "Recyclization of 4-Cyanobenzo[c]Pyrylium Salts Upon Reaction with Hydrazine", Institute of Physical Organic Chemistry and Coal Chemistry, Academy of Sciences of the Ukranian SSR, Donetsk 340114, No. 7, 1987, p. 807.
Nikolyukin, Y. A. et al., "Synthesis of Azolo[5,4-c]Isoquinolines", Institute of Physical Organic Chemisty and Coal Chemistry, Academy of Sciences of the Ukranian SSR, Donetsk, No. 8, 1991, 914-917.
Kondratov, R.V. et al., "Small Molecules that Dramatically Alter Multidrug Resistance Phenotype by Modulating the Substrate Specificity of P-glycoprotein", PNAS, 98(24), 2001, 14078-14083.
STN International Registry Search, printed on Jan. 28, 2009, 3 pages.
Bogza, S. L. et al., "Participation of Molecular Oxygen in Cyclization of 5-Arylmethyleneamino-4-(3,4-dimethoxyphenyl)pyrazoles", Russian Journal of Organic Chemistry, 38(4), 2002, 609-610.
Nagahira, A. et al., "Identification of a Novel Inhibitor of LPS-Induced TNF-a Production with Antiproliferative Activity in Monocyte/Macrophages", Biochemical and Biophysical Research Communications, vol. 281, 2001, 1030-1036.

(Continued)

Primary Examiner—Zinna N Davis
(74) Attorney, Agent, or Firm—McDonnell Boehnen Hulbert & Berghoff LLP

(57) ABSTRACT

The present invention comprises compounds and pharmaceutical compositions comprising the compounds that are inhibitors of ALK. The invention also comprises methods of using the compounds and compositions to treat diseases mediated by ALK, including diseases such as cancer, immunological disorders, cardiovascular diseases, and other degenerative disorders.

24 Claims, 2 Drawing Sheets

OTHER PUBLICATIONS

Durr, H. et al., "Cycloalkenecarbenes. X. Spiro[2,4]heptatrienes by photolysis of diazocyclopentadienes in alkynes", Justus Liebigs Annalen Der Chemie, vol. 7, 1150-61, Aug. 16, 1974.

Ito, K. et al., "Synthesis of Furo[2,3-] isoquinoline Derivatives", Journal of Heterocyclic Chemistry, vol. 15, 1978, pp. 301-305.

Tikk, I. et al., "Hydroxyiminoisoquinolin-3(2H)-ones. 9 [1]. Synthesis of some Oxazolo[5,4-c]-, Thiazolo[5,4-c]- and 2,3- Dihydro-1H-[1,4]oxazino[2,3-c]isoquinolines", Journal of Heterocyclic Chemistry, vol. 25, 1988, pp. 273-277.

Rao, U. N. et al., "Convenient synthesis of 3H-pyrrolo[2,3-c]isoquinolines and 3-H-pyrrolo[2,3-c][1,7]-,3,4-benzo[c][1,7], and dihydro-pyrido [4,3-c][1,8]naphthyridines via palladium-assisted nucleophilic amination", Heterocycles, vol. 56, 2002, pp. 443-455.

Jain, S. et al., "A novel synthesis of di(1-methylazacycloalkeno)[2,3-b:2',3'-d]pyridines through annulation on lactam acetals", Tetrahedron Letters, 31(1), 1990, pp. 131-134.

Fischer, E. et al., "Synthesis of new sulfur heteroaromatics isoelectronic with dibenzo[g,p]chrysene by photocyclization of thienyl- and phenyl-substituted ethenes", Journal of Organic Chemistry, vol. 61, 1996, pp. 6997-7005.

Al-Kaabi, S. S. et al., "Studies on fused 2(1H)-pyridenethiones: New routes for the synthesis of fused 1H-pyrazolo [3,4-b]pyridines and fused thieno[2,3-b]pyridines", Bulletin of the Chemical Society of Japan, vol. 65, 1992, pp. 2241-2245.

Wiersema, A. K. et al., "Thiophene analogues of fluorene. IV. An Unusual behaviour of a cyclopentadithiophenone in the reaction with dienophiles", Acta Chemica Scandinavica, Munksgaard, Copenhagen, DK, 24(7), 1970, pp. 2653-2665.

Tikk, I. et al., "Hydroxyiminoisouinolin-3(2H)-ones. Part 7. Rearrangemetn of 4-Hydroxyimino-1,4-dihydroisoquinolin-3 (2H) -ones under Wolfi-Semmler type reaction conditions", Journal of Chemical Research, Miniprint, Scientific Reviews, Northwood, GB, vol. 4, No. Paper E/265/86, 1987, pp. 1101-1119.

Freslon, G. et al., "Nouveau type de cycloaddition donnant accès à un furoisobanzofuranne", Bulletin de la Societe Chimique de France, Societe Fransaise de Chimie, Paris, France, 1974, pp. 2105-2110.

* cited by examiner

ANAPLASTIC LYMPHOMA KINASE MODULATORS AND METHODS OF USE

This application is the National Stage of International Application No. PCT/US2004/023762, filed Jul. 23, 2004, which claims the benefit of priority of U.S. provisional application No. 60/489,658, filed Jul. 23, 2003.

BACKGROUND OF THE INVENTION

1. Field of the Invention

This invention relates to compounds for modulating protein kinase enzymatic activity for modulating cellular activities such as proliferation, differentiation, programmed cell death, migration and chemoinvasion. Even more specifically, the invention relates to pyrazoloisoquinolines which inhibit, regulate and/or modulate Anaplastic Lymphoma Kinase (ALK) signal transduction pathways related to the changes in cellular activities as mentioned above, compositions which contain these compounds, and methods of using them to treat ALK-dependent diseases and conditions.

2. Summary of Related Art

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Protein kinases are enzymes that catalyze the phosphorylation of proteins, in particular, hydroxy groups on tyrosine, serine and threonine residues of proteins. The consequences of this seemingly simple activity on cell differentiation and proliferation are staggering; i.e., virtually all aspects of cell life in one way or another depend on protein kinase activity. Furthermore, abnormal protein kinase activity has been related to a host of disorders, ranging from relatively non-life threatening diseases such as psoriasis to extremely virulent diseases such as glioblastoma (brain cancer).

Protein kinases can be categorized as receptor type or non-receptor type. Receptor-type tyrosine kinases have an extracellular, a transmembrane, and an intracellular portion, while non-receptor type tyrosine kinases are wholly intracellular.

Receptor-type tyrosine kinases are comprised of a large number of transmembrane receptors with diverse biological activity. In fact, about 20 different subfamilies of receptor-type tyrosine kinases have been identified. One tyrosine kinase subfamily, designated the HER subfamily, is comprised of EGFR (HER1), HER2, HER3, and HER4. Ligands of this subfamily of receptors identified so far include epithelial growth factor, TGF-alpha, amphiregulin, HB-EGF, betacellulin and heregulin. Another subfamily of these receptor-type tyrosine kinases is the insulin subfamily, which includes INS-R, IGF-IR, and IR-R. The PDGF subfamily includes the PDGF-alpha and beta receptors, CSFIR, c-kit and FLK-II. Then there is the FLK family, which is comprised of the kinase insert domain receptor (KDR), fetal liver kinase-1 (FLK-1), fetal liver kinase-4 (FLK-4) and the fms-like tyrosine kinase-1 (flt-1). The PDGF and FLK families are usually considered together due to the similarities of the two groups. For a detailed discussion of the receptor-type tyrosine kinases, see Plowman et al., DN&P 7(6):334-339, 1994, which is hereby incorporated by reference.

The non-receptor type of tyrosine kinases is also comprised of numerous families, including Src, Frk, Btk, Csk, Abl, Zap70, Fes/Fps, Fak, Jak, Ack, and LIMK. Each of these families is then further sub-divided into varying subfamilies. For example, the Src family is one of the largest and includes Src, Yes, Fyn, Lyn, Lck, Blk, Hck, Fgr, and Yrk. The Src subfamily of kinases has been linked to oncogenesis. For a more detailed discussion of the non-receptor type of tyrosine kinases, see Bolen, Oncogene, 8:2025-2031 (1993), which is hereby incorporated by reference.

Since protein kinases and their ligands play critical roles in various cellular activities, deregulation of protein kinase enzymatic activity can lead to altered cellular properties, such as uncontrolled cell growth, associated with cancer. In addition to cancer, altered kinase signaling is implicated in numerous other pathological diseases. These include, but are not limited to: immunological disorders such as rheumatoid arthritis, graft-host diseases, multiple sclerosis, psoriasis; cardiovascular diseases such as atherosclerosis, myocardio-infarction, ischemia, stroke and restenosis; other inflammatory and degenerative diseases such as interbowel diseases, osteoarthritis, macular degeneration, diabetic retinopathy. Therefore, both receptor and non-receptor protein kinases are attractive targets for small molecule drug discovery.

One particularly attractive goal for therapeutic use of kinase modulation relates to oncological indications. For example, modulation of protein kinase activity for the treatment of cancer has been demonstrated successfully with the FDA approval of Gleevec® (imatinib mesylate, produced by Novartis Pharmaceutical Corporation of East Hanover, N.J.) for the treatment of Chronic Myeloid Leukemia (CML) and gastrointestinal stromal cancers (GIST). Gleevec is a c-Kit and Abl kinase inhibitor.

Modulation (particularly inhibition) of cell proliferation and apoptosis, two key cellular processes needed for tumor grown and survival (Matter, A., Drug Disc. Technol. 2001 6, 1005-1024), is an attractive goal for development of small-molecule drugs. Anti-proliferative and pro-apoptotic therapy represents a potentially important approach for the treatment of solid tumors and other disease associated with dysregulated cell growth, including ischemic coronary artery disease, diabetic retinopathy, psoriasis and rheumatoid arthritis.

One particularly attractive target for small-molecule modulation, with respect to antiproliferative and proapoptotic activity is Anaplastic Lymphoma Kinase (ALK). ALK is a novel receptor tyrosine kinase (RTK) belonging to the insulin receptor subfamily. ALK is present in tumors as a result of a (2:5)(p23'q35) chromosomal translocation, which produces fusion proteins between ALK and other proteins such as nucleophosmin (NPM). The immunocytochemical detection of the NPM-ALK fusion protein (and proteins encoded by other ALK fusion genes) has allowed the definition of a tumor classification as "ALK-positive lymphoma." Eight variant ALK fusion proteins have been detected to date and all contain ALK kinase activity.

Activation of ALK occurs either by binding of the endogenous ALK mitogenic ligand, pleiotrophin, or by self-aggregation of the ALK fusion proteins, which causes autophosphorylation resulting in an increase of receptor dependent signaling. ALK activation causes increased cell proliferation and apoptosis via activation of the PKC, MAPK and PIP3K pathways.

ALK fusion proteins or full-length ALK proteins have been detected not only in ALK-positive lymphomas but also in B-cell lymphoma, neuroblastoma and inflammatory myofibroblastic tumors. Recent analysis shows that ALK expression is a marker for a lymphoma subtype with a good prognosis and there are reports of a five-year survival of approximately 80% for ALK-positive lymphomas, compared to 15-45% for ALK-negative lymphomas of anaplastic large cell morphology. (See Morris, et al., Brit. J. Hematol. (2001) 113, 275-295; Stein, et al., Blood (2000) 96, 3681-3695; Drexler, et al. Leukemia (2000) 14, 1533-1559). Thus modulation of ALK is desirable as a means to treat certain cancers and cancer-related disease.

Accordingly, the identification of small-molecule compounds that specifically inhibit, regulate and/or modulate the signal transduction of kinases, particularly ALK, is desirable as a means to treat or prevent disease states associated with abnormal cell proliferation and apoptosis, and is an object of this invention.

SUMMARY OF THE INVENTION

The present invention provides compounds for modulating ALK activity and methods of treating diseases mediated by ALK activity utilizing the compounds and pharmaceutical compositions thereof. Diseases mediated by ALK activity include, but are not limited to, diseases characterized in part by abnormalities in cell proliferation (i.e. tumor growth), programmed cell death (apoptosis), cell migration and invasion, and angiogenesis associated with tumor growth or inflammatory disorders or vascularization disorders.

In another aspect, the invention provides methods of screening for modulators of receptor tyrosine kinase activity, for example activity of ALK. The methods comprise combining a composition of the invention, a receptor tyrosine kinase, and at least one candidate agent and determining the effect of the candidate agent on the kinase activity.

In yet another aspect, the invention also provides pharmaceutical kits comprising one or more containers filled with one or more of the ingredients of pharmaceutical compounds and/or compositions of the present invention, including, one or more tyrosine receptor kinase activity modulators as described herein. Such kits can also include, for example, other compounds and/or compositions (for example, diluents, permeation enhancers, lubricants, and the like), a device(s) for administering the compounds and/or compositions, and written instructions in a form prescribed by a governmental agency regulating the manufacture, use or sale of pharmaceuticals or biological products, which instructions can also reflects approval by the agency of manufacture, use or sale for human administration.

In still yet another aspect, the invention also provides a diagnostic agent comprising a compound of the invention and, optionally, pharmaceutically acceptable adjuvants and excipients.

These and other features and advantages of the present invention will be described in more detail below with reference to the associated drawings.

DETAILED DESCRIPTION OF THE INVENTION

Figure 1:
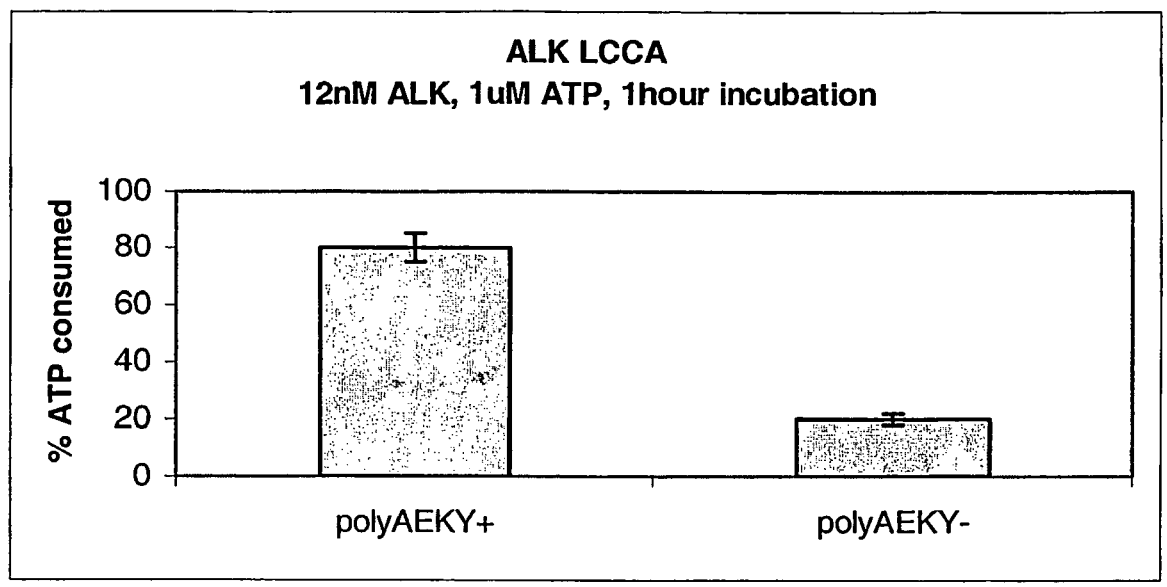
FIG. 1 shows a graph of percent ATP remaining following kinase reaction, determined using a Luciferase-Coupled Chemiluminescent Kinase Assay (LCCA).
Figure 2:
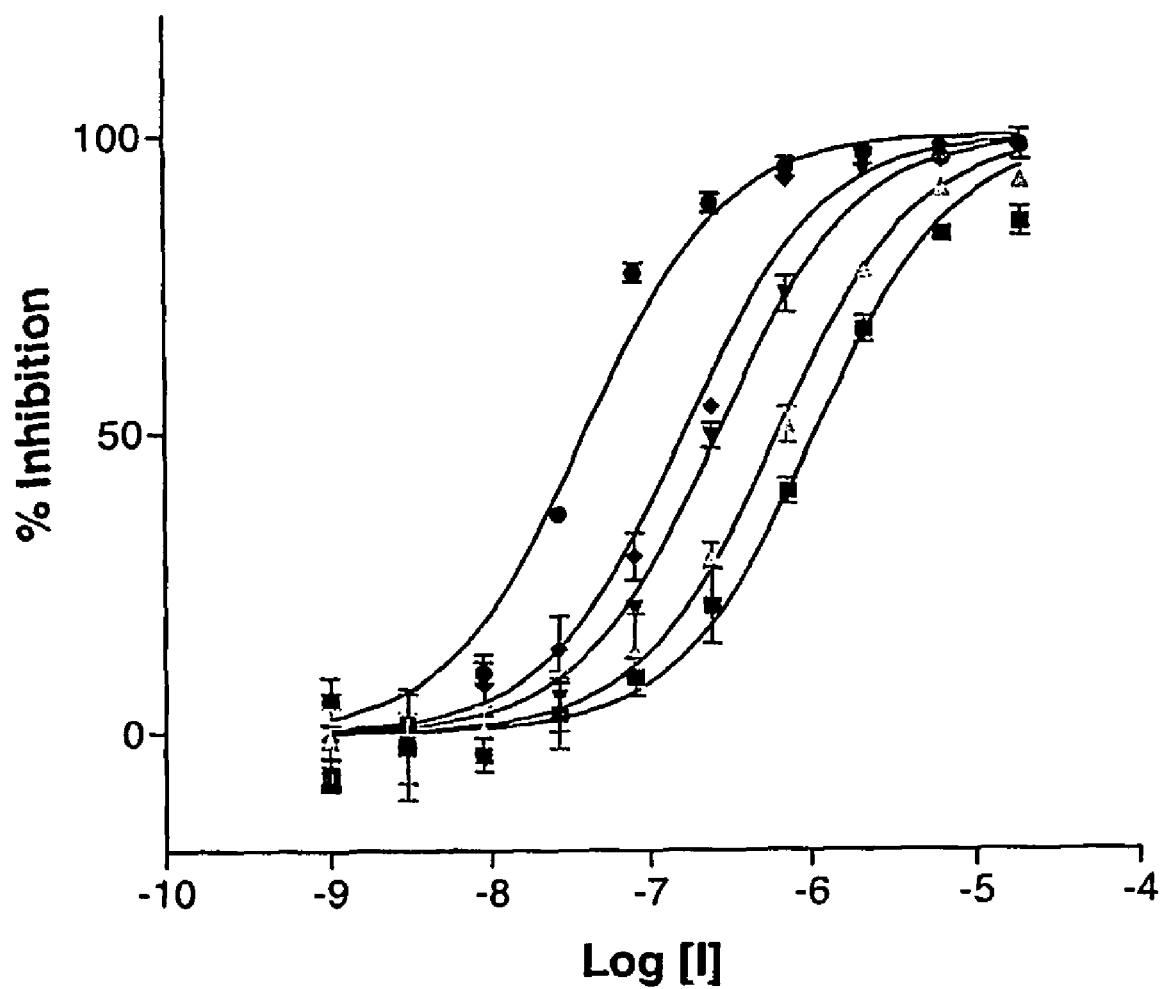
FIG. 2 shows a graph illustrating the percent inhibition of ALK autophosphorylation at varying concentration of inhibitors tested.

The compositions of the invention are used to treat diseases associated with abnormal and or unregulated cellular activities. Disease states which can be treated by the methods and compositions provided herein include, but are not limited to, cancer (further discussed below), immunological disorders such as rheumatoid arthritis, graft-host diseases, multiple sclerosis, psoriasis; cardiovascular diseases such as arteriosclerosis, myocardioinfarction, ischemia, stroke and restenosis; other inflammatory and degenerative diseases such as interbowel diseases, osteoarthritis, macular degeneration, diabetic retinopathy.

It is appreciated that in some cases the cells may not be in a hyper- or hypo-proliferative and/or migratory state (abnormal state) and still require treatment. For example, during wound healing, the cells may be proliferating "normally", but proliferation and migration enhancement may be desired. Alternatively, reduction in "normal" cell proliferation and/or migration rate may be desired.

The present invention comprises compounds for modulating ALK activity and methods of treating diseases mediated by ALK activity utilizing the compounds and pharmaceutical compositions thereof. Diseases mediated by ALK activity include, but are not limited to, diseases characterized in part by abnormalities in cell proliferation (i.e. tumor growth), programmed cell death (apoptosis), cell migration and invasion, and angiogenesis associated with tumor growth.

One aspect of the invention, Example [0024], is a compound for inhibiting ALK according to formula I,

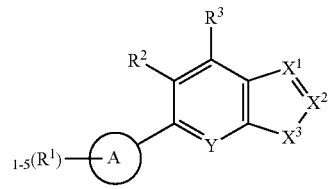

or a pharmaceutically acceptable salt, or stereoisomer, prodrug or metabolite thereof, wherein, A is a five- to ten-membered ring containing up to three heteroatoms; provided A is not a saturated alicyclic when $X^2$ is =N—, $X^3$ is —O—, and A is a pyridin-4-yl;

each of $R^1$, $R^2$ and $R^3$ is independently selected from —H, halo, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(=O)N(R$^4$) R$^4$, —C(=O)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, optionally substituted alkoxy, optionally substituted $C_{1-6}$ alkyl, optionally substituted aryl, optionally substituted aryl $C_{1-6}$ alkyl, optionally substituted heterocyclyl, and optionally substituted heterocyclyl $C_{1-6}$ alkyl;

two adjacent of $R^1$, together with the annular atoms to which they are attached, can form a five- to six-membered ring containing up to two heteroatoms and optionally substituted with up to four of $R^{10}$;

$R^2$ and $R^3$, together with the annular atoms to which they are attached, can form a five- to six-membered ring containing up to two heteroatoms and optionally substituted with up to five of $R^6$;

each $R^4$ is selected from —H, optionally substituted $C_{1-6}$ alkyl, optionally substituted aryl, optionally substituted aryl $C_{1-6}$ alkyl, optionally substituted heterocyclyl, and optionally substituted heterocyclyl $C_{1-6}$ alkyl;

two of $R^4$, when taken together with a common nitrogen to which they are attached, form an optionally substituted five- to seven-membered heterocyclyl, said optionally substituted five- to seven-membered heterocyclyl optionally containing at least one additional heteroatom selected from N, O, S, and P;

each $R^5$ is selected from —H, —CN, —NO$_2$, —OR$^4$, —S(O)$_{0-2}$R$^4$, —CO$_2$R$^4$, optionally substituted C$_{1-6}$ alkyl, optionally substituted C$_{2-6}$ alkenyl, and optionally substituted C$_{2-6}$ alkynyl;

Y is =N— or =C(R$^8$)—;

$X^1$ and $X^2$ are each independently either =N— or =C(R$^9$)—;

$X^3$ is selected from —N(R$^7$)—, —O—, and —S—;

$R^7$ is selected from —H, optionally substituted C$_{1-6}$alkyl, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —C(=O)R$^4$, optionally substituted alkoxy, optionally substituted aryl, optionally substituted aryl C$_{1-6}$ alkyl, optionally substituted heterocyclyl, and optionally substituted heterocyclyl C$_{1-6}$ alkyl;

each of $R^6$, $R^8$, $R^9$ and $R^{10}$ is independently selected from —H, halo, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, —C(=O)R$^4$, optionally substituted alkoxy, optionally substituted C$_{1-6}$ alkyl, optionally substituted aryl, optionally substituted aryl C$_{1-6}$ alkyl, optionally substituted heterocyclyl, and optionally substituted heterocyclyl C$_{1-6}$ alkyl; provided when $R^9$ is aryl, heteroaryl, —C(H)=C(H)R or —C(H)=NR, where R is an optionally substituted alkyl, cycloalkyl, heteroalicyclic, aryl, or heteroaryl, then Y is not =C(H)—; and two adjacent of $R^6$, together with the annular atoms to which they are attached, can form an optionally substituted five- to seven-membered ring containing up to two heteroatoms.

In one example [0024], the compound is according to example [0024], wherein $R^2$ and $R^3$, together with the carbons to which they are attached, form a five- to six-membered ring containing up to two heteroatoms and optionally substituted with up to four of $R^6$.

In another example [0026], the compound is according to example [0025], wherein said five- to six-membered ring is an aryl or a heteroaryl.

In another example [0027], the compound is according to example [0026], wherein said five- to six-membered ring is phenyl or pyridyl.

In another example [0028], the compound is according to example [0027], of formula II,

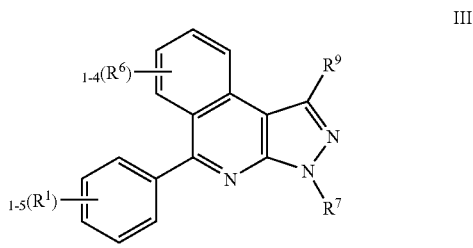

II

In another example [0029], the compound is according to example [0028], wherein $X^1$ is =C(R$^9$)—, $X^2$ is =N—, and $X^3$ is =N(R$^7$)—.

In another example [0030], the compound is according to example [0029], wherein Y is =N—.

In another example [0031], the compound is according to example [0030], wherein A is either a six to ten-membered aryl or a five- to ten-membered heteroaryl containing up to three heteroatoms.

In another example [0032], the compound is according to example [0031], wherein A is either a six membered aryl or a five- or six-membered heteroaryl containing up to three heteroatoms.

In another example [0033], the compound is according to example [0032], wherein $R^1$ is selected from —H, halo, trihalomethyl, —CN, —OR$^4$, —N(R$^4$)R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, —NCO$_2$R$^4$, optionally substituted alkoxy, optionally substituted C$_{1-6}$ alkyl, optionally substituted heterocyclyl, and optionally substituted heterocyclyl C$_{1-6}$ alkyl.

In another example [0034], the compound is according to example [0033], of formula III,

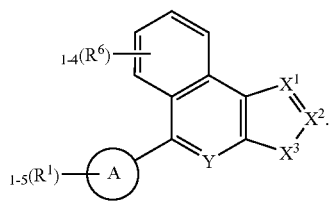

III wherein at least one of $R^1$ is —OH.

In another example [0035], the compound is according to example [0034], wherein the compound is either a 3-(3H-pyrazolo[3,4-c]isoquinolin-5-yl)-phenol or a 4-(3H-pyrazolo[3,4-c]isoquinolin-5-yl)-phenol.

In another example [0036], the compound is according to example [0035], wherein $R^9$ is selected from —H, trihalomethyl, optionally substituted alkoxy, optionally substituted C$_{1-6}$ alkyl, optionally substituted aryl C$_{1-6}$ alkyl, optionally substituted heterocyclyl, and optionally substituted heterocyclyl C$_{1-6}$ alkyl.

In another example [0037], the compound is according to example [0036], wherein $R^6$ is selected from —H, halo, trihalomethyl, —CN, —OR$^4$, —N(R$^4$)R$^4$, —CO$_2$R$^4$, —C(=O)N(R$^4$)R$^4$, —N(R$^4$)SO$_2$R$^4$, —N(R$^4$)C(O)R$^4$, —NCO$_2$R$^4$, —C(=O)R$^4$, optionally substituted C$_{1-6}$ alkyl, optionally substituted heterocyclyl, optionally substituted heterocyclyl C$_{1-6}$ alkyl, and a six- or seven-membered heteroalicyclic formed by two adjacent of $R^6$, together with the annular atoms to which they are attached, said six- or seven-membered heteroalicyclic containing up to two heteroatoms.

In another example [0038], the compound is according to example [0037], wherein $R^6$ is selected from —H, halo, —OR$^4$, —N(R$^4$)R$^4$, optionally substituted C$_{1-6}$ alkyl, optionally substituted heterocyclyl, optionally substituted heterocyclyl C$_{1-6}$ alkyl, and a six-or seven-membered heteroalicyclic formed by two adjacent of $R^6$, together with the annular atoms to which they are attached, said six- or seven-membered heteroalicyclic containing up to two heteroatoms.

In another example [0039], the compound is according to example [0038], wherein at least one of $R^6$ is optionally substituted C$_{1-6}$ alkoxy.

In another example [0040], the compound is according to example [0039], wherein at least one of $R^1$ is halogen or methyl.

In another example [0041], the compound is according to example [0040], wherein $R^9$ is selected from —H, trihalomethyl, and optionally substituted $C_{1-6}$ alkyl.

In another example [0042], the compound is according to example [0038], wherein at least one of $R^6$ is $C_{1-6}$ alkoxy substituted with a heteroalicyclic.

In another example [0043], the compound is according to example [0042], wherein said heteroalicyclic is selected from the group consisting of dioxolanyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, morpholinyl, quinuclidinyl, tetrahydrofuryl, tetrahydropyranyl, thiamorpholinyl, thiamorpholinyl sulfoxide, 2,5-diaza-bicyclo[2.2.1]heptanyl, and thiamorpholinyl sulfone.

In another example [0044], the compound is according to example [0038], wherein at least one of $R^6$ is $C_{1-6}$ alkoxy substituted with at least one additional of an optionally substituted alkoxyl, an amino, an optionally substituted dialkylamino, and an optionally substituted monoalkylamino.

In another example [0045], the compound is according to example [0024], selected from Table 1.

TABLE 1

| Entry | Name | Structure |
|---|---|---|
| 1 | 7,8-bis(methoxy)-5-phenyl-1-(phenylmethyl)-3H-pyrazolo[3,4-c]isoquinoline | 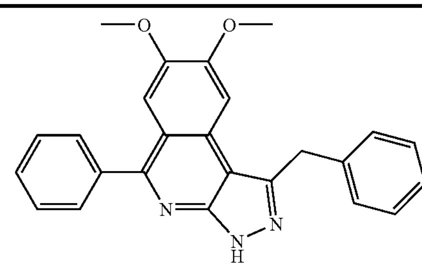 |
| 2 | 2-[7,8-bis(methyloxy)-1-(phenylmethyl)-3H-pyrazolo[3,4-c]isoquinolin-5-yl]phenol | 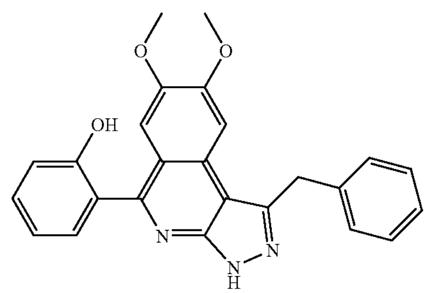 |
| 3 | 4-[7,8-bis(methyloxy)-1-(phenylmethyl)-3H-pyrazolo[3,4-c]isoquinolin-5-yl]phenol | 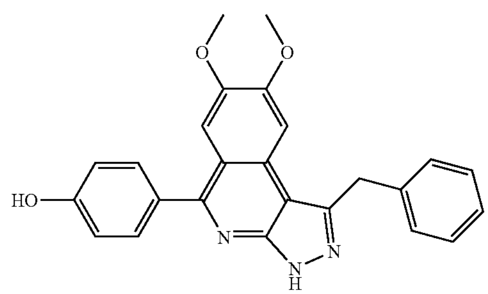 |
| 4 | 4-[7,8-bis(methyloxy)-1-(phenylmethyl)-3H-pyrazolo[3,4-c]isoquinolin-5-yl]-N,N-dimethylaniline | 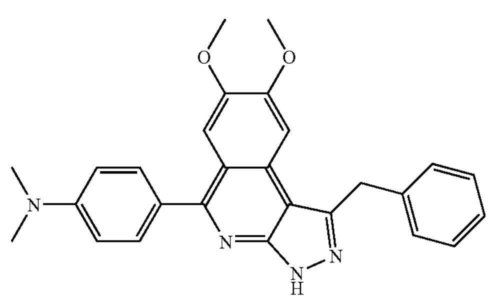 |

TABLE 1-continued

| Entry | Name | Structure |
|---|---|---|
| 5 | 5-(4-fluorophenyl)-7,8-bis(methyloxy)-1-(phenylmethyl)-3H-pyrazolo[3,4-c]isoquinoline | 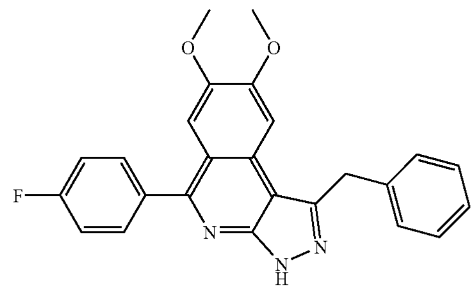 |
| 6 | 5-(4-nitrophenyl)-7,8-bis(methyloxy)-1-(phenylmethyl)-3H-pyrazolo[3,4-c]isoquinoline | 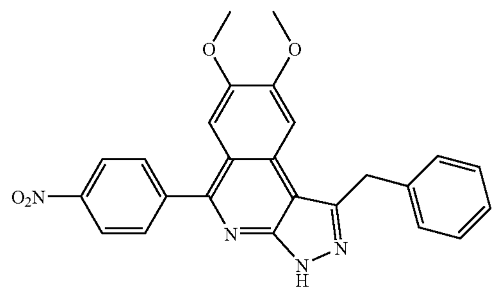 |
| 7 | 4-[3-methyl-7,8-bis(methyloxy)-1-(phenylmethyl)-3H-pyrazolo[3,4-c]isoquinolin-5-yl]phenol | 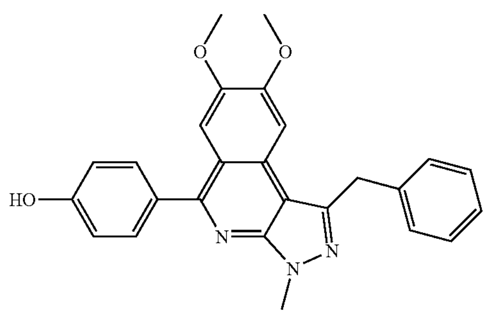 |
| 8 | 3-[7,8-bis(methyloxy)-1-(phenylmethyl)-3H-pyrazolo[3,4-c]isoquinolin-5-yl]phenol | 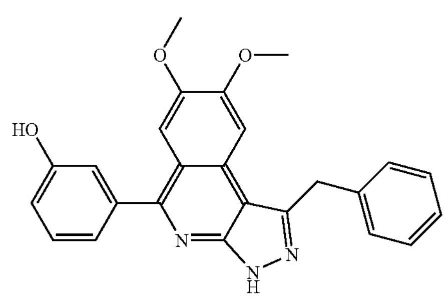 |
| 9 | 4-[7,8-bis(methyloxy)-1-(phenylmethyl)-3H-pyrazolo[3,4-c]isoquinolin-5-yl]benzene-1,2-diol | 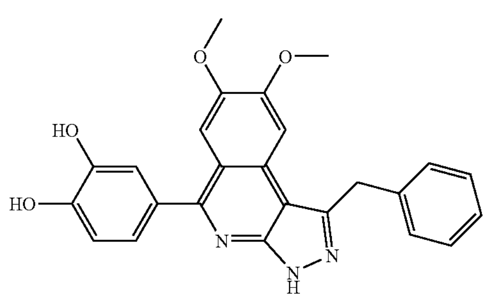 |

TABLE 1-continued

| Entry | Name | Structure |
|---|---|---|
| 10 | 4-{7,8-bis(methyloxy)-1-[(4-methylphenyl)methyl]-3H-pyrazolo[3,4-c]isoquinolin-5-yl}phenol | 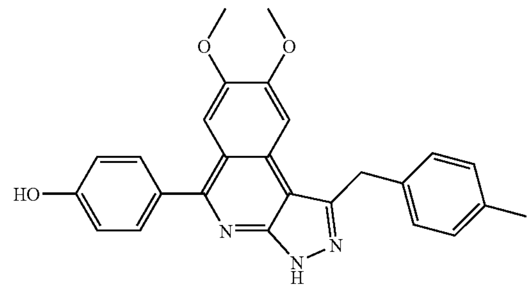 |
| 11 | 5-(1,3-benzodioxol-5-yl)-7,8-bis(methyloxy)-1-(phenylmethyl)-3H-pyrazolo[3,4-c]isoquinoline | 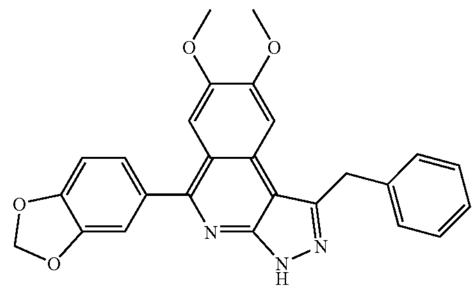 |
| 12 | 4-(7,8-bis(methyloxy)-1-{[4-(methyloxy)phenyl]methyl}-3H-pyrazolo[3,4-c]isoquinolin-5-yl)phenol | 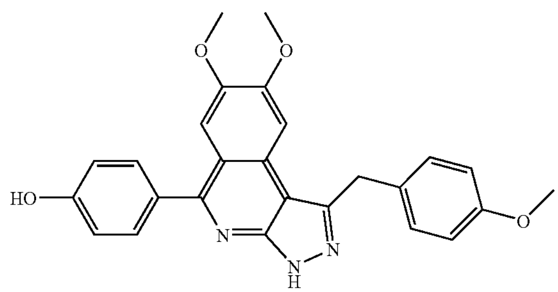 |
| 13 | 4-{7,8-bis(methyloxy)-1-[(2-methylphenyl)methyl]-3H-pyrazolo[3,4-c]isoquinolin-5-yl}phenol | 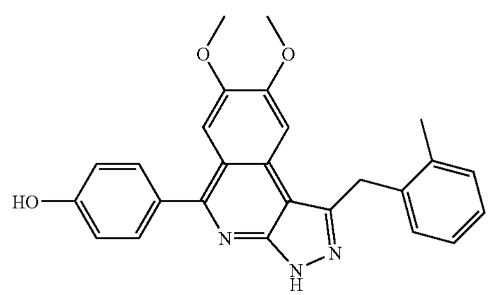 |
| 14 | 4-{7,8-bis(methyloxy)-1-[(3-methylphenyl)methyl]-3H-pyrazolo[3,4-c]isoquinolin-5-yl}phenol | 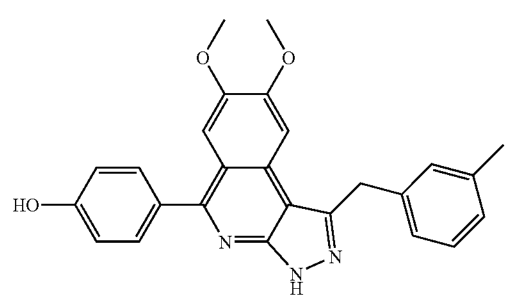 |

TABLE 1-continued

| Entry | Name | Structure |
|---|---|---|
| 15 | 4-[1-methyl-7,8-bis(methyloxy)-3H-pyrazolo[3,4-c]isoquinolin-5-yl]phenol | 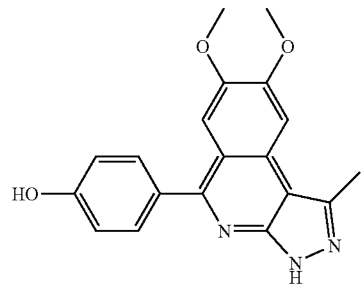 |
| 16 | 2-[7,8-bis(methyloxy)-1-(phenylmethyl)-3H-pyrazolo[3,4-c]isoquinolin-5-yl]-6-fluorophenol | 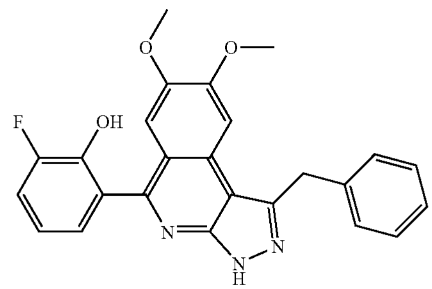 |
| 17 | 3-[7,8-bis(methyloxy)-1-(phenylmethyl)-3H-pyrazolo[3,4-c]isoquinolin-5-yl]-4-nitrophenol | 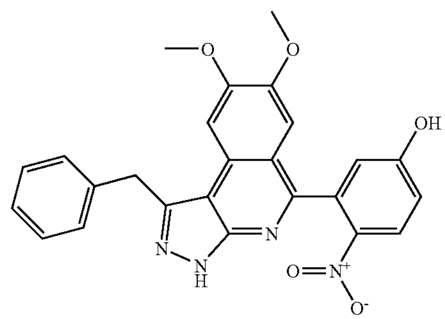 |
| 18 | 4-[7,8-bis(methyloxy)-1-(phenylmethyl)-3H-pyrazolo[3,4-c]isoquinolin-5-yl]benzoic acid | 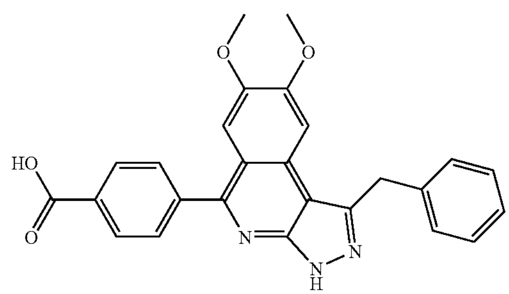 |
| 19 | 4-[7,8-bis(methyloxy)-1-(1-phenylethyl)-3H-pyrazolo[3,4-c]isoquinolin-5-yl]phenol | 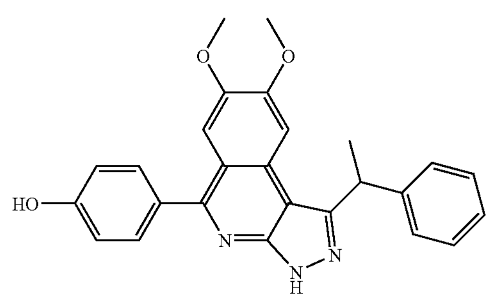 |

TABLE 1-continued

| Entry | Name | Structure |
|---|---|---|
| 20 | 4-[1-{[3,4-bis(methyloxy)phenyl]methyl}-7,8-bis(methyloxy)-3H-pyrazolo[3,4-c]isoquinolin-5-yl]phenol | 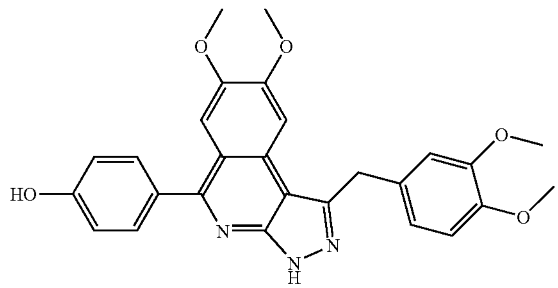 |
| 21 | 4-(7,8-bis(methyloxy)-1-{[3-(methyloxy)phenyl]methyl}-3H-pyrazolo[3,4-c]isoquinolin-5-yl)phenol | 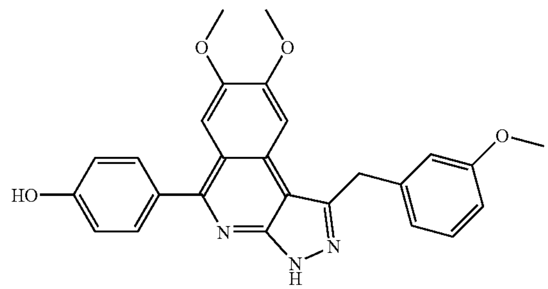 |
| 22 | 4-[1-ethyl-7,8-bis(methyloxy)-3H-pyrazolo[3,4-c]isoquinolin-5-yl]phenol | 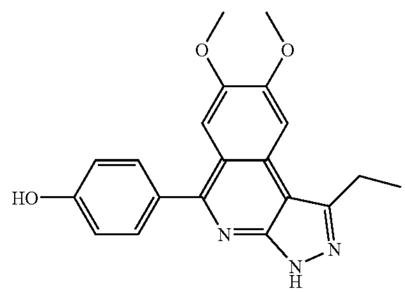 |
| 23 | 7,8-bis(methyloxy)-1-(phenylmethyl)-5-pyridin-4-yl-3H-pyrazolo[3,4-c]isoquinoline | 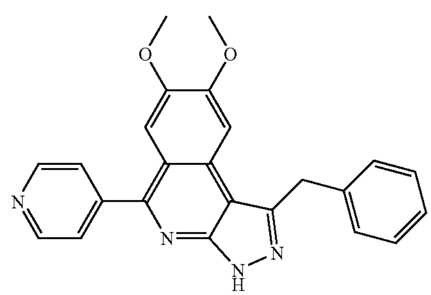 |
| 24 | 4-[6,7,8-tris(methyloxy)-1-(phenylmethyl)-3H-pyrazolo[3,4-c]isoquinolin-5-yl]phenol | 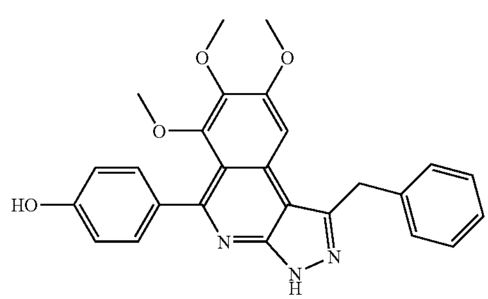 |

TABLE 1-continued

| Entry | Name | Structure |
|---|---|---|
| 25 | 4-[1-methyl-6,7,8-tris(methyloxy)-3H-pyrazolo[3,4-c]isoquinolin-5-yl]phenol | 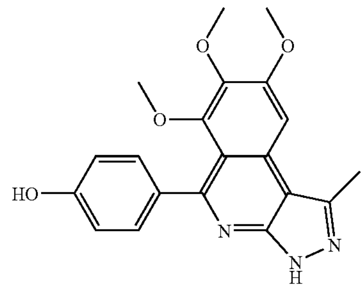 |
| 26 | 4-[8-(methyloxy)-1-(phenylmethyl)-3H-pyrazolo[3,4-c]isoquinolin-5-yl]phenol | 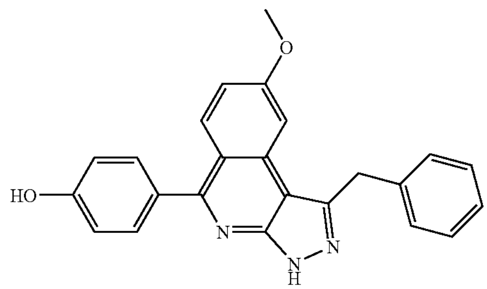 |
| 27 | 4-[7,8-bis(methyloxy)-1-(trifluoromethyl)-3H-pyrazolo[3,4-c]isoquinolin-5-yl]phenol | 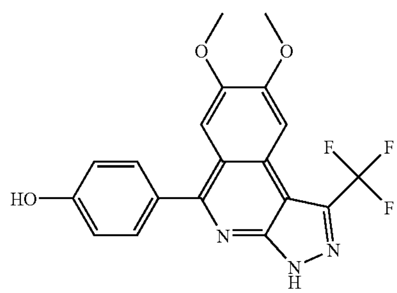 |
| 28 | 4-[1-(1-methylethyl)-7,8-bis(methyloxy)-3H-pyrazolo[3,4-c]isoquinolin-5-yl]phenol | 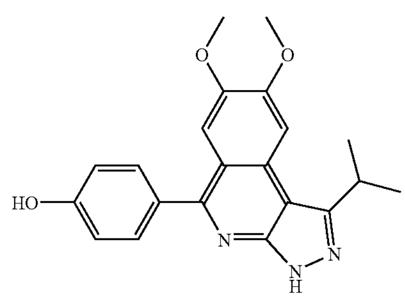 |
| 29 | 4-[7,8-bis(methyloxy)-3H-pyrazolo[3,4-c]isoquinolin-5-yl]phenol | 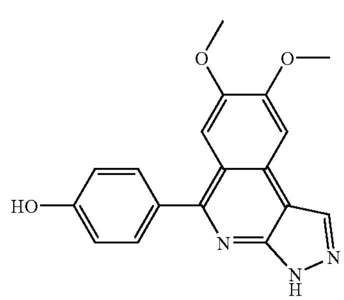 |

TABLE 1-continued

| Entry | Name | Structure |
|---|---|---|
| 30 | 4-[7-methyl-8-(methyloxy)-1-(phenylmethyl)-3H-pyrazolo[3,4-c]isoquinolin-5-yl]phenol | 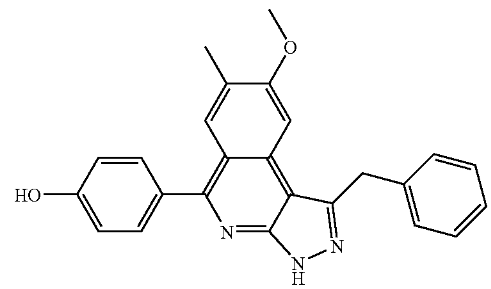 |
| 31 | 4-[1-methyl-6,8-bis(methyloxy)-3H-pyrazolo[3,4-c]isoquinolin-5-yl]phenol | 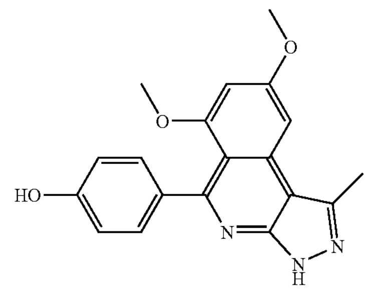 |
| 32 | 4-[6,8-bis(methyloxy)-3H-pyrazolo[3,4-c]isoquinolin-5-yl]phenol | 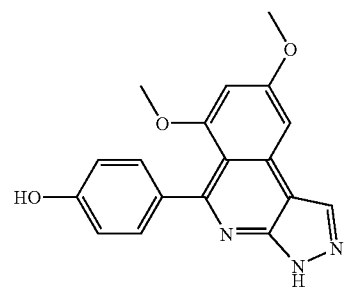 |
| 33 | 4-[6,8-bis(methyloxy)-1-(phenylmethyl)-3H-pyrazolo[3,4-c]isoquinolin-5-yl]phenol | 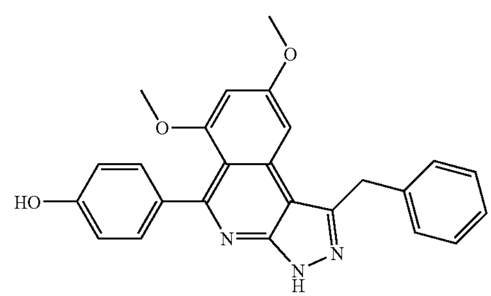 |
| 34 | 4-[6,7,8-tris(methyloxy)-3H-pyrazolo[3,4-c]isoquinolin-5-yl]phenol | 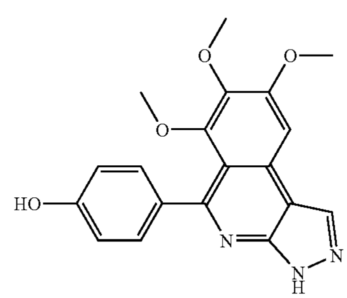 |

TABLE 1-continued

| Entry | Name | Structure |
|---|---|---|
| 35 | 4-[1-methyl-7,8,9-tris(methyloxy)-3H-pyrazolo[3,4-c]isoquinolin-5-yl]phenol | 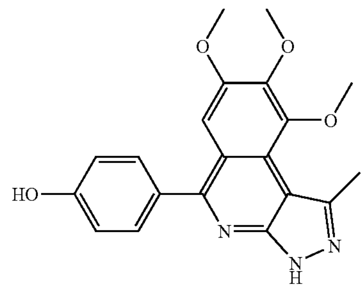 |
| 36 | 4-[1-methyl-8-(methyloxy)-3H-pyrazolo[3,4-c]isoquinolin-5-yl]phenol | 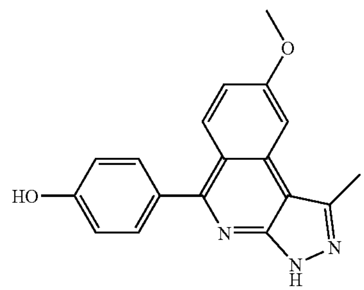 |
| 37 | 2-methyl-4-[1-methyl-7,8-bis(methyloxy)-3H-pyrazolo[3,4-c]isoquinolin-5-yl]phenol | 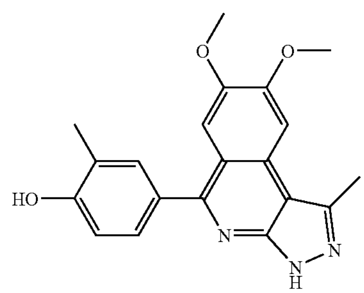 |
| 38 | 4-[1-methyl-7,8-bis(methyloxy)-3H-pyrazolo[3,4-c]isoquinolin-5-yl]-2-(methyloxy)phenol | 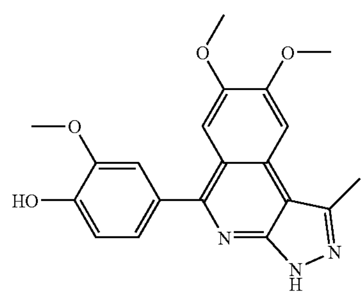 |
| 39 | 4-{1-methyl-8-(methyloxy)-7-[(2-morpholin-4-ylethyl)oxy]-3H-pyrazolo[3,4-c]isoquinolin-5-yl}phenol | 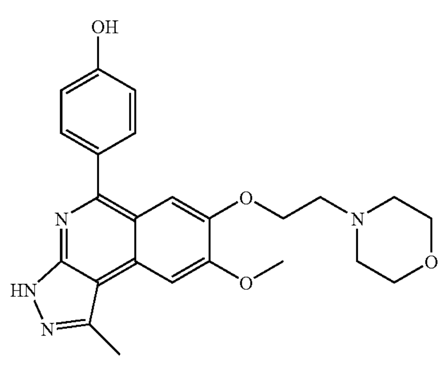 |

TABLE 1-continued

| Entry | Name |
|---|---|
| 40 | 2-(ethyloxy)-4-[1-methyl-7,8-bis(methyloxy)-3H-pyrazolo[3,4-c]isoquinolin-5-yl]phenol |
| 41 | 2-chloro-4-[1-methyl-7,8-bis(methyloxy)-3H-pyrazolo[3,4-c]isoquinolin-5-yl]phenol |
| 42 | 2-fluoro-4-[1-methyl-7,8-bis(methyloxy)-3H-pyrazolo[3,4-c]isoquinolin-5-yl]phenol |
| 43 | 4-[1-methyl-7,8-bis(methyloxy)-3H-pyrazolo[3,4-c]isoquinolin-5-yl]-2-nitrophenol |
| 44 | 2-bromo-4-[1-methyl-7,8-bis(methyloxy)-3H-pyrazolo[3,4-c]isoquinolin-5-yl]phenol |

TABLE 1-continued

| Entry | Name | Structure |
|---|---|---|
| 45 | 1-{[5-(4-hydroxyphenyl)-7,8-bis(methyloxy)-3H-pyrazolo[3,4-c]isoquinolin-1-yl]methyl}pyrrolidin-2-one | 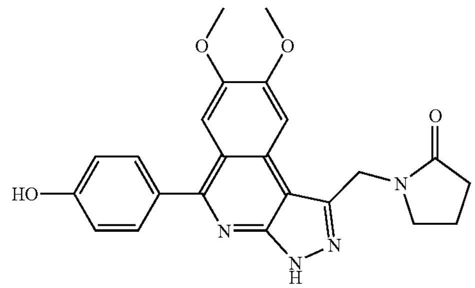 |
| 46 | 5-(4-fluorophenyl)-1-methyl-7,8-bis(methyloxy)-3H-pyrazolo[3,4-c]isoquinoline | 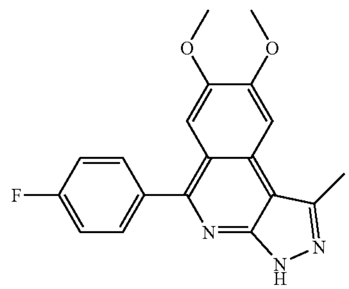 |
| 47 | 2,6-dimethyl-4-[1-methyl-7,8-bis(methyloxy)-3H-pyrazolo[3,4-c]isoquinolin-5-yl]phenol | 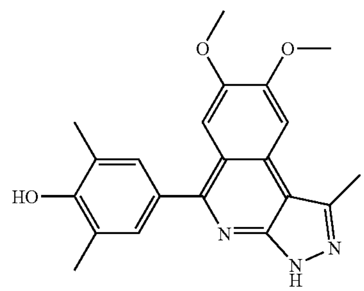 |
| 48 | 5-[4-fluoro-3-(trifluoromethyl)phenyl]-1-methyl-7,8-bis(methyloxy)-3H-pyrazolo[3,4-c]isoquinoline | 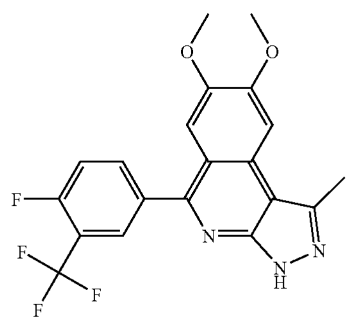 |
| 49 | 5-(3-chloro-4-fluorophenyl)-1-methyl-7,8-bis(methyloxy)-3H-pyrazolo[3,4-c]isoquinoline | 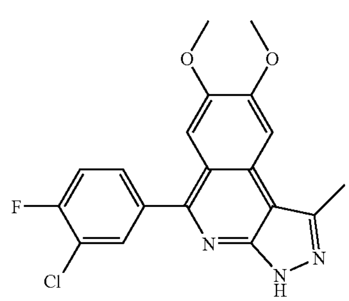 |

TABLE 1-continued

| Entry | Name | Structure |
|---|---|---|
| 50 | 5-(3,4-difluorophenyl)-1-methyl-7,8-bis(methyloxy)-3H-pyrazolo[3,4-c]isoquinoline | 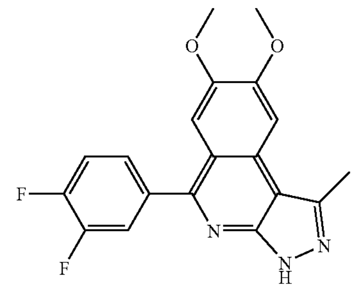 |
| 51 | 1-methyl-7,8-bis(methyloxy)-5-[3-(trifluoromethyl)phenyl]-3H-pyrazolo[3,4-c]isoquinoline | 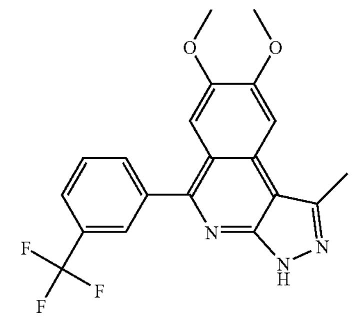 |
| 52 | 5-(4-fluoro-3-methylphenyl)-1-methyl-7,8-bis(methyloxy)-3H-pyrazolo[3,4-c]isoquinoline | 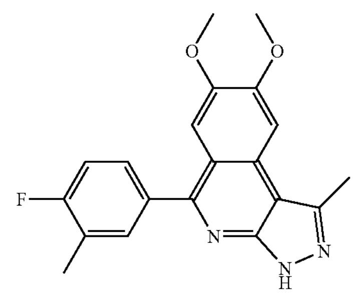 |
| 53 | 5-(3-bromo-4-fluorophenyl)-1-methyl-7,8-bis(methyloxy)-3H-pyrazolo[3,4-c]isoquinoline | 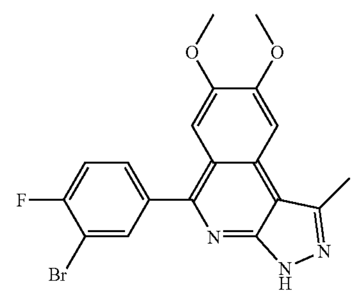 |
| 54 | 4-{1-methyl-7-(methyloxy)-8-[(piperidin-4-ylmethyl)oxy]-3H-pyrazolo[3,4-c]isoquinolin-5-yl}phenol | 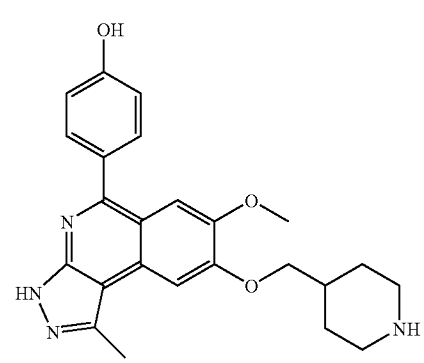 |

TABLE 1-continued

| Entry | Name |
|---|---|
| 55 | 4-{1-methyl-8-(methyloxy)-7-[(piperidin-4-ylmethyl)oxy]-3H-pyrazolo[3,4-c]isoquinolin-5-yl}phenol |
| 56 | 1-methyl-7,8-bis(methyloxy)-5-(3-methylphenyl)-3H-pyrazolo[3,4-c]isoquinoline |
| 57 | 5-(3-bromophenyl)-1-methyl-7,8-bis(methyloxy)-3H-pyrazolo[3,4-c]isoquinoline |
| 58 | 4-[8-(ethyloxy)-1-methyl-7-(methyloxy)-3H-pyrazolo[3,4-c]isoquinolin-5-yl]phenol |
| 59 | 4-[1-methyl-8,9-bis(methyloxy)-3H-pyrazolo[3,4-c]isoquinolin-5-yl]phenol |

TABLE 1-continued

| Entry | Name | Structure |
|---|---|---|
| 60 | 4-[7-(ethyloxy)-1-methyl-8-(methyloxy)-3H-pyrazolo[3,4-c]isoquinolin-5-yl]phenol | 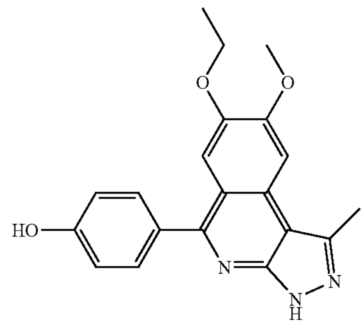 |
| 61 | 4-{1-methyl-8-(methyloxy)-9-[(piperidin-4-ylmethyl)oxy]-3H-pyrazolo[3,4-c]isoquinolin-5-yl}phenol | 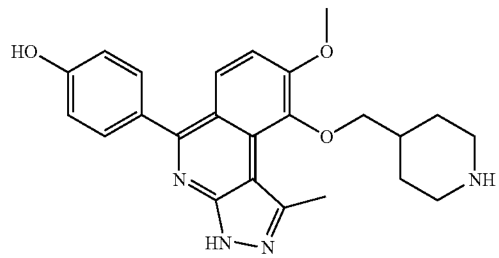 |
| 62 | 4-[1-methyl-7,8-bis(methyloxy)-3H-pyrazolo[3,4-c]isoquinolin-5-yl]-2-(1-methylethyl)phenol | 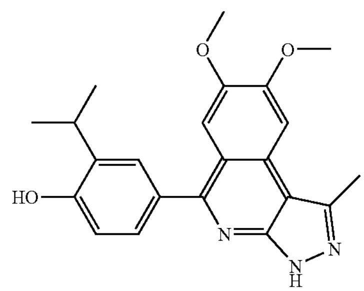 |
| 63 | 2-ethyl-4-[1-methyl-7,8-bis(methyloxy)-3H-pyrazolo[3,4-c]isoquinolin-5-yl]phenol | 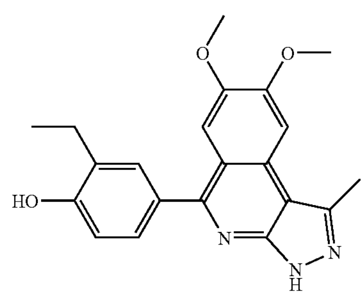 |
| 64 | 4-(1-methyl-8-(methyloxy)-9-{[(1-methylpiperidin-4-yl)methyl]oxy}-3H-pyrazolo[3,4-c]isoquinolin-5-yl)phenol | 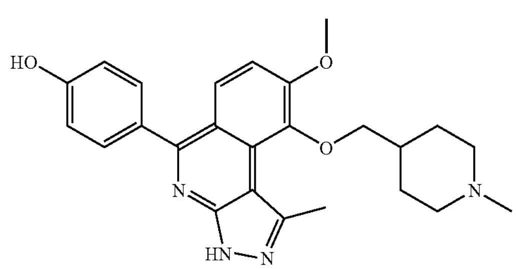 |

TABLE 1-continued

| Entry | Name | Structure |
|---|---|---|
| 65 | 4-(1-methyl-7-(methyloxy)-8-{[(1-methylpiperidin-4-yl)methyl]oxy}-3H-pyrazolo[3,4-c]isoquinolin-5-yl)phenol | 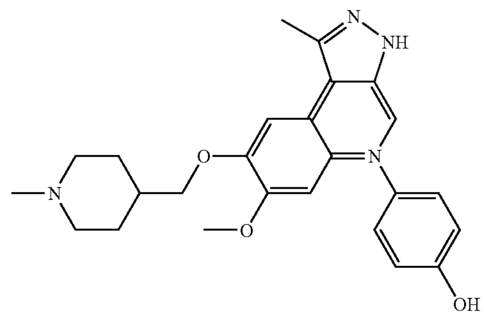 |
| 66 | 4-[1,7-dimethyl-8-(methyloxy)-3H-pyrazolo[3,4-c]isoquinolin-5-yl]phenol | 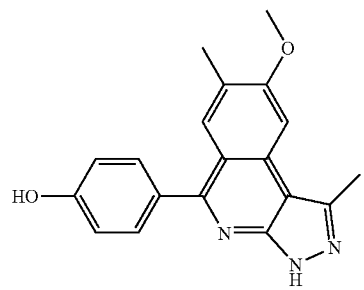 |
| 67 | 1,1-dimethylethyl 4-[5-(4-hydroxyphenyl)-7,8-bis(methyloxy)-3H-pyrazolo[3,4-c]isoquinolin-1-yl]piperidine-1-carboxylate | 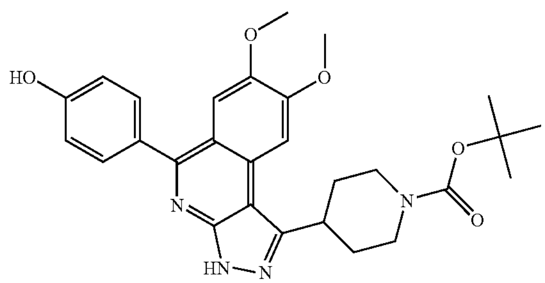 |
| 68 | 4-[7,8-bis(methyloxy)-1-piperidin-4-yl-3H-pyrazolo[3,4-c]isoquinolin-5-yl]phenol | 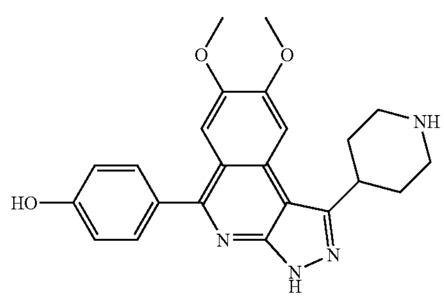 |
| 69 | 2-chloro-4-[1-methyl-8,9-bis(methyloxy)-3H-pyrazolo[3,4-c]isoquinolin-5-yl]phenol | 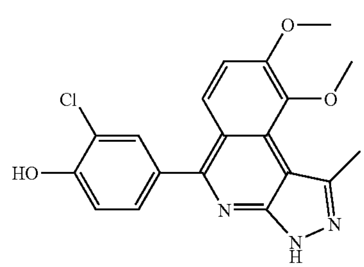 |

TABLE 1-continued

| Entry | Name | Structure |
|---|---|---|
| 70 | 2-fluoro-4-[1-methyl-8,9-bis(methyloxy)-3H-pyrazolo[3,4-c]isoquinolin-5-yl]phenol | 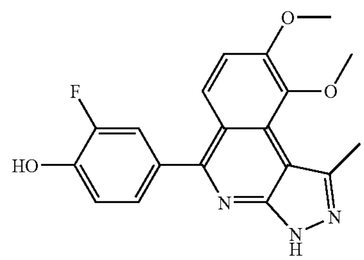 |
| 71 | 2-methyl-4-[1-methyl-8,9-bis(methyloxy)-3H-pyrazolo[3,4-c]isoquinolin-5-yl]phenol | 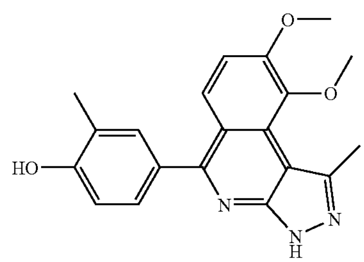 |
| 72 | 2-bromo-4-[1-methyl-8,9-bis(methyloxy)-3H-pyrazolo[3,4-c]isoquinolin-5-yl]phenol | 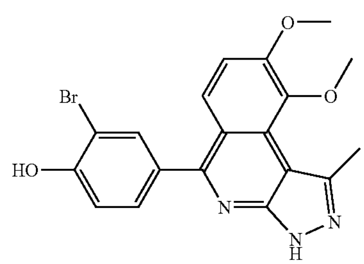 |
| 73 | 4-[1-methyl-7,8-bis(methyloxy)-3H-pyrazolo[3,4-c]isoquinolin-5-yl]benzonitrile | 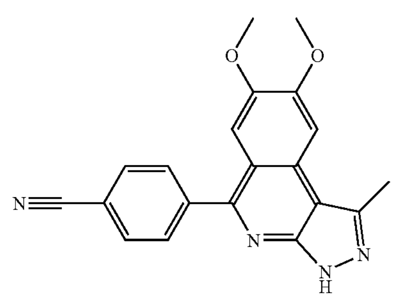 |
| 74 | N'-hydroxy-4-[1-methyl-7,8-bis(methyloxy)-3H-pyrazolo[3,4-c]isoquinolin-5-yl]benzenecarboximidamide | 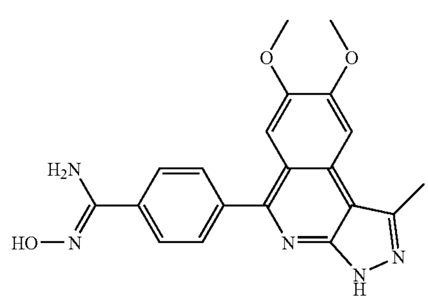 |

TABLE 1-continued

| Entry | Name | Structure |
|---|---|---|
| 75 | 5-hydroxy-2-[1-methyl-7,8-bis(methyloxy)-3H-pyrazolo[3,4-c]isoquinolin-5-yl]-4H-pyran-4-one | 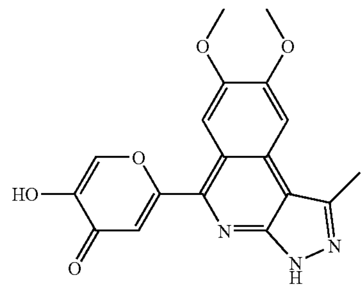 |
| 76 | 2-[(difluoromethyl)oxy]-4-[1-methyl-7,8-bis(methyloxy)-3H-pyrazolo[3,4-c]isoquinolin-5-yl]phenol | 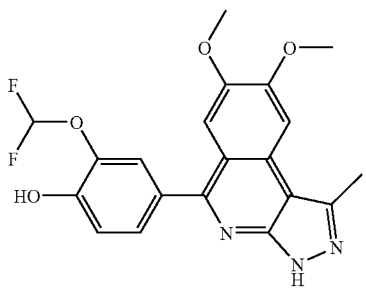 |
| 77 | 5-[1-methyl-7,8-bis(methyloxy)-3H-pyrazolo[3,4-c]isoquinolin-5-yl]pyridin-2-ol | 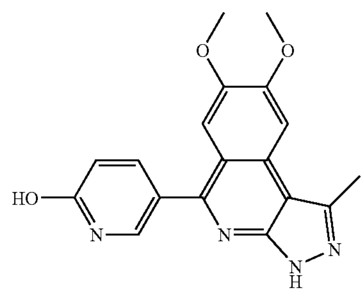 |
| 78 | 4-[1,9-dimethyl-8-(methyloxy)-3H-pyrazolo[3,4-c]isoquinolin-5-yl]phenol | 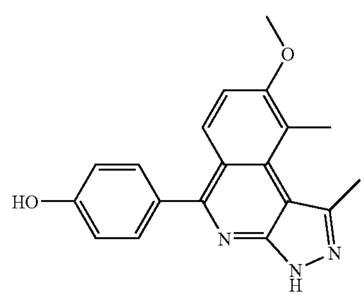 |
| 79 | 4-[6,9-difluoro-1-methyl-8-(methyloxy)-3H-pyrazolo[3,4-c]isoquinolin-5-yl]phenol | 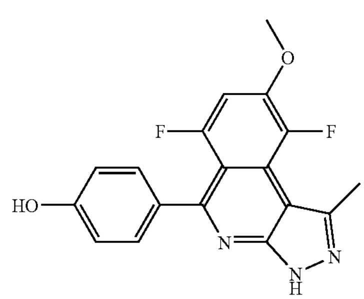 |

TABLE 1-continued

| Entry | Name | Structure |
|---|---|---|
| 80 | 2-bromo-4-{1-methyl-8-(methyloxy)-9-[(2-morpholin-4-yl-ethyl)oxy]-3H-pyrazolo[3,4-c]isoquinolin-5-yl}phenol | 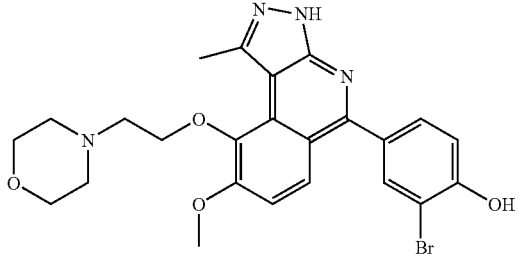 |
| 81 | 2-chloro-4-{1-methyl-8-(methyloxy)-9-[(2-morpholin-4-yl-ethyl)oxy]-3H-pyrazolo[3,4-c]isoquinolin-5-yl}phenol | 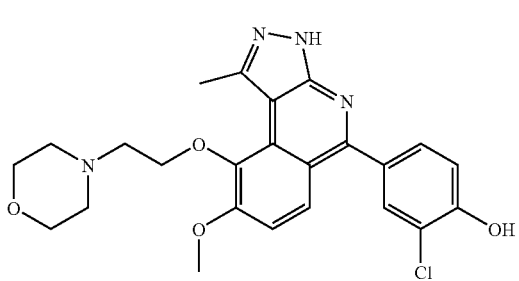 |
| 82 | 4-(7,8-bis(methyloxy)-1-{[(phenylmethyl)amino]methyl}-3H-pyrazolo[3,4-c]isoquinolin-5-yl)phenol | 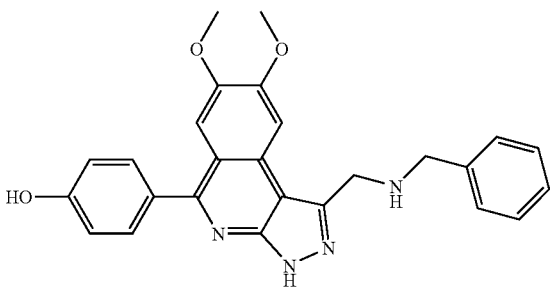 |
| 83 | 2,5-dimethyl-4-[1-methyl-7,8-bis(methyloxy)-3H-pyrazolo[3,4-c]isoquinolin-5-yl]phenol | 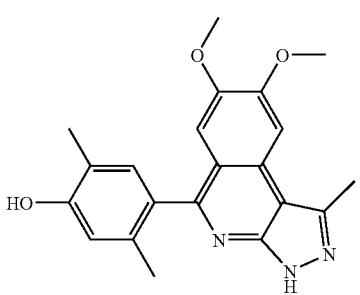 |
| 84 | 2,3-dichloro-4-[1-methyl-7,8-bis(methyloxy)-3H-pyrazolo[3,4-c]isoquinolin-5-yl]phenol | 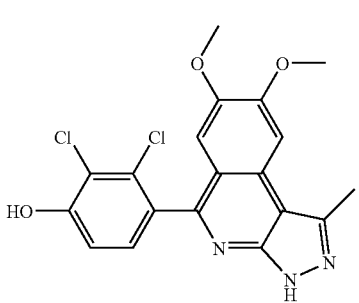 |

TABLE 1-continued

| Entry | Name | Structure |
|---|---|---|
| 85 | 2,5-dichloro-4-[1-methyl-7,8-bis(methyloxy)-3H-pyrazolo[3,4-c]isoquinolin-5-yl]phenol | 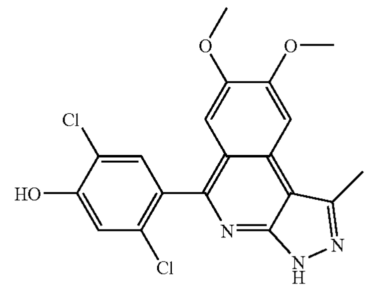 |
| 86 | 2,3-dimethyl-4-[1-methyl-7,8-bis(methyloxy)-3H-pyrazolo[3,4-c]isoquinolin-5-yl]phenol | 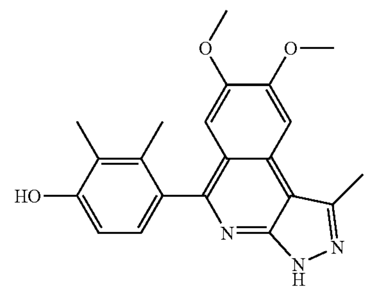 |
| 87 | 2-bromo-4-(1-methyl-8-(methyloxy)-9-{[(1-methylpiperidin-4-yl)methyl]oxy}-3H-pyrazolo[3,4-c]isoquinolin-5-yl)phenol | 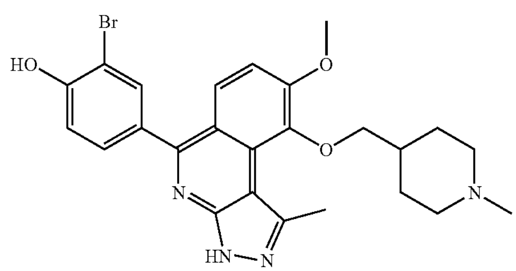 |
| 88 | 2-chloro-4-(1-methyl-7-(methyloxy)-8-{[(1-methylpiperidin-4-yl)methyl]oxy}-3H-pyrazolo[3,4-c]isoquinolin-5-yl)phenol | 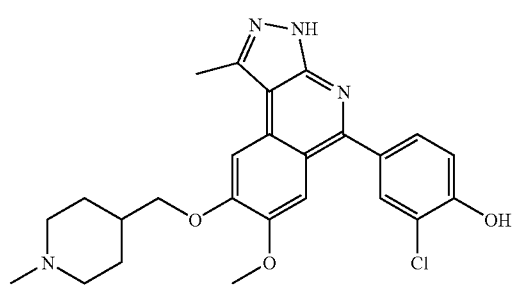 |
| 89 | 4-[9-fluoro-1-methyl-8-(methyloxy)-3H-pyrazolo[3,4-c]isoquinolin-5-yl]phenol | 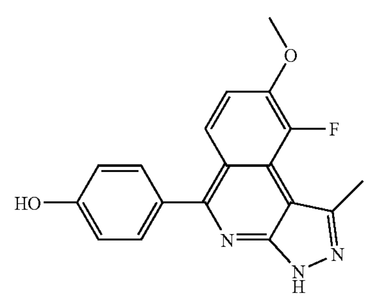 |

TABLE 1-continued

| Entry | Name | Structure |
|---|---|---|
| 90 | 4-(1-methyl-8-(methyloxy)-9-{[2-(methyloxy)ethyl]oxy}-3H-pyrazolo[3,4-c]isoquinolin-5-yl)phenol | 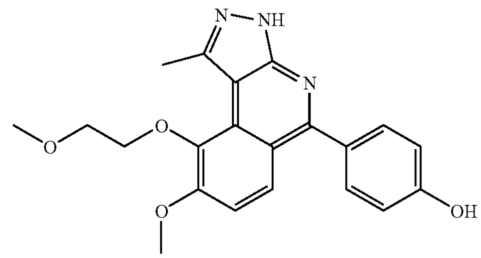 |
| 91 | 2-chloro-4-(1-methyl-8-(methyloxy)-9-{[(1-methylpiperidin-4-yl)methyl]oxy}-3H-pyrazolo[3,4-c]isoquinolin-5-yl)phenol | 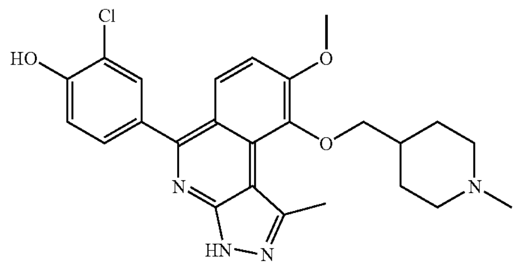 |
| 92 | 4-[6-bromo-1,7-dimethyl-8-(methyloxy)-3H-pyrazolo[3,4-c]isoquinolin-5-yl]phenol | 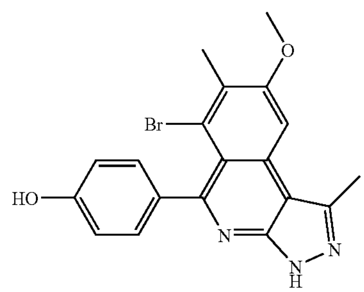 |
| 93 | 4-[6-fluoro-1-methyl-7,8-bis(methyloxy)-3H-pyrazolo[3,4-c]isoquinolin-5-yl]phenol | 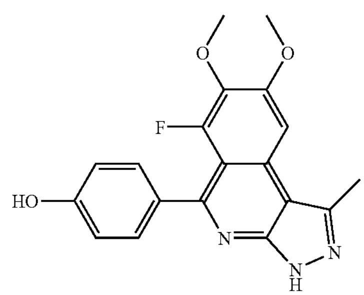 |
| 94 | 4-[9-chloro-1,7-dimethyl-8-(methyloxy)-3H-pyrazolo[3,4-c]isoquinolin-5-yl]phenol | 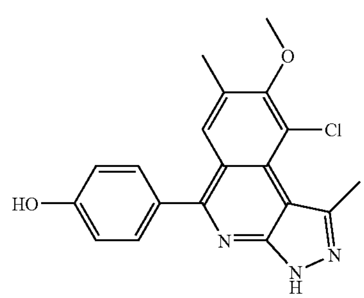 |

TABLE 1-continued

| Entry | Name | Structure |
|---|---|---|
| 95 | 2-chloro-4-[8-{[(1-eth-ylpiperidin-4-yl)meth-yl]oxy}-1-methyl-7-(meth-yloxy)-3H-pyrazolo[3,4-c]iso-quinolin-5-yl]phenol | 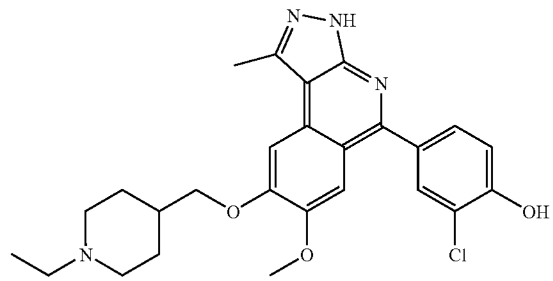 |
| 96 | 3-chloro-4-[1-methyl-7,8-bis(meth-yloxy)-3H-pyra-zolo[3,4-c]isoquinolin-5-yl]phenol | 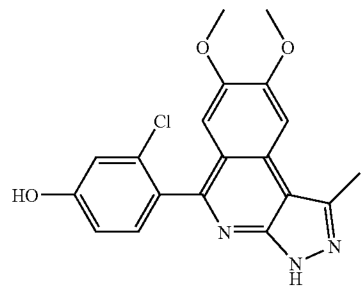 |
| 97 | 4-(1-methyl-8,9-bis{[2-(meth-yloxy)ethyl]oxy}-3H-pyra-zolo[3,4-c]isoquinolin-5-yl)phenol | 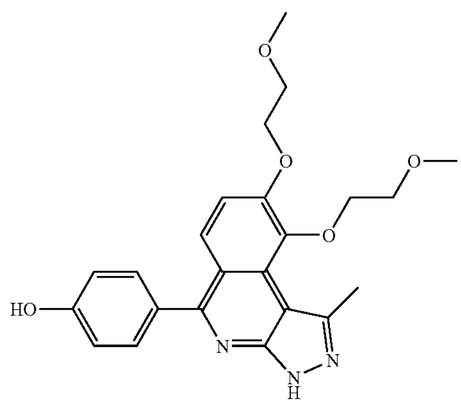 |
| 98 | 4-(1-methyl-3H-pyrazolo[3,4-c]iso-quinolin-5-yl)phenol | 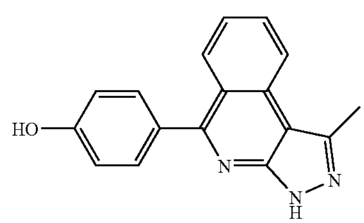 |
| 99 | 2-chloro-4-(1-methyl-3H-pyra-zolo[3,4-c]isoquinolin-5-yl)phenol | 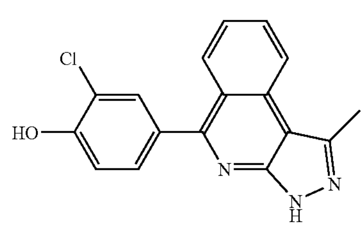 |

TABLE 1-continued

| Entry | Name | Structure |
|---|---|---|
| 100 | 2-bromo-4-(1-methyl-3H-pyrazolo[3,4-c]isoquinolin-5-yl)phenol | 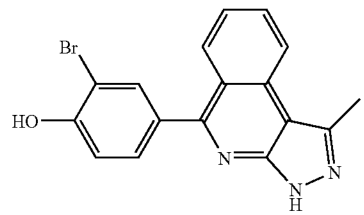 |
| 101 | 2-chloro-4-[1,7-dimethyl-8-(methyloxy)-3H-pyrazolo[3,4-c]isoquinolin-5-yl]phenol | 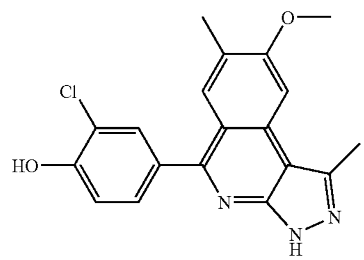 |
| 102 | 2-bromo-4-[1,7-dimethyl-8-(methyloxy)-3H-pyrazolo[3,4-c]isoquinolin-5-yl]phenol | 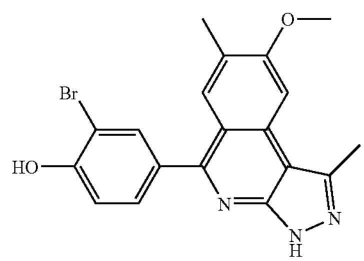 |
| 103 | 2-chloro-4-[1-methyl-8-({[1-(1-methylethyl)piperidin-4-yl]methyl}oxy)-7-(methyloxy)-3H-pyrazolo[3,4-c]isoquinolin-5-yl]phenol | 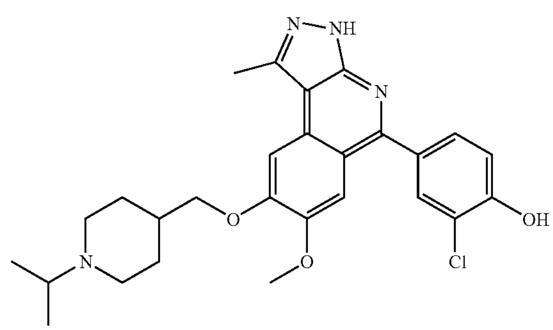 |
| 104 | 4-[9-bromo-1-methyl-8-(methyloxy)-3H-pyrazolo[3,4-c]isoquinolin-5-yl]phenol | 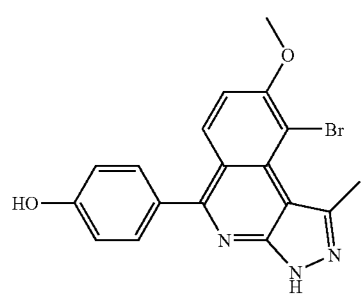 |

TABLE 1-continued

| Entry | Name | Structure |
|---|---|---|
| 105 | 4-[7-chloro-9-fluoro-1-methyl-8-(methyloxy)-3H-pyrazolo[3,4-c]isoquinolin-5-yl]phenol | 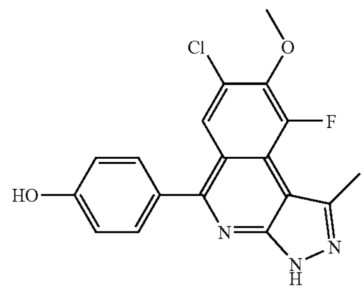 |
| 106 | 4-[8-{[(1-acetylpiperidin-4-yl)methyl]oxy}-1-methyl-7-(methyloxy)-3H-pyrazolo[3,4-c]isoquinolin-5-yl]-2-chlorophenol | 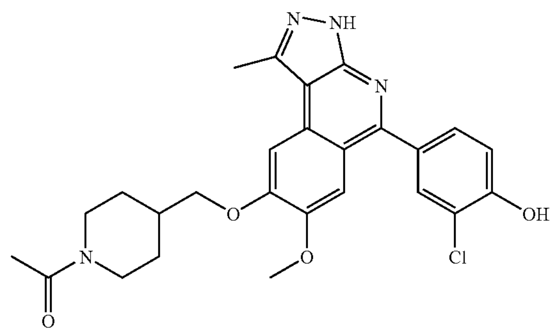 |
| 107 | 4-[9-{[(1-acetylpiperidin-4-yl)methyl]oxy}-1-methyl-8-(methyloxy)-3H-pyrazolo[3,4-c]isoquinolin-5-yl]-2-bromophenol | 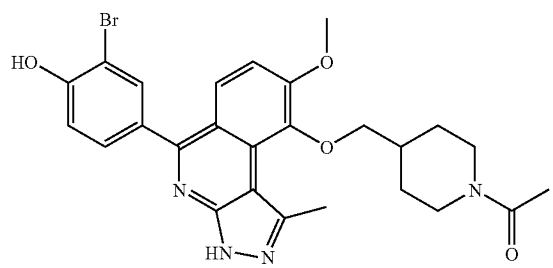 |
| 108 | 2-chloro-4-(1-methyl-9-(methyloxy)-8-{[2-(methyloxy)ethyl]oxy}-3H-pyrazolo[3,4-c]isoquinolin-5-yl)phenol | 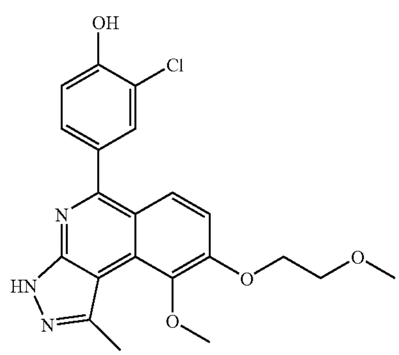 |
| 109 | 4-[7-fluoro-1-methyl-8-(methyloxy)-3H-pyrazolo[3,4-c]isoquinolin-5-yl]phenol | 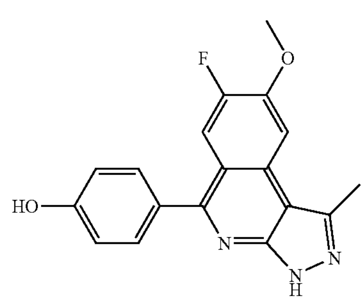 |

TABLE 1-continued

| Entry | Name | Structure |
|---|---|---|
| 110 | 2-chloro-4-(1-methyl-8,9-bis{[2-(methyloxy)ethyl]oxy}-3H-pyrazolo[3,4-c]isoquinolin-5-yl)phenol | 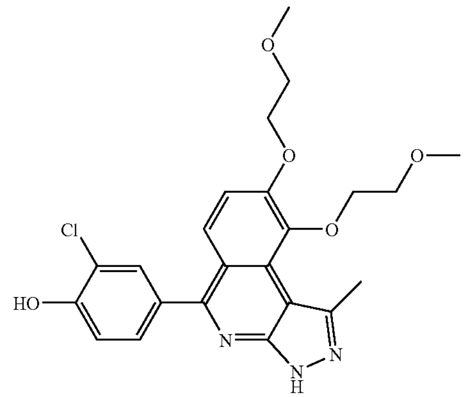 |
| 111 | 2-bromo-4-(1-methyl-8,9-bis{[2-(methyloxy)ethyl]oxy}-3H-pyrazolo[3,4-c]isoquinolin-5-yl)phenol | 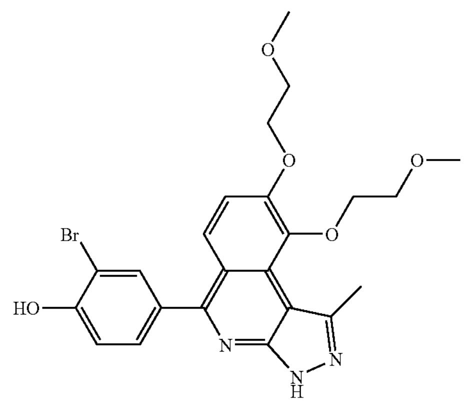 |
| 112 | 2-chloro-4-(1-methyl-8-(methyloxy)-9-{[2-(methyloxy)ethyl]oxy}-3H-pyrazolo[3,4-c]isoquinolin-5-yl)phenol | 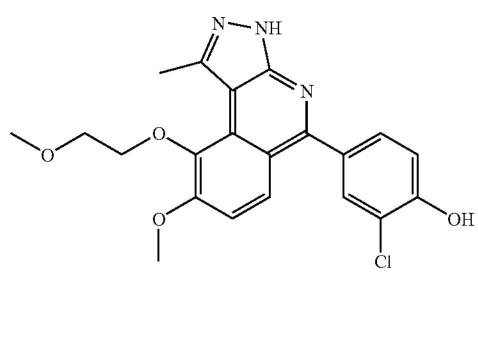 |
| 113 | 2-bromo-4-(1-methyl-8-(methyloxy)-9-{[2-(methyloxy)ethyl]oxy}-3H-pyrazolo[3,4-c]isoquinolin-5-yl)phenol | 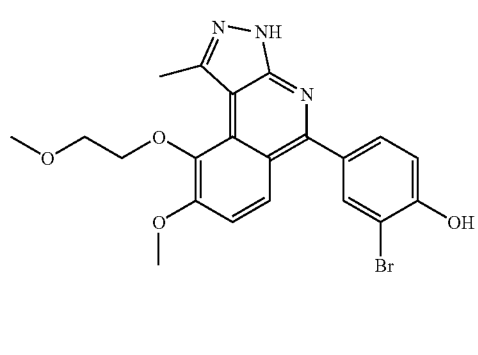 |

TABLE 1-continued

| Entry | Name | Structure |
|---|---|---|
| 114 | 3-fluoro-4-[1-methyl-7,8-bis(methyloxy)-3H-pyrazolo[3,4-c]isoquinolin-5-yl]phenol | 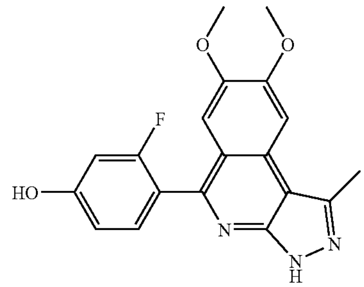 |
| 115 | 2-chloro-4-(1-methyl-7-(methyloxy)-8-{[2-(methyloxy)ethyl]oxy}-3H-pyrazolo[3,4-c]isoquinolin-5-yl)phenol | 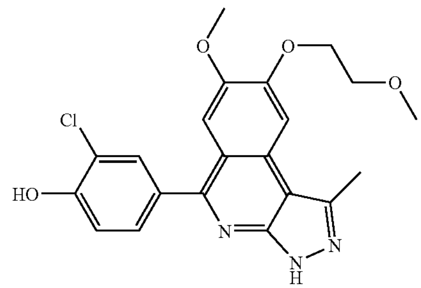 |
| 116 | 2-bromo-4-(1-methyl-7-(methyloxy)-8-{[2-(methyloxy)ethyl]oxy}-3H-pyrazolo[3,4-c]isoquinolin-5-yl)phenol | 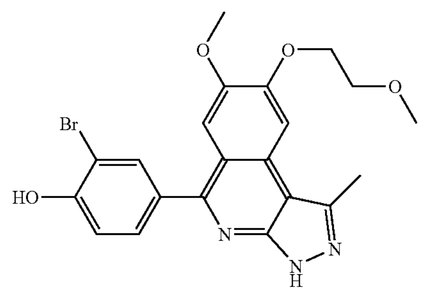 |
| 117 | 2-chloro-4-(1-methyl-7,8-bis{[2-(methyloxy)ethyl]oxy}-3H-pyrazolo[3,4-c]isoquinolin-5-yl)phenol | 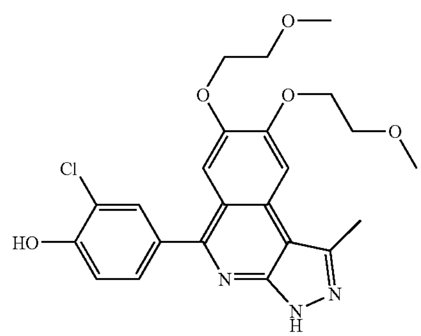 |
| 118 | 2-bromo-4-(1-methyl-7,8-bis{[2-(methyloxy)ethyl]oxy}-3H-pyrazolo[3,4-c]isoquinolin-5-yl)phenol | 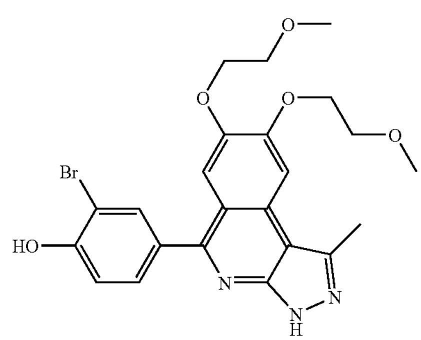 |

TABLE 1-continued

| Entry | Name |
|---|---|
| 119 | 1-methyl-7,8-bis(methyloxy)-5-(1H-pyrazol-5-yl)-3H-pyrazolo[3,4-c]isoquinoline |
| 120 | 4-(6,9-difluoro-1-methyl-8-{[2-(methyloxy)ethyl]oxy}-3H-pyrazolo[3,4-c]isoquinoln-5-yl)phenol |
| 121 | 2-chloro-5-fluoro-4-[1-methyl-7,8-bis(methyloxy)-3H-pyrazolo[3,4-c]isoquinolin-5-yl]phenol |
| 122 | 2-bromo-5-fluoro-4-[1-methyl-7,8-bis(methyloxy)-3H-pyrazolo[3,4-c]isoquinolin-5-yl]phenol |
| 123 | 4-[9-fluoro-1-methyl-7,8-bis(methyloxy)-3H-benzo[e]indazol-5-yl]phenol |

TABLE 1-continued

| Entry | Name | Structure |
|---|---|---|
| 124 | 2-hydroxy-5-[1-methyl-7,8-bis(methyloxy)-3H-pyrazolo[3,4-c]isoquinolin-5-yl]benzoic acid | 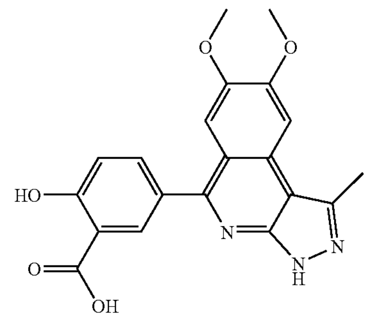 |
| 125 | 3-fluoro-4-(1-methyl-7-(methyloxy)-8-{[2-(methyloxy)ethyl]oxy}-3H-pyrazolo[3,4-c]isoquinolin-5-yl)phenol | 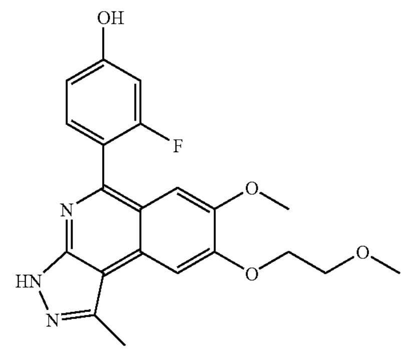 |
| 126 | 4-(6,9-difluoro-1-methyl-8-{[2-(methyloxy)ethyl]oxy}-3H-pyrazolo[3,4-c]isoquinolin-5-yl)-3-fluorophenol | 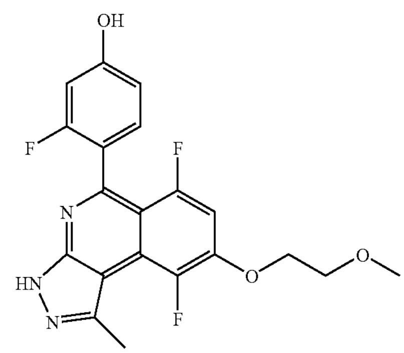 |
| 127 | 2-chloro-4-(6,9-difluoro-1-methyl-8-{[2-(methyloxy)ethyl]oxy}-3H-pyrazolo[3,4-c]isoquinolin-5-yl)phenol | 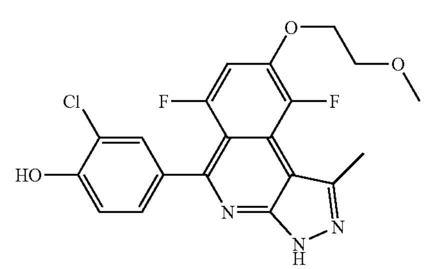 |
| 128 | 2-chloro-4-[8-(ethyloxy)-1-methyl-7-(methyloxy)-3H-pyrazolo[3,4-c]isoquinolin-5-yl]phenol | 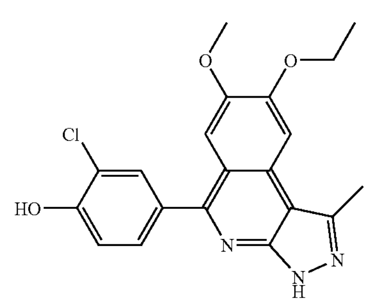 |

TABLE 1-continued

| Entry | Name | Structure |
|---|---|---|
| 129 | 2-chloro-4-[6-chloro-1-methyl-7,8-bis(methyloxy)-3H-pyrazolo[3,4-c]isoquinolin-5-yl]phenol | 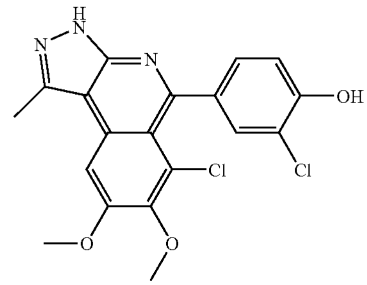 |
| 130 | 3-fluoro-4-(1-methyl-9-(methyloxy)-8-{[2-(methyloxy)ethyl]oxy}-3H-pyrazolo[3,4-c]isoquinolin-5-yl)phenol | 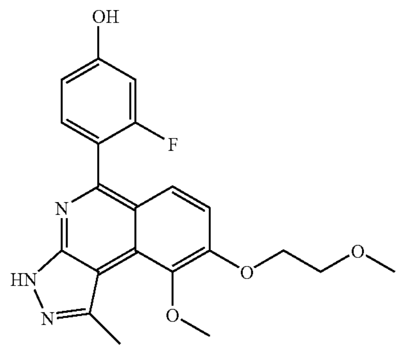 |
| 131 | 2-chloro-4-(1,7-dimethyl-8-{[2-(methyloxy)ethyl]oxy}-3H-pyrazolo[3,4-c]isoquinolin-5-yl)phenol | 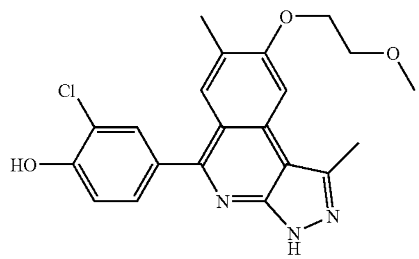 |
| 132 | 3-fluoro-4-(6-fluoro-1-methyl-7-(methyloxy)-8-{[2-(methyloxy)ethyl]oxy}-3H-pyrazolo[3,4-c]isoquinolin-5-yl)phenol | 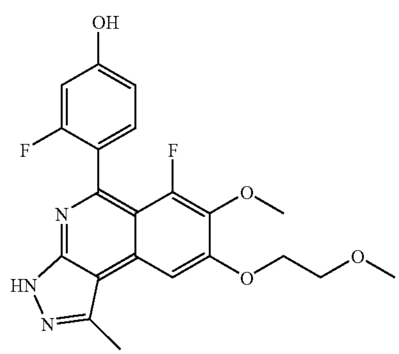 |
| 133 | 2-chloro-4-[1-methyl-8-[(1-methylethyl)oxy]-7-(methyloxy)-3H-pyrazolo[3,4-c]isoquinolin-5-yl]phenol | 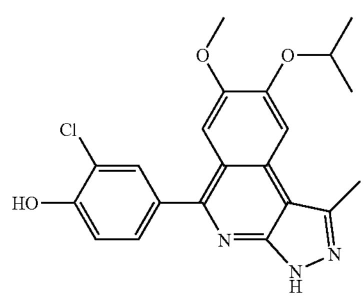 |

TABLE 1-continued

| Entry | Name | Structure |
|---|---|---|
| 134 | 2-chloro-4-{1-methyl-7-(methyloxy)-8-[(2-methylpropyl)oxy]-3H-pyrazolo[3,4-c]isoquinolin-5-yl}phenol | 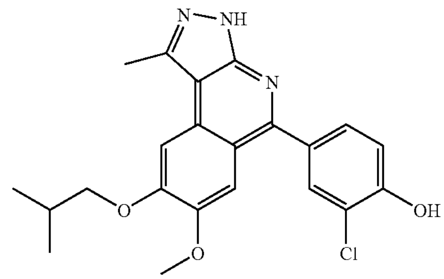 |
| 135 | 2-bromo-5-fluoro-4-(1-methyl-7-(methyloxy)-8-{[2-(methyloxy)ethyl]oxy}-3H-pyrazolo[3,4-c]isoquinolin-5-yl)phenol | 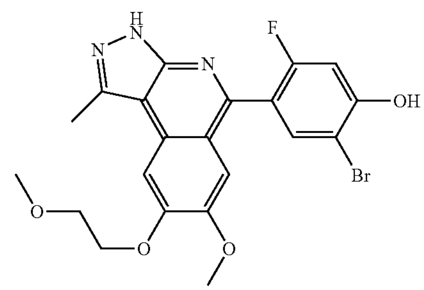 |
| 136 | 4-[7,8-bis(methyloxy)-3H-pyrazolo[3,4-c]isoquinolin-5-yl]-2-chlorophenol | 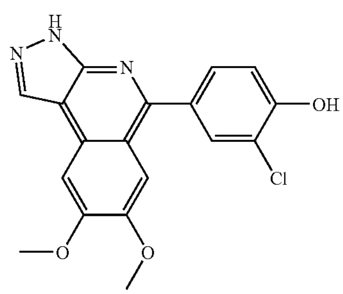 |
| 137 | 4-[7,8-bis(methyloxy)-1-(trifluoromethyl)-3H-pyrazolo[3,4-c]isoquinolin-5-yl]-2-chlorophenol | 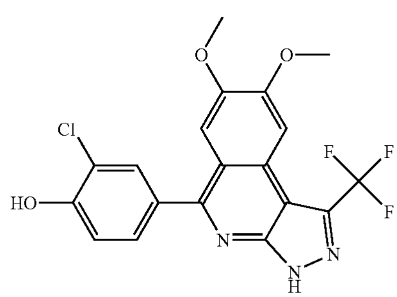 |
| 138 | 4-{7,8-bis(methyloxy)-1-[(methyloxy)methyl]-3H-pyrazolo[3,4-c]isoquinolin-5-yl}-2-chlorophenol | 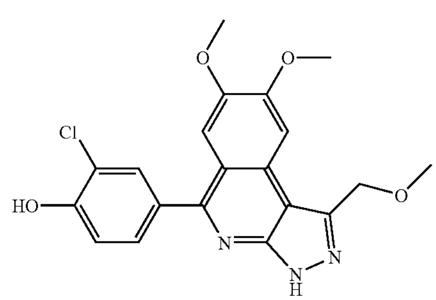 |

TABLE 1-continued

| Entry | Name | Structure |
|---|---|---|
| 139 | 2-chloro-4-(1-methyl-3H-[1,3]dioxolo[4,5-g]pyrazolo[3,4-c]isoquinolin-5-yl)phenol | 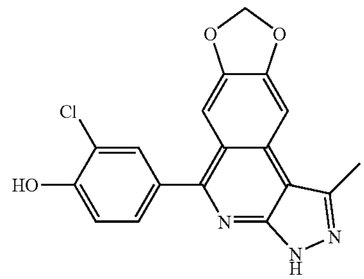 |
| 140 | 2-chloro-4-(1-methyl-8,9-dihydro-3H-[1,4]dioxino[2,3-g]pyrazolo[3,4-c]isoquinolin-5-yl)phenol | 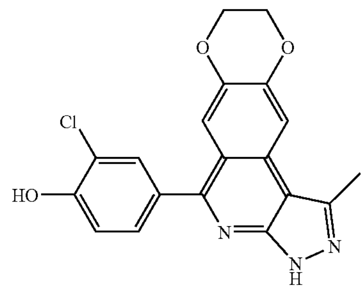 |
| 141 | 2-chloro-4-(1-methyl-9,10-dihydro-3H,8H-[1,4]dioxepino[2,3-g]pyrazolo[3,4-c]isoquinolin-5-yl)phenol | 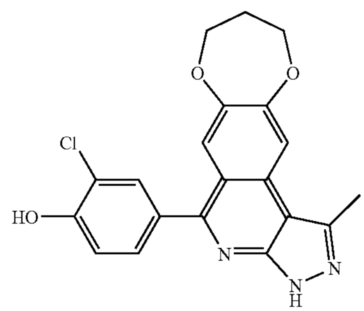 |
| 142 | 2-chloro-4-[7-[(difluoromethyl)oxy]-1-methyl-8-(methyloxy)-3H-pyrazolo[3,4-c]isoquinolin-5-yl]phenol | 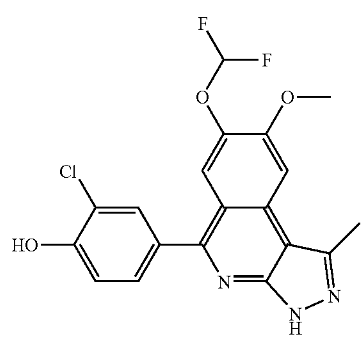 |
| 143 | 2-chloro-5-fluoro-4-(6-fluoro-1-methyl-9-(methyloxy)-8-{[2-(methyloxy)ethyl]oxy}-3H-pyrazolo[3,4-c]isoquinolin-5-yl)phenol | 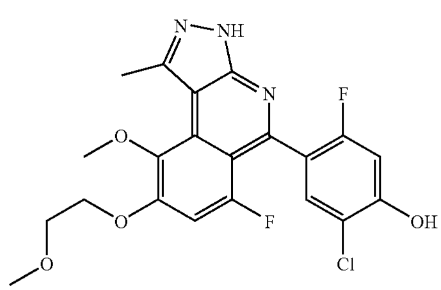 |

TABLE 1-continued

| Entry | Name | Structure |
|---|---|---|
| 144 | 2-chloro-4-(6,9-difluoro-1-methyl-8-{[2-(methyloxy)ethyl]oxy}-3H-pyrazolo[3,4-c]isoquinolin-5-yl)-5-fluorophenol | 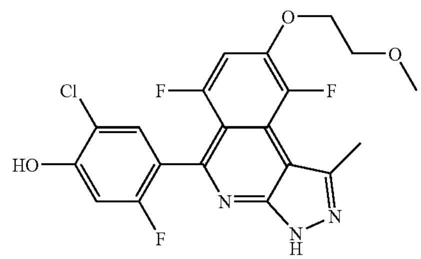 |
| 145 | 2-chloro-4-(11-methyl-2,3-dihydro-9H-[1,4]dioxino[2,3-f]pyrazolo[3,4-c]isoquinolin-7-yl)phenol | 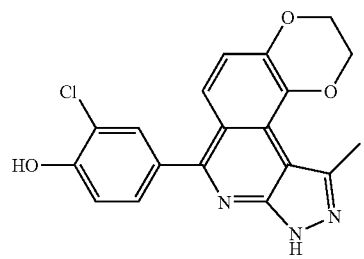 |
| 146 | 2-chloro-5-fluoro-4-(11-methyl-2,3-dihydro-9H-[1,4]dioxino[2,3-f]pyrazolo[3,4-c]isoquinolin-7-yl)phenol | 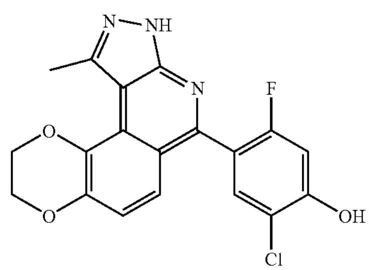 |
| 147 | 2-chloro-4-[1-methyl-6,7,8-tris(methyloxy)-3H-pyrazolo[3,4-c]isoquinolin-5-yl]phenol | 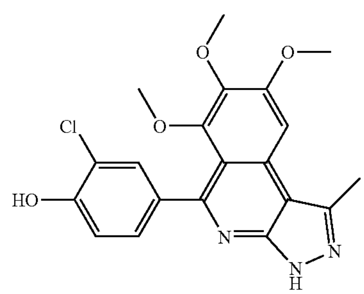 |
| 148 | 2-bromo-4-(6,9-difluoro-1-methyl-8-{[2-(methyloxy)ethyl]oxy}-3H-pyrazolo[3,4-c]isoquinolin-5-yl)-5-fluorophenol | 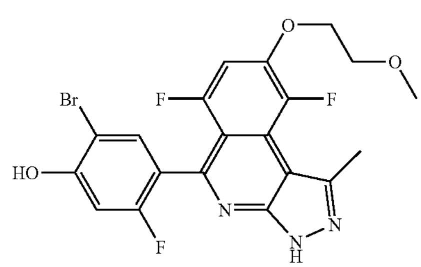 |
| 149 | 7-(3-chlorophenyl)-11-methyl-2,3-dihydro-9H-[1,4]dioxino[2,3-f]pyrazolo[3,4-c]isoquinoline | 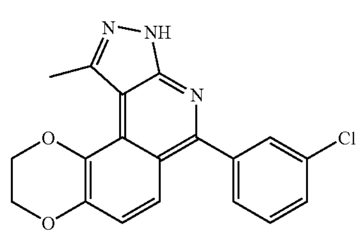 |

TABLE 1-continued

| Entry | Name | Structure |
|---|---|---|
| 150 | 2-chloro-5-fluoro-4-(6-fluoro-1-methyl-8,9-dihydro-3H-[1,4]dioxino[2,3-g]pyrazolo[3,4-c]isoquinolin-5-yl)phenol | 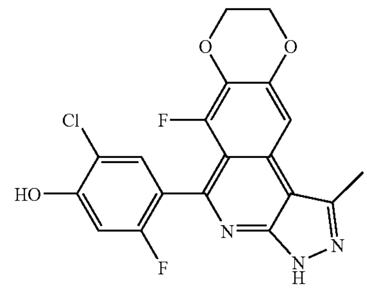 |
| 151 | 2-chloro-4-{1-methyl-7-(methyloxy)-8-[(tetrahydrofuran-2-ylmethyl)oxy]-3H-pyrazolo[3,4-c]isoquinolin-5-yl}phenol | 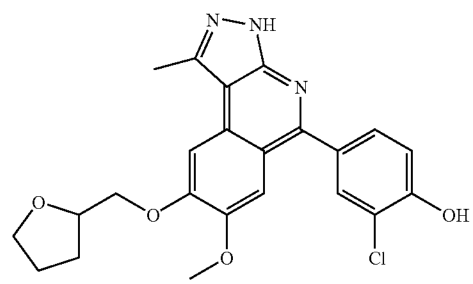 |
| 152 | 2-chloro-4-{1-methyl-7-(methyloxy)-8-[(tetrahydro-2H-pyran-2-ylmethyl)oxy]-3H-pyrazolo[3,4-c]isoquinolin-5-yl}phenol | 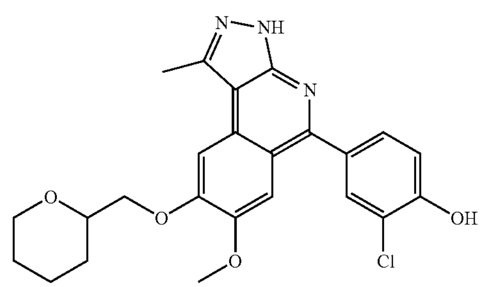 |
| 153 | 2-chloro-4-{1-methyl-7-(methyloxy)-8-[(2,2,2-trifluoroethyl)oxy]-3H-pyrazolo[3,4-c]isoquinolin-5-yl}phenol | 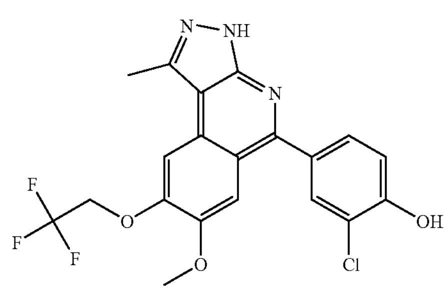 |
| 154 | 2-chloro-5-fluoro-4-[9-fluoro-1-methyl-6,7,8-tris(methyloxy)-3H-pyrazolo[3,4-c]isoquinolin-5-yl]phenol | 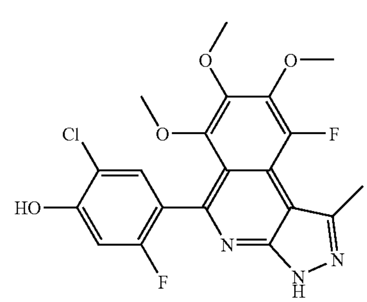 |

TABLE 1-continued

| Entry | Name | Structure |
|---|---|---|
| 155 | 5-(3-chloro-4-hydroxyphenyl)-6,9-difluoro-1-methyl-3H-pyrazolo[3,4-c]isoquinolin-8-ol | 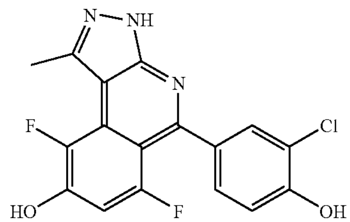 |
| 156 | 6,9-difluoro-5-(2-fluorophenyl)-1-methyl-8-{[2-(methyloxy)ethyl]oxy}-3H-pyrazolo[3,4-c]isoquinoline | 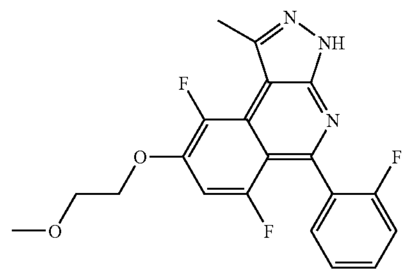 |
| 157 | 2-chloro-4-{8-[(difluoromethyl)oxy]-6,9-difluoro-1-methyl-3H-pyrazolo[3,4-c]isoquinolin-5-yl}phenol | 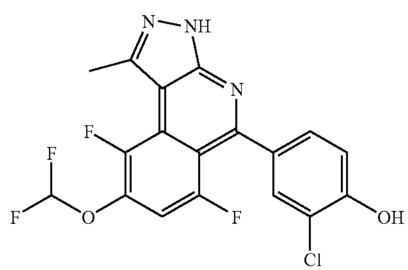 |
| 158 | 2-chloro-4-(6,11-difluoro-1-methyl-8,9-dihydro-3H-[1,4]dioxino[2,3-g]pyrazolo[3,4-c]isoquinolin-5-yl)-5-fluorophenol | 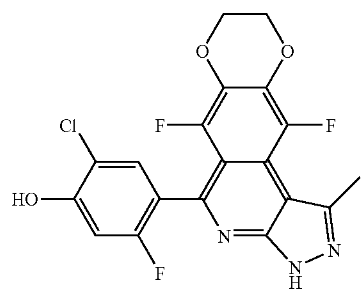 |
| 159 | 4-(1-methyl-3H-benzo[e]indazol-5-yl)phenol | 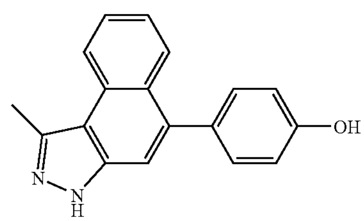 |
| 160 | 6-fluoro-7-(2-fluorophenyl)-11-methyl-2,3-dihydro-9H-[1,4]dioxino[2,3-f]pyrazolo[3,4-c]isoquinoline | 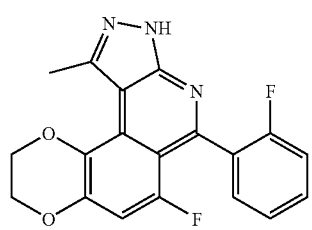 |

TABLE 1-continued

| Entry | Name | Structure |
|---|---|---|
| 161 | 2-chloro-4-{1-methyl-7-(methyloxy)-8-[(tetrahydro-2H-pyran-4-ylmethyl)oxy]-3H-pyrazolo[3,4-c]isoquinolin-5-yl}phenol | 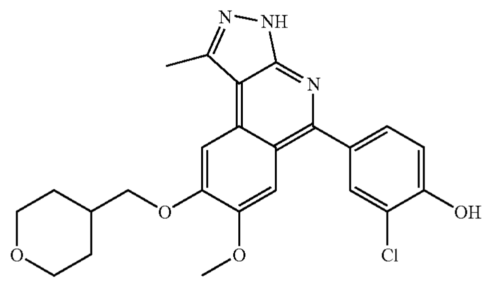 |
| 162 | 2-chloro-4-[8-{[2-(ethyloxy)ethyl]oxy}-1-methyl-7-(methyloxy)-3H-pyrazolo[3,4-c]isoquinolin-5-yl]phenol | 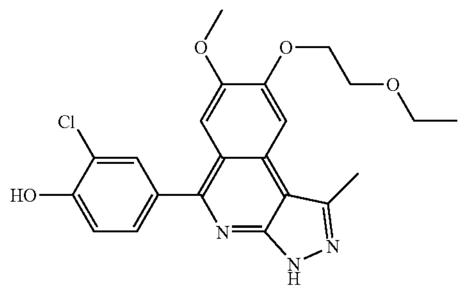 |
| 163 | N-[4-(6-fluoro-11-methyl-2,3-dihydro-9H-[1,4]dioxino[2,3-f]pyrazolo[3,4-c]isoquinolin-7-yl)phenyl]acetamide | 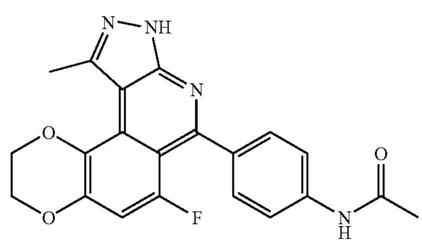 |
| 164 | 3-fluoro-4-(6-fluoro-11-methyl-2,3-dihydro-9H-[1,4]dioxino[2,3-f]pyrazolo[3,4-c]isoquinolin-7-yl)phenol | 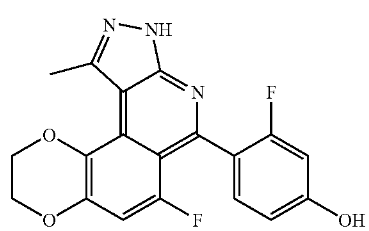 |
| 165 | 2-chloro-5-fluoro-4-(6-fluoro-11-methyl-2,3-dihydro-9H-[1,4]dioxino[2,3-f]pyrazolo[3,4-c]isoquinolin-7-yl)phenol | 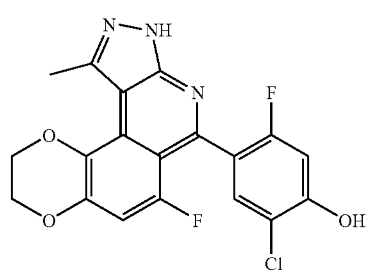 |

TABLE 1-continued

| Entry | Name | Structure |
|---|---|---|
| 166 | 2-chloro-4-[8-(cyclopentyloxy)-1-methyl-7-(methyloxy)-3H-pyrazolo[3,4-c]isoquinolin-5-yl]phenol | 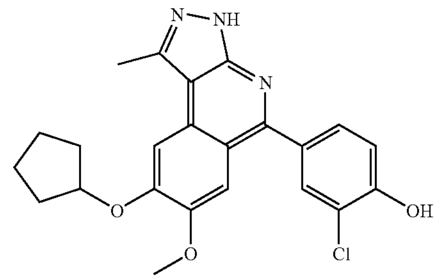 |
| 167 | 2-chloro-4-(1-methyl-7-(1-methylethyl)-8-{[2-(methyloxy)ethyl]oxy}-3H-pyrazolo[3,4-c]isoquinolin-5-yl)phenol | 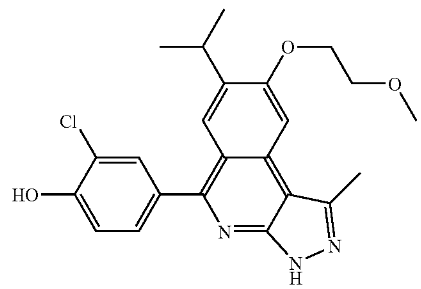 |
| 168 | 2-chloro-4-[9-ethyl-1-methyl-8-(methyloxy)-3H-pyrazolo[3,4-c]isoquinolin-5-yl]phenol | 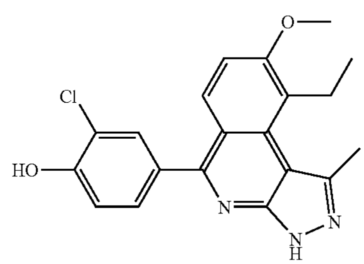 |
| 169 | 2-chloro-4-(6,9-difluoro-1-methyl-8-{[(1-methylpiperidin-4-yl)methyl]oxy}-3H-pyrazolo[3,4-c]isoquinolin-5-yl)phenol | 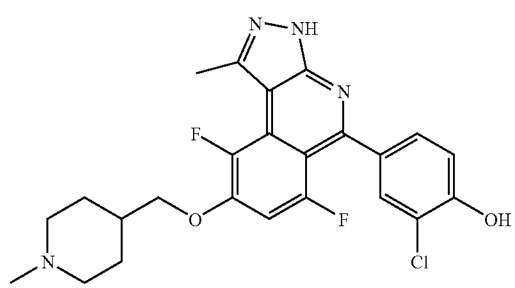 |
| 170 | 5-(3-chloro-4-hydroxyphenyl)-8-fluoro-1-methyl-7-(methyloxy)-3H-pyrazolo[3,4-c]isoquinolin-6-ol | 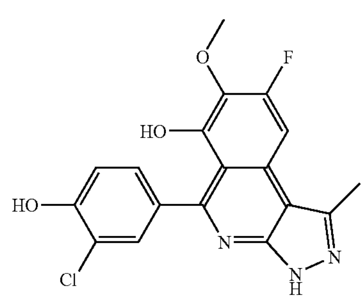 |

TABLE 1-continued

| Entry | Name | Structure |
|---|---|---|
| 171 | 2-chloro-4-(6-fluoro-1-methyl-7-(methyloxy)-8-{[(1-methylpiperidin-4-yl)methyl]oxy}-3H-pyrazolo[3,4-c]isoquinolin-5-yl)phenol | 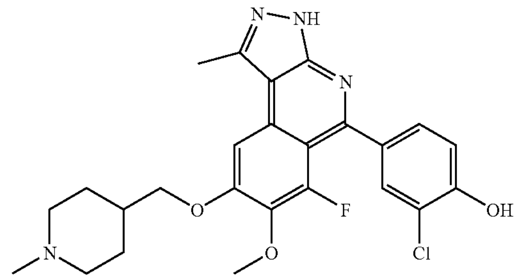 |
| 172 | 2-chloro-4-(6-fluoro-1-methyl-8,9-bis{[2-(methyloxy)ethyl]oxy}-3H-pyrazolo[3,4-c]isoquinolin-5-yl)phenol | 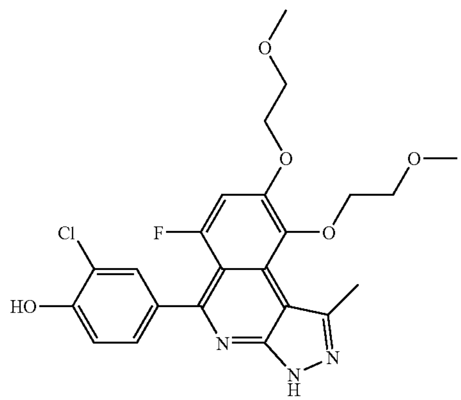 |
| 173 | 5-[3-chloro-4-(methyloxy)phenyl]-6-fluoro-1-methyl-7-(methyloxy)-8-{[(1-methylpiperidin-4-yl)methyl]oxy}-3H-pyrazolo[3,4-c]isoquinoline | 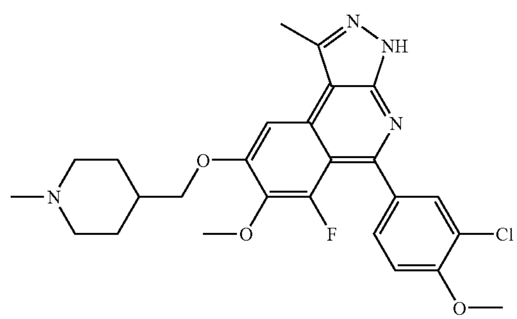 |
| 174 | 5-[3-chloro-4-(methyloxy)phenyl]-8-fluoro-1-methyl-7-(methyloxy)-3H-pyrazolo[3,4-c]isoquinolin-6-ol | 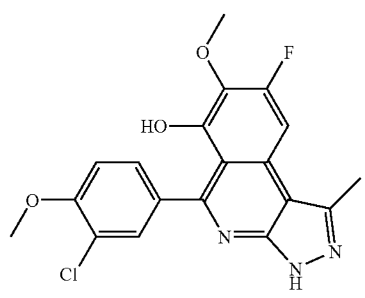 |
| 175 | 5-[3-chloro-4-(methyloxy)phenyl]-1-methyl-7,8-bis(methyloxy)-3H-pyrazolo[3,4-c]isoquinoline | 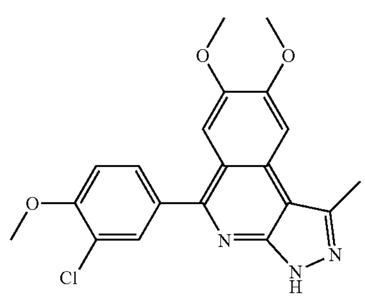 |

TABLE 1-continued

| Entry | Name |
|---|---|
| 176 | 2-chloro-4-{6-fluoro-1-methyl-7-(methyloxy)-8-[(2-piperidin-1-yl-ethyl)oxy]-3H-pyrazolo[3,4-c]isoquinolin-5-yl}phenol |
| 177 | 2-chloro-4-[8-{[2-(4-ethyl-piperazin-1-yl)ethyl]oxy}-6-fluoro-1-methyl-7-(methyloxy)-3H-pyrazolo[3,4-c]isoquinolin-5-yl]phenol |
| 178 | 2-chloro-4-[8-{[2-(di-ethylamino)ethyl]oxy}-6-fluoro-1-methyl-7-(methyloxy)-3H-pyrazolo[3,4-c]isoquinolin-5-yl]phenol |
| 179 | 2-chloro-4-(6-fluoro-1-methyl-7-(methyloxy)-8-{[2-(methyloxy)ethyl]oxy}-3H-pyrazolo[3,4-c]isoquinolin-5-yl)phenol |
| 180 | 6,9-difluoro-5-furan-3-yl-1-methyl-3H-pyrazolo[3,4-c]isoquinolin-8-ol |

TABLE 1-continued

| Entry | Name | Structure |
|---|---|---|
| 181 | 6,9-difluoro-5-furan-2-yl-1-methyl-3H-pyrazolo[3,4-c]isoquinolin-8-ol | 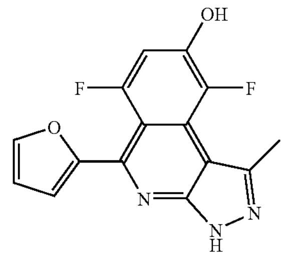 |
| 182 | 2-chloro-4-(6-fluoro-1-methyl-9-(methyloxy)-8-{[(1-methylpiperidin-4-yl)methyl]oxy}-3H-pyrazolo[3,4-c]isoquinolin-5-yl)phenol | 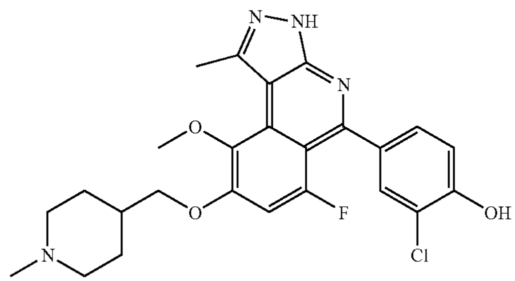 |
| 183 | 2-bromo-4-(6-fluoro-1-methyl-9-(methyloxy)-8-{[(1-methylpiperidin-4-yl)methyl]oxy}-3H-pyrazolo[3,4-c]isoquinolin-5-yl)phenol | 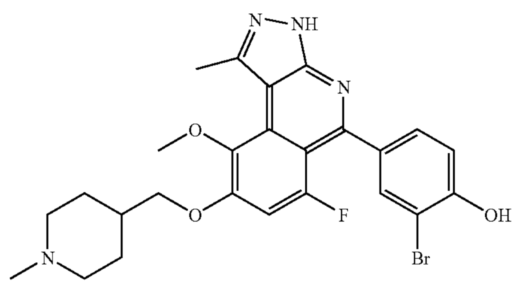 |
| 184 | 2-chloro-5-fluoro-4-(6-fluoro-1-methyl-9-(methyloxy)-8-{[(1-methylpiperidin-4-yl)methyl]oxy}-3H-pyrazolo[3,4-c]isoquinolin-5-yl)phenol | 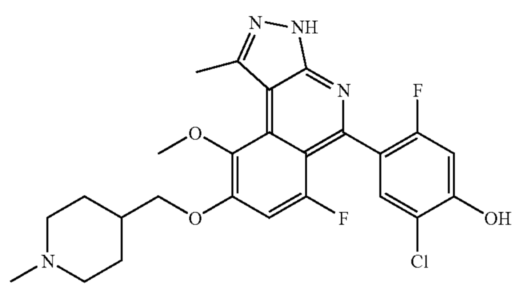 |
| 185 | 4-(6-fluoro-1-methyl-9-(methyloxy)-8-{[(1-methylpiperidin-4-yl)methyl]oxy}-3H-pyrazolo[3,4-c]isoquinolin-5-yl)-2-methylphenol | 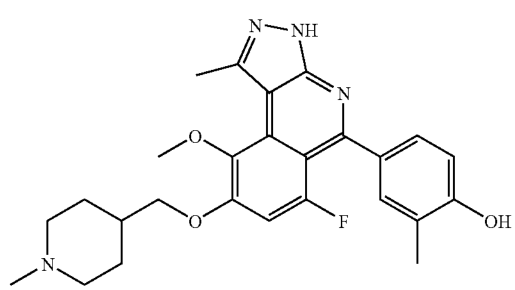 |

TABLE 1-continued

| Entry | Name | Structure |
|---|---|---|
| 186 | 2-chloro-4-{6,9-difluoro-1-methyl-8-[(2-piperidin-1-yl-ethyl)oxy]-3H-pyrazolo[3,4-c]isoquinolin-5-yl}phenol | 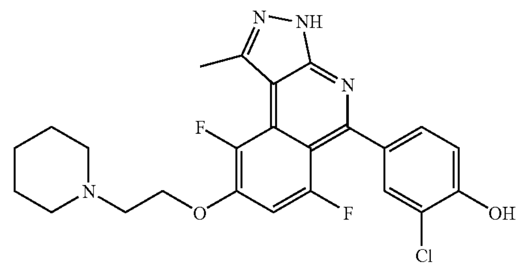 |
| 187 | 2-chloro-4-(8-{[2-(4-ethyl-piperazin-1-yl)ethyl]oxy}-6,9-difluoro-1-methyl-3H-pyrazolo[3,4-c]isoquinolin-5-yl)phenol | 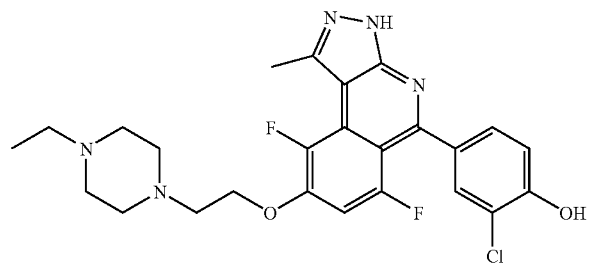 |
| 188 | 2-chloro-4-(8-{[2-(diethylamino)ethyl]oxy}-6,9-difluoro-1-methyl-3H-pyrazolo[3,4-c]isoquinolin-5-yl)phenol | 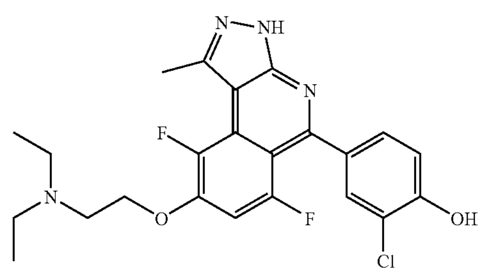 |
| 189 | 4-(6,9-difluoro-8-hydroxy-1-methyl-3H-pyrazolo[3,4-c]isoquinolin-5-yl)-N-hydroxybenzenecarboximidamide | 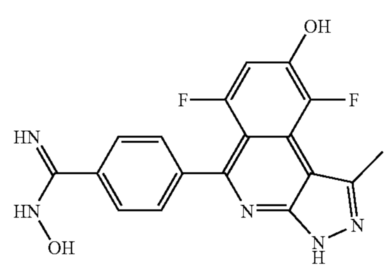 |
| 190 | 3-(6,9-difluoro-8-hydroxy-1-methyl-3H-pyrazolo[3,4-c]isoquinolin-5-yl)-N-hydroxybenzenecarboximidamide | 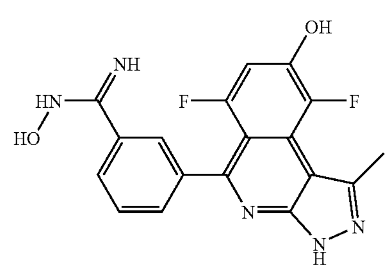 |

TABLE 1-continued

| Entry | Name | Structure |
|---|---|---|
| 191 | 6,9-difluoro-5-(1H-indol-5-yl)-1-methyl-3H-pyrazolo[3,4-c]isoquinolin-8-ol | 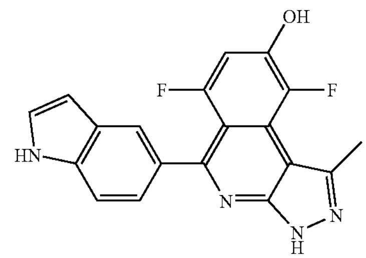 |
| 192 | 5-(1H-benzimidazol-6-yl)-6,9-difluoro-1-methyl-3H-pyrazolo[3,4-c]isoquinolin-8-ol | 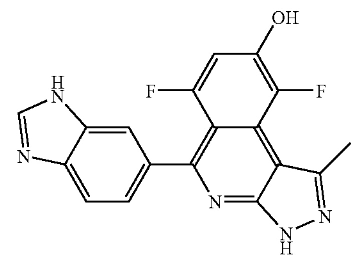 |
| 193 | 5-(4-aminophenyl)-6,9-difluoro-1-methyl-3H-pyrazolo[3,4-c]isoquinolin-8-ol | 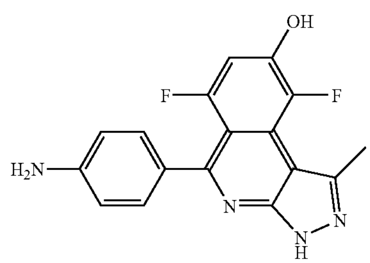 |
| 194 | 2-chloro-4-(6-fluoro-1-methyl-7-(methyloxy)-8-{[2-(4-methylpiperazin-1-yl)ethyl]oxy}-3H-pyrazolo[3,4-c]isoquinolin-5-yl)phenol | 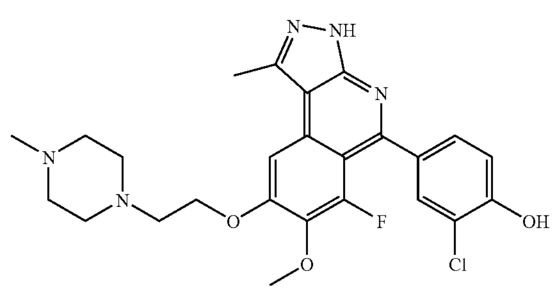 |
| 195 | 5-(2-amino-1,3-thiazol-5-yl)-6,9-difluoro-1-methyl-3H-pyrazolo[3,4-c]isoquinolin-8-ol | 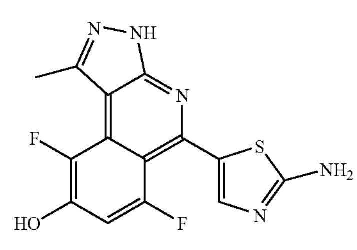 |

TABLE 1-continued

| Entry | Name | Structure |
|---|---|---|
| 196 | 2-chloro-4-[8-{[2-(4-ethyl-piperazin-1-yl)ethyl]oxy}-6-fluoro-1-methyl-9-(methyloxy)-3H-pyrazolo[3,4-c]isoquinolin-5-yl]phenol | 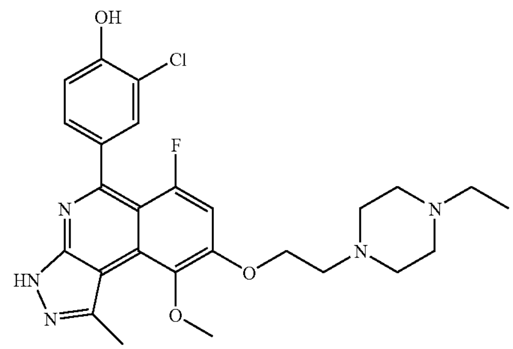 |
| 197 | 2-chloro-4-(6-fluoro-1-methyl-9-(methyloxy)-8-{[2-(4-methyl-piperazin-1-yl)ethyl]oxy}-3H-pyrazolo[3,4-c]isoquinolin-5-yl)phenol | 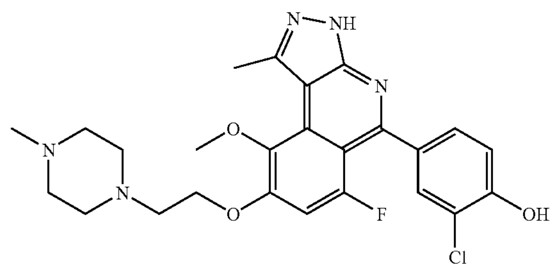 |
| 198 | 5-(6-aminopyridin-3-yl)-6,9-difluoro-1-methyl-3H-pyrazolo[3,4-c]isoquinolin-8-ol | 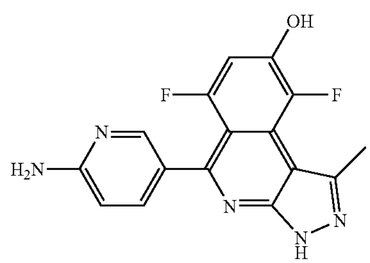 |
| 199 | 5-(5-amino-2-thienyl)-6,9-difluoro-1-methyl-3H-pyrazolo[3,4-c]isoquinolin-8-ol | 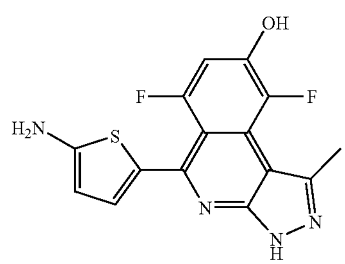 |
| 200 | 2-chloro-4-[8-{[3-(4-ethyl-piperazin-1-yl)propyl]oxy}-6-fluoro-1-methyl-9-(methyloxy)-3H-pyrazolo[3,4-c]isoquinolin-5-yl]phenol | 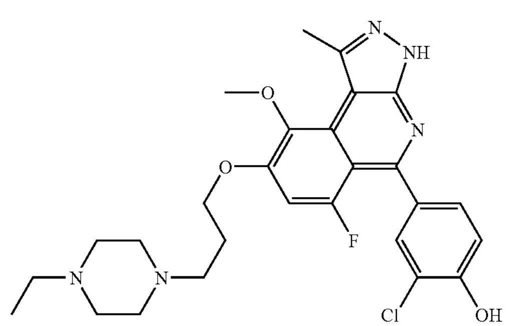 |

TABLE 1-continued

| Entry | Name | Structure |
|---|---|---|
| 201 | 2-chloro-4-(6-fluoro-1-methyl-9-(methyloxy)-8-{[3-(4-methyl-piperazin-1-yl)propyl]oxy}-3H-pyrazolo[3,4-c]isoquinolin-5-yl)phenol | 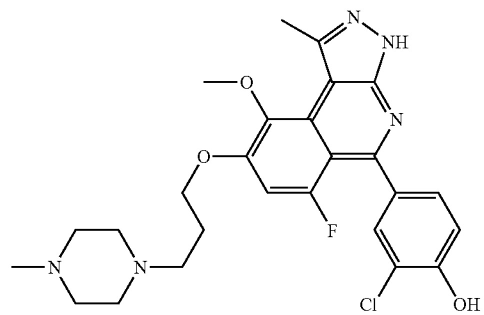 |
| 202 | 6,9-difluoro-5-(1H-indol-6-yl)-1-methyl-3H-pyrazolo[3,4-c]isoquinolin-8-ol | 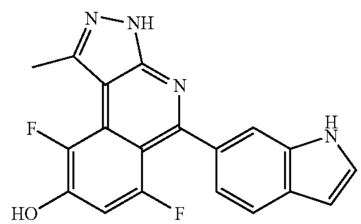 |
| 203 | N-[5-(6,9-difluoro-8-hydroxy-1-methyl-3H-pyrazolo[3,4-c]isoquinolin-5-yl)-1,3-thiazol-2-yl]acetamide | 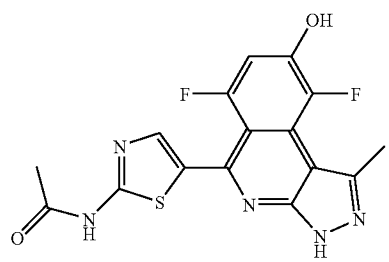 |
| 204 | 5-(3-chlorophenyl)-8-{[2-(4-ethyl-piperazin-1-yl)ethyl]oxy}-6-fluoro-1-methyl-9-(methyloxy)-3H-pyrazolo[3,4-c]isoquinoline | 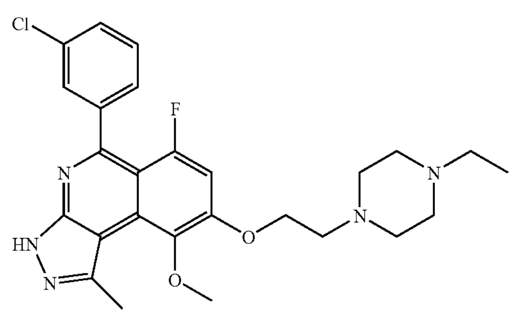 |
| 205 | 5-(3-aminophenyl)-6,9-difluoro-1-methyl-3H-pyrazolo[3,4-c]isoquinolin-8-ol | 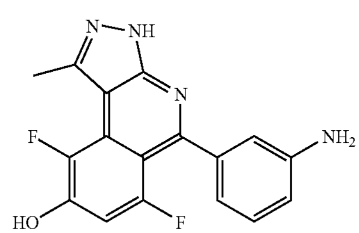 |

TABLE 1-continued

| Entry | Name | Structure |
|---|---|---|
| 206 | 2-chloro-4-{6-fluoro-1-methyl-9-(methyloxy)-8-[(2-morpholin-4-ylethyl)oxy]-3H-pyrazolo[3,4-c]isoquinolin-5-yl}phenol | 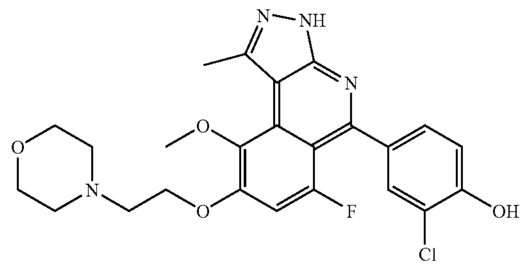 |
| 207 | 4-[8-({2-[butyl(ethyl)amino]ethyl}oxy)-6-fluoro-1-methyl-9-(methyloxy)-3H-pyrazolo[3,4-c]isoquinolin-5-yl]-2-chlorophenol | 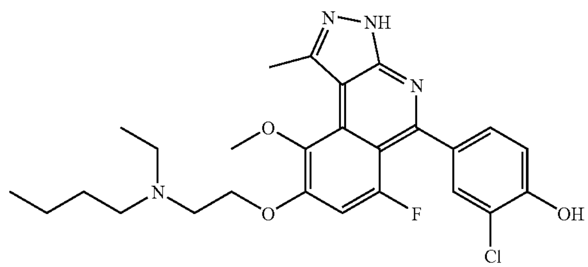 |
| 208 | 4-[8-{[(2R)-2-amino-3-methylbutyl]oxy}-6-fluoro-1-methyl-9-(methyloxy)-3H-pyrazolo[3,4-c]isoquinolin-5-yl]-2-chlorophenol | 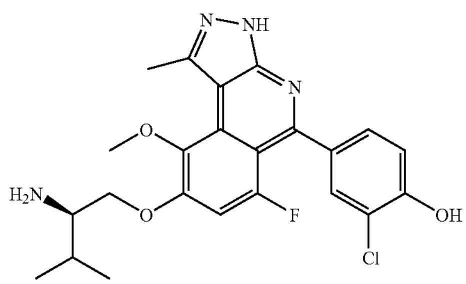 |
| 209 | 2-chloro-4-(6-fluoro-1-methyl-9-(methyloxy)-8-{[2-(1-methylpiperidin-4-yl)ethyl]oxy}-3H-pyrazolo[3,4-c]isoquinolin-5-yl)phenol | 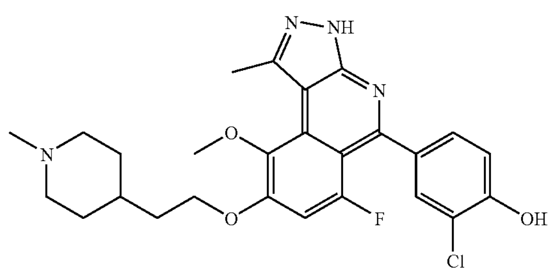 |
| 210 | 2-chloro-4-[8-{[(1-ethylpiperidin-4-yl)methyl]oxy}-6-fluoro-1-methyl-9-(methyloxy)-3H-pyrazolo[3,4-c]isoquinolin-5-yl]phenol | 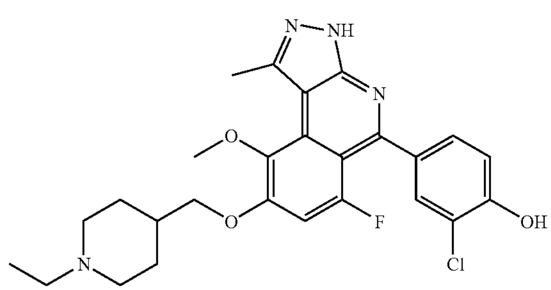 |

TABLE 1-continued

| Entry | Name | Structure |
|---|---|---|
| 211 | 5-(2-amino-1,3-thiazol-4-yl)-6,9-difluoro-1-methyl-3H-pyrazolo[3,4-c]isoquinolin-8-ol | 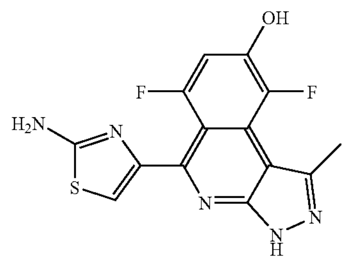 |
| 212 | 5-(5-amino-1,3,4-thiadiazol-2-yl)-6,9-difluoro-1-methyl-3H-pyrazolo[3,4-c]isoquinolin-8-ol | 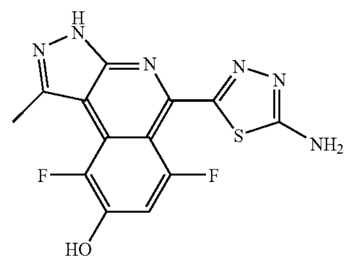 |
| 213 | 4-[8-{[(2R)-2-amino-3,3-dimethylbutyl]oxy}-6-fluoro-1-methyl-9-(methyloxy)-3H-pyrazolo[3,4-c]isoquinolin-5-yl]-2-chlorophenol | 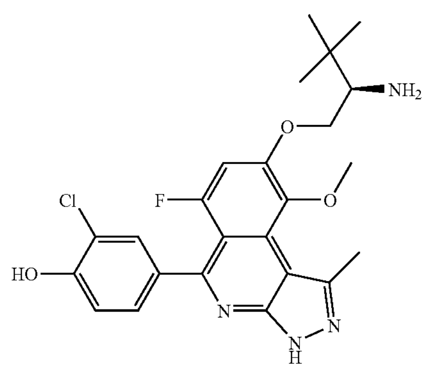 |
| 214 | 2-chloro-4-[6-fluoro-1-methyl-9-(methyloxy)-8-({2-[4-(2-methylpropyl)piperazin-1-yl]ethyl}oxy)-3H-pyrazolo[3,4-c]isoquinolin-5-yl]phenol | 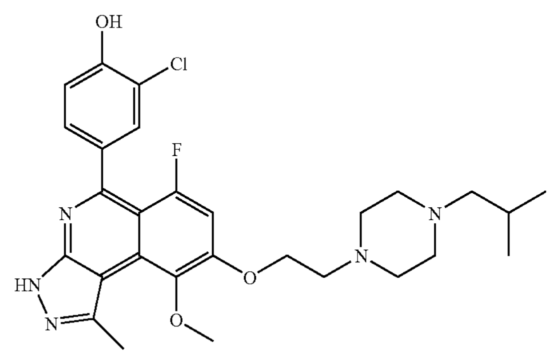 |
| 215 | 2-chloro-4-[8-{[2-(5-ethyl-2,5-diazabicyclo[2.2.1]hept-2-yl)ethyl]oxy}-6-fluoro-1-methyl-9-(methyloxy)-3H-pyrazolo[3,4-c]isoquinolin-5-yl]phenol | 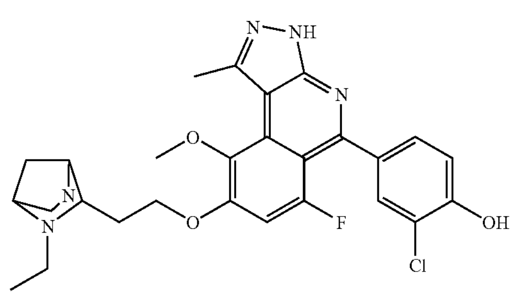 |

TABLE 1-continued

| Entry | Name |
|---|---|
| 216 | 2-chloro-4-[6-fluoro-1-methyl-8-({2-[4-(1-methyl-ethyl)piperazin-1-yl]ethyl}oxy)-9-(methyloxy)-3H-pyrazolo[3,4-c]isoquinolin-5-yl]phenol |
| 217 | 4-[8-{[2-(3-amino-8-aza-bicyclo[3.2.1]oct-8-yl)ethyl]oxy}-6-fluoro-1-methyl-9-(methyloxy)-3H-pyrazolo[3,4-c]isoquinolin-5-yl]-2-chlorophenol |
| 218 | 2-chloro-4-[8-{[2-(1-ethyl-piperidin-4-yl)ethyl]oxy}-6-fluoro-1-methyl-9-(methyloxy)-3H-pyrazolo[3,4-c]isoquinolin-5-yl]phenol |
| 219 | 2-chloro-4-[8-{[2-(di-ethylamino)ethyl]oxy}-6-fluoro-1-methyl-9-(methyloxy)-3H-pyrazolo[3,4-c]isoquinolin-5-yl]phenol |
| 220 | 2-chloro-5-{6-fluoro-1-methyl-9-(methyloxy)-8-[(2-pyrrolidin-1-yl-ethyl)oxy]-3H-pyrazolo[3,4-c]isoquinolin-5-yl}phenol |

TABLE 1-continued

| Entry | Name | Structure |
|---|---|---|
| 221 | 6,9-difluoro-5-(2-imino-3-methyl-2,3-dihydro-1,3-thiazol-5-yl)-1-methyl-3H-pyrazolo[3,4-c]isoquinolin-8-ol | 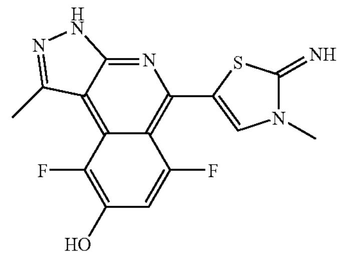 |
| 222 | 6,9-difluoro-1-methyl-5-(1,3-thiazol-5-yl)-3H-pyrazolo[3,4-c]isoquinolin-8-ol | 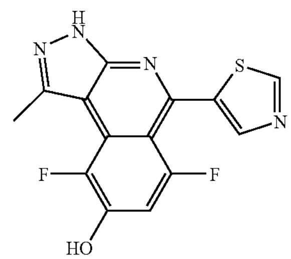 |
| 223 | 2-chloro-4-[6-fluoro-1-methyl-8-[(8-methyl-8-azabicyclo[3.2.1]oct-3-yl)oxy]-9-(methyloxy)-3H-pyrazolo[3,4-c]isoquinolin-5-yl]phenol | 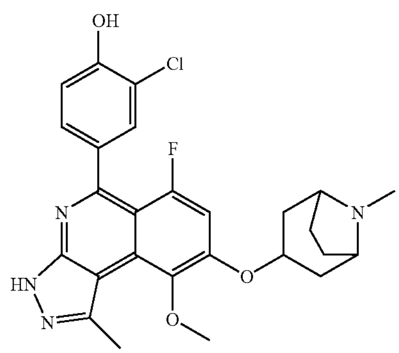 |
| 224 | 2-chloro-4-{6-fluoro-1-methyl-9-(methyloxy)-8-[(3-pyrrolidin-1-yl-propyl)oxy]-3H-pyrazolo[3,4-c]isoquinolin-5-yl}phenol | 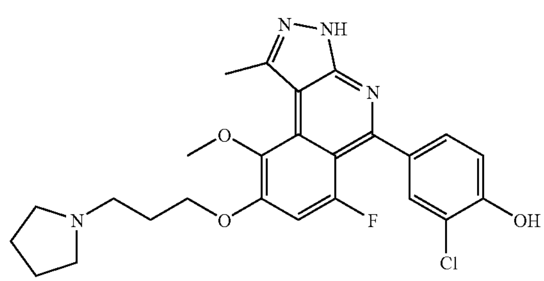 |
| 225 | 2-chloro-4-{6-fluoro-1-methyl-9-(methyloxy)-8-[(3-piperidin-1-yl-propyl)oxy]-3H-pyrazolo[3,4-c]isoquinolin-5-yl}phenol | 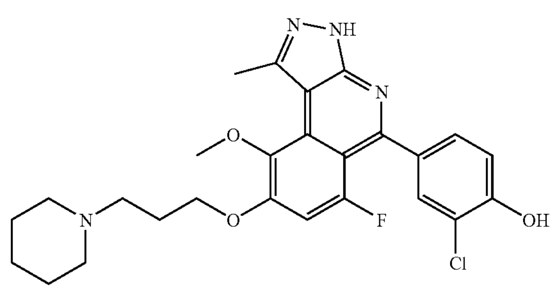 |

TABLE 1-continued

| Entry | Name | Structure |
|---|---|---|
| 226 | 2-chloro-4-{6-fluoro-1-methyl-9-(methyloxy)-8-[(3-morpholin-4-ylpropyl)oxy]-3H-pyrazolo[3,4-c]isoquinolin-5-yl}phenol | 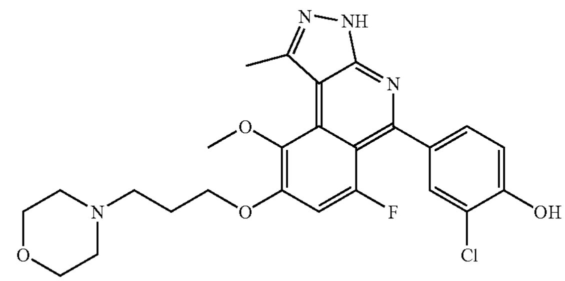 |
| 227 | 2-chloro-4-[8-({2-[[2-(dimethylamino)ethyl](methyl)amino]ethyl}oxy)-6-fluoro-1-methyl-9-(methyloxy)-3H-pyrazolo[3,4-c]isoquinolin-5-yl]phenol | 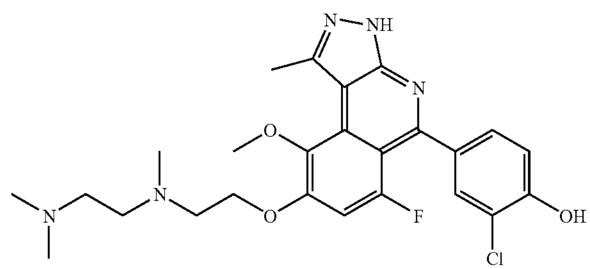 |
| 228 | 2-chloro-4-[8-({2-[[2-(diethylamino)ethyl](methyl)amino]ethyl}oxy)-6-fluoro-1-methyl-9-(methyloxy)-3H-pyrazolo[3,4-c]isoquinolin-5-yl]phenol | 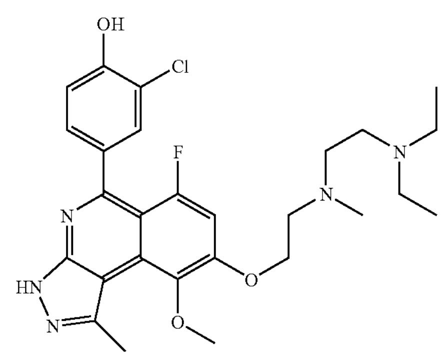 |
| 229 | 2-chloro-4-[8-({2-[[2-(dimethylamino)ethyl](ethyl)amino]ethyl}oxy)-6-fluoro-1-methyl-9-(methyloxy)-3H-pyrazolo[3,4-c]isoquinolin-5-yl]phenol | 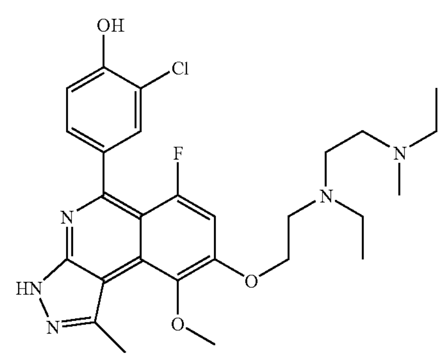 |

TABLE 1-continued

| Entry | Name |
|---|---|
| 230 | 4-[8-[(2-{bis[3-(dimethylamino)propyl]amino}ethyl)oxy]-6-fluoro-1-methyl-9-(methyloxy)-3H-pyrazolo[3,4-c]isoquinolin-5-yl]-2-chlorophenol |
| 231 | 2-chloro-4-[6-fluoro-1-methyl-8-({2-[methyl(1-methylpyrrolidin-3-yl)amino]ethyl}oxy)-9-(methyloxy)-3H-pyrazolo[3,4-c]isoquinolin-5-yl]phenol |
| 232 | 2-chloro-4-{6-fluoro-1-methyl-9-(methyloxy)-8-[(2-{(2S)-2-[(methyloxy)methyl]pyrrolidin-1-yl}ethyl)oxy]-3H-pyrazolo[3,4-c]isoquinolin-5-yl}phenol |
| 233 | 2-chloro-4-(6-fluoro-1-methyl-9-(methyloxy)-8-{[2-(4-pyrrolidin-1-ylpiperidin-1-yl)ethyl]oxy}-3H-pyrazolo[3,4-c]isoquinolin-5-yl)phenol |
| 234 | 2-chloro-4-[8-{[2-(4-cyclohexylpiperazin-1-yl)ethyl]oxy}-6-fluoro-1-methyl-9-(methyloxy)-3H-pyrazolo[3,4-c]isoquinolin-5-yl]phenol |

TABLE 1-continued

| Entry | Name | Structure |
|---|---|---|
| 235 | 2-[4-(2-{[5-(3-chloro-4-hydroxy-phenyl)-6-fluoro-1-methyl-9-(methyloxy)-3H-pyrazolo[3,4-c]isoquinolin-8-yl]oxy}ethyl)piperazin-1-yl]-N-(1-methylethyl)acetamide | 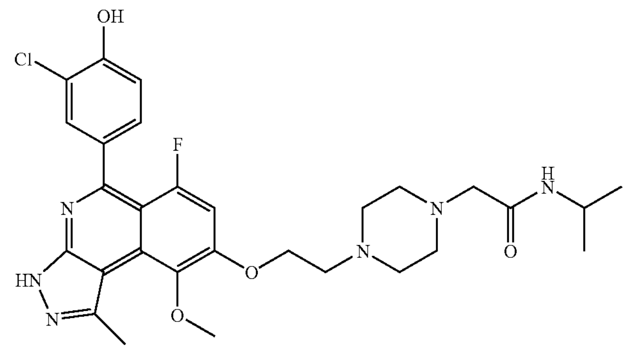 |
| 236 | 4-[8-{[2-(1,4'-bipiperidin-1'-yl)ethyl]oxy}-6-fluoro-1-methyl-9-(methyloxy)-3H-pyrazolo[3,4-c]isoquinolin-5-yl]-2-chlorophenol | 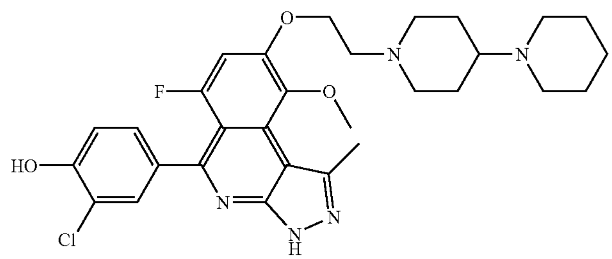 |
| 237 | 2-chloro-4-[6-fluoro-1-methyl-8-{[2-(4-methyl-1,4-diazepan-1-yl)ethyl]oxy}-9-(methyloxy)-3H-pyrazolo[3,4-c]isoquinolin-5-yl]phenol | 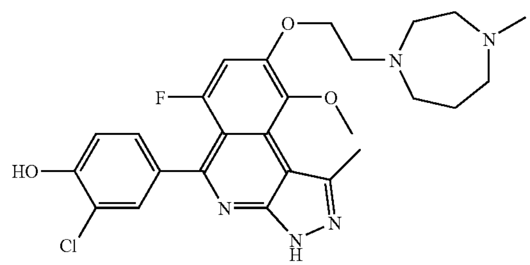 |
| 238 | 2-chloro-4-(6-fluoro-1-methyl-9-(methyloxy)-8-{[2-(4-pyridin-2-ylpiperazin-1-yl)ethyl]oxy}-3H-pyrazolo[3,4-c]isoquinolin-5-yl)phenol | 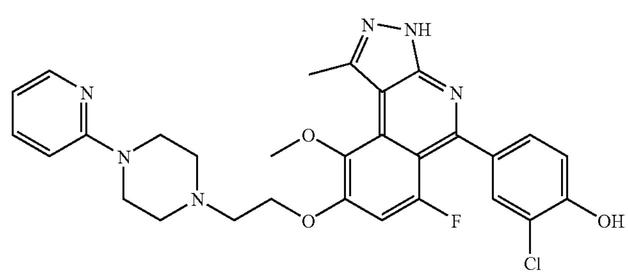 |
| 239 | 2-chloro-4-[8-{[2-(2,6-dimethylmorpholin-4-yl)ethyl]oxy}-6-fluoro-1-methyl-9-(methyloxy)-3H-pyrazolo[3,4-c]isoquinolin-5-yl]phenol | 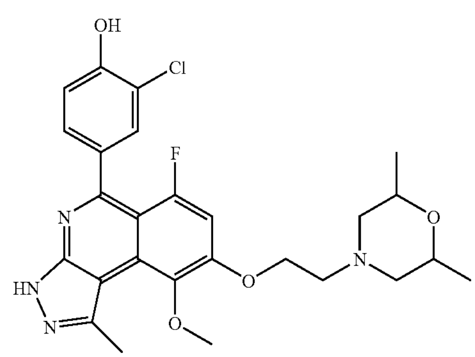 |

TABLE 1-continued

| Entry | Name | Structure |
|---|---|---|
| 240 | 2-chloro-4-{6-fluoro-1-methyl-9-(methyloxy)-8-[(2-thiomorpholin-4-ylethyl)oxy]-3H-pyrazolo[3,4-c]isoquinolin-5-yl}phenol | 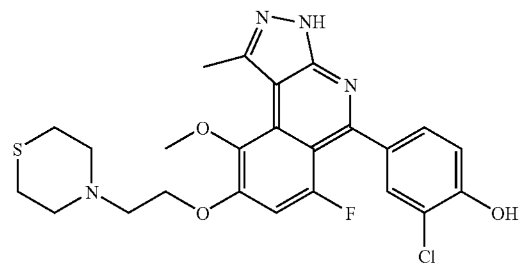 |
| 241 | 2-chloro-4-[8-{[2-(2,6-dimethylpiperidin-1-yl)ethyl]oxy}-6-fluoro-1-methyl-9-(methyloxy)-3H-pyrazolo[3,4-c]isoquinolin-5-yl]phenol | 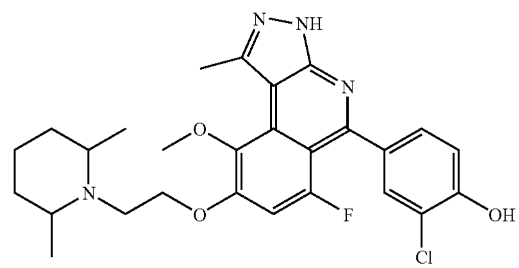 |
| 242 | 2-chloro-4-(6-fluoro-1-methyl-9-(methyloxy)-8-{[2-(octahydroquinolin-1(2H)-yl)ethyl]oxy}-3H-pyrazolo[3,4-c]isoquinolin-5-yl)phenol | 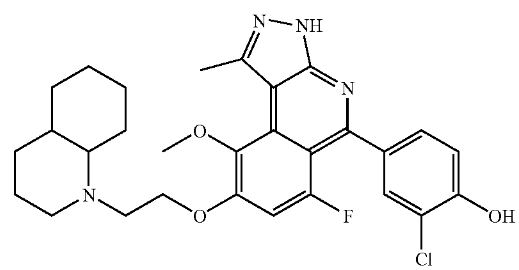 |
| 243 | 4-[8-({2-[bis(1-methylethyl)amino]ethyl}oxy)-6-fluoro-1-methyl-9-(methyloxy)-3H-pyrazolo[3,4-c]isoquinolin-5-yl]-2-chlorophenol | 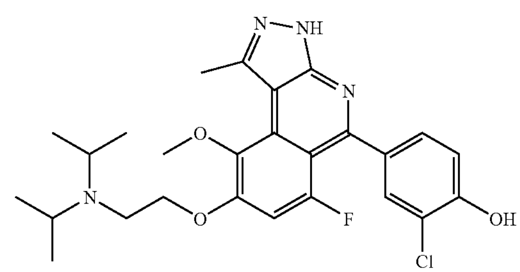 |
| 244 | 4-[8-[(2-{bis[2-(methyloxy)ethyl]amino}ethyl)oxy)-6-fluoro-1-methyl-9-(methyloxy)-3H-pyrazolo[3,4-c]isoquinolin-5-yl]-2-chlorophenol | 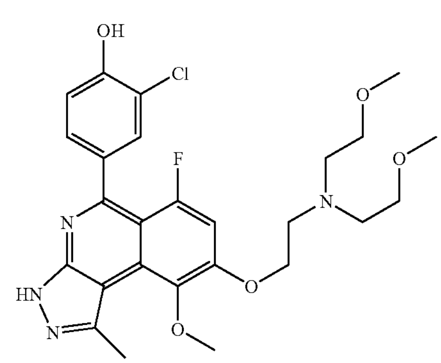 |

TABLE 1-continued

| Entry | Name | Structure |
|---|---|---|
| 245 | 2-chloro-4-{6-fluoro-1-methyl-9-(methyloxy)-8-[(2-piperidin-1-yl-ethyl)oxy]-3H-pyrazolo[3,4-c]isoquinolin-5-yl}phenol | 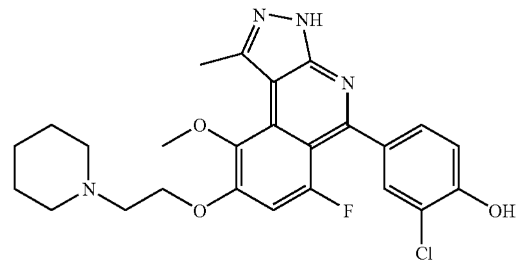 |
| 246 | 6,9-difluoro-1-methyl-5-(1-oxido-pyridin-4-yl)-3H-pyrazolo[3,4-c]isoquinolin-8-ol | 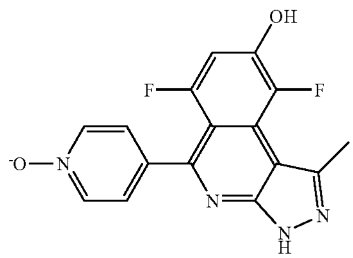 |

Another aspect of the invention is a pharmaceutical composition comprising a compound according to any one of paragraphs [0024]-[0045] and a pharmaceutically acceptable carrier.

Another aspect of the invention is a metabolite of the compound or the pharmaceutical composition according to any one of paragraphs [0024]-[0046].

Another aspect of the invention is a method of modulating the in vivo activity of a kinase, the method comprising administering to a subject an effective amount of the compound or the pharmaceutical composition according to any of paragraphs [0024]-[0046].

Another aspect of the invention is the method according to paragraph [0048], wherein the kinase is ALK.

Another aspect of the invention is the method according to paragraph [0049], wherein modulating the in vivo activity of ALK comprises inhibition of ALK.

Another aspect of the invention is a method of treating diseases or disorders associated with uncontrolled, abnormal, and/or unwanted cellular activities, the method comprising administering, to a mammal in need thereof, a therapeutically effective amount of the compound or the pharmaceutical composition as described in any one of paragraphs [0024]-[0046].

Another aspect of the invention is a method of screening for modulators of ALK, the method comprising combining a compound according to any one of paragraphs [0024]-[0045], and at least one candidate agent and determining the effect of the candidate agent on the ALK activity.

Another aspect of the invention is a method of inhibiting proliferative activity in a cell, the method comprising administering an effective amount of a composition comprising a compound according any one of paragraphs [0024]-[0045] to a cell or a plurality of cells.

Definitions

As used in the present specification, the following words and phrases are generally intended to have the meanings as set forth below, except to the extent that the context in which they are used indicates otherwise or they are expressly defined to mean something different.

The symbol "—" means a single bond, "=" means a double bond, "≡" means a triple bond. The symbol refers to a group on a double-bond as occupying either position on the terminus of a double bond to which the symbol is attached; that is, the geometry, E- or Z-, of the double bond is ambiguous. When a group is depicted removed from its parent formula, the "~"symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —CH₂CH₂—. It is understood by one of ordinary skill in the art that the aforementioned descriptive techniques are common in the chemical arts to provide brevity and simplicity to description of otherwise complex structures.

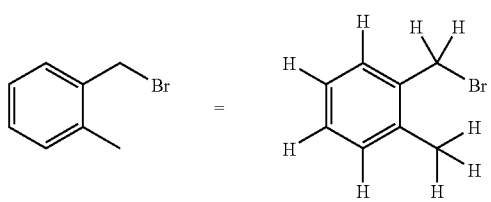

In this application, some ring structures are depicted generically and will be described textually. For example, in the schematic below, if in the structure on the left, ring A is used to describe a "spirocyclyl," then if ring A is cyclopropyl, there are at most four hydrogens on ring A (when "R" can also be —H). In another example, as depicted on the right side of the schematic below, if ring B is used to describe a "phenylene" then there can be at most four hydrogens on ring B (assuming depicted cleaved bonds are not C—H bonds).

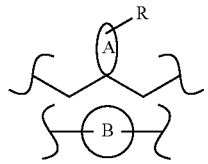

If a group "R" is depicted as "floating" on a ring system, as for example in the formula:

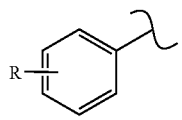

then, unless otherwise defined, a substituent "R" may reside on any atom of the ring system, assuming replacement of a depicted, implied, or expressly defined hydrogen from one of the ring atoms, so long as a stable structure is formed.

If a group "R" is depicted as floating on a fused ring system, as for example in the formulae:

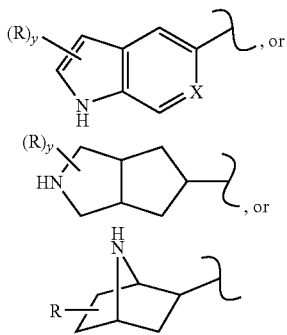

then, unless otherwise defined, a substituent "R" may reside on any atom of the fused ring system, assuming replacement of a depicted (for example the —NH— in the formula above), implied (for example as in the formula above, where the hydrogens are not shown but understood to be present), or expressly defined hydrogen (for example where in the formula above, "X" equals =CH—) from one of the ring atoms, so long as a stable structure is formed. In the example depicted, the "R" group may reside on either the 5-membered or the 6-membered ring of the fused ring system. In the formula depicted above, when y is 2 for example, then the two "R's" may reside on any two atoms of the ring system, again assuming each replaces a depicted, implied, or expressly defined hydrogen on the ring.

When there are more than one such depicted "floating" groups, as for example in the formulae:

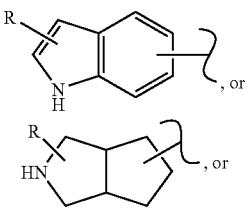

-continued

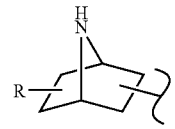

where there are two groups, namely, the "R" and the bond indicating attachment to a parent structure; then, unless otherwise defined, the "floating" groups may reside on any atoms of the ring system, again assuming each replaces a depicted, implied, or expressly defined hydrogen on the ring.

When a group "R" is depicted as existing on a ring system containing saturated carbons, as for example in the formula:

where, in this example, "y" can be more than one, assuming each replaces a currently depicted, implied, or expressly defined hydrogen on the ring; then, unless otherwise defined, where the resulting structure is stable, two "R's" may reside on the same carbon. A simple example is when R is a methyl group; there can exist a geminal dimethyl on a carbon of the depicted ring (an "annular" carbon).

In another example, two R's on the same carbon, including that carbon, may form a ring, thus creating a spirocyclic ring (a "spirocyclyl" group) structure with the depicted ring as for example in the formula:

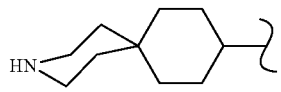

When a compound is described using a generic functional group descriptor, it is understood to mean that any compound of that class would fit into such a description, unless limited by previous language pertaining to such a class. For example if a compound is called "a phenol," then all phenols are included, unless previous descriptive language pertaining to other substitution on that class of compounds is expressed.

"Alicyclic" refers to a saturated carbocyclic ring system, for example cyclopropane and the like.

"Alkyl" is intended to include linear, branched, or cyclic hydrocarbon structures and combinations thereof, inclusively. For example, "$C_8$ alkyl" may refer to an n-octyl, iso-octyl, cyclohexylethyl, and the like. Lower alkyl refers to alkyl groups of from one to six carbon atoms. Examples of lower alkyl groups include methyl, ethyl, propyl, isopropyl, butyl, s-butyl, t-butyl, isobutyl, pentyl, hexyl and the like. Higher alkyl refers to alkyl groups containing more that eight carbon atoms. Exemplary alkyl groups are those of $C_{20}$ or below. Cycloalkyl is a subset of alkyl and includes cyclic hydrocarbon groups of from three to thirteen carbon atoms. Examples of cycloalkyl groups include c-propyl, c-butyl, c-pentyl, norbornyl, adamantyl and the like. In this application, alkyl refers to alkanyl, alkenyl, and alkynyl residues (and combinations thereof); it is intended to include cyclohexylmethyl, vinyl, allyl, isoprenyl, and the like. Thus when an alkyl residue having a specific number of carbons is named, all geometric isomers having that number of carbons are intended to be encompassed; thus, for example, either "butyl" or "$C_4$ alkyl" is meant to include n-butyl, sec-butyl, isobutyl, t-butyl, isobutenyl and but-2-yne radicals; and for example, "propyl" or "$C_3$ alkyl" each include n-propyl, pro-penyl, and isopropyl.

"Alkylene" refers to straight or branched chain divalent radical consisting solely of carbon and hydrogen atoms, containing no unsaturation and having from one to ten carbon atoms, for example, methylene, ethylene, propylene, n-butylene and the like. Alkylene is a subset of alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), and cyclohexylpropylene (—$CH_2CH_2CH(C_6H_{13})$).

"Alkylidene" refers to a straight or branched chain unsaturated divalent radical consisting solely of carbon and hydrogen atoms, having from two to ten carbon atoms, for example, ethylidene, propylidene, n-butylidene, and the like. Alkylidene is a subset of alkyl, referring to the same residues as alkyl, but having two points of attachment and, specifically, double bond unsaturation. The unsaturation present includes at least one double bond.

"Alkylidyne" refers to a straight or branched chain unsaturated divalent radical consisting solely of carbon and hydrogen atoms having from two to ten carbon atoms, for example, propylid-2-ynyl, n-butylid-1-ynyl, and the like. Alkylidyne is a subset of alkyl, referring to the same residues as alkyl, but having two points of attachment and, specifically, triple bond unsaturation. The unsaturation present includes at least one triple bond.

Any of the above radicals, "alkylene," "alkylidene" and "alkylidyne," when optionally substituted, may contain alkyl substitution which itself contains unsaturation. For example, 2-(2-phenylethynyl-but-3-enyl)-naphthalene (IUPAC name) contains an n-butylid-3-ynyl radical with a vinyl substituent at the 2-position of said radical.

"Alkoxy" or "alkoxyl" refers to the group —O-alkyl, for example including from one to eight carbon atoms of a straight, branched, cyclic configuration, unsaturated chains, and combinations thereof attached to the parent structure through an oxygen atom. Examples include methoxy, ethoxy, propoxy, isopropoxy, cyclopropyloxy, cyclohexyloxy and the like. Lower-alkoxy refers to groups containing one to six carbons.

"Substituted alkoxy" refers to the group —O-(substituted alkyl), the substitution on the alkyl group generally containing more than only carbon (as defined by alkoxy). One exemplary substituted alkoxy group is "polyalkoxy" or —O-optionally substituted alkylene-optionally substituted alkoxy, and includes groups such as —$OCH_2CH_2OCH_3$, and glycol ethers such as polyethyleneglycol and —$O(CH_2CH_2O)_xCH_3$, where x is an integer of between about two and about twenty, in another example, between about two and about ten, and in a further example between about two and about five. Another exemplary substituted alkoxy group is hydroxyalkoxy or —$OCH_2(CH_2)_yOH$, where y is for example an integer of between about one and about ten, in another example y is an integer of between about one and about four.

"Acyl" refers to groups of from one to ten carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to six carbons.

"α-Amino Acids" refer to naturally occurring and commercially available amino acids and optical isomers thereof. Typical natural and commercially available α-amino acids are glycine, alanine, serine, homoserine, threonine, valine, norvaline, leucine, isoleucine, norleucine, aspartic acid, glutamic acid, lysine, ornithine, histidine, arginine, cysteine, homocysteine, methionine, phenylalanine, homophenylalanine, phenylglycine, ortho-tyrosine, meta-tyrosine, para-tyrosine, tryptophan, glutamine, asparagine, proline and hydroxyproline. A "side chain of an α-amino acid" refers to the radical found on the α-carbon of an α-amino acid as defined above, for example, hydrogen (for glycine), methyl (for alanine), benzyl (for phenylalanine), and the like.

"Amino" refers to the group —$NH_2$. "Substituted amino," refers to the group —N(H)R or —N(R)R where each R is independently selected from the group: optionally substituted alkyl, optionally substituted alkoxy, optionally substituted aryl, optionally substituted heterocyclyl, acyl, carboxy, alkoxycarbonyl, sulfanyl, sulfinyl and sulfonyl, for example, diethylamino, methylsulfonylamino, furanyl-oxy-sulfonamino.

"Annular" refers to a single ring system either aromatic or alicyclic.

"Aryl" refers to aromatic six- to fourteen-membered carbocyclic ring, for example, benzene, naphthalene, indane, tetralin, fluorene and the like, univalent radicals. As univalent radicals, the aforementioned ring examples are named, phenyl, naphthyl, indanyl, tetralinyl, and fluorenyl.

"Arylene" generically refers to any aryl that has at least two groups attached thereto. For a more specific example, "phenylene" refers to a divalent phenyl ring radical. A phenylene, thus may have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. Both the aryl, and the corresponding alkylene, alkylidene, or alkylidyne radical portion of an arylalkyl group may be optionally substituted. "Lower arylalkyl" refers to an arylalkyl where the "alkyl" portion of the group has one to six carbons; this can also be referred to as $C_{1-6}$ arylalkyl.

"Exo-alkenyl" refers to a double bond that emanates from an annular carbon, and is not within the ring system, for example the double bond depicted in the formula below.

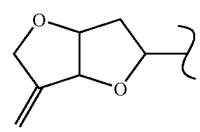

In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Fused-polycyclic" or "fused ring system" refers to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the invention may themselves have spiro rings attached thereto via a single ring atom of the fused-polycyclic.

"Halogen" or "halo" refers to fluorine, chlorine, bromine or iodine. "Haloalkyl" and "haloaryl" refer generically to alkyl and aryl radicals that are substituted with one or more halogens, respectively. Thus, "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is within the scope of dihaloaryl.

"Heteroarylene" generically refers to any heteroaryl that has at least two groups attached thereto. For a more specific example, "pyridylene" refers to a divalent pyridyl ring radical. A pyridylene, thus may have more than two groups attached, but is defined by a minimum of two non-hydrogen groups attached thereto.

"Heteroatom" refers to O, S, N, or P.

"Heterocyclyl" refers to a stable three- to fifteen-membered ring radical that consists of carbon atoms and from one to five heteroatoms selected from the group consisting of nitrogen, phosphorus, oxygen and sulfur. For purposes of this invention, the heterocyclyl radical may be a monocyclic, bicyclic or tricyclic ring system, which may include fused or bridged ring systems as well as spirocyclic systems; and the nitrogen, phosphorus, carbon or sulfur atoms in the heterocyclyl radical may be optionally oxidized to various oxidation states. In a specific example, the group —S(O)$_{0-2}$—, refers to —S— (sulfide), —S(O)— (sulfoxide), and —SO$_2$— (sulfone). For convenience, nitrogens, particularly but not exclusively, those defined as annular aromatic nitrogens, are meant to include their corresponding N-oxide form, although not explicitly defined as such in a particular example. Thus, for a compound of the invention having, for example, a pyridyl ring; the corresponding pyridyl-N-oxide is meant to be included as another compound of the invention. In addition, annular nitrogen atoms may be optionally quaternized; and the ring radical may be partially or fully saturated or aromatic. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroalicyclic" refers specifically to a non-aromatic heterocyclyl radical. A heteroalicyclic may contain unsaturation, but is not aromatic.

"Heteroaryl" refers specifically to an aromatic heterocyclyl radical.

"Heterocyclylalkyl" refers to a residue in which a heterocyclyl is attached to a parent structure via one of an alkylene, alkylidene, or alkylidyne radical. Examples include (4-methylpiperazin-1-yl) methyl, (morpholin-4-yl) methyl, (pyridine-4-yl) methyl, 2-(oxazolin-2-yl) ethyl, 4-(4-methylpiperazin-1-yl)-2-butenyl, and the like. Both the heterocyclyl, and the corresponding alkylene, alkylidene, or alkylidyne radical portion of a heterocyclylalkyl group may be optionally substituted. "Lower heterocyclylalkyl" refers to a heterocyclylalkyl where the "alkyl" portion of the group has one to six carbons. "Heteroalicyclylalkyl" refers specifically to a heterocyclylalkyl where the heterocyclyl portion of the group is non-aromatic; and "heteroarylalkyl" refers specifically to a heterocyclylalkyl where the heterocyclyl portion of the group is aromatic Such terms may be described in more than one way, for example, "lower heterocyclylalkyl" and "heterocyclyl C$_{1-6}$alkyl" are equivalent terms.

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only sterically practical and/or synthetically feasible compounds are meant to be included. "Optionally substituted" refers to all subsequent modifiers in a term, for example in the term "optionally substituted arylC$_{1-8}$ alkyl," optional substitution may occur on both the "C$_{1-8}$ alkyl" portion and the "aryl" portion of the molecule; and for example, optionally substituted alkyl includes optionally substituted cycloalkyl groups. A list of exemplary optional substitution are listed below in the definition of "substituted."

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings B and B'), but not a bridgehead atom, can be a shared atom between the saturated bridged ring system and a spirocyclyl (ring A) attached thereto. A spirocyclyl can be carbocyclic or heteroalicyclic.

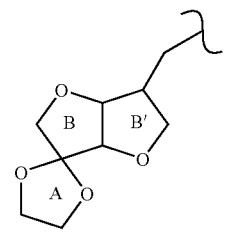

"Substituted" alkyl, aryl, alkoxyl, and heterocyclyl, refer respectively to alkyl, aryl, alkoxyl, and heterocyclyl, wherein one or more (for example up to about five, in another example, up to about three) hydrogen atoms are replaced by a substituent independently selected from: optionally substituted alkyl (for example, fluoromethyl), optionally substituted aryl (for example, 4-hydroxyphenyl), optionally substituted arylalkyl (for example, 1-phenyl-ethyl), optionally substituted heterocyclylalkyl (for example, 1-pyridin-3-yl-ethyl or [1,4']bipiperidinyl), optionally substituted heterocyclyl (for example, 5-chloro-pyridin-3-yl or 1-methyl-piperidin-4-yl), optionally substituted alkoxy, alkylenedioxy (for example methylenedioxy), optionally substituted amino (for example, alkylamino, dialkylamino, optionally substituted dialkylamino (wherein each alkyl on the amino is optionally substituted)), optionally substituted amidino, optionally substituted aryloxy (for example, phenoxy), optionally substituted arylalkyloxy (for example, benzyloxy), carboxy (—$CO_2H$), carboalkoxy (that is, acyloxy or —OC(=O)R), carboxyalkyl (that is, esters or —$CO_2R$), carboxamido, benzyloxycarbonylamino (CBZ-amino), cyano, acyl, halogen, hydroxy, nitro, sulfanyl, sulfinyl, sulfonyl, thiol, halogen, hydroxy, oxo, carbamyl, acylamino, and sulfonamido.

"Sulfanyl" refers to the groups: —S-(optionally substituted alkyl), —S-(optionally substituted aryl), and —S-(optionally substituted heterocyclyl).

"Sulfinyl" refers to the groups: —S(O)—H, —S(O)-(optionally substituted alkyl), —S(O)-optionally substituted aryl), and —S(O)-(optionally substituted heterocyclyl).

"Sulfonyl" refers to the groups: —$S(O_2)$—H, —$S(O_2)$-(optionally substituted alkyl), —$S(O_2)$-optionally substituted aryl), —$S(O_2)$-(optionally substituted heterocyclyl), —$S(O_2)$-(optionally substituted alkoxy), —$S(O_2)$-optionally substituted aryloxy), and —$S(O_2)$-(optionally substituted heterocyclyloxy).

"Yield" for each of the reactions described herein is expressed as a percentage of the theoretical yield.

Some of the compounds of the invention may have imino, amino, oxo or hydroxy substituents off aromatic heterocyclyl systems. For purposes of this disclosure, it is understood that such imino, amino, oxo or hydroxy substituents may exist in their corresponding tautomeric form, i.e., amino, imino, hydroxy or oxo, respectively.

Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the invention, or their pharmaceutically acceptable salts, may have asymmetric carbon atoms, oxidized sulfur atoms or quaternized nitrogen atoms in their structure.

The compounds of the invention and their pharmaceutically acceptable salts may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention.

It is assumed that when considering generic descriptions of compounds of the invention for the purpose of constructing a compound, such construction results in the creation of a stable structure. That is, one of ordinary skill in the art would recognize that there can theoretically be some constructs which would not normally be considered as stable compounds (that is, sterically practical and/or synthetically feasible, supra).

When a particular group with its bonding structure is denoted as being bonded to two partners; that is, a divalent radical, for example, —$OCH_2$—, then it is understood that either of the two partners may be bound to the particular group at one end, and the other partner is necessarily bound to the other end of the particular group, unless stated explicitly otherwise. Stated another way, divalent radicals are not to be construed as limited to the depicted orientation, for example "—$OCH_2$—" is meant to mean not only "—$OCH_2$—" as drawn, but also "—$CH_2O$—."

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Patient" for the purposes of the present invention includes humans and other animals, particularly mammals, and other organisms. Thus the methods are applicable to both human therapy and veterinary applications. In a preferred embodiment the patient is a mammal, and in a most preferred embodiment the patient is human.

"Kinase-dependent diseases or conditions" refer to pathologic conditions that depend on the activity of one or more protein kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example protein substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinorna, glucagonoma, gastrinoma, carcinoid tumors, vipoma), small bowel (adenocarcinorna, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitoulinary tract: kidney (adenocarcinoma, Wilm's tumor [neplrroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis defornians), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, SertoliLeydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplasia nevi, lipoma, angioma, dermatofibroma, keloids, psoriasis; and Adrenal lands: neuroblastoma. Thus, the term "cancerous cell" as provided herein, includes a cell afflicted by any one of the above-identified conditions.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) wherein the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In addition, it is intended that the present invention cover compounds made either using standard organic synthetic techniques, including combinatorial chemistry or by biological methods, such as bacterial digestion, metabolism, enzymatic conversion, and the like.

"Treating" or "treatment" as used herein covers the treatment of a disease-state in a human, which disease-state is characterized by abnormal cellular proliferation, and invasion and includes at least one of: (i) preventing the disease-state from occurring in a human, in particular, when such human is predisposed to the disease-state but has not yet been diagnosed as having it; (ii) inhibiting the disease-state, i.e., arresting its development; and (iii) relieving the disease-state, i.e., causing regression of the disease-state. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

One of ordinary skill in the art would understand that certain crystallized, protein-ligand complexes, in particular ALK-ligand complexes, and their corresponding x-ray structure coordinates can be used to reveal new structural information useful for understanding the biological activity of kinases as described herein. As well, the key structural features of the aforementioned proteins, particularly, the shape of the ligand binding site, are useful in methods for designing or identifying selective modulators of kinases and in solving the structures of other proteins with similar features. Such protein-ligand complexes, having compounds of the invention as their ligand component, are an aspect of the invention.

As well, one of ordinary skill in the art would appreciate that such suitable x-ray quality crystals can be used as part of a method of identifying a candidate agent capable of binding to and modulating the activity of kinases. Such methods may be characterized by the following aspects: a) introducing into a suitable computer program, information defining a ligand binding domain of a kinase in a conformation (e.g. as defined by x-ray structure coordinates obtained from suitable x-ray quality crystals as described above) wherein the computer program creates a model of the three dimensional structures of the ligand binding domain, b) introducing a model of the three dimensional structure of a candidate agent in the computer program, c) superimposing the model of the candidate agent on the model of the ligand binding domain, and d) assessing whether the candidate agent model fits spatially into the ligand binding domain. Aspects a-d are not necessarily carried out in the aforementioned order. Such methods may further entail: performing rational drug design with the model of the three-dimensional structure, and selecting a potential candidate agent in conjunction with computer modeling.

Additionally, one skilled in the art would appreciate that such methods may further entail: employing a candidate agent, so-determined to fit spatially into the ligand binding domain, in a biological activity assay for kinase modulation, and determining whether said candidate agent modulates kinase activity in the assay. Such methods may also include administering the candidate agent, determined to modulate kinase activity, to a mammal suffering from a condition treatable by kinase modulation, such as those described above.

Also, one skilled in the art would appreciate that compounds of the invention can be used in a method of evaluating the ability of a test agent to associate with a molecule or molecular complex comprising a ligand binding domain of a kinase. Such a method may be characterized by the following aspects: a) creating a computer model of a kinase binding pocket using structure coordinates obtained from suitable x-ray quality crystals of the kinase, b) employing computational algorithms to perform a fitting operation between the test agent and the computer model of the binding pocket, and c) analyzing the results of the fitting operation to quantify the association between the test agent and the computer model of the binding pocket.

General Administration

Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

The compositions will include a conventional pharmaceutical carrier or excipient and a compound of the invention as the/an active agent, and, in addition, may include other medicinal agents, pharmaceutical agents, carriers, adjuvants, etc. Compositions of the invention may be used in combination with anticancer or other agents that are generally administered to a patient being treated for cancer. Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One preferable route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alginates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Generally, depending on the intended mode of administration, the pharmaceutically acceptable compositions will contain about 1% to about 99% by weight of a compound(s) of the invention, or a pharmaceutically acceptable salt thereof, and 99% to 1% by weight of a suitable pharmaceutical excipient. In one example, the composition will be between about 5% and about 75% by weight of a compound(s) of the invention, or a pharmaceutically acceptable salt thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to those skilled in the art.

Utility of Compounds of the Invention as Screening Agents

To employ the compounds of the invention in a method of screening for candidate agents that bind to ALK, the protein is bound to a support, and a compound of the invention is added to the assay. Alternatively, the compound of the invention is bound to the support and the protein is added. Classes of candidate agents among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate agent to the ALK protein may be done in a number of ways. In one example, the candidate agent (the compound of the invention) is labeled, for example, with a fluorescent or radioactive moiety and binding determined directly. For example, thus may be done by attaching all or a portion of the ALK protein to a solid support, adding a labeled agent (for example a compound of the invention in which at least one atom has been replaced by a detectable isotope), washing off excess reagent, and determining the amount of the label that is present on the solid support. Various blocking and washing steps may be utilized as are known in the art.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the ALK protein may be labeled at tyrosine positions using $^{125}$I, or with fluorophores. Alternatively, more than one component may be labeled with different labels; using $^{125}$I for the proteins, for example, and a fluorophor for the candidate agents.

The compounds of the invention may also be used as competitors to screen for additional drug candidates. "Candidate bioactive agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. In the case where protein binding or activity is screened, some embodiments exclude molecules already known to bind to that particular protein. Exemplary embodiments of assays described herein include candidate agents, which do not bind the target protein in its endogenous native state, termed herein as "exogenous" agents. In one example, exogenous agents further exclude antibodies to ALK.

Candidate agents can encompass numerous chemical classes, though typically they are organic molecules having a molecular weight of more than about 100 and less than about 2,500 daltons. Candidate agents comprise functional groups necessary for structural interaction with proteins, particularly hydrogen bonding and lipophilic binding, and typically include at least an amine, carbonyl, hydroxyl, ether, or carboxyl group, for example at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs, or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In one example, the binding of the candidate agent is determined through the use of competitive binding assays. In this example, the competitor is a binding moiety known to bind to ALK, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to ALK for a time sufficient to allow binding, if present. Incubations may be performed at any temperature that facilitates optimal activity, typically between 4 and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In one example, the competitor is added first, followed by the candidate agent. Displacement of the competitor is an indication the candidate agent is binding to ALK and thus is capable of binding to, and potentially modulating, the activity of ALK. In this embodiment, either component can be labeled. Thus, for example, if the competitor is labeled, the presence of label in the wash solution indicates displacement by the agent. Alternatively, if the candidate agent is labeled, the presence of the label on the support indicates displacement.

In an alternative embodiment, the candidate agent is added first, with incubation and washing, followed by the competitor. The absence of binding by the competitor may indicate the candidate agent is bound to ALK with a higher affinity. Thus, if the candidate agent is labeled, the presence of the label on the support, coupled with a lack of competitor binding, may indicate the candidate agent is capable of binding to ALK.

It may be of value to identify the binding site of ALK. This can be done in a variety of ways. In one embodiment, once ALK has been identified as binding to the candidate agent, ALK is fragmented or modified and the assays repeated to identify the necessary components for binding.

Modulation is tested by screening for candidate agents capable of modulating the activity of ALK comprising the steps of combining a candidate agent with ALK, as above, and determining an alteration in the biological activity of ALK. Thus, in this embodiment, the candidate agent should both bind to (although this may not be necessary), and alter its biological or biochemical activity as defined herein. The methods include both in vitro screening methods and in vivo screening of cells for alterations in cell viability, morphology, and the like.

Alternatively, differential screening may be used to identify drug candidates that bind to the native ALK, but cannot bind to modified ALK.

Positive controls and negative controls may be used in the assays. For example, all control and test samples are performed in at least triplicate to obtain statistically significant results. Incubation of samples is for a time sufficient for the binding of the agent to the protein. Following incubation, samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Assays

For assay of activity, generally either ALK or a compound according to the invention is non-diffusably bound to an insoluble support having isolated sample-receiving areas (e.g., a microtiter plate, an array, etc.). The insoluble support may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the composition is not crucial so long as it is compatible with the reagents and overall methods of the invention, maintains the activity of the composition and is nondiffusable. Exemplary methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

One measure of inhibition is $K_i$. For compounds with $IC_{50}$'s less than 1 µM, the $K_i$ or $K_d$ is defined as the dissociation rate constant for the interaction of the agent with ALK. Exemplary compositions have $K_i$'s of, for example, less than about 100 µM, less than about 10 µM, less than about 1 µM, and further for example having $K_i$'s of less than about 100 nM, and still further, for example, less than about 10 nM. The $K_i$ for a compound is determined from the $IC_{50}$ based on three assumptions. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max} E_0 \left[ 1 - \frac{(E_0 + I_0 + K_d) - \sqrt{(E_0 + I_0 + K_d)^2 - 4E_0 I_0}}{2E_0} \right]$$

where V is the observed rate, $V_{max}$, is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the compound that results in a decrease in the rate of cell growth by fifty percent. Exemplary compounds have $GI_{50}$'s of, for example, less than about 1 mM, less than about 10 µM, less than about 1 µM, and further, for example, having $GI_{50}$'s of less than about 100 nM, still further having $GI_{50}$'s of less than about 10 nM. Measurement of $GI_{50}$ is done using a cell proliferation assay.

Tyrosine kinase activity is determined by 1) measurement of kinase-dependent ATP consumption in the presence of a generic substrate such as, polyglutamic acid, tyrosine, 4:1 (pEY), using luciferase/luciferin-mediated chemiluminescence or; 2) incorporation of radioactive phosphate derived from $^{32}$P-ATP into a generic substrate which has been adsorbed onto the well surface of polystyrene microtiter plates. Phosphorylated ($^{32}$P) substrate products are quantified by scintillation spectrometry.

Abbreviations and Their Definitions

The following abbreviations and terms have the indicated meanings throughout:

| Abbreviation | Meaning |
| --- | --- |
| Ac | acetyl |
| ACN | acetonitrile |
| ATP | adenosine triphosphate |
| BNB | 4-bromomethyl-3-nitrobenzoic acid |
| Boc | t-butyloxy carbonyl |
| br | broad |
| Bu | butyl |
| ° C. | degrees Celsius |
| c- | cyclo |
| CBZ | CarboBenZoxy = benzyloxycarbonyl |
| d | doublet |
| dd | doublet of doublet |
| dt | doublet of triplet |
| DBU | Diazabicyclo[5.4.0]undec-7-ene |
| DCM | dichloromethane = methylene chloride = $CH_2Cl_2$ |
| DCE | dichloroethylene |
| DEAD | diethyl azodicarboxylate |
| DIC | diisopropylcarbodiimide |
| DIEA | N,N-diisopropylethyl amine |
| DMAP | 4-N,N-dimethylaminopyridine |
| DMF | N,N-dimethylfonnamide |
| DMSO | dimethyl sulfoxide |
| DVB | 1,4-divinylbenzene |
| EEDQ | 2-ethoxy-1-ethoxycarbonyl-1,2-dihydroquinoline |
| EI | Electron Impact ionization |
| Et | ethyl |

| Abbreviation | Meaning |
|---|---|
| Fmoc | 9-fluorenylmethoxycarbonyl |
| g | gram(s) |
| GC | gas chromatography |
| H or hr | hour(s) |
| HATU | O-(7-Azabenzotriazol-1-yl)-1,1,3,3-tetramethyluronium hexafluorophosphate |
| HMDS | hexamethyldisilazane |
| HOAc | acetic acid |
| HOBt | hydroxybenzotriazole |
| HPLC | high pressure liquid chromatography |
| L | liter(s) |
| M | molar or molarity |
| m | multiplet |
| Me | methyl |
| mesyl | methanesulfonyl |
| mg | milligram(s) |
| MHz | megahertz (frequency) |
| Min | minute(s) |
| mL | milliliter(s) |
| mM | millimolar |
| mmol | millimole(s) |
| mol | mole(s) |
| MS | mass spectral analysis |
| MTBE | methyl t-butyl ether |
| N | normal or normality |
| NBS | N-bromosuccinimide |
| NCS | N-chlorosuccinimide |
| nM | nanomolar |
| NMO | N-methylmorpholine oxide |
| NMR | nuclear magnetic resonance spectroscopy |
| PEG | polyethylene glycol |
| pEY | poly-glutamine, tyrosine |
| Ph | phenyl |
| PhOH | phenol |
| PfP | pentafluorophenol |
| PfPy | pentafluoropyridine |
| PPTS | Pyridinium p-toluenesulfonate |
| Py | pyridine |
| PyBroP | bromo-tris-pyrrolidono-phosphonium hexafluorophosphate |
| q | quartet |

| Abbreviation | Meaning |
|---|---|
| RT | Room temperature |
| Sat'd | saturated |
| s | singlet |
| SEM-Cl | chloromethyl 2-trimethylsilylethyl ether |
| s- | secondary |
| t- | tertiary |
| T or tr | triplet |
| TBDMS | t-butyldimethylsilyl |
| TES | triethylsilane |
| TFA | trifluoroacetic acid |
| THF | tetrahydrofuran |
| TMOF | trimethyl orthoformate |
| TMS | trimethylsilyl |
| tosyl | p-toluenesulfonyl |
| Trt | triphenylmethyl |
| µL | microliter(s) |
| µM | Micromole(s) or micromolar |

Synthesis of Compounds

The compounds encompassed by the instant application can be synthesized by methods known to one of ordinary skill in the art. Compounds of the invention generally may be prepared by methods illustrated in Scheme 1; however, Scheme 1 and its corresponding description are not intended to be limiting. For example, scheme 1 depicts the synthesis of compounds of the invention according to formula I, where $R^2$ and $R^3$ combine to form an aromatic ring (which itself is substituted with up to three of $R^6$, in this case one of $R^6$ is —$OR^4$) that is ultimately fused to a pyrazoloisoquinoline. Of course there are other embodiments in which $R^2$ and $R^3$ represent different functionality but are nonetheless consistent with formula I. One of ordinary skill in the art would recognize that functionality of compounds according to formula I can be introduced at various stages of the synthesis of the compounds and likewise protecting groups can be used in such synthetic strategies.

Scheme 1

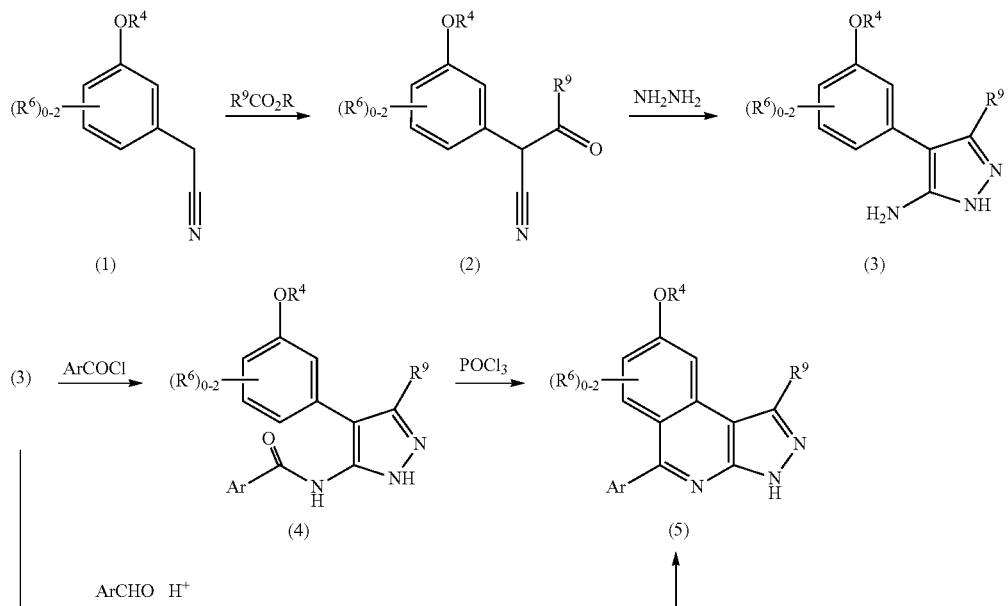

Referring to Scheme 1, the synthesis of phenylacetonitriles represented by (1) bearing a broad range of aromatic ring functional groups are well known in the art (March, *Advanced Organic Chemistry*, Wiley-Interscience; Larock, *Comprehensive Organic Transformations*, VCH Publishers; both incorporated by reference herein) and may be readily reacted with a range of esters as well as suitably activated acyl derivatives to provide Claisen-like condensation products such as (2) as a means of introducing $R^9$ functional group. Such transformations may be carried out under basic conditions using hydroxide, alkoxide or alkali metal hydride and the like in either protic or aprotic solvent depending on the choice of base. Solvents such as methanol, ethanol, THF or DMF and the like are suitable for carrying out such transformations. Temperatures ranging from room temperature to solvent reflux may be employed depending on the reactivity of the selected ester and phenylacetonitrile substrate. In some cases it may be desirable to employ or generate in situ a suitably activated acyl derivative to enhance the reactivity of an ester toward reaction with the phenylacetonitrile. These reagents include, but are not limited to acyl halides, anhydrides, acylimidazoles N-hydroxysuccinyl esters and the like.

Treatment of an intermediate such as (2) with hydrazine, preferably in a polar protic solvent such as methanol or ethanol at elevated temperature affords the corresponding aminopyrazole (3). In one approach to the synthesis of compounds of the invention, aminopyrazole (3) can be acylated by treatment with an aromatic acid chloride or suitably activated ester of the corresponding benzoic acid to form amide intermediate (4). Amide (4) is subjected to Bischler-Napieralski cyclodehydration conditions [Fodor and Nagubandi, *Tetrahedron* 36, 1279-1300 (1980), incorporated by reference herein] by treatment with phosphorous oxychloride and heating with or without the presence of a suitably high boiling inert solvent such as toluene to afford the pyrazoloisoquinoline ring system represented by (5). The amide may alternatively be first treated with phosphorous pentachloride to generate an intermediate imino chloride and subsequently made to undergo cyclodehydration on heating [Fodor, Gal and Philips, *Angew. Chem. Int. Ed. Engl.* 11, 919 (1972), incorporated by reference herein].

In another synthetic approach to the pyrazoloisoquinoline ring system, the ring-forming step may be carried out directly using Pictet-Spengler methodology [Kametani and Fukumoto, *Isoquinolines*, Wiley Interscience; Bogza et al., *J. Heterocyclic Chem.* 38, 523-525 (2001), incorporated by reference herein]. In this approach, treatment of the aminopyrazole (3) with an aromatic aldehyde in the presence of a suitable acidic solvent such a trifluoroacetic acid with heating is a preferred method for generation of the pyrazoloisoquinoline (5). The choice of reaction conditions depends greatly on the functional groups present on the aromatic ring ($R^6$ according to formula I, and that functionality needed to introduce L and ring A according to formula I). The cyclization is facilitated by the presence of electron-donating functionality on the aromatic ring in positions ortho- and para- to the bond-forming ring atom, in particular hydroxy or alkoxy groups are preferred. In some embodiments, acetic acid as a reaction solvent is well suited for the Pictet-Spengler ring closure step and allows for the incorporation of acid sensitive functional groups in the synthetic sequence. In other embodiments, a phenylacetonitrile substrate that does not bear either alkoxy or hydroxy functional groups may be required. These substrates may be employed in the synthesis of pyrazoloisoquinolines by the use of transition-metal Lewis acids in the ring forming step or alternatively, by using a very strong acid such as methanesulfonic acid as the reaction solvent. It is recognized that for some cyclization substrates the choice of aromatic ring substitution pattern may result in the availability of two possible Pictet-Spengler reaction products and both products may be isolated from the reaction mixtures obtained.

As mentioned, the pyrazoloisoquinolines may bear a suitably protected functional groups at any suitable stage in their synthesis. This protecting group may be introduced or removed at any stage in the synthetic sequence to afford a compound of the invention or a key intermediate along the synthetic pathway. The choice of a suitable protecting group and its introduction or removal is a well-established practice in synthetic organic chemistry [Green and Wuts, *Protective Groups in Organic Synthesis*, Wiley Interscience, incorporated by reference herein]. For example in Scheme 2, in the conversion of intermediate (2a) to aminopyrazole (6), a functionalized hydrazine may be employed. In particular, the use of tert-butyl hydrazine readily affords protected aminopyrazole (6). An intermediate of this type is particularly useful for the synthesis of more complex compounds of the invention, which may require multi-step synthesis involving, for example, the manipulation of functionality on the pyrazoloisoquinoline aromatic ring. In such instances, either the introduction of specifically targeted or a broad range of functional groups in an efficient manner may be carried out. In the case illustrated, the Pictet-Spengler reaction may be carried out under mildly acidic conditions, typically in acetic acid with reaction temperatures in the range of 50-110° C., to afford intermediate (7). This intermediate can then be selectively derivatized, for example at the hydroxyl position, to provide a range of phenyl ether analogs followed by removal of the pyrazole ring tert-butyl group under appropriate conditions to give (8) which is in accord with formula I.

Scheme 2

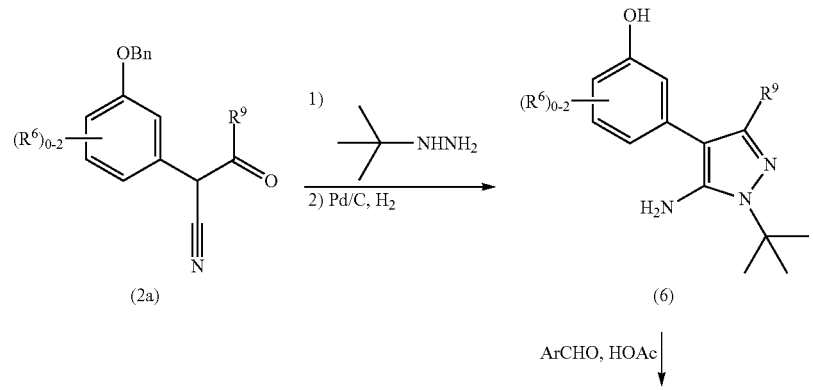

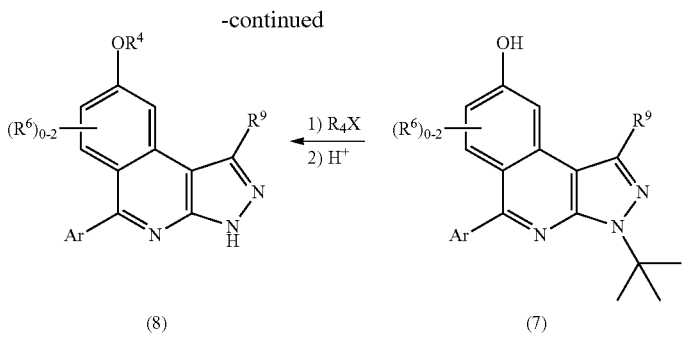

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

4-[8-(methyloxy)-1-(phenylmethyl)-3H-pyrazolo[3,4-c]isoquinolin-5-yl]phenol trifluoroacetic acid salt: To a mixture of [3-(methyloxy)phenyl]acetonitrile (2.0 g, 14 mmol) and ethyl phenylacetate (2.8 g, 17 mmol) in ethanol (4 mL) was added a sodium ethoxide solution (21%, 10.2 mL, 27 mmol), and the resulting mixture was heated at reflux for 18 hours. After cooling to room temperature, it was poured into a mixture of ice-water (50 mL). This aqueous mixture was washed with dichloromethane (3×20 mL) then acidified to pH 1. The acidified mixture was extracted with ethyl acetate (3×30 mL). The combined extract was washed with aqueous sodium bicarbonate solution, brine, dried over sodium sulfate, filtered and concentrated to give 2-[3-(methyloxy)phenyl]-3-oxo-4-phenylbutanenitrile as a brown oil (0.8 g, 3.4 mmol, 38% yield), MS (EI) for $C_{17}H_{15}NO_2$: 266 (MH$^+$).

2-[3-(methyloxy)phenyl]-3-oxo-4-phenylbutanenitrile (100 mg, 0.38 mmol) was dissolved in ethanol (1 mL), and anhydrous hydrazine (98%, 14 µL, 0.45 mmol) was added. The resulting mixture was heated at reflux for 1 hour. It was cooled, concentrated, and the residue was dried under vacuum for one hour. To this residue was added of 4-hydroxybenzaldehyde (69 mg, 0.57 mmol) and trifluoroacetic acid (1 mL), and the mixture was heated at 70° C. for 18 hours. Then the reaction mixture was concentrated, dissolved in 10 mL of N,N-dimethylformamide and purified by preparatory reverse phase HPLC (Shimadzu LC-8A HPLC, Waters Xterra C18 30 mm×100 mm column, acetonitrile-water-trifluoroacetic eluent). After concentration then lyophillization of the pure fractions 4-[8-(methyloxy)-1-(phenylmethyl)-3H-pyrazolo[3,4-c]isoquinolin-5-yl]phenol trifluoroacetic acid salt (63 mg, 0.13 mmol, 34% yield) was obtained. $^1$H NMR (400 MHz, d$_6$-DMSO): 7.97-7.94 (d, 1H), 7.50-7.48 (d, 2H), 7.30-7.25 (m, 6H), 7.06-7.02 (m, 1H), 6.95-6.93 (d, 2H), 4.60 (s, 2H), 3.76 (s, 3H); MS (EI) for $C_{24}H_{19}N_3O_2$: 382 (MH$^+$).

Using the same or analogous synthetic techniques and/or substituting with alternative reagents, the following compounds of the invention were prepared:

4-(7,8-bis(methyloxy)-1-{[4-(methyloxy)phenyl]methyl}-3H-pyrazolo[3,4-c]isoquinolin-5-yl)phenol trifluoroacetic acid salt: $^1$H NMR (400 MHz, d$_6$-DMSO): 7.66-7.64 (d, 2H), 7.50 (s, 1H), 7.36 (s, 1H), 7.26-7.24 (d, 2H), 7.16-7.14 (d, 2H), 6.86-6.84 (d, 2H), 4.64 (s, 2H), 3.82 (s, 3H), 3.78 (s, 3H), 3.70 (s, 3H); MS (EI) for $C_{26}H_{23}N_3O_4$: 442 (MH$^+$).

4-{7,8-bis(methyloxy)-1-[(2-methylphenyl)methyl]-3H-pyrazolo[3,4-c]isoquinolin-5-yl}phenol trifluoroacetic acid salt: $^1$H NMR (400 MHz, d$_6$-DMSO): 7.61-7.59 (d, 2H), 7.46 (s, 1H), 7.28-7.26 (d, 2H), 7.17-7.10 (m, 3H), 7.10 (s, 1H), 6.96-6.94 (d, 2H), 4.25 (s, 2H), 3.70 (s, 3H), 3.58 (s, 3H), 2.42 (s, 3H); MS (EI) for $C_{26}H_{23}N_3O_4$: 442 (MH$^+$). MS (EI) for $C_{26}H_{23}N_3O_3$: 426 (MH$^+$).

4-{7,8-bis(methyloxy)-1-[(3-methylphenyl)methyl]-3H-pyrazolo[3,4-c]isoquinolin-5-yl}phenol trifluoroacetic acid salt: $^1$H NMR (400 MHz, d$_6$-DMSO): 9.80 (b, 1H), 7.58-7.56 (d, 2H), 7.44 (s, 1H), 7.27 (s, 1H), 7.18-7.13 (m, 2H), 7.06-7.00 (m, 2H), 6.96-6.92 (d, 2H), 4.25 (s, 2H), 3.77 (s, 3H), 3.70 (s, 3H), 2.23 (s, 3H); MS (EI) for $C_{26}H_{23}N_3O_3$: 426 (MH$^+$).

2-[7,8-bis(methyloxy)-1-(phenylmethyl)-3H-pyrazolo[3,4-c]isoquinolin-5-yl]-6-fluorophenol trifluoroacetic acid salt: $^1$H NMR (400 MHz, d$_6$-DMSO): 9.78 (b, 1H), 7.40-7.18 (m, 7H), 7.00-6.90 (m, 3H), 4.61 (s, 2H), 3.78 (s, 3H), 3.62 (s, 3H); MS (EI) for $C_{25}H_{20}N_3O_3F$: 430 (MH$^+$).

3-[7,8-bis(methyloxy)-1-(phenylmethyl)-3H-pyrazolo[3,4-c]isoquinolin-5-yl]-4-nitrophenol trifluoroacetic acid salt: $^1$H NMR (400 MHz, d$_6$-DMSO): 11.05 (b, 1H), 8.12-8.10 (d, 1H), 7.45 (s, 1H), 7.43-7.30 (m, 4H), 7.20-7.15 (m, 2H), 7.10-6.95 (m, 2H), 4.61 (s, 2H), 3.78 (s, 3H), 3.61 (s, 3H); MS (EI) for $C_{25}H_{20}N_4O_5$: 457 (MH$^+$).

4-[7,8-bis(methyloxy)-1-(phenylmethyl)-3H-pyrazolo[3,4-c]isoquinolin-5-yl]benzoic acid trifluoroacetic acid salt: $^1$H NMR (400 MHz, d$_6$-DMSO): 8.16-8.13 (d, 2H) 7.87-7.84 (d, 2H), 7.36-7.18 (m, 7H), 4.65 (s, 2H), 3.75 (s, 3H), 3.68 (s, 3H), 3.48 (b, 1H); MS (EI) for $C_{26}H_{21}N_3O_4$: 440 (MH$^+$).

4-[1-{[3,4-bis(methyloxy)phenyl]methyl}-7,8-bis(methyloxy)-3H-pyrazolo[3,4-c]isoquinolin-5-yl]phenol trifluoroacetic acid salt: $^1$H NMR (400 MHz, d$_4$-Methanol): 7.66-7.64 (d, 2H), 7.48 (s, 1H), 7.31 (s, 1H), 7.08-7.06 (d, 2H), 6.92-6.91 (d, 1H), 6.90-6.88 (d, 1H), 6.76-6.75 (d, 1H), 4.68 (s, 2H), 3.82 (s, 3H), 3.79 (s, 3H), 3.78 (s, 3H), 3.72 (s, 3H); MS (EI) for $C_{27}H_{25}N_3O_5$: 472 (MH$^+$).

4-(7,8-bis(methyloxy)-1-{[3-(methyloxy)phenyl]methyl}-3H-pyrazolo[3,4-c]isoquinolin-5-yl)phenol trifluoroacetic acid salt: $^1$H NMR (400 MHz, d$_6$-DMSO): 9.80 (b, 1H)

7.56-7.54 (d, 2H), 7.42 (s, 1H), 7.24 (s, 1H), 7.19-7.15 (t, 1H), 6.94-6.92 (d, 2H), 6.86- (s, 1H), 6.80-6.78 (m, 2H), 4.56 (s, 2H), 3.75 (s, 3H), 3.69 (s, 3H), 3.66 (s, 3H); MS (EI) for $C_{26}H_{23}N_3O_4$: 442 (MH$^+$).

7,8-bis(methyloxy)-1-(phenylmethyl)-5-pyridin-4-yl-3H-pyrazolo[3,4-c]isoquinoline trifluoroacetic acid salt: $^1$H NMR (400 MHz, $d_6$-DMSO): 8.86-8.84 (d, 2H), 7.92-7.90 (d, 2H), 7.32-7.20 (m, 7H), 4.63 (s, 2H), 3.74 (s, 3H), 3.70 (s, 3H); MS (EI) for $C_{24}H_{20}N_4O_2$: 397 (MH$^+$).

4-[6,7,8-tris(methyloxy)-1-(phenylmethyl)-3H-pyrazolo[3,4-c]isoquinolin-5-yl]phenol trifluoroacetic acid salt: $^1$H NMR (400 MHz, $d_6$-DMSO): 7.42-7.40 (d, 2H), 7.34-7.24 (m, 5H), 7.11 (s, 1H), 6.95-6.93 (d, 2H), 4.75 (s, 2H), 3.80 (s, 3H), 3.77 (s, 3H), 3.37 (s, 3H); MS (EI) for $C_{26}H_{23}N_3O_4$: 442 (MH$^+$).

4-[7-methyl-8-(methyloxy)-1-(phenylmethyl)-3H-pyrazolo[3,4-c]isoquinolin-5-yl]phenol trifluoroacetic acid salt: $^1$H NMR (400 MHz, $d_6$-DMSO): 9.91 (b, 1H), 7.92 (s, 1H), 7.60-7.58 (d, 2H), 7.46 (s, 1H), 7.32-7.21 (m, 5H), 6.90-6.88 (d, 2H), 4.56 (s, 2H), 3.74 (s, 3H), 2.28 (s, 3H); MS (EI) for $C_{25}H_{21}N_3O_2$: 396 (MH$^+$).

4-[6,8-bis(methyloxy)-1-(phenylmethyl)-3H-pyrazolo[3,4-c]isoquinolin-5-yl]phenol trifluoroacetic acid salt: $^1$H NMR (400 MHz, $d_6$-DMSO): 7.30-7.19 (m, 6H), 6.90-6.85 (m, 2H), 6079-6.77 (d, 2H), 6.50 (s, 1H), 4.58 (s, 2H), 3.72 (s, 6H); MS (EI) for $C_{25}H_{21}N_3O_3$: 412 (MH$^+$).

4-[7,8-bis(methyloxy)-1-(phenylmethyl)-3H-pyrazolo[3,4-c]isoquinolin-5-yl]benzene-1,2-diol: $^1$H NMR (400 MHz, $d_6$-DMSO): 13.46 (bs, 1H), 9.25 (s, 2H), 7.53 (s, 1H), 7.31 (m, 6H), 7.01 (d, 1H), 6.88 (d, 1H), 4.57 (s, 2H), 3.73 (s, 3H), 3.71 (s, 3H); MS (EI) for $C_{25}H_{21}N_3O_4$: 428 (MH$^+$).

4-[7,8-bis(methyloxy)-1-(phenylmethyl)-3H-pyrazolo[3,4-c]isoquinolin-5-yl]-N,N-dimethylaniline: $^1$H NMR (400 MHz, $d_6$-DMSO): 8.57 (s, 1H), 7.71 (t, 2H), 7.65 (d, 2H), 7.53 (s, 1H), 7.3 (d, 2H), 7.28 (s, 2H), 7.21 (s, 1H) 6.92 (d, 2H), 6.80 (t, 2H), 4.62 (s, 2H), 3.74 (s, 3H), 3.71 (s, 3H); MS (EI) for $C_{27}H_{26}N_4O_2$: 439 (MH$^+$).

5-(4-fluorophenyl)-7,8-bis(methyloxy)-1-(phenylmethyl)-3H-pyrazolo[3,4-c]isoquinoline: $^1$H NMR (400 MHz, $d_6$-DMSO): 8.73 (s, 1H), 7.96 (m, 1H), 7.79 (m, 2H), 7.42 (m, 3H), 7.29 (m, 5H), 7.19 (s, 1H), 4.62 (s, 2H), 3.74 (s, 3H), 3.68 (s, 3H); MS (EI) for $C_{25}H_{20}N_3O_2F$: 414 (MH$^+$).

5-(4-nitrophenyl)-7,8-bis(methyloxy)-1-(phenylmethyl)-3H-pyrazolo[3,4-c]isoquinoline: $^1$H NMR (400 MHz, $d_6$-DMSO): 8.43 (d, 2H), 8.03 (d, 2H), 7.31 (m, 6H), 7.21 (m, 1H), 4.64 (s, 2H), 3.75 (s, 3H), 3.69 (s, 3H); MS (EI) for $C_{25}H_{21}N_4O_4$: 441 (MH$^+$).

3-[7,8-bis(methyloxy)-1-(phenylmethyl)-3H-pyrazolo[3,4-c]isoquinolin-5-yl]phenol: $^1$H NMR (400 MHz, $d_6$-DMSO): 7.42 (s, 1H), 7.25 (m, 7H), 7.17 (m, 1H), 7.08 (m, 2H), 6.90 (m, 1H), 4.62 (s, 2H), 3.74 (s, 3H), 3.68 (s, 3H); MS (EI) for $C_{25}H_{21}N_3O_3$: 411 (MH$^+$).

5-(1,3-benzodioxol-5-yl)-7,8-bis(methyloxy)-1-(phenylmethyl)-3H-pyrazolo[3,4-c]isoquinoline: $^1$H NMR (400 MHz, $d_6$-DMSO): 7.55 (d, 1H), 7.39 (s, 1H), 7.25 (m, 5H), 7.12 (m, 1H), 7.08 (s, 1H), 6.90 (d, 1H), 5.88 (s, 2H), 4.68 (s, 2H), 3.75 (s, 3H), 3.68 (s, 3H); MS (EI) for $C_{26}H_{21}N_3O_4$: 439 (MH$^+$).

4-{7,8-bis(methyloxy)-1-[(4-methylphenyl)methyl]-3H-pyrazolo[3,4-c]isoquinolin-5-yl}phenol: $^1$H NMR (400 MHz, $d_6$-DMSO): 9.81 (s, 1H), 7.55 (d, 2H), 7.44 (s, 1H), 7.24 (s, 1H), 7.16 (d, 2H), 7.08 (d, 2H), 6.95 (d, 2H), 4.53 (s, 2H), 3.74 (s, 3H), 3.69 (s, 3H); MS (EI) for $C_{26}H_{23}N_3O_3$: 425 (MH$^+$).

4-[7,8-bis(methyloxy)-1-(1-phenylethyl)-3H-pyrazolo[3,4-c]isoquinolin-5-yl]phenol: $^1$H NMR (400 MHz, CD$_3$OD): 7.63-7.61 (d, 2H), 7.43 (s, 1H), 7.38-7.20 (m, 6H), 5.09-5.06 (m, 1H), 3.80 (s, 3H), 3.75 (s, 3H), 1.98-1.96 (d, 3H); MS (EI) for $C_{26}H_{23}N_3O_3$: 426 (MH$^+$).

Example 2

4-[1-methyl-7,8-bis(methyloxy)-3H-pyrazolo[3,4-c]isoquinolin-5-yl]phenol trifluoroacetic acid salt: To a mixture of 3,4-dimethoxyphenylacetonitrile (2.0 g, 11 mmol) and ethyl acetate (1.37 mL, 14 mmol) in ethanol (4 mL) was added a sodium ethoxide solution (21 W %, 8.4 mL, 23 mmol), and the resulting mixture was heated at reflux for 18 hours. The reaction mixture was cooled to room temperature, and then poured into ice-water (50 mL). This aqueous mixture was washed with dichloromethane (3×20 mL) and the aqueous phase acidified to pH 1. The aqueous phase was extracted with ethyl acetate (3×30 mL). The combined ethyl acetate extract was washed with saturated aqueous sodium bicarbonate solution, brine, dried over anhydrous sodium sulfate then filtered and concentrated to give 2-[3,4-bismethyloxy)phenyl]-3-oxobutanenitrile as a tan color solid (1.5 g, 6.8 mmol, 61% yield). MS (EI) for $C_{12}H_{33}NO_3$: 220 (MH$^+$).

2-[3,4-bismethyloxy)phenyl]-3-oxobutanenitrile (100 mg, 0.46 mmol) was dissolved in ethanol, and anhydrous hydrazine (98%, 18 µL, 0.59 mmol) was added. The resulting mixture was heated at reflux for 1 hour. The mixture was cooled, concentrated and dried iii vacuo for one hour to give an oily residue. To this residue was added of 4-hydroxybenzaldehyde (84 mg, 0.67 mmol) then trifluoroacetic acid (2 mL) and the mixture was heated at reflux for 18 hours. The reaction mixture was then concentrated, dissolved in 10 mL of dimethylformamide and purified by preparative reverse phase HPLC (Shimadzu LC-8A HPLC, Waters Xterra C18 30 mm×100 mm column, acetonitrile-water-trifluoroacetic eluent). Concentration and lyophillization of the pure fractions afforded 4-[1-methyl-7,8-bis(methyloxy)-3H-pyrazolo[3,4-c]isoquinolin-5-yl]phenol trifluoroacetic acid salt (55 mg, 0.16 mmol, 26% yield). $^1$H NMR (400 MHz, $d_6$-DMSO): 10.00 (b, 1H), 7.76 (s, 1H), 7.70-7.68 (d, 2H), 7.51 (s, 1H), 7.01-6.98 (d, 2H), 4.18 (s, 3H), 3.95 (s, 3H), 2.84 (s, 3H); MS (EI) for $C_{19}H_{17}N_3O_3$: 336 (MH$^+$).

Using the same or analogous synthetic techniques and/or substituting with alternative reagents, the following compounds of the invention were prepared:

4-[1-methyl-6,8-bis(methyloxy)-3H-pyrazolo[3,4-c]isoquinolin-5-yl]phenol trifluoroacetic acid salt: $^1$H NMR (400 MHz, $d_6$-DMSO): 9.52 (b, 1H), 7.26-7.21 (m, 3H), 6.80-6.78 (d, 2H), 6.62 (s, 1H), 4.02 (s, 3H), 3.55 (s, 3H), 2.80 (s, 3H); MS (EI) for $C_{19}H_{17}N_3O_3$: 336 (MH$^+$).

4-[1-methyl-7,8,9-tris(methyloxy)-3H-pyrazolo[3,4-c]isoquinolin-5-yl]phenol trifluoroacetic acid salt: $^1$H NMR (400 MHz, $d_6$-DMSO): 7.56-7.54 (d, 2H), 7.38 (s, 1H), 6.80-6.78 (d, 2H), 3.98 (s, 3H), 3.95 (s, 3H), 3.78 (s, 3H), 2.78 (s, 3H); MS (EI) for $C_{20}H_{19}N_3O_4$: 366 (MH$^+$).

2-methyl-4-[1-methyl-7,8-bis(methyloxy)-3H-pyrazolo[3,4-c]isoquinolin-5-yl]phenol trifluoroacetic acid salt: $^1$H NMR (400 MHz, $d_6$-DMSO): 9.90 (b, 1H), 7.66 (s, 1H), 7.53 (b, 2H), 7.45-43 (d, 1H), 7.05-6.95 (d, 1H), 4.09 (s, 3H), 3.77 (s, 3H), 2.85 (s, 3H), 2.24 (s, 3H); MS (EI) for $C_{20}H_{19}N_3O_3$: 350 (MH$^+$).

4-[1-methyl-7,8-bis(methyloxy)-3H-pyrazolo[3,4-c]isoquinolin-5-yl]-2-(methyloxy)phenol trifluoroacetic acid salt: $^1$H NMR (400 MHz, $d_6$-DMSO): 7.76 (s, 1H), 7.56 (s, 1H), 7.30-7.29 (d, 1H), 7.20-7.18 (d, d, 1H), 6.98-6.96 (d, 1H), 4.06 (s, 3H), 3.84 (s, 3H), 3.77 (s, 3H), 2.83 (s, 3H); MS (EI) for $C_{20}H_{19}N_3O_4$: 366 (MH$^+$).

2-chloro-4-[1-methyl-7,8-bis(methyloxy)-3H-pyrazolo[3,4-c]isoquinolin-5-yl]phenol trifluoroacetic acid salt: $^1$H NMR (400 MHz, d$_6$-DMSO): 10.65 (b, 1H), 7.71-7.70 (d, 1H), 7.66 (s, 1H), 7.57-7.53 (d, d, 1H), 7.46 (s, 1H), 7.18-7.16 (d, 1H), 4.06 (s, 3H), 3.77 (s, 3H), 2.82 (s, 3H); MS (EI) for $C_{19}H_{16}N_3O_3Cl$: 370 (MH$^+$).

2-fluoro-4-[1-methyl-7,8-bis(methyloxy)-3H-pyrazolo[3,4-c]isoquinolin-5-yl]phenol trifluoroacetic acid salt: $^1$H NMR (400 MHz, d$_6$-DMSO): 10.25 (b, 1H), 7.66 (s, 1H), 7.55-7.53 (d, 1H), 7.48 (s, 1H), 7.41-7.39 (d, 1H), 7.17-7.12 (d, d, 1H), 4.06 (s, 3H), 3.77 (s, 3H), 2.83 (s, 3H); MS (EI) for $C_{19}H_{16}N_3O_3F$: 354 (MH$^+$).

4-[1-methyl-7,8-bis(methyloxy)-3H-pyrazolo[3,4-c]isoquinolin-5-yl]-2-nitrophenol trifluoroacetic acid salt: $^1$H NMR (400 MHz, d$_6$-DMSO): 10.42 (b, 1H), 8.25 (s, 1H), 7.98-7.96 (d, 1H), 7.67 (s, 1H), 7.46 (s, 1H), 7.33-7.31 (d, 1H), 4.06 (s, 3H), 3.79 (s, 3H), 2.82 (s, 3H); MS (EI) for $C_{19}H_{16}N_4O_5$: 381 (MH$^+$).

2-bromo-4-[1-methyl-7,8-bis(methyloxy)-3H-pyrazolo[3,4-c]isoquinolin-5-yl]phenol trifluoroacetic acid salt: $^1$H NMR (400 MHz, d$_6$-DMSO): 10.72 (b, 1H), 7.85 (s, 1H), 7.66 (s, 1H), 7.61-7.59 (d, 1H), 7.47 (s, 1H), 7.14-7.12 (d, 1H), 4.08 (s, 3H), 3.77 (s, 3H), 2.82 (s, 3H); MS (EI) for $C_{19}H_{16}N_3O_3Br$: 414 (MH$^+$).

4-[1-methyl-6,7,8-tris(methyloxy)-3H-pyrazolo[3,4-c]isoquinolin-5-yl]phenol trifluoroacetate: $^1$H NMR (400 MHz, d$_6$-DMSO): 7.50 (s, 1H), 7.29 (d, 2H), 6.81 (d, 2H), 6.67 (s, 1H), 4.09 (s, 3H), 3.78 (s, 6H), 2.82 (s, 3H); MS (EI) for $C_{20}H_{19}N_3O_4$: 366 (MH$^+$).

4-[1-methyl-8-(methyloxy)-3H-pyrazolo[3,4-c]isoquinolin-5-yl]phenol trifluoroacetate: $^1$H NMR (400 MHz, d$_6$-DMSO): 8.03 (d, 1H), 7.65 (d, 1H), 7.52 (d, 2H), 7.18 (dd, 1H), 6.96 (d, 2H), 4.02 (s, 3H), 2.83 (s, 3H); MS (EI) for $C_{18}H_{15}N_3O_2$: 306 (MH$^+$).

5-(4-fluorophenyl)-1-methyl-7,8-bis(methyloxy)-3H-pyrazolo[3,4-c]isoquinoline: $^1$H NMR (400 MHz, DMSO-d$_6$): 13.32 (s, 1H), 7.78 (m, 2H), 7.67 (s, 1H), 7.40 (m, 3H), 4.06 (s, 3H), 3.74 (s, 3H), 2.82 (s, 3H); MS (EI) for $C_{19}H_{16}N_3O_2F$: 338 (MH$^{30}$).

2,6-dimethyl-4-[1-methyl-7,8-bis(methyloxy)-3H-pyrazolo[3,4-c]isoquinolin-5-yl]phenol: $^1$H NMR (400 MHz, DMSO-d$_6$): 7.64 (s, 1H), 7.55 (s, 1H), 7.35 (s, 2H), 4.07 (s, 3H), 3.76 (s, 3H), 2.83 (s, 3H), 2.28 (s, 6H); MS (EI) for $C_{21}H_{21}N_3O_3$: 364 (MH$^+$).

5-[4-fluoro-3-(trifluoromethyl)phenyl]-1-methyl-7,8-bis(methyloxy)-3H-pyrazolo[3,4-c]isoquinoline: $^1$H NMR (400 MHz, DMSO-d$_6$): 13.40 (s, 1H), 8.16 (m, 1H), 8.10 (m, 1H), 7.72 (m, 1H), 7.68 (s, 1H), 7.35 (s, 1H), 4.07 (s, 3H), 3.77 (s, 3H), 2.83 (s, 3H); MS (EI) for $C_{20}H_{15}N_3O_2F_4$: 406 (MH$^+$).

5-(3-chloro-4-fluorophenyl)-1-methyl-7,8-bis(methyloxy)-3H-pyrazolo[3,4-c]isoquinoline: $^1$H NMR (400 MHz, DMSO-d$_6$): 13.36 (s, 1H), 7.93 (m, 1H), 7.76 (m, 1H), 7.67 (s, 1H), 7.61 (t, J=8.9 Hz, 1H), 7.35 (s, 1H), 4.06 (s, 3H), 3.76 (s, 3H), 2.82 (s, 3H); MS (EI) for $C_{19}H_{15}N_3O_2ClF$: 372 (MH$^+$).

5-(3,4-difluorophenyl)-1-methyl-7,8-bis(methyloxy)-3H-pyrazolo[3,4-c]isoquinoline: $^1$H NMR (400 MHz, DMSO-d$_6$): 13.36 (s, 1H), 7.81 (m, 1H), 7.67 (s, 1H), 7.61 (m, 2H), 7.36 (s, 1H), 4.08 (s, 3H), 3.78 (s, 3H), 2.82 (s, 3H); MS (EI) for $C_{19}H_{15}N_3O_2F_2$: 356 (MH$^+$).

1-methyl-7,8-bis(methyloxy)-5-[3-(trifluoromethyl)phenyl]-3H-pyrazolo[3,4-c]isoquinoline: $^1$H NMR (400 MHz, DMSO-d$_6$): 13.40 (s, 1H), 8.08 (m, 2H), 7.94 (d, J=7.8 Hz, 1H), 7.83 (t, J=7.8 Hz, 1H), 7.68 (s, 1H), 7.36 (s, 1H), 4.07 (s, 3H), 3.74 (s, 3H), 2.83 (s, 3H); MS (EI) for $C_{20}H_{16}N_3O_2F_3$: 388 (MH$^+$).

5-(4-fluoro-3-methylphenyl)-1-methyl-7,8-bis(methyloxy)-3H-pyrazolo[3,4-c]isoquinoline: $^1$H NMR (400 MHz, DMSO-d$_6$): 7.66 (m, 2H), 7.58 (m, 1H), 7.41 (s, 1H), 7.33 (t, J=9.0 Hz, 1H), 4.06 (s, 3H), 3.75 (s, 3H), 2.83 (s, 3H), 2.36 (s, 3H); MS (EI) for $C_{20}H_{18}N_3O_2F$: 352 (MH$^+$).

5-(3-bromo-4-fluorophenyl)-1-methyl-7,8-bis(methyloxy)-3H-pyrazolo[3,4-c]isoquinoline: $^1$H NMR (400 MHz, DMSO-d$_6$): 13.36 (s, 1H), 8.05 (m, 1H), 7.80 (m, 1H), 7.67 (s, 1H), 7.57 (t, J=8.7 Hz, 1H), 7.36 (s, 1H), 4.06 (s, 3H), 3.76 (s, 3H), 2.83 (s, 3H); MS (EI) for $C_{19}H_{15}N_3O_2BrF$: 416, 418 (MH$^+$).

2-(ethyloxy)-4-[1-methyl-7,8-bis(methyloxy)-3H-pyrazolo[3,4-c]isoquinolin-5-yl]phenol: $^1$H NMR (400 MHz, MeOH-d$_4$): 7.68 (s, 1H), 7.53 (s, 1H), 7.35 (d, J=2.2 Hz, 1H), 7.23 (dd, J=2.2/8.2 Hz, 1H), 7.08 (d, J=8.2 Hz, 1H), 4.18 (q, J=7.0 Hz, 2H), 4.16 (s, 3H), 3.82 (s, 3H), 2.94 (s, 3H), 1.47 (t, J=7.0 Hz, 3H); MS (EI) for $C_{21}H_{21}N_3O_4$: 380 (MH$^+$).

4-[1,9-dimethyl-8-(methyloxy)-3H-pyrazolo[3,4-c]isoquinolin-5-yl]phenol: $^1$H NMR (400 MHz, d$_6$-DMSO): 13.46 (s, 1H), 9.81 (s, 1H), 7.96 (d, J=9.6 Hz, 1H), 7.44 (d, J=8.4 Hz, 2H), 7.32 (d, J=9.6 Hz, 1H), 6.93 (d, J=8.4 Hz, 2H), 3.96 (s, 3H), 2.79 (s, 3H), 2.72 (s, 3H); MS (EI) for $C_{19}H_{17}N_3O_2$: 320 (MH$^+$).

4-[6-bromo-1,7-dimethyl-8-(methyloxy)-3H-pyrazolo[3,4-c]isoquinolin-5-yl]phenol. $^1$H NMR (400 MHz, d$_6$-DMSO): 9.63 (broad s, 1H), 7.63 (s, 1H), 7.20 (d, 2H), 6.80 (d, 2H), 4.09 (s, 3H), 2.81 (s, 3H), 2.40 (s, 3H); MS (EI) for $C_{19}H_{16}N_3O_2Br$: 398 (MH$^+$).

2-chloro-4-(1-methyl-7-(1-methylethyl)-8-{[2-(methyloxy)ethyl]oxy}-3H-pyrazolo[3,4-c]isoquinolin-5-yl)phenol. $^1$H NMR (400 MHz, d$_6$-DMSO): 13.31 (broad s, 1H), 10.64 (s, 1H), 7.91 (s, 1H), 7.65 (d, 2H), 7.49 (dd, 1H), 7.16 (d, 1H), 4.43 (t, 2H), 3.82 (t, 2H), 3.39 (s, 3H), 3.31 (q, 1H), 2.81 (s, 3H), 1.17 (d, 6H); MS (EI) for $C_{23}H_{24}N_3O_3Cl$: 426 (MH$^+$).

4-[1-methyl-8,9-bis(methyloxy)-3H-pyrazolo[3,4-c]isoquinolin-5-yl]phenol $^1$H-NMR (400 MHz, DMSO-d$_6$): δ7.87 (d, 1H), 7.52-7.50 (m, 2H), 7.44 (d, 1H), 6.99-6.95 (m, 2H), 4.02 (s, 3H), 3.91 (s, 3H), 2.82 (s, 3H); MS (EI) for $C_{19}H_{17}N_3O_3$: 336 (MH$^+$).

2-chloro-4-[1-methyl-8,9-bis(methyloxy)-3H-pyrazolo[3,4-c]isoquinolin-5-yl]phenol $^1$H NMR (400 MHz, DMSO-d$_6$): δ7.80 (d, 1H), 7.59 (d, 1H), 7.41 (dd, 1H), 7.40 (d, 1H), 7.12 (d, 1H), 3.99 (s, 3H), 3.89 (s, 3H), 2.79 (s, 3H); MS (EI) for $C_{19}H_{16}ClN_3O_3$: 370 (MH$^+$).

2-fluoro-4-[1-methyl-8,9-bis(methyloxy)-3H-pyrazolo[3,4-c]isoquinolin-5-yl]phenol MS (EI) for $C_{19}H_{16}FN_3O_3$: 354 (MH$^+$).

2-methyl-4-[1-methyl-8,9-bis(methyloxy)-3H-pyrazolo[3,4-c]isoquinolin-5-yl]phenol hydrochloride $^1$H NMR (400 MHz, CD$_3$OD): δ8.10 (d, 1H), 7.56 (d, 1H), 7.54-7.53 (m, 1H), 7.47 (dd, 1H), 7.05 (d, 1H), 4.16 (s, 3H), 4.04 (s, 3H), 3.00 (s, 3H), 2.35 (s, 3H); MS (EI) for $C_{20}H_{19}N_3O_3$: 350 (MH$^+$).

2-bromo-4-[1-methyl-8,9-bis(methyloxy)-3H-pyrazolo[3,4-c]isoquinolin-5-yl]phenol MS (EI) for $C_{19}H_{16}BrN_3O_3$: 414, 416 (MH$^+$).

2-chloro-4-[1-methyl-6,7,8-tris(methyloxy)-3H-pyrazolo[3,4-c]isoquinolin-5-yl]phenol $^1$H NMR (400 MHz, DMSO-d$_6$): δ13.30 (s, 1H), 10.28 (s, 1H), 7.50 (s, 1H), 7.40 (d, 1H), 7.21 (dd, 1H), 7.00 (d, 1H), 4.08 (s, 3H), 3.78 (s, 3H), 3.31 (s, 3H), 2.81 (s, 3H); MS (EI) for $C_{20}H_{18}N_3O_4$: 400 (MH$^+$).

4-[1-methyl-7,8-bis(methyloxy)-3H-pyrazolo[3,4-c]isoquinolin-5-yl]benzonitrile: $^1$H-NMR (400 MHz, d$_6$-DMSO): 8.02 (d, 2H), 7.90 (d, 2H), 7.66 (s, 1H), 7.28 (s, 1H), 4.05 (s, 3H), 3.73 (s, 3H), 2.82 (s, 3H), MS (EI) for $C_{20}H_{16}N_4O_2$: 345.1 (MH$^+$).

N'-hydroxy-4-[1-methyl-7,8-bis(methyloxy)-3H-pyrazolo[3,4-c]isoquinolin-5-yl]benzenecarboximidamide:

¹H-NMR (400 MHz, d₆-DMSO): 11.21 (bs, 1H), 8.87 (bs, 1H), 7.81 (dd, 4H), 7.67 (s, 1H), 7.34 (s, 1H), 4.05 (s, 3H), 3.73 (s, 3H), 2.82 (s, 3H), MS (EI) for $C_{20}H_{19}N_5O_3$: 378.2 (MH⁺).

2-hydroxy-5-[1-methyl-7,8-bis(methyloxy)-3H-pyrazolo[3,4-c]isoquinolin-5-yl]benzoic acid: ¹H-NMR (400 MHz, d₆-DMSO): 8.14 (d, 1H), 7.88 (dd, 1H), 7.63 (s, 1H), 7.43 (s, 1H), 7.13 (d, 1H), 4.04 (s, 3H), 3.74 (s, 3H), 2.81 (s, 3H), MS (EI) for $C_{20}H_{17}N_3O_5$: 380.2 (MH⁺).

2-chloro-4-(1-methyl-3H-[1,3]dioxolo[4,5-g]pyrazolo[3,4-c]isoquinolin-5-yl)phenol: MS (EI) for $C_{18}H_{12}ClN_3O_3$: 354.2 (MH⁺)

2-chloro-4-(1,7-dimethyl-8-{[2-(methyloxy)ethyl]oxy}-3H-pyrazolo[3,4-c]isoquinolin-5-yl)phenol: ¹H-NMR (400 MHz, d₆-DMSO): 10.78 (bs, 1H), 7.80 (d, 1H), 7.65 (d, 1H), 7.62 (s, 1H), 7.44 (dd, 1H), 7.17 (d, 1H), 4.38 (m, 2H), 3.80 (m, 2H), 3.37 (s, 3H), 2.84 (s, 3H), 2.26 (s, 3H), MS (EI) for $C_{21}H_{22}ClN_3O_3$: 400.2 (MH⁺).

1-methyl-7,8-bis(methyloxy)-5-(3-methylphenyl)-3H-pyrazolo[3,4-c]isoquinoline: ¹H NMR (400 MHz, d₆-DMSO) δ7.66 (s, 1H), 7.55-7.44 (m, 4H), 7.43 (s, 1H), 7.37 (d, 1H), 4.06 (s, 3H), 3.72 (s, 3H), 2.83 (s, 3H), 2.44 (s, 3H); MS (EI) for $C_{20}H_{19}N_3O_2$: 334 (MH⁺).

5-(3-bromophenyl)-1-methyl-7,8-bis(methyloxy)-3H-pyrazolo[3,4-c]isoquinoline: ¹H NMR (400 MHz, d₆-DMSO) δ13.36 (br. s, 1H), 7.89 (s, 1H), 7.75 (m, 2H), 7.67 (s, 1H), 7.54 (t, 1H), 7.34 (s, 1H), 4.06 (s, 3H), 3.75 (s, 3H), 2.82 (s, 3H); MS (EI) for $C_{19}H_{16}BrN_3O_2$: 398 (MH⁺).

4-[1-methyl-7,8-bis(methyloxy)-3H-pyrazolo[3,4-c]isoquinolin-5-yl]-2-(1-methylethyl)phenol: ¹H NMR (400 MHz, d₆-DMSO) δ9.83 (br. s, 1H), 7.65 (s, 1H), 7.53 (m, 2H), 7.43 (m, 1H), 6.99 (d, 1H), 4.07 (s, 3H), 3.76 (s, 3H), 3.33 (h, 1H), 2.83 (s, 3H), 1.23 (d, 6H); MS (EI) for $C_{22}H_{23}N_3O_3$: 378 (MH⁺).

2-ethyl-4-[1-methyl-7,8-bis(methyloxy)-3H-pyrazolo[3,4-c]isoquinolin-5-yl]phenol: ¹H NMR (400 MHz, d₆-DMSO) δ9.76 (br. s, 1H), 7.62 (s, 1H), 7.52 (s, 1H), 7.47 (m, 1H), 7.41 (m, 1H), 6.96 (d, 1H), 4.05 (s, 3H), 3.75 (s, 3H), 2.82 (s, 3H), 2.65 (q, 2H), 1.20 (t, 3H); MS (EI) for $C_{21}H_{21}N_3O_3$: 364 (MH⁺).

5-hydroxy-2-[1-methyl-7,8-bis(methyloxy)-3H-pyrazolo[3,4-c]isoquinolin-5-yl]-4H-pyran-4-one: ¹H NMR (400 MHz, d₆-DMSO) δ13.60 (br. s, 1H), 9.53 (s, 1H), 8.34 (s, 1H), 7.69 (s, 1H), 7.59 (s, 1H), 6.93 (s, 1H), 4.08 (s, 3H), 3.89 (s, 3H), 2.85 (s, 3H); MS (EI) for $C_{18}H_{15}N_3O_5$: 354 (MH⁺).

2-[(difluoromethyl)oxy]-4-[1-methyl-7,8-bis(methyloxy)-3H-pyrazolo[3,4-c]isoquinolin-5-yl]phenol: ¹H NMR (400 MHz, d₆-DMSO) δ13.27 (s, 1H), 10.39 (s, 1H), 7.65 (s, 1H), 7.53-6.98 (m, 5H), 4.06 (s, 3H), 3.77 (s, 3H), 2.81 (s, 3H); MS (EI) for $C_{20}H_{17}F_2N_3O_4$: 402 (MH⁺).

5-[1-methyl-7,8-bis(methyloxy)-3H-pyrazolo[3,4-c]isoquinolin-5-yl]pyridin-2-ol: ¹H NMR (400 MHz, d₆-DMSO) δ13.28 (s, 1H), 11.95 (br. s, 1H), 7.88 (m, 1H), 7.82 (s, 1H), 7.64 (s, 1H), 7.46 (s, 1H), 6.51 (d, 1H), 4.05 (s, 3H), 3.84 (s, 3H), 2.80 (s, 3H); MS (EI) for $C_{18}H_{16}N_4O_3$: 337 (MH⁺).

2,5-dimethyl-4-[1-methyl-7,8-bis(methyloxy)-3H-pyrazolo[3,4-c]isoquinolin-5-yl]phenol: ¹H NMR (400 MHz, d₆-DMSO) δ9.52 (br. s, 1H), 7.63 (s, 1H), 7.05 (s, 1H), 6.97 (s, 1H), 6.77 (s, 1H), 4.05 (s, 3H), 3.64 (s, 3H), 2.84 (s, 3H), 2.15 (s, 3H), 1.92 (s, 3H); MS (EI) for $C_{21}H_{21}N_3O_3$: 364 (MH⁺).

2,3-dichloro-4-[1-methyl-7,8-bis(methyloxy)-3H-pyrazolo[3,4-c]isoquinolin-5-yl]phenol: ¹H NMR (400 MHz, d₆-DMSO) δ11.01 (br. s, 1H), 7.66 (s, 1H), 7.33 (d, 1H), 7.14 (d, 1H), 6.89 (s, 1H), 4.06 (s, 3H), 3.64 (s, 3H), 2.83 (s, 3H); MS (EI) for $C_{19}H_{15}C_{12}N_3O_3$: 404 (MH⁺).

2,5-dichloro-4-[1-methyl-7,8-bis(methyloxy)-3H-pyrazolo[3,4-c]isoquinolin-5-yl]phenol: ¹H NMR (400 MHz, d₆-DMSO) δ11.06 (s, 1H), 7.65 (s, 1H), 7.56 (s, 1H), 7.20 (s, 1H), 6.93 (s, 1H), 4.06 (s, 3H), 3.70 (s, 3H), 2.83 (s, 3H); MS (EI) for $C_{19}H_{15}C_{12}N_3O_3$: 404 (MH⁺).

2,3-dimethyl-4-[1-methyl-7,8-bis(methyloxy)-3H-pyrazolo[3,4-c]isoquinolin-5-yl]phenol: ¹H NMR (400 MHz, d₆-DMSO) δ9.60 (br. s, 1H), 7.66 (s, 1H), 7.01 (d, 1H), 6.95 (s, 1H), 6.84 (d, 1H), 4.07 (s, 3H), 3.64 (s, 3H), 2.86 (s, 3H), 2.17 (s, 3H), 1.89 (s, 3H); MS (EI) for $C_{21}H_{21}N_3O_3$: 364 (MH⁺).

3-chloro-4-[1-methyl-7,8-bis(methyloxy)-3H-pyrazolo[3,4-c]isoquinolin-5-yl]phenol: ¹H NMR (400 MHz, d₆-DMSO) δ10.20 (br. s, 1H), 7.63 (s, 1H), 7.33 (d, 1H), 6.99 (d, 1H), 6.90 (m, 2H), 4.06 (s, 3H), 3.55 (s, 3H), 2.82 (s, 3H); MS (EI) for $C_{19}H_{16}ClN_3O_3$: 370 (MH⁺).

3-fluoro-4-[1-methyl-7,8-bis(methyloxy)-3H-pyrazolo[3,4-c]isoquinolin-5-yl]phenol: ¹H NMR (400 MHz, d₆-DMSO) δ10.25 (br. s, 1H), 7.63 (s, 1H), 7.40 (t, 1H), 7.10 (s, 1H), 6.76 (m, 2H), 4.40 (s, 3H), 3.70 (s, 3H), 2.82 (s, 3H); MS (EI) for $C_{19}H_{16}FN_3O_3$: 354 (MH⁺).

2-chloro-5-fluoro-4-[1-methyl-7,8-bis(methyloxy)-3H-pyrazolo[3,4-c]isoquinolin-5-yl]phenol: ¹H NMR (400 MHz, d₆-DMSO) δ11.11 (br. s, 1H), 7.63 (s, 1H), 7.59 (d, 1H), 7.09 (d, 1H), 6.95 (d, 1H), 4.05 (s, 3H), 3.53 (s, 3H), 2.82 (s, 3H); MS (EI) for $C_{19}H_{15}ClFN_3O_3$: 388 (MH⁺).

2-bromo-5-fluoro-4-[1-methyl-7,8-bis(methyloxy)-3H-pyrazolo[3,4-c]isoquinolin-5-yl]phenol: ¹H NMR (400 MHz, d₆-DMSO) δ13.31 (br. s, 1H), 11.15 (s, 1H), 7.71 (d, 1H), 7.63 (s, 1H), 7.09 (d, 1H), 6.93 (d, 1H), 4.04 (s, 3H), 3.73 (s, 3H), 2.82 (s, 3H); MS (EI) for $C_{19}H_{15}BrFN_3O_3$: 432 (MH⁺).

4-[1,7-dimethyl-8-(methyloxy)-3H-pyrazolo[3,4-c]isoquinolin-5-yl]phenol. ¹H NMR (400 MHz, d₆-DMSO): 7.81 (s, 1H), 7.57 (s, 1H), 7.49 (d, 2H), 6.97 (d, 2H), 4.06 (s, 3H), 2.84 (s, 3H), 2.25 (s, 3H); MS (EI) for $C_{19}H_{17}N_3O_2$: 320 (MH⁺).

4-[9-chloro-1,7-dimethyl-8-(methyloxy)-3H-pyrazolo[3,4-c]isoquinolin-5-yl]phenol. ¹H NMR (400 MHz, d₆-DMSO): 10.10 (broad s, 1H), 7.80 (s, 1H), 7.28 (d, 2H), 6.90 (d, 2H), 2.90 (s, 3H), 2.31 (s, 3H); MS (EI) for $C_{19}H_{16}N_3O_2Cl$: 354 (MH⁺).

2-chloro-4-[1,7-dimethyl-8-(methyloxy)-3H-pyrazolo[3,4-c]isoquinolin-5-yl]phenol. ¹H NMR (400 MHz, d₆-DMSO): 7.80 (d, 1H), 7.65 (d, 1H), 7.60 (s, 1H), 7.46 (dd, 1H), 7.19 (d, 1H), 4.08 (s, 3H), 2.85 (s, 3H), 2.27 (s, 3H); MS (EI) for $C_{19}H_{16}N_3O_2Cl$: 354 (MH⁺).

2-bromo-4-[1,7-dimethyl-8-(methyloxy)-3H-pyrazolo[3,4-c]isoquinolin-5-yl]phenol. ¹H NMR (400 MHz, d₆-DMSO): 10.84 (broad s, 1H), 7.82 (dd, 2H), 7.63 (s, 1H), 7.51 (dd, 1H), 7.18 (d, 1H), 4.09 (s, 3H), 2.86 (s, 3H), 2.28 (s, 3H); MS (EI) for $C_{19}H_{16}N_3O_2Br$: 400 (MH⁺).

2-chloro-4-[9-ethyl-1-methyl-8-(methyloxy)-3H-pyrazolo[3,4-c]isoquinolin-5-yl]phenol. ¹H NMR (400 MHz, d₆-DMSO): 7.97 (d, 1H), 7.57 (d, 1H), 7.38 (dd, 2H), 7.14 (d, 1H), 3.98 (s, 3H), 3.30 (q, 2H), 2.87 (s, 3H), 1.24 (t, 3H); MS (EI) for $C_{20}H_{18}N_3O_2Cl$: 368 (MH⁺).

5-(3-chloro-4-hydroxyphenyl)-8-fluoro-1-methyl-7-(methyloxy)-3H-pyrazolo[3,4-c]isoquinolin-6-ol. ¹H NMR (400 MHz, d₄-MeOH): 7.49 (d, 1H), 7.41 (d, 1H), 7.21 (dd, 1H), 6.92 (d, 1H), 3.81 (s, 3H), 2.75 (s, 3H). MS (EI) for $C_{18}H_{14}N_3O_3ClF$: 375 (MH⁺).

4-[1-methyl-6,7,8-tris(methyloxy)-3H-pyrazolo[3,4-c]isoquinolin-5-yl]phenol: ¹H NMR (400 MHz, d₆-DMSO): 7.50 (s, 1H), 7.29 (d, 2H), 6.81 (d, 2H), 6.67 (s, 1H), 4.09 (s, 3H), 3.78 (s, 6H), 2.82 (s, 3H); MS (EI) for $C_{20}H_{19}N_3O_4$: 366 (MH⁺).

4-[1-methyl-8-(methyloxy)-3H-pyrazolo[3,4-c]isoquinolin-5-yl]phenol: $^1$H NMR (400 MHz, d$_6$-DMSO): 8.03 (d, 1H), 7.65 (d, 1H), 7.52 (d, 2H), 7.18 (dd, 1H), 6.96 (d, 2H), 4.02 (s, 3H), 2.83 (s, 3H); MS (EI) for $C_{18}H_{15}N_3O_2$: 306 (MH$^+$).

4-[7-chloro-9-fluoro-1-methyl-8-(methyloxy)-3H-pyrazolo[3,4-c]isoquinolin-5-yl]phenol $^1$H NMR (400 MHz, CD$_3$OD): 7.96 (br s, 1H), 7.48 (d, 2H), 6.98 (d, 2H), 4.17 (s, 3H), 2.83 (br d, 3H); MS (EI) for $C_{18}H_{13}N_3O_2FCl$: 358 (MH$^+$).

1-methyl-7,8-bis(methyloxy)-5-(1H-pyrazol-5-yl)-3H-pyrazolo[3,4-c]isoquinoline hydrochloric acid salt: $^1$H NMR (400 MHz, d$_6$-DMSO): 10.80 (b, 1H), 8.88 (s, 1H), 7.92 (s, 1H), 7.62 (s, 1H), 7.02 (s, 1H), 4.06 (s, 3H), 3.88 (s, 3H), 2.82 (s, 3H); MS (EI) for $C_{16}H_{15}N_5O_2$: 310 (MH$^+$).

2-chloro-4-[6-chloro-1-methyl-7,8-bis(methyloxy)-3H-pyrazolo[3,4-c]isoquinolin-5-yl]phenol hydrochloric acid salt $^1$H NMR (400 MHz, d$_6$-DMSO): 10.40 (b, 1H), 7.50 (s, 1H), 7.35 (s, 1H), 7.19-7.18 (d, 1H), 7.16-7.15 (d, 1H), 4.02 (s, 3H), 3.88 (s, 3H), 2.77 (s, 3H); MS (EI) for $C_{19}H_{15}Cl_2N_3O_3$: 459 (MH$^+$).

5-[3-chloro-4-(methyloxy)phenyl]-1-methyl-7,8-bis(methyloxy)-3H-pyrazolo[3,4-c]isoquinoline hydrochloric acid salt $^1$H NMR (400 MHz, d$_6$-DMSO): 7.81 (s, 1H), 7.75-7.73 (d, 1H), 7.67 (s, 1H), 7.45 (d, 1H), 7.36-7.34 (d, 1H), 4.07 (s, 3H), 3.98 (s, 3H), 3.57 (s, 3H), 2.84 (s, 3H); MS (EI) for $C_{20}H_{18}ClN_3O_3$: 384 (MH$^+$).

Example 3

4-[1-ethyl-7,8-bis(methyloxy)-3H-pyrazolo[3,4-c]isoquinolin-5-yl]phenol trifluoroacetic acid salt: To a mixture of [3,4-bis(methyloxy)phenyl]acetonitrile (2.0 g, 11 mmol) and ethyl propanoate (1.61 mL, 14 mmol) in ethanol (4 mL) was added a sodium ethoxide solution (21%, 8.4 mL, 23 mmol), and the resulting mixture was heated at reflux for 18 hours. After cooling to room temperature, it was poured into a mixture of ice-water (50 mL). This aqueous mixture was washed with dichloromethane (3×20 mL) then acidified to pH 1. The acidified mixture was extracted with ethyl acetate (3×30 mL). The combined extract was washed with saturated sodium bicarbonate solution, brine, dried over sodium sulfate, filtered and concentrated to give 2-[3,4-bis(methyloxy)phenyl]-3-oxopentanenitrile as a brown oil (0.8 g, 3.4 mmol, 30% yield), MS (EI) for $C_{13}H_{15}NO_3$: 234 (MH$^+$).

2-[3,4-bis(methyloxy)phenyl]-3-oxopentanenitrile (100 mg, 0.43 mmol) was dissolved in ethanol (1 mL), and anhydrous hydrazine (98%, 16 µL, 0.52 mmol) was added. The resulting mixture was heated at reflux for 1 hour. It was cooled, concentrated, and the residue was dried in vacuum for one hour. To this residue was added of 4-hydroxybenzaldehyde (79 mg, 0.64 mmol) and trifluoroacetic acid (1 mL), and the mixture was heated at 70° C. for 18 hours. Then the reaction mixture was concentrated, dissolved in 10 mL of N,N-dimethylformamide and purified by preparatory HPLC (Shimadzu LC-8A HPLC, Waters Xterra C18 30 mm×100 mm column, acetonitrile-water-trifluoroacetic eluent). After concentration then lyophillization of the pure fractions 4-[1-ethyl-7,8-bis(methyloxy)-3H-pyrazolo[3,4-c]isoquinolin-5-yl]phenol trifluoroacetic acid salt (55 mg, 0.12 mmol, 28% yield) was obtained. $^1$H NMR (400 MHz, d$_6$-DMSO): 7.77 (s, 1H), 7.71-7.69 (d, 2H), 7.51 (s, 1H), 7.01-6.98 (d, 2H), 4.05 (s, 3H), 3.76 (s, 3H), 3.26-3.21 (q, 2H), 1.44-1.40 (t, 3H); MS (EI) for $C_{20}H_{19}N_3O_3$: 349 (MH$^+$).

Example 4

4-[7,8-bis(methyloxy)-1-(trifluoromethyl)-3H-pyrazolo[3,4-c]isoquinolin-5-yl]phenol trifluoroacetic acid salt: To a mixture of [3,4-bis(methyloxy)phenyl]acetonitrile (2.0 g, 11 mmol) and ethyl trifluoroacetate (1.7 mL, 14 mmol) in ethanol (4 mL) was added a sodium ethoxide solution (21%, 8.4 mL, 23 mmol), and the resulting mixture was heated at reflux for 18 hours. After cooling to room temperature, it was poured into a mixture of ice-water (50 mL). This aqueous mixture was washed with dichloromethane (3×20 mL) then acidified to pH 1. The acidified mixture was extracted with ethyl acetate (3×30 mL). The combined extract was washed with aqueous sodium bicarbonate solution, brine, dried over sodium sulfate, filtered and concentrated to give 2-[3,4-bis(methyloxy)phenyl]-4,4,4-trifluoro-3-oxobutanenitrile as a brown oil (0.8 g, 3.4 mmol, 30% yield), MS (EI) for $C_{12}H_{10}F_3NO_3$: 274 (MH$^+$).

2-[3,4-bis(methyloxy)phenyl]4,4,4-trifluoro-3-oxobutanenitrile (100 mg, 0.37 mmol) was dissolved in benzene (10 mL), acetic acid (1 mL), and anhydrous hydrazine (98%, 12 µL, 0.44 mmol). The resulting mixture was heated at reflux for 3 hours. It was cooled, concentrated, and the residue was basified with solid sodium bicarbonate, diluted with ethyl acetate (50 mL), washed with water and brine (50 mL each), dried over sodium sulfate, filtered, concentrated, and the residue was dried in vacuum to give an oily residue. To this residue was added of 4-hydroxybenzaldehyde (67 mg, 0.55 mmol) and trifluoroacetic acid (1 mL), and the mixture was heated at 70° C. for 18 hours. Then the reaction mixture was concentrated, dissolved in 10 mL of N,N-dimethylformamide and purified by preparatory HPLC (Shimadzu LC-8A HPLC, Waters Xterra C18 30 mm×100 mm column, acetonitrile-water-trifluoroacetic eluent). After concentration then then lyophillization of the pure fractions 4-[7,8-bis(methyloxy)-1-(trifluoromethyl)-3H-pyrazolo[3,4-c]isoquinolin-5-yl] phenol trifluoroacetic acid salt (56 mg, 0.11 mmol, 30% yield) was obtained. $^1$H NMR (400 MHz, d$_6$-DMSO): 7.63-7.61 (d, 2H), 7.59 (s, 1H), 7.58 (s, 1H), 6.99-6.97 (d, 2H), 4.00 (s, 3H), 3.80 (s, 3H); MS (EI) for $C_{19}H_{14}N_3O_3F_3$: 340 (MH$^+$).

Example 5

4-[1-(1-methylethyl)-7,8-bis(methyloxy)-3H-pyrazolo[3,4-c]isoquinolin-5-yl]phenol trifluoroacetic acid salt: To a mixture of [3,4-bis(methyloxy)phenyl]acetonitrile (2.0 g, 11 mmol) and ethyl 2-methylpropanoate (1.9 mL, 14 mmol) in ethanol (4 mL) was added a sodium ethoxide solution (21%, 8.4 mL, 23 mmol), and the resulting mixture was heated at reflux for 18 hours. After cooling to room temperature, it was poured into a mixture of ice-water (50 mL). This aqueous mixture was washed with dichloromethane (3×20 mL) then acidified to pH 1. The acidified mixture was extracted with ethyl acetate (3×30 mL). The combined extract was washed with aqueous sodium bicarbonate solution, brine, dried over sodium sulfate, filtered and concentrated to give 2-[3,4-bis(methyloxy)phenyl]-4-methyl-3-oxopentanenitrile as a brown oil (0.7 g, 3.4 mmol, 28% yield), MS (EI) for $C_{14}H_{17}NO_3$: 248 (MH$^+$).

2-[3,4-bis(methyloxy)phenyl]-4-methyl-3-oxopentanenitrile (100 mg, 0.40 mmol) was dissolved in ethanol (1 mL), and anhydrous hydrazine (98%, 16 µL, 0.52 mmol) was added. The resulting mixture was heated at reflux for 1 hour. It was cooled, concentrated, and the residue was dried in vacuum for one hour. To this residue was added of 4-hydroxybenzaldehyde (74 mg, 0.61 mmol) and trifluoroacetic acid (1 mL), and the mixture was heated at 70° C. for 18 hours. Then the reaction mixture was concentrated, dissolved in 10 mL of N,N-dimethylformamide and purified by preparatory HPLC (Shimadzu LC-8A HPLC, Waters Xterra C18 30 mm×100 mm column, acetonitrile-water-trifluoroacetic eluent). After concentration and lyophillization of the pure fractions 4-[1-(1-methylethyl)-7,8-bis(methyloxy)-3H-pyrazolo[3,4-c]isoquinolin-5-yl]phenol trifluoroacetic acid salt (60 mg, 0.13 mmol, 33% yield) was obtained. $^1$H NMR (400 MHz, $d_6$-DMSO): 7.62-7.60 (d, 2H), 7.58 (s, 1H), 7.55 (s, 1H), 6.98-6.96 (d, 2H), 4.04 (s, 3H), 3.77-3.75 (m, 1H), 3.76 (s, 3H), 1.49-1.46 (d, 2H); MS (EI) for $C_{21}H_{21}N_3O_3$: 363 (MH$^+$).

Example 6

4-[7,8-bis(methyloxy)-3H-pyrazolo[3,4-c]isoquinolin-5-yl]phenol trifluoroacetic acid salt: To a mixture of [3,4-bis(methyloxy)phenyl]acetonitrile (2.0 g, 11 mmol) and ethyl formate (1.1 mL, 14 mmol) in ethanol (4 mL) was added a sodium ethoxide solution (21%, 8.4 mL, 23 mmol), and the resulting mixture was heated at reflux for 18 hours. After cooling to room temperature, it was poured into a mixture of ice-water (50 mL). This aqueous mixture was washed with dichloromethane (3×20 mL) then acidified to pH 1. The acidified mixture was extracted with ethyl acetate (3×30 mL). The combined extract was washed with aqueous sodium bicarbonate solution, brine, dried over sodium sulfate, filtered and concentrated to give 2-[3,4-bis(methyloxy)phenyl]-3-oxo-propanenitrile as a brown oil (2.0 g, 9.8 mmol, 89% yield). MS (EI) for $C_{11}H_{11}NO_3$: 206 (MH$^+$).

2-[3,4-bis(methyloxy)phenyl]-3-oxopropanenitrile (100 mg, 0.49 mmol) was dissolved in ethanol (1 mL), and anhydrous hydrazine (98%, 19 µL, 0.52 mmol) was added. The resulting mixture was heated at reflux for 1 hour. It was cooled, concentrated, and the residue was dried in vacuum for one hour. To this residue was added of 4-hydroxybenzaldehyde (89 mg, 0.61 mmol) and trifluoroacetic acid (1 mL), and the mixture was heated at 70° C. for 18 hours. Then the reaction mixture was concentrated, dissolved in 10 mL of N,N-dimethylformamide and purified by preparatory HPLC (Shimadzu LC-8A HPLC, Waters Xterra C18 30 mm×100 mm column, acetonitrile-water-trifluoroacetic eluent). After concentration and lyophillization of the pure fractions 4-[7,8-bis(methyloxy)-3H-pyrazolo[3,4-c]isoquinolin-5-yl]phenol trifluoroacetic acid salt (60 mg, 0.15 mmol, 31% yield) was obtained. $^1$H NMR (400 MHz, $d_6$-DMSO): 8.62 (s, 1H), 7.90 (s, 1H), 7.62-7.60 (d, 2H), 7.48 (s, 1H), 6.98-6.96 (d, 2H), 4.06 (s, 3H), 3.78 (s, 3H); MS (EI) for $C_{18}H_{15}N_3O_3$: 322 (MH$^+$).

Using the same or analogous synthetic techniques and/or substituting with alternative reagents, the following compounds of the invention were prepared:

4-[6,8-bis(methyloxy)-3H-pyrazolo[3,4-c]isoquinolin-5-yl]phenol trifluoroacetic acid salt: $^1$H NMR (400 MHz, $d_6$-DMSO): 8.64 (s, 1H), 7.47 (s, 1H), 7.27-7.25 (d, 2H), 6.80-6.78 (d, 2H), 6.61 (s, 1H), 4.00 (s, 3H), 3.56 (s, 3H); MS (EI) for $C_{18}H_{15}N_3O_3$: 322 (MH$^+$).

4-[6,7,8-tris(methyloxy)-3H-pyrazolo[3,4-c]isoquinolin-5-yl]phenol trifluoroacetic acid salt: $^1$H NMR (400 MHz, $d_6$-DMSO): 8.62 (s, 1H), 7.73 (s, 1H), 7.32-7.30 (d, 2H), 6.82-6.80 (d, 2H), 4.05 (s, 3H), 3.80 (s, 6H); MS (EI) for $C_{19}H_{17}N_3O_4$: 352 (MH$^+$).

Example 7

1-{[5-(4-hydroxyphenyl)-7,8-bis(methyloxy)-3H-pyrazolo[3,4-c]isoquinolin-1-yl]methyl}pyrrolidin-2-one: To a mixture of [3,4-bis(methyloxy)phenyl]acetonitrile (1.0 g, 5.5 mmol) and methyl (2-oxopyrrolidin-1-yl)acetate (1.0 g, 7.0 mmol) in ethanol (4 mL) was added a sodium ethoxide solution (21%, 4.2 mL, 11 mmol), and the resulting mixture was heated at reflux for 18 hours. After cooling to room temperature, it was poured into a mixture of ice-water (50 mL). This aqueous mixture was washed with dichloromethane (3×20 mL) then acidified to pH 1. The acidified mixture was extracted with ethyl acetate (3×30 mL). The combined extract was washed with aqueous sodium bicarbonate solution, brine, dried over sodium sulfate, filtered and concentrated to give 2-[3,4-bis(methyloxy)phenyl]-3-oxo-4-(2-oxopyrrolidin-1-yl)butanenitrile as a brown oil (0.43 g, 1.4 mmol, 25% yield), MS (EI) for $C_{16}H_{18}N_2O_4$: 303 (MH$^+$).

2-[3,4-bis(methyloxy)phenyl]-3-oxo-4-(2-oxopyrrolidin-1-yl)butanenitrile (200 mg, 0.66 mmol) was dissolved in ethanol (2 mL), and anhydrous hydrazine (98%, 26 µL, 0.79 mmol) was added. The resulting mixture was heated at reflux for 1 hour. It was cooled, concentrated, and the residue was dried in vacuum for one hour. To this residue was added of 4-hydroxybenzaldehyde (121 mg, 1.00 mmol) and trifluoroacetic acid (2 mL), and the mixture was heated at 70° C. for 18 hours. Then the reaction mixture was concentrated, dissolved in 10 mL of N,N-dimethylformamide and purified by preparatory HPLC (Shimadzu LC-8A HPLC, Waters Xterra C18 30 mm×100 mm column, acetonitrile-water-trifluoroacetic eluent). After concentration and lyophillization of the pure fractions 5-{[5-(4-hydroxyphenyl)-7,8-bis(methyloxy)-3H-pyrazolo[3,4-c]iso-quinolin-1-yl]methyl}pyrrolidin-2-one trifluoroacetic acid salt (65 mg, 0.12 mmol, 18% yield) was obtained. $^1$H NMR (400 MHz, $d_6$-DMSO): 9.80 (b, 1H), 7.74 (s, 1H), 7.56-7.54 (d, 2H), 7.48 (s, 1H), 6.94-6.92 (d, 2H), 4.01 (s, 3H), 3.73 (s, 3H), 3.41-3.35 (m, 1H), 3.18-3.13 (m, 2H), 2.36-2.28 (m, 2H), 1.88-1.77 (m, 2H); MS (EI) for $C_{23}H_{22}N_4O_4$: 419 (MH$^+$).

Example 8

4-[7,8-bis(methyloxy)-1-piperidin-4-yl-3H-pyrazolo[3,4-c]isoquinolin-5-yl]phenol hydrochloride: To an ice-cooled solution of [3,4-bis(methylox)phenyl]acetonitrile (3.5 g, 20.0 mmol) in a mixture of tetrahydrofuran-DMF (4:1, 50 mL) 60% sodium hydride in mineral oil (0.97 g, 24.0 mmol) was added and the reaction mixture was stirred for 30 minutes, followed by the addition of 1-(1,1-dimethylethyl) 4-ethyl piperidine-1,4-dicarboxylate (5.15 g, 20.0 mmol). The reaction mixture was allowed to warm to room temperature and it was stirred for 18 h. The excess sodium hydride was quenched by the addition of methanol. It was diluted with water and ethyl acetate. The organic layer was separated and discarded. The aqueous layer was acidified to pH 2 by the addition of 2 M hydrochloric acid. It was extracted with ethyl acetate. The organic layer was separated and it was washed with brine, dried over anhydrous sodium sulfate and concentrated in vacuo. The resulting crude product was purified by column chromatography (hexane-acetone 4:1) to result in 1,1-dimethylethyl 4-[[3,4-bis(methyloxy)phenyl](cyano)acetyl]piperidine1-carboxylate (6.4 g, 83%). MS (EI) for $C_{21}H_{28}N_2O_5$: 411.1 (MNa$^+$), 332.2 (M-tBu$^+$).

A mixture of 1,1-dimethylethyl 4-[[3,4-bis(methyloxy)phenyl](cyano)acetyl] piperidine1-carboxylate (2.2 g, 5.7 mmol), hydrazine dihydrochloride (0.72 g, 6.84 mmol) and triethyl amine (0.95 mL, 6.84 mmol) in ethanol (30 mL) was heated to 70° C. and stirred for 18 h. After cooling it to room temperature the solvent was evaporated and the crude was dissolved in ethyl acetate. The organic layer was washed with water, 10% aqueous citric acid and brine, dried over anhydrous sodium sulfate and concentrated in vacuo to give 1,1-dimethylethyl 4-{5-amino-4-[3,4-bis(methyloxy)phenyl]-1H-pyrazol-3-yl}piperidine-1-carboxylate (2.1 g, 91%). $^1$H-NMR (400 MHz, d$_6$-DMSO): 6.94 (d, 1H), 6.78 (d, 1H), 7.74 (dd, 1H), 4.26 (m, 2H), 3.88 (m, 2H), 3.75 (2 s, 6H), 2.66 (m, 1H), 1.62 (m, 4H), 1.39 (s, 9H), MS (EI) for $C_{21}H_{30}N_4O_4$: 403.2 (MH$^+$).

A solution of 1,1-dimethylethyl 4-{5-amino-4-[3,4-bis(methyloxy)phenyl]-1H-pyrazol-3-yl}piperidine-1-carboxylate (0.39 g, 0.97 mmol) and 4-hydroxybenzaldehyde (0.12 g, 0.97 mmol) was heated to 72° C. in trifluoroacetic acid (5 mL) for 18 h. The solvent was evaporated under reduced pressure and the residue was purified by reverse phase HPLC (CH$_3$CN/H$_2$O with 0.1% TFA) to give 4-[7,8-bis(methyloxy)-1-piperidin-4-yl-3H-pyrazolo[3,4-c]isoquinolin-5-yl]phenol trifluoroacetate (0.24 g, 61%). 53 mg (0.12 mmol) 4-[7,8-bis(methyloxy)-1-piperidin-4-yl-3H-pyrazolo[3,4-c]isoquinolin-5-yl]phenol trifluoroacetate was dissolved in ethanol (10 mL) and it was treated with polymer bound Hunig's base (Argonaut Technologies Inc. PS-DIEA, 3.44 mmol/g) for 30 minutes to adjust the pH to 7. The resin was filtered off and the filtrate was concentrated to dryness. The residue was treated with hydrogen chloride (4M in 1,4-dioxane, 3.0 mL). The precipitating solid was collected by filtration to result in 4-[7,8-bis(methyloxy)-1-piperidin-4-yl-3H-pyrazolo[3,4-c]isoquinolin-5-yl]phenol hydrochloride (42 mg, 89%). $^1$H-NMR (400 MHz, d$_6$-DMSO): 9.18 (s, 1H), 8.78 (s, 1H), 7.48 (d, 2H), 7.44 (d, 2H), 6.88 (d, 2H), 4.00, 3.68 (2 s, 2×3H), 3.34 (m, 2H), 3.16 (m, 2H), 2.22 (m, 2H), 2.02 (m, 2H), 1.22 (m, 1H), MS (EI) for $C_{23}H_{24}N_4O_3$: 405.1 (MH$^+$).

Example 9

4-(7,8-bis(methyloxy)-1-{[(phenylmethyl)amino]methyl}-3H-pyrazolo[3,4-c]isoquinolin-5-yl)phenol: To an ice-cooled solution of benzyl-glycine ethyl ester (5.50 mL, 30.0 mmol) in tetrahydrofuran (100 mL) triethylamine (12.54 mL, 90.0 mmol) was added, followed by the dropwise addition of a solution of di-tert-butyl-dicarbonate (7.20 g, 33.0 mmol) in tetrahydrofuran (50 mL). The reaction mixture was stirred for 18 h at room temperature. The solvent was evaporated and the crude was dissolved in ethyl acetate. The organic layer was washed with water, 10% aqueous citric acid and brine, dried over anhydrous sodium sulfate and concentrated in vacuo. The resulting crude product was purified by column chromatography (hexane-ethyl acetate 9:1) to give ethyl N-{[(1,1-dimethylethyl)oxy]carbonyl}-N-(phenylmethyl)glycinate (7.6 g, 86%). $^1$H-NMR (400 MHz, CDCl$_3$): 7.28 (m, 5H), 4.51, 4.55 (2 s, 2H), 4.16 (2 dd, 4H), 3.91, 3.78 (2 s, 2H), 1.47 (s, 9H), 1.25 (2 t, 3H), GCMS for $C_{16}H_{23}NO_4$: 192 (M-Boc$^+$), 237 (M-tBu$^+$).

1,1-dimethylethyl {3-[3,4-bis(methyloxy)phenyl]-3-cyano-2-oxypropyl}(phenylmethyl)carbamate was prepared from [3,4-bis(methylox)phenyl]acetonitrile (2.72 g, 15.35 mmol) and ethyl N-{[(1,1-dimethylethyl)oxy]carbonyl}-N-(phenylmethyl)glycinate (4.50 g, 15.34 mmol) as described in EXAMPLE 8 (6.2 g, 95%). MS (EI) for $C_{24}H_{28}N_2O_5$: 447.3 (MNa$^+$), 325.3 (M-Boc$^+$).

A mixture of 1,1-dimethylethyl {3-[3,4-bis(methyloxy)phenyl]-3-cyano-2-oxypropyl}(phenylmethyl)carbamate (0.51 g, 1.20 mmol) and benzenesulfonohydrazide (0.21 g, 1.20 mmol) in ethanol (10 mL) was heated to 70° C. for 18 h. The solvent was evaporated and replaced with xylene (10 mL) The reaction mixture was stirred at 120° C. for another 18 h. The solvent was removed under reduced pressure and the crude product was purified by column chromatography (hexane-acetone 4:1) to give 1,1-dimethylethyl {[(5-amino-4-[3,4-bis(methyloxy)phenyl]-1-(phenylsulfonyl)-1H-pyrazol-3-yl]methyl}(phenylmethyl)carbamate (0.15 g, 21%). MS (EI) for $C_{30}H_{34}N_4O_6S$: 601.3 (MNa$^+$), 579.3 (MH+), 523.2 (M-tBu$^+$).

A solution of 1,1-dimethylethyl {[(5-amino-4-[3,4-bis(methyloxy)phenyl]-1-(phenylsulfonyl)-1H-pyrazol-3-yl]methyl}(phenylmethyl)carbamate (0.15 g, 0.26 mmol) and 4-hydroxybenzaldehyde (0.032 g, 0.26 mmol) was heated to 72° C. in trifluoroacetic acid (5 mL) for 18 h. The solvent was evaporated and the resulting crude product was purified by reverse phase HPLC (CH$_3$CN/H$_2$O with 0.1% TFA) to give 4-(7,8-bis(methyloxy)-1-{[(phenylmethyl)amino]methyl}-3H-pyrazolo[3,4-c]isoquinolin-5-yl)phenol (0.062 g, 54%). MS (EI) for $C_{26}H_{24}N_4O_3$: 441.3 (MH$^+$).

Example 10

4-(1-methyl-3H-pyrazolo[3,4-c]isoquinolin-5-yl)phenol: To a solution of α-acetylacetonitrile (2 g, 12.6 mmol) in ethanol was added triethylamine (1.05 mL, 7.6 mmol) and hydrazine dihydrochloride (1.6 g, 15.1 mmol). The mixture was heated to 80° C. and stirred for 2 h before cooling to rt. The volatile materials were removed in vacuo. The crude residue was purified by flash chromatography (gradient: 5% methanol in CH$_2$Cl$_2$ to 10% methanol in CH$_2$Cl$_2$) to provide 1.92 g of 3-methyl-4-phenyl-1H-pyrazol-5-amine (11.1 mmol, 88% yield). $^1$H NMR (400 MHz, CDCl$_3$): δ7.40 (m, 2H), 7.34-7.32 (m, 2H), 7.27-7.23 (m, 1H), 3.71 (br s, 2H), 2.30 (s, 3H); MS (EI) for $C_{10}H_{11}N_3$: 174 (MH$^+$).

To 3-methyl-4-phenyl-1H-pyrazol-5-amine (173 mg, 1 mmol) was added 4-hydroxybezaldehyde (244 mg, 2 mmol) and methanesulfonic acid (3 mL). The mixture was heated to 120° C. for 16 h. After cooling to rt, the mixture was diluted with ethyl acetate and then filtered through celite. The product was then extracted from the organic phase with NaOH (aq). The organic phase was discarded, and the aqueous extract was carefully neutralized with HCl (conc) and then extracted with ethyl acetate. The ethyl acetate extract was dried over sodium sulfate, filtered, and concentrated in vacuo. The crude residue was purified by flash chromatography (ethyl acetate) to provide 41.2 mg of 4-(1-methyl-3H-pyrazolo[3,4-c]isoquinolin-5-yl)phenol (0.15 mmol, 15% yield). $^1$H-NMR (400 MHz, DMSO-d$_6$): δ13.42 (s, 1H), 9.81 (s, 1H), 8.34 (d, 1H), 8.11 (d, 1H), 7.87 (t, 1H), 7.50 (d, 2H), 6.94 (d, 2H), 2.79 (s, 3H); MS (EI) for $C_{17}H_{13}N_3O$: 276 (MH$^+$).

Using the same or analogous synthetic techniques and/or substituting with alternative reagents, the following compounds of the invention were prepared:

2-chloro-4-(1-methyl-3H-pyrazolo[3,4-c]isoquinolin-5-yl)phenol $^1$H NMR (400 MHz, DMSO-d$_6$): δ13.53 (s, 1H), 10.65 (s, 1H), 8.39 (d, 1H), 8.12 (d, 1H), 7.92 (t, 1H), 7.67 (d, 1H), 7.58 (t, 1H), 7.50 (dd, 1H), 7.16 (m, 1H), 2.81 (s, 3H); MS (EI) for $C_{17}H_{12}ClN_3O$: 310 (MH$^+$).

2-bromo-4-(1-methyl-3H-pyrazolo[3,4-c]isoquinolin-5-yl)phenol $^1$H NMR (400 MHz, DMSO-d$_6$): δ13.48 (s, 1H), 10.69 (s, 1H), 8.36 (d, 1H), 8.09 (d, 1H), 7.89 (t, 1H), 7.78 (d, 1H), 7.57-7.50 (m, 2H), 7.12 (d, 1H), 2.80 (s, 3H); MS (EI) for $C_{17}H_{12}BrIN_3O$: 354, 356 (MH$^+$).

Example 11

4-{7,8-bis(methyloxy)-1-[(methyloxy)methyl]-3H-pyrazolo[3,4-c]isoquinolin-5-yl}-2-chlorophenol hydrochloride salt: To a mixture of [3,4-bis(methyloxy)phenyl]acetonitrile (2.0 g, 11 mmol) and ethyl (methyloxy)acetate (1.65 g, 14 mmol) in ethanol (4 mL) was added a sodium ethoxide solution (21%, 8.4 mL, 23 mmol), and the resulting mixture was heated at reflux for 18 hours. After cooling to room temperature, it was poured into a mixture of ice-water (50 mL). This aqueous mixture was washed with dichloromethane (3×20 mL) to remove all non-basic organic impurities, and then it was acidified to pH of 1. The acidified mixture was extracted with ethyl acetate (3×30 mL). The combined extract was washed with aqueous sodium bicarbonate solution, brine, dried over sodium sulfate, filtered and concentrated to give 2-[3,4-bis(methyloxy)phenyl]-4-(methyloxy)-3-oxobutanenitrile as a brown oil (1.8 g, 7.2 mmol, 66% yield), MS (EI) for $C_{13}H_{15}NO_4$: 250 (MH$^+$).

To a solution of 2-[3,4-bis(methyloxy)phenyl]-4-(methyloxy)-3-oxobutanenitrile (200 mg, 0.8 mmol) in ethanol (5 mL) was added hydrazine dihydrochloride (101 mg, 0.9 mmol). The resulting mixture was heated at reflux for 1 hour. It was cooled, pour into a saturated sodium bicarbonate solution (10 mL), and the mixture was extracted with ethyl acetate (3×10 mL). The combined extract was washed with water and brine (30 mL each), dried over sodium sulfate, filtered and concentrated to give oily residue. To this residue was added of 3-chloro-4-hydroxybenzaldehyde (189 mg, 1.2 mmol) and trifluoroacetic acid (3 mL), and the resulting mixture was heated at 70° C. for 18 hours. Then the reaction mixture was concentrated, dissolved in 10 mL of N,N-dimethylformamide and purified by preparatory reverse phase HPLC (Shimadzu LC-8A HPLC, Waters Xterra C18 30 mm×100 mm column, acetonitrile-water-trifluoroacetic buffer). After lyophillization of the pure fractions a yellow powder was obtained. The solid was dissolved in 4 mL of 1:1 methanol: 4N hydrogen chloride in dioxane, and evaporated to dryness (repeated three times) to give 4-{7,8-bis(methyloxy)-1-[(methyloxy)methyl]-3H-pyrazolo[3,4-c]isoquinolin-5-yl}-2-chlorophenol hydrochloride salt (101 mg, 0.23 mmol, 29% yield). $^1$H NMR (400 MHz, d$_6$-DMSO): 10.64 (b, 1H), 7.82 (s, 1H), 7.71 (s, 1H), 7.58-7.56 (d, 1H), 7.45 (s, 1H), 7.17-7.15 (d, 1H), 4.92 (s, 2H), 4.02 (s, 3H), 3.78 (s, 3H); MS (EI) for $C_{20}H_{18}ClN_3O_4$: 400 (MH$^+$).

Example 12

4-(1-methyl-3H-benzo[e]indazol-5-yl)phenol: To a solution of 0.625 g (2.80 mmol) 4-bromonapthalen-2-ol in dichloroethane (2.5 mL) was added aluminum chloride (0.561 g, 4.20 mmol), followed by acetyl chloride (0.20 mL, 2.8 mmol). The solution was refluxed for 2 h, then poured into 50 mL ice-cold 1M hydrochloric acid. This solution was extracted with dichloromethane (2×100 mL). The combined organic layers were dried over sodium sulfate, filtered and concentrated in vacuo. Column chromatography (SiO$_2$, 3:1 hexanes/ethyl acetate) gave 0.619 g (83%) of 1-(4-bromo-2-hydroxynapthalen-1-yl)ethanone as a pale pink solid. $^1$H NMR (400 MHz, d$_6$-DMSO): 13.22 (s, 1H), 8.25 (d, 1H), 8.04 (d, 1H), 7.61 (dt, 1H), 7.51 (s, 1H), 7.49 (t, 1H), 2.83 (s, 3H); MS (EI) for $C_{12}H_9O_2Br$: 265 (MH$^+$), 267 (M+2).

A mixture of 1-(4-bromo-2-hydroxynapthalen-1-yl)ethanone (0.255 g, 0.96 mmol), (4-hydroxyphenyl)boronic acid (0.140 g, 1.06 mmol), Pd(PPh$_3$)$_4$ (0.056 g, 0.048 mmol) and potassium carbonate (0.4 g, 2.88 mmol) in water (9.7 mL) in dioxane (32.0 mL) was flushed with nitrogen, sealed and heated for 2 h in a 100° C. oil bath. The solution was cooled to room temperature and partitioned between 200 mL of 10% methanol in ethyl acetate and 100 mL saturated aqueous sodium chloride. The layers were separated and the aqueous layer was extracted (2×50 mL 10% methanol in ethyl acetate). The combined organic layers were dried over sodium sulfate, filtered and concentrated in vacuo. Column chromatography (SiO$_2$, 5:1 hexanes/ethyl acetate) gave 0.223 g (83%) of 1-[2-hydroxy-4-(4-hydroxyphenyl)napthalen-1-yl]ethanone. $^1$H NMR (400 MHz, d$_6$-DMSO): 8.11 (d, 1H), 7.87 (d, 1H), 7.56 (dt, 1H), 7.33 (m, 3H), 7.07 (s, 1H), 6.99 (d, 2H), 2.89 (s, 3H); MS (EI) for $C_{18}H_{14}O_3$: 279 (MH$^+$).

A solution of 1-[2-hydroxy-4-(4-hydroxyphenyl)napthalen-1-yl]ethanone (0.223 g, 0.8 mmol), and 35% aqueous hydrazine (0.72 mL, 8.0 mmol) in diethylene glycol (2.7 mL) was heated using a reflux condenser in a 170° C. oil bath for 12 h, then 190° C. for 2 h until 95% complete conversion was observed. The crude solution was purified directly via preparative reverse phase HPLC (CH$_3$CN/H$_2$O/TFA eluent) to give 0.132 g (60% yield) of 4-(1-methyl-3H-benzo[e]indazol-5-yl)phenol. $^1$H NMR (400 MHz, d$_6$-DMSO): 9.62 (broad s, 1H), 8.37 (d, 1H), 7.82 (d, 1H), 7.65 (dt, 1H), 7.42 (dt, 1H), 7.39 (s, 1H), 7.30 (dd, 2H), 6.93 (s, 2H), 2.82 (s, 3H); MS (EI) for $C_{18}H_{14}N_2O$: 275 (MH$^+$).

Example 13

4-{1-methyl-8-(methyloxy)-7-[(piperidin-4-ylmethyl)oxy]-3H-pyrazolo[3,4-c]isoquinolin-5-yl}phenol: 4-Hydroxy-3-methoxyphenylacetonitrile (1.01 g, 6.20 mmol) was dissolved in dimethylformamide (4 mL) and potassium carbonate (4.28 g, 31.0 mmol) was added followed by 1,1-dimethylethyl 4-{[(methylsulfonyl)oxy]methyl piperidine-1-carboxylate (2.00 g, 6.82 mmol). The mixture was stirred at 70° C. for 14 h and then concentrated in vacuo. The residual oil was partitioned between ethyl acetate and 1N sodium hydroxide. The organic portion was washed with 1 N sodium hydroxide. The aqueous portion was back-extracted with ethyl acetate. The combined organic portion was washed with water, brine, dried over sodium sulfate, filtered and concentrated in vacuo to afford a semi-solid which was collected by filtration after trituration with hexanes/ether to afford 1,1-dimethylethyl 4-({[4-(cyanomethyl)-2-(methyloxy)phenyl]oxy}methyl) piperidine-1-carboxylate as a light brown solid (1.72 g, 4.78 mmol, 77% yield). $^1$H NMR (400 MHz, CDCl$_3$): 6.84-6.83 (m, 2H), 6.82-6.81 (m, 1H), 4.28-4.02 (m, 2H), 3.85 (s, 3H), 3.83 (d, 2H), 3.70 (s, 2H), 2.81-2.66 (m, 2H), 2.10-1.98 (m, 1H), 1.89-1.82 (m, 2H), 1.46 (s, 9H), 1.25 (qd, 2H); MS (EI) for $C_{20}H_{28}N_2O_4$: 383 (MNa$^+$).

To NaH (60 wt. % dispersion in oil; 0.42 g, 10.5 mmol) suspended in THF (20 mL) was added 1,1-dimethylethyl 4-({[4-(cyanomethyl)-2-(methyloxy)phenyl]oxy}methyl)piperidine-1-carboxylate (1.73 g, 4.81 mmol) and then anhydrous ethyl acetate (0.559 mL, 5.73 mmol). The mixture was stirred at 60° C. for 15 h. The mixture was cooled to room temperature, was acidified with 4 N HCl in dioxane (2 mL, 8 mmol) and was concentrated in vacuo. The residue was partitioned between 1 N hydrochloric acid and ethyl acetate. The organic portion was washed with water, brine, dried over sodium sulfate, filtered and concentrated in vacuo to afford a red oil which was dissolved in ethanol (20 mL) and treated with hydrazine (0.185 mL, 5.84 mmol) at reflux for 1 h. The mixture was concentrated in vacuo and dried in vacuo to afford 1,1-dimethylethyl 4-({[4-(5-amino-3-methyl-1H-pyrazol-4-yl)-2-(methyloxy)phenyl]oxy}methyl)piperidine-1-carboxylate as a red foam (2.00 g, 4.81 mmol, 100% yield). MS (EI) for $C_{22}H_{32}N_4O_4$: 417 (MH$^+$), 439 (MNa$^+$).

A mixture of 1,1-dimethylethyl 4-({[4-(5-amino-3-methyl-1H-pyrazol-4-yl)-2-(methyloxy)phenyl]oxy}methyl)piperidine-1-carboxylate (100 mg, 0.24 mmol) and 4-hydroxybenzaldehyde (44 mg, 0.36 mmol) was dissolved in TFA (1 mL) and heated to 75° C. for 15 h. After cooling to rt, the mixture was diluted with DMF and purified by preparative reverse phase HPLC. The fractions containing the desired product were concentrated and lyophilized to yield 4-{1-methyl-8-(methyloxy)-7-[(piperidin-4-ylmethyl)oxy]-3H-pyrazolo[3,4-c]isoquinolin-5-yl}phenol hydrogen trifluoroacetate (26.2 mg, 20% yield). $^1$H NMR (400 MHz, d$_6$-DMSO): 8.64-8.54 (m, 1H), 8.28-8.18 (m, 1H), 7.64 (s, 1H), 7.57-7.54 (m, 2H), 7.49 (s, 1H), 6.95-6.91 (m, 2H), 4.05 (s, 3H), 3.82 (d, 2H), 3.31 (d, 2H), 2.92 (q, 2H), 2.81 (s, 3H), 2.16-2.04 (m, 1H), 1.94 (d, 2H), 1.53-1.42 (m, 2H); MS (EI) for $C_{24}H_{26}N_4O_3$: 419 (MH$^+$).

Using the same or analogous synthetic techniques and/or substituting with alternative reagents, the following compounds of the invention were prepared:

4-{1-methyl-8-(methyloxy)-7-[(2-morpholin-4-ylethyl)oxy]-3H-pyrazolo[3,4-c]isoquinolin-5-yl}phenol: $^1$H NMR (400 MHz, d$_6$-DMSO): 13.2 (br s, 1H), 9.78 (s, 1H), 7.62 (s, 1H), 7.54 (s, 1H), 7.51 (d, 2H), 6.92 (d, 2H), 4.08-4.02 (m, 5H), 3.56-3.50 (m, 4H), 2.79 (s, 3H), 2.67 (t, 2H), 2.46-2.40 (m, 4H); MS (EI) for $C_{24}H_{26}N_4O_4$: 435 (MH$^+$).

4-[7-(ethyloxy)-1-methyl-8-(methyloxy)-3H-pyrazolo[3,4-c]isoquinolin-5-yl]phenol. $^1$H NMR (400 MHz, CD$_3$OD): 7.74 (s, 1H), 7.65-7.63 (m, 2H), 7.49 (s, 1H), 7.10-7.07 (m, 2H), 6.78-6.74 (m, 1H), 4.17 (s, 3H), 3.83.00 (s, 2H), 2.97 (s, 3H), 1.45-1.41 (m, 3H). MS (EI) for $C_{20}H_{19}N_3O_3$: 350 (MH$^+$).

4-{1-methyl-8-(methyloxy)-7-[(2-morpholin-4-ylethyl)oxy]-3H-pyrazolo[3,4-c]isoquinolin-5-yl}phenol: $^1$H NMR (400 MHz, d$_6$-DMSO): 13.2 (br s, 1H), 9.78 (s, 1H), 7.62 (s, 1H), 7.54 (s, 1H), 7.51 (d, 2H), 6.92 (d, 2H), 4.08-4.02 (m, 5H), 3.56-3.50 (m, 4H), 2.79 (s, 3H), 2.67 (t, 2H), 2.46-2.40 (m, 4H); MS (EI) for $C_{24}H_{26}N_4O_4$: 435 (MH$^+$).

Example 14

4-(1-methyl-7-(methyloxy)-8-{[(1-methylpiperidin-4-yl)methyl]oxy}-3H-pyrazolo[3,4-c]isoquinolin-5-yl)phenol hydrochloride: To a solution of methyl 3-hydroxy-4-methoxy benzoate (2.0 g, 11 mmol) in DMF (25 mL) was added cesium carbonate (7.2 g, 22 mmol) and 1,1-dimethylethyl 4-{[(methylsulfonyl)oxy]methyl}piperidine-1-carboxylate (3.2 g, 11 mmol). The mixture was heated to 70° C. and stirred for 2 h. After cooling to rt, water was added and the resulting aqueous mixture was extracted with ether followed by ethyl acetate. The organic layers were combined, dried over sodium sulfate, filtered, and concentrated in vacuo. The crude residue was purified by flash chromatography (70% hexanes, 30% ethyl acetate) to provide 3.54 g of 1,1-dimethylethyl 4-[({2-(methyloxy)-5-[(methyloxy)carbonyl]phenyl}oxy)methyl]piperidine-1-carboxylate (9.3 mmol, 85% yield). $^1$H NMR (400 MHz, CDCl$_3$): δ7.69-7.66 (dd, 1H), 7.52 (d, 1H), 6.88 (d, 1H), 4.15 (br m, 2H), 3.92 (s, 3H), 3.91-3.88 (m, 2H), 3.90 (s, 3H), 2.76 (br m, 2H), 2.06 (m, 1H), 1.88 (br d, 2H), 1.47 (s, 9H), 1.31-1.25 (m, 2H); MS (EI) for $C_{20}H_{29}NO_6$: 402 (MNa$^+$).

1,1-Dimethylethyl 4-[({2-(methyloxy)-5-[(methyloxy)carbonyl]phenyl}oxy)methyl]piperidine-1-carboxylate (3.34 g, 8.8 mmol) was dissolved in THF (30 mL) and the resulting solution was cooled with an ice bath. A solution of LAH in THF (1 M, 8.8 mmol, 8.8 mL) was added by syringe. The reaction vessel was removed from the ice bath, and the reaction mixture was allowed to warm to rt. After 2 h at rt, the mixture was quenched by cautious sequential addition of water (0.33 mL), 15% NaOH (aq) (0.33 mL), and water (1 mL). During the quench, a white precipitate formed. The solid was removed by filtration through celite and was rinsed with ether. The combined organic layers were washed with dilute hydrochloric acid to then dried over sodium sulfate, filtered, and concentrated to provide 1.88 g of 1,1-dimethylethyl 4-({[5-(hydroxymethyl)-2-(methyloxy)phenyl]oxy}methyl)piperidine-1-carboxylate (5.4 mmol, 61% yield). $^1$H NMR (400 MHz, CDCl$_3$): δ6.93-6.85 (m, 3H), 4.62 (d, 2H), 4.15 (br m, 2H), 3.87 (m, 2H), 3.86 (s, 3H), 2.76 (br m, 2H), 2.06 (m, 1H), 1.88 (br d, 2H), 1.47 (s, 9H), 1.28 (m, 2H).

To a solution of 1,1-dimethylethyl 4-({[5-(hydroxymethyl)-2-(methyloxy) phenyl]oxy}methyl)piperidine-1-carboxylate (1.88 g, 5.4 mmol) in dichloromethane (14 mL) was added triethylamine (2.3 mL, 16.2 mmol). The resulting mixture was cooled with an ice bath, and methanesulfonyl chloride (0.84 mL, 10.8 mmol) was added dropwise. The mixture was allowed to warm to room temperature and a white precipitate formed. After 2.5 h, the solvent was removed and the residue was dissolved in water, which was subsequently extracted twice with ethyl acetate. The organic layers were combined, dried over sodium sulfate, filtered, and concentrated to provide a yellow oil. To the oil was added DMF (10 mL) and potassium cyanide (703 mg, 10.8 mmol). The resulting mixture was stirred at rt for 15 h. Water was then added, and the aqueous mixture was extracted twice with ethyl acetate. The organic layers were combined, washed with brine, dried over sodium sulfate, filtered, and concentrated. The residue was purified by flash chromatography (60% hexanes, 40% ethyl acetate) to provide 800 mg of 1,1-dimethylethyl 4-({[5-(cyanomethyl)-2-(methyloxy)phenyl]oxy}methyl)piperidine-1-carboxylate (2.2 mmol, 41% yield). $^1$H NMR (400 MHz, CDCl$_3$): δ6.89-6.81 (m, 3H), 4.15 (br m, 2H), 3.86 (s, 3H), 3.86-3.83 (m, 2H), 3.69 (s, 2H), 2.76 (br m, 2H), 2.10-2.00 (m, 1H), 1.87 (br d, 2H), 1.47 (s, 9H), 1.31-1.20 (m, 2H); MS (EI) for $C_{20}H_{28}N_2O_4$: 383 (MNa$^+$).

1,1-Dimethylethyl 4-({[5-(cyanomethyl)-2-(methyloxy)phenyl]oxy}methyl) piperidine-1-carboxylate (800 mg, 2.2 mmol) was dissolved in THF (5 mL) to which was added sodium hydride (60% dispersion in mineral oil, 176 mg, 4.4 mmol) followed by ethyl acetate (258 μL, 2.6 mmol). The mixture was heated to 60° C. and stirred for 16 h. After cooling to rt, the mixture was neutralized with HCl (4 N in dioxane, 1 mL). The solvents were removed and to the residue was added dilute hydrochloric acid. The aqueous mixture was extracted twice with ethyl acetate. The organic extracts were combined, dried over sodium sulfate, filtered, and concentrated to provide a brown oil. The brown oil was dissolved in ethanol (10 mL). After the addition of hydrazine (108 μL, 3.5 mmol), the solution was heated to 90° C. for 3 hours then cooled to room temperature. The solvent was removed in vacuo, and the residue purified by flash chromatography (5% methanol in dichloromethane) to provide 682 mg of 1,1-dimethylethyl 4-({[5-(5-amino-3-methyl-1H-pyrazol-4-yl)-2-(methyloxy)-phenyl]oxy}methyl)piperidine-1-carboxylate as a yellow solid (1.7 mmol, 77% yield). $^1$H NMR (400 MHz, CDCl$_3$): δ6.95-6.86 (m, 3H), 4.14 (br m, 2H), 3.88 (s, 3H), 3.85 (d, 2H), 3.08-2.78 (br m, 4H), 2.26 (s, 3H), 2.06 (m, 1H), 1.87 (br d, 2H), 1.46 (s, 9H), 1.30-1.21 (m, 2H); MS (EI) for $C_{22}H_{32}N_4O_4$: 417 (MH$^+$).

To 1,1-dimethylethyl 4-({[5-(5-amino-3-methyl-1H-pyrazol-4-yl)-2-(methyloxy)-phenyl]oxy}methyl)piperidine-1-carboxylate (529 mg, 1.27 mmol) in dichloromethane was added 4-hydroxybenzaldehyde (232 mg, 1.9 mmol) and TFA (5 mL). The mixture was heated to 70° C. in a open reaction vessel. After stirring 22 h at 70° C. the volatile residue was removed in vacuo. To the resulting orange oil was added 37% aqueous formaldehyde (1 mL) and formic acid (10 mL). The mixture was heated to 95° C. for 17 h then cooled to room temperature. The solvents were removed in vacuo. The residue was subsequently dissolved in DMF (2 mL) to which was added DMAP (165 mg, 1.35 mmol) and di-t-butyl dicarbonate (100 mg, 0.45 mmol). The mixture was stirred at room temperature for 15 h. The reaction mixture was diluted with water and the resulting aqueous mixture was extracted with ethyl acetate. The organic phase was then dried over sodium sulfate, filtered, and concentrated in vacuo. The residue was purified by flash chromatography (90% $CHCl_3$: 9.2% methanol: 0.8% concentrated ammonium hydroxide). The fractions containing the desired product were concentrated, and then further purified by preparative reverse phase HPLC. The clean fractions were concentrated providing 32.0 mg of 1,1-dimethylethyl 4-{1-methyl-7-(methyloxy)-8-{[(1-methylpiperidin-4-yl)methyl]oxy}-3H-pyrazolo[3,4-c]isoquinolin-5-yl}phenyl carbonate trifluoroacetate (0.06 mmol, 5% yield).

1,1-Dimethylethyl 4-{1-methyl-7-(methyloxy)-8-{[(1-methylpiperidin-4-yl)methyl]oxy}-3H-pyrazolo[3,4-c]isoquinolin-5-yl}phenyl carbonate trifluoroacetate (32 mg, 0.049 mmol) was taken into 4 N HCl in dioxane and the mixture was stirred for 1 h at rt. The reaction mixture was concentrated in vacuo. The resulting residue was dissolved in water, frozen, and lyophilized. 4-(1-methyl-7-(methyloxy)-8-{[(1-methylpiperidin-4-yl)methyl]oxy}-3H-pyrazolo[3,4-c]isoquinolin-5-yl)phenol hydrochloride was isolated as a solid (13.0 mg, 0.028 mmol, 57% yield). $^1$H NMR (400 MHz, DMSO-$d_6$): δ9.71 (br m, 2H), 7.59 (d, 2H), 7.54 (d, 2H), 6.94 (m, 2H), 4.18 (d, 2H), 3.76 (s, 3H), 3.04-2.96 (m, 2H), 2.81 (s, 3H), 2.82-2.74 (m, 2H), 2.15 (m, 1H), 2.04 (br d, 2H), 1.67-1.61 (m, 2H); MS (EI) for $C_{25}H_{28}N_4O_3$: 433 (MH$^+$).

Using the same or analogous synthetic techniques and/or substituting with alternative reagents, the following compounds of the invention were prepared:

4-{1-methyl-7-(methyloxy)-8-[(piperidin-4-ylmethyl)oxy]-3H-pyrazolo[3,4-c]isoquinolin-5-yl}phenol trifluoroacetate: $^1$H NMR (400 MHz, $d_6$-DMSO): 9.82 (s br, 1H), 8.60 (d, 1H), 8.31-8.29 (m, 1H), 7.62 (s, 1H), 7.57-7.53 (m, 2H), 7.50 (s, 1H), 6.95-6.90 (m, 2H), 4.18 (d, 2H), 3.75 (s, 3H), 3.35 (d, 2H), 2.96 (q, 2H), 2.80 (s, 3H), 2.25-2.15 (m, 1H), 1.99 (d, 2H), 1.60-1.50 (m, 2H); MS (EI) for $C_{24}H_{26}N_4O_3$: 419 (MH$^+$).

4-[8-{[(1-acetylpiperidin-4-yl)methyl]oxy}-1-methyl-7-(methyloxy)-3H-pyrazolo[3,4-c]isoquinolin-5-yl]-2-chlorophenol hydrochloride $^1$H NMR (400 MHz, DMSO-$d_6$): δ13.23 (s, 1H), 7.67 (s, 1H), 7.61 (s, 1H), 7.52 (d, 1H), 7.46 (s, 1H), 7.12 (d, 1H), 4.42 (d, 1H), 4.16 (d, 2H), 3.87 (d, 1H), 3.76 (s, 3H), 3.08 (t, 1H), 2.79 (s, 3H), 2.59 (t, 1H), 2.14 (br s, 1H), 2.01 (s, 3H), 1.85 (br t, 2H), 1.34-1.18 (m, 2H); MS (EI) for $C_{26}H_{27}ClN_4O_4$: 497 (MH$^+$).

2-chloro-4-[1-methyl-8-[(1-methylethyl)oxy]-7-(methyloxy)-3H-pyrazolo[3,4-c]isoquinolin-5-yl]phenol hydrochloride $^1$H NMR (400 MHz, DMSO-$d_6$): δ10.79 (s, 1H), 7.75 (d, 1H), 7.64 (s, 1H), 7.58 (dd, 1H), 7.46 (s, 1H), 7.19 (d, 1H), 5.03 (m, 1H), 3.77 (s, 3H), 2.82 (s, 3H), 1.43 (d, 6H); MS (EI) for $C_{21}H_{20}ClN_3O_3$: 398 (MH$^+$).

2-chloro-4-{1-methyl-7-(methyloxy)-8-[(2-methylpropyl)oxy]-3H-pyrazolo[3,4-c]isoquinolin-5-yl}phenol hydrochloride $^1$H NMR (400 MHz, DMSO-$d_6$): δ10.73 (s, 1H), 7.73 (d, 1H), 7.64 (s, 1H), 7.57 (dd, 1H), 7.47 (s, 1H), 7.18 (d, 1H), 4.08 (d, 2H), 3.79 (s, 3H), 2.82 (s, 3H), 2.18 (m, 1H), 1.07 (d, 6H); MS (EI) for $C_{22}H_{22}ClN_3O_3$: 412 (MH$^+$).

2-chloro-4-{1-methyl-7-(methyloxy)-8-[(2,2,2-trifluoroethyl)oxy]-3H-pyrazolo[3,4-c]isoquinolin-5-yl}phenol. MS (EI) for $C_{20}H_{18}N_3O_3Cl$: 438 (MH$^+$).

2-chloro-4-(1-methyl-7-(methyloxy)-8-{[(1-methylpiperidin-4-yl)methyl]oxy}-3H-pyrazolo[3,4-c]isoquinolin-5-yl)phenol. $^1$H NMR (400 MHz, $d_4$-MeOH): 7.87 (d, 1H), 7.76 (s, 1H), 7.63 (dd, 1H), 7.48 (s, 1H), 7.24 (d, 1H), 4.36 (d, 2H), 3.85 (s, 3H), 3.62 (d, 2H), 3.13 (tr, 2H), 3.02 (s, 3H), 2.90 (s, 3H), 2.32 (br s, 1H), 2.22 (d, 2H), 1.84 (q, 2H). MS (EI) for $C_{25}H_{28}N_4O_3Cl$: 468 (MH$^+$).

2-chloro-4-[1-methyl-8-({[1-(1-methylethyl)piperidin-4-yl]methyl}oxy)-7-(methyloxy)-3H-pyrazolo[3,4-c]isoquinolin-5-yl]phenol. $^1$H NMR (400 MHz, $d_4$-MeOH): 7.75 (d, 1H), 7.63 (s, 1H), 7.54 (dd, 1H), 7.44 (s, 1H), 7.17 (d, 1H), 4.26 (d, 2H), 3.82 (s, 3H), 3.58-3.55 (m, 3H), 3.16 (tr, 2H), 2.92 (s, 3H), 2.32 (br s, 1H), 2.25 (d, 2H), 1.89 (q, 2H), 1.41 (d, 6H). MS (EI) for $C_{27}H_{32}N_4O_3Cl$: 496 (MH$^+$).

2-chloro-4-[8-{[(1-ethylpiperidin-4-yl)methyl]oxy}-1-methyl-7-(methyloxy)-3H-pyrazolo[3,4-c]isoquinolin-5-yl]phenol. $^1$H NMR (400 MHz, $d_4$-MeOH): 7.78 (d, 1H), 7.68 (s, 1H), 7.56 (dd, 1H), 7.46 (s, 1H), 7.19 (d, 1H), 4.29 (d, 2H), 3.83 (s, 3H), 3.68 (d, 2H), 3.21 (q, 2H), 3.05 (tr, 2H), 2.94 (s, 3H), 2.32 (br s, 1H), 2.23 (d, 2H), 1.84 (q, 2H), 1.39 (tr, 3H). MS (EI) for $C_{26}H_{30}N_4O_3Cl$: 482 (MH$^+$).

4-[8-(ethyloxy)-1-methyl-7-(methyloxy)-3H-pyrazolo[3,4-c]isoquinolin-5-yl]phenol. $^1$H NMR (400 MHz, $CD_3OD$): 7.72 (s, 1H), 7.65-7.63 (m, 2H), 7.52 (s, 1H), 7.08-7.06 (m, 2H), 4.40 (q, J=8.0 Hz, 2H), 3.82 (s, 3H), 2.94 (s, 3H), 1.57 (t, J=8.0 Hz, 3H). MS (EI) for $C_{20}H_{19}N_3O_3$: 350 (MH$^+$).

2-chloro-4-(1-methyl-7-(methyloxy)-8-{[2-(methyloxy)ethyl]oxy}-3H-pyrazolo[3,4-c]isoquinolin-5-yl)phenol hydrochloric acid salt: $^1$H NMR (400 MHz, $d_6$-DMSO): 10.61 (b, 1H), 7.70-7.66 (m, 2H), 7.55-7.53 (d, d, 1H), 7.45 (s, 1H), 7.16-7.14 (d, 1H), 4.43-4.41 (m, 1H), 3.80-3.78 (m, 1H), 3.76 (s, 3H), 3.72-3.64 (m, 1H), 3.50-3.44 (m, 1H), 3.35 (s, 3H), 2.81 (s, 3H); MS (EI) for $C_{21}H_{20}ClN_3O_4$: 414 (MH$^+$).

2-bromo-4-(1-methyl-7-(methyloxy)-8-{[2-(methyloxy)ethyl]oxy}-3H-pyrazolo[3,4-c]isoquinolin-5-yl)phenol hydrochloric acid salt: $^1$H NMR (400 MHz, $d_6$-DMSO): 10.80 (b, 1H), 7.86 (s, 1H), 7.66 (s, 1H), 7.61-7.58 (d, 1H), 7.45 (s, 1H), 7.16-7.14 (d, 1H), 4.43-4.41 (m, 2H), 3.77 (s, 3H), 3.72-3.64 (m, 2H), 3.35 (s, 3H), 2.81 (s, 3H); MS (EI) for $C_{21}H_{20}BrN_3O_4$: 459 (MH$^+$).

3-fluoro-4-(1-methyl-7-(methyloxy)-8-{[2-(methyloxy)ethyl]oxy}-3H-pyrazolo[3,4-c]isoquinolin-5-yl)phenol hydrochloric acid salt $^1$H NMR (400 MHz, $d_6$-DMSO): 11.15 (b, 1H), 7.69 (s, 1H), 7.47-7.42 (d, d, 1H), 7.14-7.13 (d, 1H), 6.85-6.78 (m, 2H), 4.45-4.43 (m, 2H), 3.81-3.79 (m, 2H), 3.73 (s, 3H), 3.36 (s, 3H), 2.83 (s, 3H); MS (EI) for $C_{21}H_{20}FN_3O_4$: 398 (MH$^+$).

2-chloro-4-[8-(ethyloxy)-1-methyl-7-(methyloxy)-3H-pyrazolo[3,4-c]isoquinolin-5-yl]phenol hydrochloric acid salt $^1$H NMR (400 MHz, $d_6$-DMSO): 10.82 (b, 1H), 7.66 (s, 1H), 7.62 (s, 1H), 7.52-7.49 (d, 1H), 7.41 (s, 1H), 7.14-7.12 (d, 1H), 4.05 (s, 3H), 3.99-3.97 (q, 2H), 2.81 (s, 3H), 1.37-1.34 (t, 3H); MS (EI) for $C_{20}H_{18}ClN_3O_3$: 384 (MH$^+$).

2-bromo-5-fluoro-4-(1-methyl-7-(methyloxy)-8-{[2-(methyloxy)ethyl]oxy}-3H-pyrazolo[3,4-c]isoquinolin-5-yl)phenol hydrochloric acid salt $^1$H NMR (400 MHz, $d_6$-DMSO): 11.22 (b, 1H), 7.75-7.73 (d, 1H), 7.68 (s, 1H), 7.12 (s, 1H), 6.99-6.97 (s, 1H), 4.44-4.42 (m, 2H), 3.81-3.78 (m, 2H), 3.74 (s, 3H), 3.36 (s, 3H), 2.82 (s, 3H); MS (EI) for $C_{21}H_{19}BrFN_3O_4$: 477 (MH$^+$).

2-chloro-4-{1-methyl-7-(methyloxy)-8-[(tetrahydrofuran-2-ylmethyl)oxy]-3H-pyrazolo[3,4-c]isoquinolin-5-yl}phenol hydrochloric acid salt $^1$H NMR (400 MHz, $d_6$-DMSO): 10.66 (b, 1H), 7.69 (s, 1H), 7.65 (s, 1H), 7.55-

7.52 (d, 1H), 7.44 (s, 1H), 7.16-7.14 (d, 1H), 4.24-4.22 (m, 2H), 3.93-3.90 (m, 1H), 3.78-3.76 (m, 2H), 3.77 (s, 3H), 2.80 (s, 3H), 1.87-1.84 (m, 1H), 1.74-1.71 (m, 1H), 1.51-1.40 (m, 2H); MS (EI) for $C_{23}H_{22}ClN_3O_4$: 440 (MH$^+$).

2-chloro-4-{1-methyl-7-(methyloxy)-8-[(tetrahydro-2H-pyran-2-ylmethyl)oxy]-3H-pyrazolo[3,4-c]isoquinolin-5-yl}phenol hydrochloric acid salt $^1$H NMR (400 MHz, d$_6$-DMSO): 10.66 (b, 1H), 7.69 (s, 1H), 7.65 (s, 1H), 7.55-7.52 (d, 1H), 7.44 (s, 1H), 7.16-7.14 (d, 1H), 4.24-4.22 (m, 2H), 3.93-3.90 (m, 1H), 3.78-3.76 (m, 2H), 3.77 (s, 3H), 2.80 (s, 3H), 1.86-1.84 (m, 1H), 1.75-1.71 (m, 1H), 1.51-1.40 (m, 4H); MS (EI) for $C_{24}H_{24}ClN_3O_4$: 454 (MH$^+$).

2-chloro-4-{1-methyl-7-(methyloxy)-8-[(tetrahydro-2H-pyran-2-ylmethyl)oxy]-3H-pyrazolo[3,4-c]isoquinolin-5-yl}phenol hydrochloric acid salt $^1$H NMR (400 MHz, d$_6$-DMSO): 10.65 (b, 1H), 7.71 (s, 1H), 7.64 (s, 1H), 7.57-7.55 (d, 1H), 7.47 (s, 1H), 7.18-7.15 (d, 1H), 4.17-4.15 (d, 2H), 3.93-3.89 (m, 2H), 3.77 (s, 3H), 3.75-3.66 (m, 2H), 2.82 (s, 3H), 2.15 (b, 1H), 1.76-1.73 (m, 2H), 1.46-1.41 (m, 2H); MS (EI) for $C_{24}H_{24}ClN_3O_4$: 454 (MH$^+$).

2-chloro-4-[8-{[2-(ethyloxy)ethyl]oxy}-1-methyl-7-(methyloxy)-3H-pyrazolo[3,4-c]isoquinolin-5-yl]phenol hydrochloric acid salt $^1$H NMR (400 MHz, d$_6$-DMSO): 10.76 (b, 1H), 7.72 (s, 1H), 7.69 (s, 1H), 7.58-7.55 (d, 1H), 7.47 (s, 1H), 7.19-7.16 (d, 1H), 4.42-4.40 (m, 2H), 3.85-3.82 (m, 2H), 3.78 (s, 3H), 3.59-3.55 (q, 2H), 2.82 (s, 3H), 1.17-1.14 (t, 3H); MS (EI) for $C_{22}H_{22}ClN_3O_4$: 428 (MH$^+$).

Example 15

4-(1-methyl-8-(methyloxy)-9-{[(1-methylpiperidin-4-yl)methyl]oxy}-3H-pyrazolo[3,4-c]isoquinolin-5-yl)phenol trifluoroacetate: To a solution of 2-hydroxy-3-methoxyphenylacetonitrile (1 g, 6.1 mmol) in DMF (12 mL) was added 1,1-dimethylethyl 4-{[(methylsulfonyl)oxy]methyl}piperidine-1-carboxylate (1.8 g, 6.1 mmol) and cesium carbonate (4.0 g, 12.2 mmol). The mixture was heated to 70° C. for 3 h and then cooled to rt. Water and ethyl acetate were added followed by brine to reduce emulsification. The layers were partitioned, and the aqueous phase was extracted with ethyl acetate. The organic extracts were combined, dried over sodium sulfate, filtered, and concentrated in vacuo. The residue was purified by flash chromatography (70% hexanes, 30% ethyl acetate) to provide 1.77 g of 1,1-dimethylethyl 4-({[2-(cyanomethyl)-6-(methyloxy)phenyl]oxy}methyl)piperidine-1-carboxylate (4.9 mmol, 81% yield) as a yellow syrup. $^1$H NMR (400 MHz, CDCl$_3$): δ7.03 (t, 1H), 6.93 (dd, 1H), 6.88 (dd, 1H), 4.14 (br m, 2H), 3.88 (br d, 2H), 3.84 (s, 3H), 3.70 (s, 2H), 2.00 (m, 1H), 1.86 (br d, 2H), 1.47 (s, 9H), 1.35-1.25 (m, 2H).

1,1-Dimethylethyl 4-({[2-(cyanomethyl)-6-(methyloxy)phenyl]oxy}methyl) piperidine-1-carboxylate (742 mg, 2.06 mmol) was dissolved in THF (4 mL) to which was added sodium hydride (60% dispersion in mineral oil, 165 mg, 4.12 mmol) followed by ethyl acetate (1.0 mL, 10.3 mmol). The mixture was heated to 60° C. and stirred for 6 h. After cooling to rt, water was added and the resulting mixture was neutralized with HCl (conc) (340 μL). The aqueous mixture was extracted with ethyl acetate. The organic extract was dried over sodium sulfate, filtered, and concentrated in vacuo. The residue was dissolved in ethanol (10 mL). After the addition of hydrazine (100 μL, 3.2 mmol), the solution was heated to 90° C. for 1.5 h and then cooled to rt. The volatile materials were removed in vacuo, and the resulting residue was purified by flash chromatography (95% CH$_2$Cl$_2$, 5% methanol) to provide 397 mg of 1,1-dimethylethyl 4-({[2-(5-amino-3-methyl-1H-pyrazol-4-yl)-6-(methyloxy)phenyl]oxy}methyl}piperidine-1-carboxylate as a yellow solid (0.95 mmol, 45% yield). $^1$H NMR (400 MHz, CDCl$_3$): δ7.09 (t, 1H), 6.88 (dd, 1H), 6.82 (dd, 1H), 4.03 (br m, 2H), 3.89 (s, 3H), 3.55 (br d, 2H), 3.40 (br s, 2H), 2.64 (br t, 2H), 2.23 (s, 3H), 1.72 (m, 1H), 1.63 (d, 2H), 1.47 (s, 9H), 1.08-0.99 (m, 2H); MS (EI) for $C_{22}H_{32}N_4O_4$: 417 (MH$^+$).

To 1,1-dimethylethyl 4-({[2-(5-amino-3-methyl-1H-pyrazol-4-yl)-6-(methyloxy)phenyl]oxy}methyl}piperidine-1-carboxylate (397 mg, 0.95 mmol) was added 4-hydroxybenzaldehyde (174 mg, 1.4 mmol) and TFA (5 mL). The mixture was heated to 75° C. and stirred for 15 h. After cooling to rt, the volatile materials were removed in vacuo. The resulting residue was dissolved in a 1:1 mixture of water:acetonitrile and purified by preparative HPLC. The fractions containing the desired product were concentrated and lyophilized to provide 4-{1-methyl-8-(methyloxy)-9-[(piperidin-4-ylmethyl)oxy]-3H-pyrazolo[3,4-c]isoquinolin-5-yl}phenol trifluoroacetate (64.1 mg, 0.12 mmol, 13% yield). $^1$H NMR (400 MHz, DMSO-d$_6$): δ9.81 (br s, 1H), 8.53 (br d, 1H), 8.21 (br m, 1H), 7.84 (d, 1H), 7.43 (m, 2H), 7.38 (d, 1H), 6.92 (m, 2H), 3.97 (s, 3H), 3.88 (d, 2H), 3.32 (br d, 2H), 3.00-2.92 (q, 2H), 2.80 (s, 3H), 2.26 (m, 1H), 2.04 (br d, 2H), 1.52-1.43 (m, 2H); MS (EI) for $C_{24}H_{26}N_4O_3$: 419 (MH$^+$).

To 4-{1-methyl-8-(methyloxy)-9-[(piperidin-4-ylmethyl) oxy]-3H-pyrazolo[3,4-c]isoquinolin-5-yl)phenol hydrogen trifluoroacetate (47 mg, 0.11 mmol) was added 37% aqueous formaldehyde (10 μL) and formic acid (150 μL). The mixture was heated to 110° C. for 1.5 h before cooling to rt. The mixture was diluted with a 1:1 mixture of water:acetonitrile and purified by preparative HPLC. The fractions containing desired product were combined, concentrated, and lyophilized to provide 4-(1-methyl-8-(methyloxy)-9-{[(1-methylpiperidin-4-yl)methyl]oxy}-3H-pyrazolo[3,4-c]isoquinolin-5-yl)phenol trifluoroacetate (14.1 mg, 0.026 mmol, 23% yield). $^1$H NMR (400 MHz, DMSO-d$_6$): δ9.93 (br m, 2H), 7.87 (d, 1H), 7.48 (d, 2H), 7.44 (d, 1H), 6.96 (m, 2H), 4.00 (s, 3H), 3.45 (m, 2H), 3.00-2.96 (q, 2H), 2.83 (s, 3H), 2.74 (d, 3 h), 2.18 (m, 1H), 2.09 (br d, 2H), 1.61-1.52 (m, 2H); MS (EI) for $C_{25}H_{28}N_4O_3$: 433 (MH$^+$).

Using the same or analogous synthetic techniques and/or substituting with alternative reagents, the following compounds of the invention were prepared:

2-bromo-4-(1-methyl-8-(methyloxy)-9-{[(1-methylpiperidin-4-yl)methyl]oxy}-3H-pyrazolo[3,4-c]isoquinolin-5-yl]phenol hydrochloride $^1$H NMR (400 MHz, DMSO-d$_6$): δ10.82 (br s, 1H), 9.98 (br s, 1H), 7.85 (d, 1H), 7.76 (d, 1H), 7.49 (dd, 1H), 7.45 (d, 1H), 7.16 (d, 1H), 4.00 (s, 3H), 3.89 (d, 2H), 3.43-3.29 (m, 2H), 2.98 (m, 2H), 2.83 (s, 3H), 2.74 (m, 3H), 2.17 (m, 1H), 2.07 (br d, 2H), 1.57 (m, 2H); MS (EI) for $C_{25}H_{27}BrN_4O_3$: 511, 513 (MH$^+$).

2-chloro-4-(1-methyl-8-(methyloxy)-9-{[(1-methylpiperidin-4-yl)methyl]oxy}-3H-pyrazolo[3,4-c]isoquinolin-5-yl]phenol hydrochloride $^1$H NMR (400 MHz, DMSO-d$_6$): δ10.64 (br s, 1H), 7.82 (d, 1H), 7.58 (br s, 1H), 7.43-7.41 (m, 2H), 7.14 (d, 1H), 3.99 (s, 3H), 3.88 (d, 2H), 3.46 (br d, 2H), 3.00 (m, 2H), 2.82 (s, 3H), 2.75 (m, 3H), 2.17 (m, 1H), 2.10 (br d, 2H), 1.53 (m, 2H); MS (EI) for $C_{25}H_{27}ClN_4O_3$: 467 (MH$^+$).

4-[9-{[(1-acetylpiperidin-4-yl)methyl]oxy}-1-methyl-8-(methyloxy)-3H-pyrazolo[3,4-c]isoquinolin-5-yl]-2-bromophenol hydrochloride $^1$H NMR (400 MHz, DMSO-d$_6$): δ13.43 (s, 1H), 7.81 (br d, 1H), 7.72 (s, 1H), 7.44 (br d, 1H), 7.40 (br d, 1H), 7.09 (d, 1H), 4.34 (d, 1H), 3.97 (s, 3H), 3.87 (d, 2H), 3.80 (d, 1H), 3.06 (t, 1H), 2.80 (s, 3H), 2.60 (t, 1H), 2.32 (br s, 1H), 2.00 (s, 3H), 1.87 (br t, 2H), 1.26-1.12 (m, 2H); MS (EI) for $C_{26}H_{27}BrN_4O_4$: 539, 541 (MH$^+$), 561, 563 (MNa$^+$).

2-chloro-4-(1-methyl-8-(methyloxy)-9-{[2-(methyloxy)ethyl]oxy}-3H-pyrazolo[3,4-c]isoquinolin-5-yl)phenol: $^1$H NMR (400 MHz, d$_6$-DMSO) δ10.63 (br. s, 1H), 7.78 (d, 1H), 7.59 (s, 1H), 7.41 (m, 2H), 7.12 (d, 1H), 4.23 (s, 2H), 3.98 (s, 3H), 3.66 (s, 2H), 3.22 (s, 3H), 2.81 (s, 3H); MS (EI) for C$_{21}$H$_{20}$ClN$_3$O$_4$: 414 (MH$^+$).

2-bromo-4-(1-methyl-8-(methyloxy)-9-{[2-(methyloxy)ethyl]oxy}-3H-pyrazolo[3,4-c]isoquinolin-5-yl)phenol: $^1$H NMR (400 MHz, d$_6$-DMSO) δ10.72 (br. s, 1H), 7.79 (d, 1H), 7.74 (d, 1H), 7.46 (dd, 1H), 7.40 (d, 1H), 7.11 (d, 1H), 4.24 (t, 2H), 3.99 (s, 3H), 3.66 (t, 2H), 3.22 (s, 3H), 2.81 (s, 3H); MS (EI) for C$_{21}$H$_{20}$BrN$_3$O$_4$: 459 (MH$^+$).

2-bromo-4-{1-methyl-8-(methyloxy)-9-[(2-morpholin-4-ylethyl)oxy]-3H-pyrazolo[3,4-c]isoquinolin-5-yl}phenol hydrochloric acid salt: $^1$H NMR (400 MHz, D$_4$-methanol): 8.14-8.12 (d, 1H), 7.94 (s, 1H), 7.65-7.58 (m, 2H), 7.19-7.17 (d, 1H), 4.53-4.50 (t, 2H), 4.22-4.18 (m, 2H), 4.19 (s, 3H) 4.00-3-72 (m, 3H), 3.68-3.64 (m, 2H), 3.59-3.56 (m, 1H), 3.48-3.43 (m, 2H), 3.05 (s, 3H); MS (EI) for C$_{24}$H$_{25}$BrN$_4$O$_4$: 514 (MH$^+$).

2-chloro-4-{1-methyl-8-(methyloxy)-9-[(2-morpholin-4-ylethyl)oxy]-3H-pyrazolo[3,4-c]isoquinolin-5-yl}phenol hydrochloric acid salt: $^1$H NMR (400 MHz, D$_4$-methanol): 8.14-8.12 (d, 1H), 7.78 (s, 1H), 7.64-7.62 (d, 1H), 7.56-7.54 (d, d, 1H), 7.22-7.20) d, 1H), 4.53-4.51 (t, 2H), 4.22-4.18 (m, 2H), 4.19 (s, 3H), 4.00-3.72 (m, 3H), 3.68-3.64 (m, 2H), 3.59-3.57 (m, 1H), 3.48-3.43 (m, 2H), 3.05 (s, 3H); MS (EI) for C$_{24}$H$_{25}$ClN$_4$O$_4$: 469 (MH$^+$).

Example 16

4-(1-methyl-8,9-bis{[2-(methyloxy)ethyl]oxy}-3H-pyrazolo[3,4-c]isoquinolin-5-yl)phenol: A mixture of methyl 2,3-dihydroxybenzoate (2.18 g, 12.97 mmol), 2-bromoethyl methyl ether (4.50 g, 32.42 mmol), and potassium carbonate (6.91 g, 50.0 mmol) in DMF (20 mL) was stirred at 60° C. for 16 h. The reaction mixture was diluted with ethyl acetate (300 mL), washed with 5% aqueous LiCl (2×50 mL), and brine (50 mL), dried with sodium sulfate, and concentrated to provide crude methyl 2,3-bis{[2-(methyloxy)ethyl]oxy}benzoate (3.49 g, 95% yield) as a brown oil. $^1$H NMR (400 MHz, CDCl$_3$) δ7.32 (dd, 1H), 7.05 (m, 2H), 4.22 (m, 2H), 4.15 (m, 2H), 3.88 (s, 3H), 3.75 (m, 4H), 3.43 (s, 6H).

To a solution of methyl 2,3-bis{[2-(methyloxy)ethyl]oxy}benzoate (2.0 g, 7.03 mmol) in dry THF (10 mL) was added dropwise a 1M solution of lithium aluminum hydride in THF (7.0 mL), and the resulting mixture was stirred at rt for 1 h. Then, water (0.27 mL) was added slowly, followed by 15% aqueous sodium hydroxide (0.27 mL), and more water (0.81 mL). The mixture was filtered, the filter cake washed with ethyl acetate, and the combined filtrate was concentrated. Column chromatography on silica (1:1 hexanes/ethyl acetate) gave (2,3-bis{[2-(methyloxy)ethyl]oxy}phenyl)methanol (1.13 g, 63% yield) as a colorless oil. $^1$H NMR (400 MHz, CDCl$_3$) δ6.96 (dd, 1H), 6.86 (m, 2H), 4.60 (d, 1H), 4.33 (m, 2H), 4.24 (t, 1H), 4.13 (m, 2H), 3.75 (m, 2H), 3.70 (m, 2H), 3.43 (s, 6H).

To a solution of (2,3-bis{[2-(methyloxy)ethyl]oxy}phenyl)methanol (1.12 g, 4.37 mmol) and triethylamine (0.49 g, 4.84 mmol) in dichloromethane (20 mL) was slowly added thionyl chloride (0.78 g, 6.58 mmol) at 0° C. The solution was stirred at 0° C. for 15 min, and then at rt for 3 h. Dichloromethane (80 mL) was added, the solution was washed with water (50 mL), sat. sodium bicarbonate (50 mL), and brine (50 mL), dried with sodium sulfate, and concentrated to give crude 1-(chloromethyl)-2,3-bis{[2-(methyloxy)-ethyl]oxy}benzene (1.15 g, 96% yield) as a yellow oil.

$^1$H NMR (400 MHz, CDCl$_3$) δ7.02 (m, 2H), 6.90 (dd, 1H), 4.72 (s, 2H), 4.27 (m, 2H), 4.14 (m, 2H), 3.77 (m, 2H), 3.73 (m, 2H), 3.46 (s, 3H), 3.44 (s, 3H).

A mixture of 1-(chloromethyl)-2,3-bis{[2-(methyloxy)ethyl]oxy}benzene (1.15 g, 4.19 mmol) and potassium cyanide (0.82 g, 12.56 mmol) in DMF (10 mL) was stirred at 70° C. for 17 h. After cooling to rt, ethyl acetate (100 mL) was added, and the mixture was washed with sat. sodium bicarbonate (30 mL), 5% aqueous LiCl (2×30 mL), and brine (30 mL), dried with sodium sulfate, and concentrated. Column chromatography on silica (2:1 hexanes/ethyl acetate) afforded (2,3-bis{[2-(methyloxy)ethyl]oxy}phenyl)acetonitrile (0.94 g, 85% yield) as a colorless oil. $^1$H NMR (400 MHz, CDCl$_3$) δ7.02 (m, 2H), 6.88 (dd, 1H), 4.28 (m, 2H), 4.13 (m, 2H), 3.84 (s, 2H), 3.75 (m, 2H), 3.63 (m, 2H), 3.43 (s, 3H), 3.41 (s, 3H).

To a solution of (2,3-bis{[2-(methyloxy)ethyl]oxy}phenyl)acetonitrile (0.93 g, 3.52 mmol) in THF (20 mL) was added sodium hydride (0.42 g, 10.56 mmol) and ethyl acetate (1.55 g, 17.60 mmol), and the mixture was stirred at 60° C. for 90 min. After cooling to 0° C., water was added (50 mL), the aqueous layer was washed with dichloro-methane (3×25 mL), acidified with 1N HCl to pH 3, and extracted with ethyl acetate (3×50 mL). The ethyl acetate layer was washed with brine (50 mL), dried with sodium sulfate, and concentrated to give a yellow oil. This oil was dissolved in dry ethanol (5 mL), and hydrazine dihydrochloride (0.44 g, 4.20 mmol) and triethylamine (0.22 g, 2.10 mmol) were added. The reaction mixture was refluxed for 90 min, cooled to rt, and added into sat. sodium bicarbonate (100 mL). The aqueous layer was extracted with dichloromethane (3×50 mL), the organic layer was dried with sodium sulfate, and concentrated. Column chromatography on silica (95:5 dichloromethane/methanol) afforded 4-(2,3-bis{[2-(methyloxy)ethyl]oxy}phenyl)-3-methyl-1H-pyrazol-5-amine (0.81 g, 71% yield) as a pale yellow oil. $^1$H NMR (400 MHz, d$_4$-methanol) δ7.08 (t, 1H), 6.97 (dd, 1H), 6.85 (dd, 1H), 4.18 (m, 2H), 3.90 (m, 2H), 3.78 (m, 2H), 3.47 (m, 2H), 3.43 (s, 3H), 3.23 (s, 3H), 2.19 (s, 3H).

A solution of 4-(2,3-bis{[2-(methyloxy)ethyl]oxy}phenyl)-3-methyl-1H-pyrazol-5-amine (70 mg, 0.22 mmol), and 4-hydroxybenzaldehyde (40 mg, 0.33 mmol) in TFA (2 mL) was stirred in a sealed pressure vessel at 90° C. for 14 h. The reaction mixture was concentrated and purified by HPLC to give 4-(1-methyl-8,9-bis{[2-(methyloxy)ethyl]oxy}-3H-pyrazolo[3,4-c]isoquinolin-5-yl)phenol (35 mg, 38% yield) as a yellow solid. $^1$H NMR (400 MHz, d$_6$-DMSO) δ9.90 (br. s, 1H), 7.79 (d, 1H), 7.46 (m, 2H), 7.38 (d, 1H), 6.93 (m, 2H), 4.32 (m, 2H), 4.27 (m, 2H), 3.76 (m, 2H), 3.69 (m, 2H), 3.34 (s, 3H), 3.23 (s, 3H), 2.82 (s, 3H); MS (EI) for C$_{23}$H$_{25}$N$_3$O$_5$: 424 (MH$^+$).

Using the same or analogous synthetic techniques and/or substituting with alternative reagents, the following compounds of the invention were prepared:

2-chloro-4-(1-methyl-8,9-bis{[2-(methyloxy)ethyl]oxy}-3H-pyrazolo[3,4-c]isoquinolin-5-yl)phenol: $^1$H NMR (400 MHz, d$_6$-DMSO) δ10.62 (br. s, 1H), 7.75 (d, 1H), 7.59 (d, 1H), 7.40 (m, 2H), 7.12 (d, 1H), 4.32 (m, 2H), 4.27 (m, 2H), 3.76 (m, 2H), 3.69 (m, 2H), 3.35 (s, 3H), 3.23 (s, 3H), 2.81 (s, 3H); MS (EI) for C$_{23}$H$_{24}$ClN$_3$O$_5$: 458 (MH$^+$).

2-bromo-4-(1-methyl-8,9-bis{[2-(methyloxy)ethyl]oxy}-3H-pyrazolo[3,4-c]isoquinolin-5-yl)phenol: $^1$H NMR (400 MHz, d$_6$-DMSO) δ10.70 (br. s, 1H), 7.75 (m, 2H), 7.46 (m, 1H), 7.39 (d, 1H), 7.10 (d, 1H), 4.32 (m, 2H), 4.27 (m, 2H), 3.76 (m, 2H), 3.69 (m, 2H), 3.34 (s, 3H), 3.23 (s, 3H), 2.82 (s, 3H); MS (EI) for C$_{23}$H$_{24}$BrN$_3$O$_5$: 503 (MH$^+$).

Example 17

2-chloro-4-(1-methyl-7,8-bis{[2-(methyloxy)ethyl]oxy}-3H-pyrazolo[3,4-c]isoquinolin-5-yl)phenol: To a mixture of methyl 3,4-dihydroxybenzoate (1.0 g, 6.0 mmol), potassium carbonate (3.3 g, 23.8 mmol) and acetonitrile (30 mL) was added 1-bromo-2-(methyloxy)ethane(1.7 mL, 17.9 mmol). The resulting mixture was heated at reflux 18 hour. After cooling to room temperature, the reaction mixture was diluted with ethyl acetate (100 mL), filtered and concentrated. The residue was then diluted with ethyl acetate (100 mL) and washed with 5% sodium hydroxide solution, water and brine (100 mL each), dried over sodium sulfate, filtered and concentrated to give an oily residue which was purified by flash chromatography (silica gel, 30%-50% ethyl acetate-hexane) to provide methyl 3,4-bis{[2-(methyloxy)ethyl]oxy}benzoate (1.1 g, 3.9 mmol, 65% yield). $^1$H NMR (400 MHz, CDCl$_3$): 7.65-7.63 (d, 1H), 7.55 (s, 1H), 6.90-6.88 (d, 1H), 4.21-4.18 (m, 4H), 3.87 (s, 3H), 3.80-3.77 (m, 4H), 3.45 (s, 6H).

To a solution of methyl 3,4-bis{[2-(methyloxy)ethyl]oxy}benzoate, (1.1 g, 3.9 mmol) at 0° C. was added a solution of lithium aluminum hydride in tetrahydrofuran (1.0M, 5.0 mL, 5.0 mmol) and the resulting mixture was stirred for one hour. It was then quenched with ethyl acetate (2 mL) and 5% sodium hydroxide solution (2 mL), diluted with ether (100 mL), and filtered. The filtrate was washed water and brine (100 mL each), dried over sodium sulfate, filtered and concentrated to give (3,4-bis{[2-(methyloxy)ethyl]oxy}phenyl)methanol (0.82 g, 3.2 mmol, 82% yield). $^1$H NMR (400 MHz, CDCl$_3$): 6.93 (s, 1H), 6.87 (s, 2H), 4.59 (s, 2H), 4.16-4.13 (m, 4H), 3.77-3.74 (m, 4H), 3.44 (s, 6H).

To a solution of (3,4-bis{[2-(methyloxy)ethyl]oxy}phenyl)methanol (0.82 g, 3.2 mmol) and pyridine (0.41 mL 5.1 mmol) in tetrahydrofuran (20 mL) at 0° C. was added thionyl chloride (0.26 mL, 3.5 mmol) and the reaction mixture warmed to room temperature and stirred for one hour. Then it was poured into water (40 mL) and extracted with ethyl acetate (3×40 mL). The combined extract was washed with water and brine (40 mL each), dried over sodium sulfate, filtered and concentrated to give 4-(chloromethyl)-1,2-bis{[2-(methyloxy)ethyl]oxy}benzene (0.65 g, 2.4 mmol, 75% yield) $^1$H NMR (400 MHz, CDCl$_3$): 6.95-6.84 (m, 3H), 4.53 (s, 2H), 4.17-4.13 (m, 4H), 3.78-3.74 (m, 4H), 3.44 (s, 6H).

4-(Chloromethyl)-1,2-bis{[2-(methyloxy)ethyl]oxy}benzene (0.65 g, 2.4 mmol) was dissolved in N,N-dimethyl formamide (2 mL) followed by the addition potassium cyanide (0.20 g, 3.1 mmol), and the resulting mixture was heated at 60° C. for 18 hours. After cooling to room temperature, it was diluted with ethyl acetate (50 mL), washed with water and brine (20 mL each), dried over sodium sulfate, filtered and concentrated to give an oily residue which was purified by flash chromatography (50% ethyl acetate-hexane) to provide (3,4-bis{[2-(methyloxy)ethyl]oxy}phenyl)acetonitrile (0.59 g, 2.2 mmol, 92% yield). $^1$H NMR (400 MHz, CDCl$_3$): 6.89-6.93 (m, 3H), 4.16-4.13 (m, 4H), 3.78-3.75 (m, 4H), 3.67 (s, 2H), 3.45 (s, 3H), 3.44 (s, 3H).

To a suspension of (3,4-bis{[2-(methyloxy)ethyl]oxy}phenyl)acetonitrile (0.59 g, 2.2 mmol), and sodium hydride (40% oil dispersion, 270 mg, 6.7 mmol) in tetrahydrofuran (10 mL), was added ethyl acetate (1.1 mL, 11.1 mmol), and the resulting mixture was stirred at 60° C. for 1.5 hours. Then it was cooled to room temperature, and poured into a mixture of ice-water (50 mL). This aqueous mixture was washed with dichloromethane (3×20 mL) then acidified to pH of 2. The acidified mixture was extracted with ethyl acetate (3×30 mL). The combined extract was washed with saturated sodium bicarbonate solution, brine, dried over sodium sulfate, filtered and concentrated to give 2-(3,4-bis{[2-(methyloxy)ethyl]oxy}phenyl)-3-oxobutanenitrile (0.57 g, 1.9 mmol, 86% yield), MS (EI) for C$_{16}$H$_{21}$NO$_5$: 308 (MH$^+$).

To a solution of 2-(3,4-bis{[2-(methyloxy)ethyl]oxy}phenyl)-3-oxobutanenitrile (0.57 g, 1.9 mmol) in ethanol (5 mL) was added hydrazine dihydrochloride (0.20 g, 2.2 mmol) The resulting mixture was heated at reflux for 1 hour. It was cooled, pour into a saturated sodium bicarbonate solution (10 mL), and the mixture was extracted with ethyl acetate (3×10 mL). The combined extract was washed with aqueous sodium bicarbonate solution, brine, dried over sodium sulfate, filtered and concentrated to give an oily residue which was purified by flash chromatography (silica gel, 5% methanol-dichloromethane) to provide 4-(3,4-bis{[2-(methyloxy)ethyl]oxy}phenyl)-3-methyl-1H-pyrazol-5-amine (0.46 g, 1.4 mmol, 74% yield). $^1$H NMR (400 MHz, CDCl$_3$): 6.96-6.92 (m, 2H), 6.87-6.84 (d, d, 1H), 4.19-4.16 (m, 4H), 3.79-3.76 (m, 4H), 3.67 (s, 2H), 3.46 (s, 3H), 3.44 (s, 3H), 2.25 (s, 3H).

A mixture of 4-(3,4-bis{[2-(methyloxy)ethyl]oxy}phenyl)-3-methyl-1H-pyrazol-5-amine (114 mg, 0.36 mmol), 3-chloro-4-hydroxybenzaldehyde (117 mg, 0.75 mmol) and trifluoroacetic acid (3 mL) was heated at 70° C. for 18 hours. Then the reaction mixture was concentrated, dissolved in 10 mL of N,N-dimethylformamide and purified by preparatory HPLC (Shimadzu LC-8A HPLC, Waters Xterra C18 30 mm×100 mm column, acetonitrile-water-trifluoroacetic eluent). After concentration then lyophillization of the pure fractions a yellow powder was obtained. It was dissolved in 4 mL of 1:1 methanol: 4M hydrogen chloride in dioxane, and evaporated to dryness (repeated three times) to give 2-chloro-4-(1-methyl-7,8-bis{[2-(methyloxy)ethyl]oxy}-3H-pyrazolo[3,4-c]isoquinolin-5-yl)phenol hydrochloride salt (84 mg, 0.17 mmol, 47% yield) $^1$H NMR (400 MHz, d$_6$-DMSO): 10.65 (b, 1H), 7.68-7.67 (b, 2H), 7.53-7.48 (m, 2H), 7.16-7.14 (d, 1H), 4.45-4.43 (m, 2H), 4.09-4.07 (m, 2H), 3.80-3.78 (m, 2H), 3.68-3.66 (m, 2H), 3.36 (s, 3H), 3.30 (s, 3H), 2.81 (s, 3H); MS (EI) for C$_{23}$H$_{24}$ClN$_3$O$_5$: 458 (MH$^+$).

Using the same or analogous synthetic techniques and/or substituting with alternative reagents, the following compounds of the invention were prepared:

2-bromo-4-(1-methyl-7,8-bis{[2-(methyloxy)ethyl]oxy}-3H-pyrazolo[3,4-c]isoquinolin-5-yl)phenol hydrochloric acid salt: $^1$H NMR (400 MHz, d$_6$-DMSO): 10.80 (b, 1H), 7.82 (s, 1H), 7.68 (s 1H), 7.57-7.55 (d, 1H), 7.49 (s, 1H), 7.15-7.13 (d, 1H), 4.45-4.43 (m, 2H), 4.09-4.07 (m, 2H), 3.80-3.78 (m, 2H), 3.68-3.66 (m, 2H), 3.36 (s, 3H), 3.30 (s, 3H), 2.81 (s, 3H); MS (EI) for C$_{23}$H$_{24}$BrN$_3$O$_5$: 503 (MH$^+$).

Example 18

2-chloro-4-(1-methyl-9-(methyloxy)-8-{[2-(methyloxy)ethyl]oxy}-3H-pyrazolo[3,4-c]isoquinolin-5-yl)phenol hydrochloric acid salt: To a mixture of methyl 3-hydroxy-2-(methyloxy)benzoate (0.48 g, 2.6 mmol), potassium carbonate (0.73 g, 5.3 mmol) and acetonitrile (30 mL) was added 1-bromo-2-(methyloxy)ethane (0.37 mL, 4.0 mmol). The resulting mixture was heated at reflux 18 hours. After cooling to room temperature, the reaction mixture was diluted with ethyl acetate (100 mL), filtered and concentrated. The residue was then diluted with ethyl acetate (100 mL) and washed with 5% sodium hydroxide solution, water and brine (100 mL each), dried over sodium sulfate, filtered and concentrated to give an oily residue which was purified by flash chromatography (silica gel, 30% ethyl acetate-hexane) to provide methyl 2-(methyloxy)-3-{[2-(methyloxy)ethyl]oxy}benzoate, (0.54 g, 2.3 mmol, 85% yield). $^1$H NMR (400 MHz, CDCl$_3$): 7.35-7.33 (m, 1H), 7.11-7.04 (m, 2H), 4.18-4.17 (m, 2H), 3.93 (s, 3H), 3.91 (s, 3H), 3.80-3.77 (m, 2H), 3.46 (s, 3H).

To a solution of methyl 2-(methyloxy)-3-{[2-(methyloxy)ethyl]oxy}benzoate (0.54 g, 2.3 mmol) at 0° C. was added a solution of lithium aluminum hydride in tetrahydrofuran (1M, 2.8 mL, 2.8 mmol) and the resulting mixture was stirred for one hour. It was then quenched with ethyl acetate (1 mL) and 5% sodium hydroxide solution (1 mL), diluted with ether (100 mL), and filtered. The filtrate was washed water and brine (100 mL each), dried over sodium sulfate, filtered and concentrated to give (2-(methyloxy)-3-{[2-(methyloxy)ethyl]oxy}phenyl)methanol (0.37 g, 1.7 mmol, 78% yield). $^1$H NMR (400 MHz, CDCl$_3$): 7.02-6.93 (d, d, 1H), 6.92-6.87 (m, 2H), 4.68 (s, 2H), 4.16-4.14 (m, 2H), 3.92 (s, 3H), 3.79-3.77 (m, 2H), 3.45 (s, 3H).

To a solution of (2-(methyloxy)-3-{[2-(methyloxy)ethyl]oxy}phenyl)methanol (0.37 g, 1.7 mmol) and pyridine (0.23 mL 2.8 mmol) in tetrahydrofuran (8 mL) at 0° C. was added thionyl chloride (0.14 mL, 1.9 mmol) and the reaction mixture warmed to room temperature and stirred for one hour. Then it was poured into water (20 mL) and extracted with ethyl acetate (3×20 mL). The combined extract was washed with water and brine (20 mL each), dried over sodium sulfate, filtered and concentrated to give 1-(chloromethyl)-2-(methyloxy)-3-{[2-(methyloxy)ethyl]oxy}benzene (0.33 g, 1.4 mmol, 82% yield). $^1$H NMR (400 MHz, CDCl$_3$): 7.01-6.89 (m, 3H), 4.63 (s, 2H), 4.16-4.13 (m, 2H), 3.95 (s, 3H), 3.79-3.77 (m, 2H), 3.44, m, 3H).

1-(Chloromethyl)-2-(methyloxy)-3-{[2-(methyloxy)ethyl]oxy}benzene (0.33 g, 1.4 mmol) was dissolved in N,N-dimethylformamide (2 mL) followed by the addition potassium cyanide (0.12 g, 1.6 mmol), and the resulting mixture was heated at 60° C. for 18 hours. After cooling to room temperature, it was diluted with ethyl acetate (50 mL), washed with water and brine (20 mL each), dried over sodium sulfate, filtered and concentrated to give an oily residue which was purified by flash chromatography (50% ethyl acetate/hexanes) to provide (2-(methyloxy)-3-{[2-(methyloxy)ethyl]oxy}phenyl)acetonitrile (0.17 g, 0.76 mmol, 54% yield). $^1$H NMR (400 MHz, CDCl$_3$): 7.03-7.00 (d, d, 1H), 6.95-6.89 (m, 2H), 4.16-4.14 (m, 2H), 3.94 (s, 3H), 3.79-3.77 (m, 2H), 3.70 (s, 2H), 3.44 (s, 3H).

To a suspension of (2-(methyloxy)-3-{[2-(methyloxy)ethyl]oxy}phenyl)acetonitrile (0.17 g, 0.76 mmol) sodium hydride (40% oil dispersion, 93 mg, 2.3 mmol) in tetrahydrofuran (5 mL), was added ethyl acetate (0.37 mL, 0.38 mmol), and the resulting mixture was stirred at 60° C. for 1.5 hours. Then it was cooled to room temperature, and poured into a mixture of ice-water (50 mL). This aqueous mixture was washed with dichloromethane (3×20 mL) then acidified to pH 2. The acidified mixture was extracted with ethyl acetate (3×30 mL). The combined extract was washed with saturated sodium bicarbonate solution, brine, dried over sodium sulfate, filtered and concentrated to give 2-(2-(methyloxy)-3-{[2-(methyloxy)ethyl]oxy}phenyl)-3-oxobutanenitrile (0.17 g, 0.65 mmol, 85% yield). MS (EI) for C$_{14}$H$_{17}$NO$_4$: 264 (MH$^+$).

To a solution of 2-(2-(methyloxy)-3-{[2-(methyloxy)ethyl]oxy}phenyl)-3-oxobutanenitrile (0.17 g, 0.65 mmol) in ethanol (5 mL) was added hydrazine dihydrochloride (99 mg, 0.94 mmol). The resulting mixture was heated at reflux for 1 hour. It was cooled, poured into a saturated sodium bicarbonate solution (10 mL), and the mixture was extracted with ethyl acetate (3×10 mL). The combined extract was washed with aqueous sodium bicarbonate solution, brine, dried over sodium sulfate, filtered and concentrated to give an oily residue which was purified by flash chromatography (silica gel, 5% methanol in dichloromethane) to provide 3-methyl-4-(2-(methyloxy)-3-{[2-(methyloxy)ethyl]oxy}phenyl)-1H-pyrazol-5-amine (115 mg, 0.42 mmol, 65% yield). MS (EI) for C$_{14}$H$_{19}$N$_3$O$_3$: 278 (MH$^+$).

A mixture of 3-methyl-4-(2-(methyloxy)-3-{[2-(methyloxy)ethyl]oxy}phenyl)-1H-pyrazol-5-amine (115 mg, 0.42 mmol), 3-chloro-4-hydroxybenzaldehyde (100 mg, 0.64 mmol) and trifluoroacetic acid (3 mL) was heated at 70° C. for 18 hours. The reaction mixture was concentrated, dissolved in 10 mL of N,N-dimethylformamide and purified by preparatory HPLC (Shimadzu LC-8A HPLC, Waters Xterra C18 30 mm×100 mm column, acetonitrile-water-trifluoroacetic acid eluent). After concentration and lyophillization of the pure fractions a yellow powder was obtained. The solid was dissolved in 4 mL of 1:1 methanol: 4M hydrogen chloride in dioxane, and evaporated to dryness (repeated three times) yielded 2-chloro-4-(1-methyl-9-(methyloxy)-8-{[2-(methyloxy)ethyl]oxy}-3H-pyrazolo[3,4-c]isoquinolin-5-yl)phenol hydrochloride salt (76 mg, 0.17 mmol, 40% yield) $^1$H NMR (400 MHz, d$_6$-DMSO): 10.82 (b, 1H), 7.80-7.78 (d, 1H), 7.65 (s, 1H), 746-7.44 (m, 2H), 7.18-7.16 (d, 1H), 4.37-4.35 (m, 2H), 3.94 (s, 3H), 3.78-3.76 (m, 2H), 3.36 (s, 3H), 2.83 (s, 3H); MS (EI) for C$_{21}$H$_{20}$ClN$_3$O$_4$: 414 (MH$^+$).

Using the same or analogous synthetic techniques and/or substituting with alternative reagents, the following compounds of the invention were prepared:

3-fluoro-4-(1-methyl-9-(methyloxy)-8-{[2-(methyloxy)ethyl]oxy}-3H-pyrazolo[3,4-c]isoquinolin-5-yl)phenol hydrochloric acid salt: $^1$H NMR (400 MHz, d$_6$-DMSO): 7.53-7.50 (d, d, 1H), 7.41-7.34 (m, 2H), 6.81-6.73 (m, 2H), 4.35-4.32 (m, 2H), 3.75-3.75 (m, 2H), 3.93 (s, 3H), 3.35 (s, 3H), 2.82 (s, 3H); MS (EI) for C$_{21}$H$_{20}$FN$_3$O$_4$: 398 (MH$^+$).

Example 19

2-chloro-4-(6,9-difluoro-1-methyl-8-{[2-(methyloxy)ethyl]oxy}-3H-pyrazolo[3,4-c]isoquinolin-5-yl)-5-fluorophenol: 2,5-Difluorophenol (10 g, 76.8 mmol) was dissolved in DMF (10 mL) and cooled in an ice bath. To the solution was added in portions, sodium hydride (60% w/w dispersion mineral oil; 4.61 g, 115.2 mmol). The mixture was warmed to room temperature and stirred for 30 min. tert-Butyldimethylsilyl chloride (11.6 g, 76.8 mmol) was added, and the mixture was stirred at room temperature for 15 hrs. The mixture was partitioned between ethyl acetate and water. The aqueous portion was extracted with ethyl acetate. The combined organic portion was washed with brine, dried over sodium sulfate, filtered and concentrated in vacuo to afford a yellow oil, which was purified by column chromatography. Eluting with n-hexane gave 14.8 g, 61 mmol (80%), of [(2,5-difluorophenyl)oxy](1,1-dimethylethyl)dimethylsilane as a colorless oil. $^1$H NMR (CDCl$_3$): 6.97-6.91 (m, 1H), 6.61-6.53 (m, 2H), 0.97 (s, 9H), 0.19 (s, 6H); MS (EI) for C$_{12}$H$_{18}$F$_2$OSi: 245 (MH$^+$).

To a solution of [(2,5-difluorophenyl)oxy](1,1-dimethylethyl)dimethylsilane (14.8 g, 60.6 mmol) in THF (150 mL) at −78° C. was added dropwise sec-butyllithium (1.4M in THF; 47.5 mL, 66.6 mmol). The mixture was stirred at −70° C. for 1 hr. While keeping the temperature below −70° C., DMF (5.9 mL, 75.8 mmol) was added dropwise. The reaction mixture was stirred at −70° C. for 30 min, then warmed to room temperature. To the mixture was quickly added 6N HCl (30 mL) and stirring was continued for 30 min. The mixture was extracted with ethyl acetate. The combined organic portion was washed with water, brine, dried over sodium sulfate, filtered and concentrated in vacuo to afford 15.7 g, 57.6 mmol (95%), of 3-{[(1,1-dimethylethyl)(dimethyl)silyl]oxy}-2,5-difluorobenzaldehyde as a yellow oil. $^1$H NMR (CDCl$_3$): 10.30 (s, 1H), 7.26-7.10 (m, 1H), 6.92-6.87 (m, 1H), 1.00 (s, 9H), 0.24 (s, 6H); MS (EI) for C$_{13}$H$_{18}$F$_2$O$_2$Si: 273 (MH$^+$).

To a solution of 3-{[(1,1-dimethylethyl)(dimethyl)silyl]oxy}-2,5-difluorobenzaldehyde (15.7 g, 57.6 mmol) in ethanol (150 mL) at 0° C. was added in portions sodium borohydride (3.27 g, 86.4 mmol). The mixture was stirred at room temperature for 30 min. The mixture was concentrated in-vacuo, and the residue was partitioned between ethyl acetate and water. The organic portion was washed with 20% citric acid, 1N HCl, water, brine, dried over sodium sulfate, filtered and concentrated in vacuo to afford a colorless oil which was purified by column chromatography. Eluting with dichloromethane gave 12.8 g, 46.8 mmol (81%), of (3-{[(1,1-dimethylethyl)(dimethyl)silyl]oxy}-2,5-difluorophenyl)methanol as a colorless oil. $^1$H NMR (CDCl$_3$): 7.07-6.53 (m, 1H), 6.39-6.34 (m, 1H), 4.53 (s, 2H), 0.79 (s, 9H), 0.002 (s, 6H); MS (EI) for C$_{13}$H$_{20}$F$_2$O$_2$Si: 275 (MH$^+$).

To a solution of (3-{[(1,1-dimethylethyl)(dimethyl)silyl]oxy}-2,5-difluorophenyl)methanol (4.0 g, 14.8 mmol) in toluene (35 mL) was added phosphorus tribromide (850 μl, 8.8 mmol). The mixture was stirred at room temperature for 15 hrs. The mixture was concentrated in vacuo, and the residue was partitioned between ethyl acetate and water. The aqueous layer was extracted with ethyl acetate. The combined organic portion was washed with brine, dried over sodium sulfate and concentrated in vacuo to afford a yellow oil which was purified by column chromatography. Eluting with n-hexane gave 3.83 g, 11.4 mmol (77%), of {[3-(bromomethyl)-2,5-difluorophenyl]oxy}(1,1-dimethylethyl)dimethylsilane as a colorless oil. $^1$H NMR (CDCl$_3$): 6.71-6.67 (m, 1H), 6.62-6.57 (m, 1H), 4.44 (s, 2H), 0.99 (s, 9H), 0.21 (s, 6H); MS (EI) for C$_{13}$H$_{19}$F$_2$BrOSi: 338 (MH$^+$).

To a solution of {[3-(bromomethyl)-2,5-difluorophenyl]oxy}(1,1-dimethylethyl)dimethylsilane (3.56 g, 10.6 mmol) in DMSO (30 mL) was added potassium cyanide (1.03 g, 15.8 mmol). The reaction mixture was stirred at room temperature for 1 hr. The reaction mixture was partitioned between ethyl acetate and water. The aqueous portion was extracted with ethyl acetate. The combined organic portion was washed with brine, dried over sodium sulfate, filtered and concentrated in vacuo to afford an orange oil which was purified by column chromatography. Eluting with n-hexane gave 1.28 g, 4.51 mmol (43%), of (3-{[(1,1-dimethylethyl)(dimethyl)silyl]oxy}-2,5-difluorophenyl)acetonitrile as colorless oil. $^1$H NMR (CDCl$_3$): 7.24-6.72 (m, 1H), 6.64-6.59 (m, 1H), 3.73 (s, 2H), 1.00 (s, 9H), 0.21 (s, 6H); MS (EI) for C$_{14}$H$_{19}$NF$_2$OSi: 338 (MH$^+$).

To a solution of (3-{[(1,1-dimethylethyl)(dimethyl)silyl]oxy}-2,5-difluorophenyl)acetonitrile (1.22 g, 4.30 mmol) in DMF (10 mL) was added 2-bromoethyl methyl ether (485 μl, 5.16 mmol) and potassium fluoride (0.5 g, 8.6 mmol). The mixture was stirred at room temperature for 15 hrs. The reaction mixture was partitioned between ethyl acetate and water. The aqueous portion was extracted with ethyl acetate. The combined organic portion was washed with brine, dried over sodium sulfate, filtered and concentrated in-vacuo to afford an orange oil, which was purified by column chromatography. Eluting with 30% ethyl acetate in hexanes gave 690 mg, 3.04 mmol (71%) of (2,5-difluoro-3-{[2-(methyloxy)ethyl]oxy}phenyl)acetonitrile as a colorless oil. $^1$H NMR (CDCl$_3$): 6.75-6.69 (m, 2H), 4.17-4.15 (m, 2H), 3.78-3.74 (m, 4H), 3.44 (s, 3H); MS (EI) for C$_{11}$H$_{11}$NO$_2$F$_2$: 228 (MH$^+$).

To a solution of (2,5-difluoro-3-([2-(methyloxy)ethyl]oxy}phenyl)acetonitrile (621 mg, 2.70 mmol) in THF (10 mL) cooled in an ice bath was added sodium hydride (60% w/w dispersion in mineral oil; 218 mg, 5.46 mmol). The mixture was stirred at room temperature for 15 min. To the mixture was added 1-acetylimidazole (452 mg, 4.1 mmol) and was stirred at 40° C. for 15 min. The reaction mixture was cooled to room temperature and partitioned between 1N HCl and ethyl acetate. The aqueous layer was extracted with ethyl acetate. The organic portion was washed with brine, dried over sodium sulfate, and concentrated in-vacuo to afford 782 mg, 2.90 mmol of an orange oil. To the residue (764 mg, 2.84 mmol) was added ethanol (10 mL), followed by triethylamine (0.24 mL, 1.70 mmol) and Hydrazine dihydrochloride (358 mg, 3.40 mmol). The reaction mixture was stirred in a sealed vessel at 75° C. for 6 hrs. The mixture cooled to room temperature and concentrated iii vacuo. The residue was partition between 1N HCl and ethyl acetate. The aqueous portion was extracted with ethyl acetate. The aqueous portion was brought to pH 9 and extracted using ethyl acetate. The organic portion was washed with brine, dried over sodium sulfate, filtered and concentrated in vacuo to afford 417 mg, 1.48 mmol (55%) of 4-(2,5-difluoro-3-{[2-(methyloxy)ethyl]oxy}phenyl)-3-methyl-1H-pyrazol-5-amine as an orange residue. MS (EI) for C$_{13}$H$_{15}$N$_3$O$_2$F$_2$: 284 (MH$^+$).

To 4-(2,5-difluoro-3-{[2-(methyloxy)ethyl]oxy}phenyl)-3-methyl-1H-pyrazol-5-amine (40 mg, 0.141 mmol) and 5-chloro-2-fluoro-4-hydroxybenaldehyde (30 mg, 0.172 mmol) was added zinc trifluoromethanesulfonate (130 mg, 0.282 mmol) followed by acetonitrile (100 μl, 1.90 mmol) and finally 1,2-Dichloroethane (5 mL). The mixture was stirred in a sealed vessel at 120° C. for 18 hrs. The mixture was cooled to room temperature and partitioned between dichloromethane and saturated ammonia chloride. The aqueous portion was extracted with ethyl acetate. The combined organic portion was washed with brine, dried over sodium sulfate and concentrated in vacuo to afford an orange residue, which was purified by column chromatography. Eluting with 10% ethyl acetate in dichloromethane gave 12.7 mg, 0.03 mmol (21%), of 2-chloro-4-(6,9-difluoro-1-methyl-8-{[2-(methyloxy)ethyl]oxy}-3H-pyrazolo[3,4-c]isoquinolin-5-yl)-5-fluorophenol as a white solid. $^1$H NMR (400 MHz, CD$_3$OD) δ: 7.45 (d, 1H), 7.09 (q, 1H), 6.70 (d, 1H), 4.38 (t, 2H), 3.82 (t, 2H), 3.42 (s, 3H), 2.80 (d, 3H); MS (EI) for C$_{20}$H$_{15}$N$_3$O$_3$F$_3$Cl: 438 (MH$^+$).

Using the same or analogous synthetic techniques and/or substituting with alternative reagents, the following compounds of the invention were prepared:

4-(6,9-difluoro-1-methyl-8-{[2-(methyloxy)ethyl]oxy}-3H-pyrazolo[3,4-c]isoquinolin-5-yl)-3-fluorophenol: $^1$H NMR (400 MHz, CD$_3$OD): 7.34 (t, 1H), 7.22-7.04 (m, 1H), 6.72 (dd, 1H), 6.57 (dd, 1H), 4.38-4.31 (m, 2H), 3.86-3.81 (m, 2H), 3.46 (s, 3H), 2.87-2.72 (m, 3H); MS (EI) for C$_{20}$H$_{16}$F$_3$N$_3$O$_3$: 404 (MH$^+$).

2-chloro-4-(6,9-difluoro-1-methyl-8-{[2-(methyloxy)ethyl]oxy}-3H-pyrazolo[3,4-c]isoquinolin-5-yl)phenol: $^1$H NMR (400 MHz, d$_6$-DMSO): 13.7 (br s, 1H), 10.5 (s, 1H), 7.49 (s, 1H), 7.43 (dd, 1H), 7.33-7.25 (m, 1H), 7.02 (d, 1H), 4.41-4.33 (m, 2H), 3.76-3.70 (m, 2H), 3.34 (s, 3H), 2.72 (d, 3H); MS (EI) for C$_{20}$H$_{16}$ClF$_2$N$_3$O$_3$: 420 (MH$^+$).

6,9-difluoro-5-(2-fluorophenyl)-1-methyl-8-{[2-(methyloxy)ethyl]oxy}-3H-pyrazolo[3,4-c]isoquinoline: $^1$H NMR (400 MHz, d$_6$-DMSO): 13.8 (br s, 1H), 7.62-7.51 (m, 2H), 7.47 (dd, 1H), 7.38-7.28 (m, 1H), 4.43-4.35 (m, 2H), 3.77-3.71 (m, 2H), 3.34 (s, 3H), 2.76 (d, 3H); MS (EI) for C$_{20}$H$_{16}$F$_3$N$_3$O$_2$: 388 (MH$^+$).

4-[6,9-difluoro-1-methyl-8-(methyloxy)-3H-pyrazolo[3,4-c]isoquinolin-5-yl]phenol $^1$H NMR (400 MHz, d$_6$-dmso): 9.69 (s, 1H), 7.38-7.31 (m, 3H), 6.81 (d, 2H), 3.99 (s, 3H), 2.69 (s, 3H); MS (EI) for C$_{18}$H$_{13}$N$_3$O$_2$F$_2$: 342 (MH$^+$).

4-(6,9-difluoro-1-methyl-8-{[2-(methyloxy)ethyl]oxy}-3H-pyrazolo[3,4-c]isoquinolin-5-yl)phenol. $^1$H NMR (400 MHz, CD$_3$OD): 7.36 (d, 2H), 7.20 (q, 1H), 6.86 (d, 1H), 4.37 (t, 2H), 3.84 (t, 2H), 3.47 (s, 3H), 2.82 (d, 3H); MS (EI) for C$_{20}$H$_{17}$N$_3$O$_3$F$_2$: 386 (MH$^+$).

Example 20

5-(3-Chloro-4-hydroxyphenyl)-6,9-difluoro-1-methyl-3H-pyrazolo[3,4-c]isoquinolin-8-ol: (3-{[(1,1-Dimethylethyl)(dimethyl)silyl]oxy}-2,5-difluorophenyl) acetonitrile (0.353 g, 1.25 mmol) was dissolved in dimethylformamide (3 mL) and potassium fluoride (0.145 g, 2.50 mmol) was added followed by chloromethyl methyl ether (0.117 mL, 1.54 mmol). The mixture was stirred at room temperature for 0.2 h and then was partitioned between ethyl acetate and water. The aqueous portion was extracted with ethyl acetate. The combined organic portion was washed with brine, dried over sodium sulfate, filtered and concentrated in vacuo to afford an oil which was purified by column chromatography (ethyl acetate-hexanes 1:6) to afford (2,5-difluoro-3-{[(methyloxy)methyl]oxy}phenyl)acetonitrile as a light brown solid (0.253 g, 1.19 mmol, 95% yield). $^1$H NMR (400 MHz, CDCl$_3$): 7.05-6.93 (m, 1H), 6.87-6.77 (m, 1H), 5.22 (s, 2H), 3.76 (s, 2H), 3.51 (s, 3H); GCMS for C$_{10}$H$_9$NO$_2$: 213 (M$^+$).

To NaH (60 wt. % dispersion in oil; 0.09 g, 2.25 mmol) suspended in THF (4 mL) was added (2,5-difluoro-3-{[(methyloxy)methyl]oxy}phenyl)acetonitrile (0.240 g, 1.13 mmol) and then 1-acetylimidazole (0.186 g, 1.69 mmol). The mixture was stirred at 40° C. for 0.3 h. The mixture was cooled to room temperature, was acidified with 1 N HCl and ethyl acetate. The organic portion was washed with brine, dried over sodium sulfate, filtered and concentrated in vacuo to afford a yellow oil which was dissolved in dichloromethane:MeOH (1:1, 8 mL) and treated with para-toluenesulfonic acid monohydrate (0.045 g, 0.237 mmol) at 40° C. for 15 h. The mixture was partitioned between ethyl acetate and saturated sodium bicarbonate solution. The aqueous portion was extracted with ethyl acetate. The combined organic portion was washed with brine, dried over sodium sulfate, filtered and concentrated in vacuo to afford a yellow oil which was dissolved in EtOH (4 mL) and treated with tert-butylhydrazine hydrochloride (0.136 g, 1.09 mmol) at 75° C. for 18 h and at room temperature for 38 h. The mixture was concentrated in vacuo and the residue was partitioned between ethyl acetate and saturated sodium bicarbonate solution. The aqueous portion was extracted with ethyl acetate. The combined organic portion was washed with brine, dried over sodium sulfate, filtered and concentrated in vacuo to afford 3-[5-amino-1-(1,1-dimethylethyl)-3-methyl-1H-pyrazol-4-yl]-2,5-difluorophenol as a pale brown solid (0.248 g, 0.883 mmol, 78% yield). MS (EI) for C$_{14}$H$_{17}$F$_2$N$_3$O: 282 (MH$^+$).

To 3-[5-amino-1-(1,1-dimethylethyl)-3-methyl-1H-pyrazol-4-yl]-2,5-difluorophenol (0.050 g, 0.178 mmol) and 3-chloro-4-[(phenylmethyl)oxy]benzaldehyde (0.044 g, 0.178 mmol) was added acetic acid (1 mL). The mixture was stirred at 120° C. for 4.5 h and then concentrated in vacuo to afford a residue which was co-evaporated with EtOH (2×) to afford a film which was purified by column chromatography (ether-dichloromethane 1:20) to afford 5-{3-chloro-4-[(phenylmethyl)oxy]phenyl}-3-(1,1-dimethylethyl)-6,9-difluoro-1-methyl-3H-pyrazolo[3,4-c]isoquinolin-8-ol as a light brown foam (0.042 g, 0.083 mmol, 47% yield). $^1$H NMR (400 MHz, CDCl$_3$): 7.63 (t, 1H), 7.55-7.51 (m, 2H), 7.46-7.34 (m, 5H), 7.06 (d, 1H), 6.86 (dd, 1H), 5.25 (s, 2H), 2.81 (d, 3H), 1.84 (s, 9H); MS (EI) for C$_{28}$H$_{24}$ClF$_2$N$_3$O$_2$: 508 (MH$^+$).

5-{3-Chloro-4-[(phenylmethyl)oxy]phenyl}-3-(1,1-dimethylethyl)-6,9-difluoro-1-methyl-3H-pyrazolo[3,4-c]isoquinolin-8-ol (0.010 g, 0.020 mmol) was dissolved in trifluoroacetic acid (0.5 mL) and stirred at room temperature for 1.3 h, then at 50° C. for 0.2 h and finally at 60° C. for 0.5 h. The mixture was then concentrated in vacuo to afford a residue which was purified by preparative HPLC to afford 5-(3-chloro-4-hydroxyphenyl)-6,9-difluoro-1-methyl-3H-pyrazolo[3,4-c]isoquinolin-8-ol as a yellow solid (0.0047 g, 0.013 mmol, 66% yield). $^1$H NMR (400 MHz, CD$_3$OD): 7.47 (t, 1H), 7.28 (dt, 1H), 6.98 (d, 1H), 6.86 (dd, 1H), 2.82 (d, 3H); MS (EI) for C$_{17}$H$_{10}$ClF$_2$N$_3$O$_2$: 362 (MH$^+$), 394 (MNa$^+$), 400 (MK$^+$).

Using the same or analogous synthetic techniques and/or substituting with alternative reagents, the following compounds of the invention were prepared:

6,9-difluoro-5-furan-3-yl-1-methyl-3H-pyrazolo[3,4-c]isoquinolin-8-ol hydrochloride: $^1$H NMR (400 MHz, CD$_3$OD): 8.18-8.15 (m, 1H), 7.80-7.77 (m, 1H), 7.09 (dd, 1H), 6.93-6.89 (m, 1H), 2.92 (d, 3H); MS (EI) for C$_{15}$H$_9$F$_2$N$_3$O$_2$: 302 (MH$^+$).

6,9-difluoro-5-furan-2-yl-1-methyl-3H-pyrazolo[3,4-c]isoquinolin-8-ol hydrochloride: $^1$H NMR (400 MHz, CD$_3$OD): 7.90-7.88 (m, 1H), 7.18 (t, 1H), 7.02 (dd, 1H), 6.76 (dd, 1H), 2.86 (d, 3H); MS (EI) for C$_{15}$H$_9$F$_2$N$_3$O$_2$: 302 (MH$^+$).

6,9-difluoro-5-(4-hydroxybutyl)-1-methyl-3H-pyrazolo[3,4-c]isoquinolin-8-ol hydrochloride: $^1$H NMR (400 MHz, CD$_3$OD): 7.17 (dd, 1H), 3.63 (t, 2H), 3.51-3.44 (m, 2H), 2.89 (d, 3H), 1.99-1.88 (m, 2H), 1.77-1.68 (m, 2H); MS (EI) for C$_{15}$H$_{15}$F$_2$N$_3$O$_2$: 308 (MH$^+$), 330 (MNa$^+$).

4-(6,9-difluoro-8-hydroxy-1-methyl-3H-pyrazolo[3,4-c]isoquinolin-5-yl)-N-hydroxybenzenecarboximidamide trifluoroacetate: $^1$H NMR (400 MHz, CD$_3$OD): 7.83-7.74 (m, 4H), 6.88 (dd, 1H), 2.86 (d, 3H); MS (EI) for C$_{18}$H$_{13}$F$_2$N$_5$O$_2$: 370 (MH$^+$).

3-(6,9-difluoro-8-hydroxy-1-methyl-3H-pyrazolo[3,4-c]isoquinolin-5-yl)-N-hydroxybenzenecarboximidamide trifluoroacetate: $^1$H NMR (400 MHz, CD$_3$OD): 7.89-7.84 (m, 2H), 7.84-7.79 (m, 1H), 7.75-7.69 (m, 1H), 6.88 (dd, 1H), 2.85 (d, 3H); MS (EI) for C$_{18}$H$_{13}$F$_2$N$_5$O$_2$: 370 (MH$^+$).

5-(4-aminophenyl)-6,9-difluoro-1-methyl-3H-pyrazolo[3,4-c]isoquinolin-8-ol trifluoroacetate: $^1$H NMR (400 MHz, CD$_3$OD): 7.61 (dd, 2H), 7.32 (d, 2H), 6.88 (dd, 1H), 2.85 (d, 3H); MS (EI) for C$_{17}$H$_{12}$F$_2$N$_4$O: 327 (MH$^+$).

6,9-difluoro-5-(3-hydroxypropyl)-1-methyl-3H-pyrazolo[3,4-c]isoquinolin-8-ol: $^1$H NMR (400 MHz, CD$_3$OD): 6.98 (dd, 1H), 3.72 (t, 2H), 3.43-3.37 (m, 2H), 2.78 (d, 3H), 2.09-2.00 (m, 2H); MS (EI) for C$_{14}$H$_{13}$F$_2$N$_3$O$_2$: 294 (MH$^+$), 316 (MNa$^+$).

5-(5-amino-2-thienyl)-6,9-difluoro-1-methyl-3H-pyrazolo[3,4-c]isoquinolin-8-ol trifluoroacetate: $^1$H NMR (400 MHz, CD$_3$OD): 7.20 (d, 1H), 6.92 (dd, 1H), 6.28 (d, 1H), 2.78 (d, 3H); MS (EI) for C$_{15}$H$_{10}$F$_2$N$_4$OS: 333 (MH$^+$).

5-(2-amino-1,3-thiazol-4-yl)-6,9-difluoro-1-methyl-3H-pyrazolo[3,4-c]isoquinolin-8-ol trifluoroacetate: $^1$H NMR (400 MHz, CD$_3$OD): 7.07 (s, 1H), 6.99 (dd, 1H), 2.83 (d, 3H); MS (EI) for C$_{14}$H$_9$F$_2$N$_5$OS: 334 (MH$^+$).

5-(5-amino-1,3,4-thiadiazol-2-yl)-6,9-difluoro-1-methyl-3H-pyrazolo[3,4-c]isoquinolin-8-ol trifluoroacetate: $^1$H NMR (400 MHz, d$_6$-DMSO): 11.5 (br s, 1H), 7.55 (br s, 2H), 7.03 (dd, 1H), 2.75 (d, 3H); MS (EI) for C$_{13}$H$_8$F$_2$N$_6$OS: 335 (MH$^+$), 357 (MNa$^+$).

6,9-difluoro-5-(2-imino-3-methyl-2,3-dihydro-1,3-thiazol-5-yl)-1-methyl-3H-pyrazolo[3,4-c]isoquinolin-8-ol trifluoroacetate: $^1$H NMR (400 MHz, d$_6$-DMSO): 11.4 (br s, 1H), 8.75 (br s, 1H), 7.56 (d, 1H), 7.04 (dd, 1H), 2.96 (s, 3H), 2.69 (d, 3H); MS (EI) for $C_{15}H_{10}F_2N_5OS$: 348 (MH$^+$).

6,9-difluoro-1-methyl-5-(1-oxidopyridin-4-yl)-3H-pyrazolo[3,4-c]isoquinolin-8-ol: MS (EI) for $C_{16}H_{10}F_2N_4O_2$: 329.2 (MH$^+$)

6,9-difluoro-5-(1H-indol-5-yl)-1-methyl-3H-pyrazolo[3,4-c]isoquinolin-8-ol $^1$H NMR (400 MHz, CD$_3$OD): 7.82 (s, 1H), 7.52 (d, 1H), 7.38 (s, 1H), 7.31 (d, 1H), 6.90 (q, 1H), 6.57 (d, 1H), 2.86 (d, 3H); MS (EI) for $C_{19}H_{12}F_2N_4O$: 351 (MH$^+$).

5-(1H-benzimidazol-6-yl)-6,9-difluoro-1-methyl-3H-pyrazolo[3,4-c]isoquinolin-8-ol $^1$H NMR (400 MHz, CD$_3$OD): 9.46 (s, 1H), 8.01 (s, 1H), 7.92 (d, 1H), 7.77 (d, 1H), 6.83 (q, 1H), 2.81 (d, 3H); MS (EI) for $C_{18}H_{11}F_2N_5O$: 352 (MH$^+$).

5-(2-aminoethyl)-6,9-difluoro-1-methyl-3H-pyrazolo[3,4-c]isoquinolin-8-ol $^1$H NMR (400 MHz, d$_6$-DMSO): 7.12 (q, 1H), 3.65-3.60 (m, 2H), 3.41-3.38 (m, 2H), 2.69 (d, 3H); MS (EI) for $C_{13}H_{12}F_2N_4O$: 279 (MH$^+$).

5-(2-amino-1,3-thiazol-5-yl)-6,9-difluoro-1-methyl-3H-pyrazolo[3,4-c]isoquinolin-8-ol $^1$H NMR (400 MHz, CD$_3$OD): 7.54 (d, 1H), 6.90 (q, 1H), 2.68 (d, 3H); MS (EI) for $C_{14}H_9F_2N_5OS$: 334 (MH$^+$).

5-(6-aminopyridin-3-yl)-6,9-difluoro-1-methyl-3H-pyrazolo[3,4-c]isoquinolin-8-ol $^1$H NMR (400 MHz, CD$_3$OD): 8.03-7.98 (m, 2H), 6.97 (d, 1H), 6.78 (q, 1H), 2.65 (d, 3H); MS (EI) for $C_{16}H_{11}F_2N_5O$: 328 (MH$^+$).

6,9-difluoro-5-(1H-indol-6-yl)-1-methyl-3H-pyrazolo[3,4-c]isoquinolin-8-ol $^1$H NMR (400 MHz, CD$_3$OD): 7.68-7.66 (m, 2H), 7.41 (d, 1H), 7.20 (d, 1H), 6.89 (q, 1H), 6.56 (d, 1H), 2.85 (d, 3H); MS (EI) for $C_{19}H_{12}F_2N_4O$: 351 (MH$^+$).

N-[5-(6,9-difluoro-8-hydroxy-1-methyl-3H-pyrazolo[3,4-c]isoquinolin-5-yl)-1,3-thiazol-2-yl]acetamide $^1$H NMR (400 MHz, d$_6$-DMSO): 7.71 (d, 1H), 7.02 (q, 1H), 2.71 (d, 3H), 2.19 (s, 3H); MS (EI) for $C_{16}H_{11}F_2N_5O_2S$: 351 (MH$^+$).

5-(3-aminophenyl)-6,9-difluoro-1-methyl-3H-pyrazolo[3,4-c]isoquinolin-8-ol $^1$H NMR (400 MHz, CD$_3$OD): 7.65-7.58 (m, 2H), 7.54 (s, 1H), 7.49 (d, 1H), 6.85 (q, 1H), 2.81 (d, 3H); MS (EI) for $C_{17}H_{12}F_2N_4O$: 327 (MH$^+$).

6,9-difluoro-1-methyl-5-(1,3-thiazol-5-yl)-3H-pyrazolo[3,4-c]isoquinolin-8-ol $^1$H NMR (400 MHz, d$_6$-DMSO): 9.24 (s, 1H), 8.13 (d, 1H), 7.18 (q, 1H), 2.73 (d, 3H); MS (EI) for $C_{14}H_8F_2N_4OS$: 319 (MH$^+$).

Example 21

2-chloro-4-(6,11-difluoro-1-methyl-8,9-dihydro-3H-[1,4]dioxino[2,3-g]pyrazolo[3,4-c]isoquinolin-5-yl)-5-fluorophenol: To a solution of 2-bromoethanol (3.5 mL, 49.3 mmol) in DCM (20 mL) was added tert-butyldimethylsilyl chloride (8.17 g, 54.2 mmol) followed by triethylamine (13.85 mL, 98.6 mmol) and finally 4-dimethylaminopyridine (55 mg, 0.394 mmol). The mixture was stirred at room temperature for 15 hrs, and then concentrated in-vacuo. The residue was partitioned between 1N HCl and ethyl acetate. The aqueous portion was extracted with ethyl acetate. The combined organic portion was washed with brine, dried over sodium sulfate, filtered and concentrated in-vacuo to afford a yellow oil, which was purified by column chromatography. Eluting with n-hexane gave 11.8 g, 49.3 mmol (100%), of [(2-bromoethyl)oxy](1,1-dimethylethyl)dimethylsilane as a colorless oil. $^1$H NMR (400 MHz, CDCl$_3$): 3.89 (t, 2H), 3.40 (t, 2H), 0.91 (s, 9H), 0.091 (s, 6H); GC/MS for $C_8H_{19}BrOSi$: 239 (M$^+$).

To a solution of [(2-bromoethyl)oxy](1,1-dimethylethyl)dimethylsilane (11.79 g, 49.3 mmol) in DMF (100 mL) was added 3-Hydroxy-2,4,5-trifluorobenzoic acid (3 g, 15.6 mmol) and potassium carbonate (7.65 g, 55.2 mmol). The mixture was stirred at 70° C. for 15 hrs. The mixture was cooled to room temperature and concentrated in-vacuo. The residue was partitioned between 1N HCl and ethyl acetate. The aqueous layer was extracted with ethyl acetate. The organic portion was washed with brine, dried over sodium sulfate, filtered and concentrated in-vacuo to afford a yellow oil, which was purified by column chromatography. Eluting with 10% ethyl acetate in hexane gave 5.8 g, 11.4 mmol (23%), of 2-{[(1,1-dimethylethyl)(dimethyl)silyl]oxy}ethyl-3-[(2-{[(1,1-dimethylethyl)(dimethyl)silyl]oxy}ethyl)oxy]-2,4,5-trifluorobenzoate as a colorless oil. $^1$H NMR (400 MHz, CDCl$_3$): 7.49-7.26 (m, 1H), 4.40 (t, 2H), 4.27 (t, 2H), 3.95-3.91 (m, 4H), 0.89 (s, 9H), 0.86 (s, 9H), 0.074 (s, 6H), 0.056 (s, 6H); MS (EI) for $C_{23}H_{39}O_5F_3Si$: 509 (MH$^+$).

2-{[(1,1-dimethylethyl)(dimethyl)silyl]oxy}ethyl-3-[(2-{[(1,1-dimethylethyl)(dimethyl)silyl]oxy}ethyl)oxy]-2,4,5-trifluorobenzoate (5.8 g, 11.4 mmol) was added dropwise to a stirred suspension of lithium aluminum hydride (1.0 M in THF; 35 mL, 35 mmol) in THF (100 mL) at 0° C. The reaction was stirred at room temperature for 1 hr. The mixture was cooled to 0° C. Ethyl acetate (3 mL) was added slowly to the suspension, followed by water (1.25 mL), 15% aqueous sodium hydroxide solution (5 mL) and water (1.25 mL). The mixture was filtered through a pad of celite and washed with diethyl ether. The filtrate was concentrated in-vacuo to afford 3.6 g, 10.7 mmol (94%), of {3-[(2-{[(1,1-dimethylethyl)(dimethyl)silyl]oxy}ethyl)oxy]-2,4,5-trifluorophenyl]methanol as a colorless oil. $^1$H NMR (400 MHz, CDCl$_3$): 7.00-6.94 (m, 1H), 4.70 (d, 2H), 4.25 (t, 2H), 3.93 (t, 2H), 0.87 (s, 9H), 0.064 (s, 6H); GC/MS for $C_{15}H_{23}O_3F_3Si$: 336 (M$^+$).

To a solution on {3-[(2-{[(1,1-dimethylethyl)(dimethyl)silyl]oxy}ethyl)oxy]-2,4,5-trifluorophenyl]methanol (3.6 g, 10.7 mmol) in dichloromethane (30 mL) was added 3,4-dihydro-2H-pyran (1.96 mL, 21.4 mmol). The solution was cooled to 0° C. and p-toluenesulfonyl chloride (20 mg, 0.107 mmol) was added. The solution was stirred at room temperature for 15 hrs. The solution was partitioned between saturated sodium bicarbonate and dichloromethane. The organic portion was washed with water, brine and dried over sodium sulfate, filtered and concentrated in-vacuo to afford an orange oil, which was purified by column chromatography. Eluting with 10% ethyl acetate in hexane gave 3.33 g, 7.9 mmol (74%) of (1,1-dimethylethyl)(dimethyl){[2-({2,3,6-trifluoro-5-[(tetrahydro-2H-pyran-2-yloxy)methyl]phenyl}oxy)ethyl]oxy}silane as a colorless oil. $^1$H NMR (400 MHz, CDCl$_3$): 7.0-6.94 (m, 1H), 4.92-4.65 (m, 2H), 4.51-4.58 (m, 1H), 4.25 (t, 2H), 3.93 (t, 2H), 3.93-3.82 (m, 1H), 3.61-3.52 (m, 1H), 1.89-1.55 (m, 6H), 0.87 (s, 9H), 0.065 (s, 6H); GC/MS for $C_{20}H_{31}O_4F_3Si$: 363 (M$^+$).

To a solution of (1,1-dimethylethyl)(dimethyl){[2-({2,3,6-trifluoro-5-[(tetrahydro-2H-pyran-2-yloxy)methyl]phenyl}oxy)ethyl]oxy}silane (3.12 g, 7.42 mmol) in DMF (22 mL) was added potassium fluoride (453 mg, 7.79 mmol). The mixture was stirred at reflux for 15 hrs. The mixture was cooled to room temperature and partitioned between 1N HCl and ethyl acetate. The aqueous portion was extracted with ethyl acetate. The combined organic portion was washed with brine, dried over sodium sulfate, filtered and concentrated in-vacuo to afford a yellow oil, which was purified by column chromatography. Eluting with 5% ethyl acetate in dichloromethane gave, 795 mg, 2.77 mmol (37%), of 5,8-difluoro-6-[(tetrahydro-2H-pyran-2-yloxy)methyl]-2,3-dihydro-1,4- benzodioxine as a colorless oil. $^1$H NMR (400 MHz, CDCl$_3$): 6.73 (q, 1H), 4.75-4.65 (m, 2H), 4.49-4.42 (m, 1H), 4.33 (s, 4H), 3.91-3.82 (m, 1H), 3.59-3.51 (m, 1H), 1.85-1.45 (m, 6H); GC/MS for C$_{14}$H$_{16}$O$_4$F$_2$: 286 (M$^+$).

To a solution of 5,8-difluoro-6-[(tetrahydro-2H-pyran-2-yloxy)methyl]-2,3-dihydro-1,4-benzodioxine (785 mg, 2.74 mmol) in toluene (5 mL) was added phosphorous tribromide (155 µl, 1.65 mmol) and the solution was stirred at room temperature for 15 hrs. The solution was concentrated in-vacuo, and the residue was partitioned between water and ethyl acetate. The aqueous layer was extracted with ethyl acetate. The combined organic portion was washed with brine, dried over sodium sulfate, filtered and concentrated in-vacuo to afford 700 mg, 2.64 mmol (96%) of 6-(bromomethyl)-5,8-difluoro-2,3-dihydro-1,4-benzodioxine as a pale yellow oil. $^1$H NMR (400 MHz, CDCl$_3$): 6.68 (q, 1H), 4.33 (s, 2H), 4.35 (s, 4H); GC/MS (EI) for C$_9$H$_7$O$_2$F$_2$Br: 265 (M$^+$).

To a solution of 6-(bromomethyl)-5,8-difluoro-2,3-dihydro-1,4-benzodioxine (686 mg, 2.59 mmol) in DMSO (3 mL) was added potassium cyanide (186 mg, 2.85 mmol). The mixture was stirred at room temperature for 4 hrs. The mixture was partitioned between water and ethyl acetate. The aqueous portion was extracted with ethyl acetate. The combined organic portion was washed with brine, dried over sodium sulfate, and concentrated in-vacuo to afford an orange residue, which was purified by column chromatography. Eluting with 20% ethyl acetate in hexanes gave 307 mg, 1.45 mmol (56%), of (5,8-difluoro-2,3-dihydro-1,4-benzodioxin-6-yl)acetonitrile as a white solid. $^1$H NMR (400 MHz, CDCl$_3$): 6.75 (q, 1H), 4.37 (s, 4H), 3.69 (s, 2H); GC/MS for C$_{10}$H$_7$NO$_2$F$_2$: 211 (M$^+$).

A solution of (5,8-difluoro-2,3-dihydro-1,4-benzodioxin-6-yl)acetonitrile (300 mg, 1.42 mmol) in THF (3 mL) was cooled in an ice bath. To the solution was added sodium hydride (60% w/w dispersion in mineral oil; 113.6 mg, 2.84 mmol) and the mixture was stirred at 40° C. for 10 min. To the mixture was added 1-acetylimidazole (234 mg, 2.84 mmol), and the mixture was stirred at 40° C. for an additional 5 min. The mixture was cooled to room temperature and partitioned between 1N HCl and ethyl acetate. The aqueous portion was extracted with ethyl acetate. The combined organic portion was washed with brine, dried over sodium sulfate, filtered and concentrated in-vacuo. To the residue (420 mg, 1.65 mmol) was added ethanol (10 mL), followed by triethylamine (140 µl, 1.0 mmol) and Hydrazine dihydrochloride (209 mg, 2.0 mmol). The mixture was stirred in a sealed vessel at 75° C. for 6 hrs. The mixture was cooled to room temperature and concentrated in-vacuo. The residue was partitioned between 1N HCl and diethyl ether. The aqueous portion was extracted with diethyl ether. The aqueous layer was brought to pH 8 and was extracted with ethyl acetate. The combined organic portion was washed with brine, dried over sodium sulfate, filtered and concentrated in-vacuo to afford 265 mg, 0.992 mmol (70%), of 4-(5,8-difluoro-2,3-dihydro-1,4-benzodioxin-6-yl)-3-methyl-1H-pyrazol-5-amine as a colorless oil. $^1$H NMR (400 MHz, CDCl$_3$): 6.62 (q, 1H), 4.37 (s, 4H), 2.20 (s, 3H); MS (EI) for C$_{12}$H$_{11}$N$_3$O$_2$F$_2$: 268 (MH$^+$).

To a mixture of 4-(5,8-difluoro-2,3-dihydro-1,4-benzodioxin-6-yl)-3-methyl-1H-pyrazol-5-amine (48 mg, 0.180 mmol) and 5-chloro-2-fluoro-4-hydroxybenaldehyde (38 mg, 0.216 mmol) and zinc trifluoromethanesulfonate (130 mg) was added acetonitrile (127 µl, 2.43 mmol) followed by 1,2-Dichloroethane (5 mL). The mixture was stirred in a sealed vessel at 120° C. for 6 days. The mixture was cooled to room temperature and poured into saturated aqueous ammonia chloride, and extracted using ethyl acetate. The combined organic portion was washed with brine, dried over sodium sulfate, filtered and concentrated in-vacuo to afford an orange solid, which was purified by column chromatography. Eluting with 50% ethyl acetate in hexane gave 21 mg, 0.050 mmol (27%), of 2-chloro-4-(6,11-difluoro-1-methyl-8,9-dihydro-3H-[1,4]dioxino[2,3-g]pyrazolo[3,4-c]isoquinolin-5-yl)-5-fluorophenol as a yellow solid. $^1$H NMR (400 MHz, CD$_3$OD): 7.48 (d, 1H), 6.74 (d, 1H), 4.52 (s, 4H), 2.77 (d, 3H); MS (EI) for C$_{19}$H$_{11}$N$_3$O$_3$F$_3$Cl: 422 (MH$^+$).

Example 22

2-Chloro-4-(6,9-difluoro-1-methyl-8-{[(1-methylpiperidin-4-yl)methyl]oxy}-3H-pyrazolo[3,4-c]isoquinolin-5-yl)phenol trifluoroacetate: 5-{3-Chloro-4-[(phenylmethyl)oxy]phenyl}-3-(1,1-dimethylethyl)-6,9-difluoro-1-methyl-3H-pyrazolo[3,4-c]isoquinolin-8-ol (0.030 g, 0.059 mmol) was dissolved in dimethylformamide (1 mL) and potassium carbonate (0.041 g, 0.296 mmol) was added followed by 1,1-dimethylethyl 4-{[(methylsulfonyl)oxy]methyl}piperidine-1-carboxylate (0.019 g, 0.065 mmol). The mixture was stirred at 70° C. for 15 h and then at 90° C. for 24 h. The mixture was partitioned between ethyl acetate and 1N NaOH. The organic portion was washed with 1 N NaOH. The aqueous portion was back-extracted with ethyl acetate. The combined organic portion was washed with water, brine, dried over sodium sulfate, filtered and concentrated in vacuo to afford a brown oil which was dissolved in trifluoroacetic acid (0.5 mL) and stirred at room temperature for 0.6 h, then at 50° C. for 0.2 h. The mixture was partitioned between ethyl acetate and saturated sodium bicarbonate solution. The organic portion was washed with saturated sodium bicarbonate solution. The combined aqueous portion was extracted with ethyl acetate and then 10% MeOH in ethyl acetate. The combined organic portion was washed with brine, dried over sodium sulfate, filtered and concentrated in vacuo to afford a brown oil which was purified by preparative HPLC to afford a yellow film which was dissolved in formic acid (0.5 mL) and heated at 95° C. for 17 h. Formaldehyde (37 wt. % solution in water; 0.015 mL, 0.200 mmol) was added and the mixture was stirred at 95° C. for 23 h. The mixture was concentrated in vacuo to afford a residue which was dissolved in EtOH and 4 N HCl in dioxan was added. The mixture was concentrated in vacuo to afford a yellow solid which was purified by preparative HPLC to afford 2-chloro-4-(6,9-difluoro-1-methyl-8-{[(1-methylpiperidin-4-yl)methyl]oxy}-3H-pyrazolo[3,4-c]isoquinolin-5-yl)phenol trifluoroacetate as a yellow oil (0.0054 g, 0.0092 mmol, 16% yield). $^1$H NMR (400 MHz, CD$_3$OD): 7.48 (t, 1H), 7.29 (dt, 1H), 7.13 (dd, 1H), 7.00 (d, 1H), 4.14-4.09 (m, 2H), 3.64-3.57 (m, 2H), 3.12-3.03 (m, 2H), 2.89 (s, 3H), 2.76 (d, 3H), 2.26-2.13 (m, 3H), 1.81-1.66 (m, 2H); MS (EI) for C$_{24}$H$_{23}$ClF$_2$N$_4$O$_2$: 473 (MH$^+$).

Using the same or analogous synthetic techniques and/or substituting with alternative reagents, the following compounds of the invention were prepared:

2-chloro-4-{8-[(difluoromethyl)oxy]-6,9-difluoro-1-methyl-3H-pyrazolo[3,4-c]isoquinolin-5-yl}phenol: $^1$H NMR (400 MHz, CD$_3$OD): 7.48 (t, 1H), 7.28 (dt, 1H), 7.22 (dd, 1H), 7.12 (t, 1H), 6.98 (d, 1H), 2.77 (d, 3H); MS (EI) for C$_{18}$H$_{10}$ClF$_4$N$_3$O$_2$: 412 (MH$^+$).

2-chloro-4-{6,9-difluoro-1-methyl-8-[(2-piperidin-1-ylethyl)oxy]-3H-pyrazolo[3,4-c]isoquinolin-5-yl}phenol. $^1$H NMR (400 MHz, d$_6$-DMSO): 13.8 (s, 1H), 10.58 (s, 1H), 9.50 (s, 1H) 7.50 (m, 2H), 7.32 (d, 1H), 7.05 (d, 1H), 4.75 (t, 2H), 3.65-3.46 (m, 4H), 3.18-3.01 (m, 2H), 2.83-2.65 (m, 2H), 1.95-1.80 (m, 2H), 1.80-1.60 (m, 3H), 1.45-1.37 (m, 1H); MS (EI) for C$_{24}$H$_{23}$N$_4$O$_2$ClF$_2$: 473 (MH$^+$).

2-chloro-4-(8-{[2-(4-ethylpiperazin-1-yl)ethyl]oxy}-6,9-difluoro-1-methyl-3H-pyrazolo[3,4-c]isoquinolin-5-yl)phenol. $^1$H NMR (400 MHz, d$_6$-DMSO): 13.8 (s, 1H), 11.18 (s, 1H), 10.8 (s, 1H), 7.65-7.55 (m, 2H), 7.37 (d, 1H), 7.18 (d, 1H), 4.39 (t, 2H), 3.20-2.45 (m, 12H), 1.25-1.05 (m, 4H); MS (EI) for C$_{25}$H$_{26}$N$_4$O$_2$ClF$_2$: 503 (MH$^+$).

2-chloro-4-(8-{[2-(diethylamino)ethyl]oxy}-6,9-difluoro-1-methyl-3H-pyrazolo[3,4-c]isoquinolin-5-yl)phenol. $^1$H NMR (400 MHz, d$_6$-DMSO): 13.8 (s, 1H), 10.58 (s, 1H), 10.1 (s, 1H), 7.50-7.43 (m, 2H), 7.32 (d, 1H), 7.07 (d, 1H), 4.65 (t, 2H), 3.64 (t, 2H), 3.30-3.26 (m, 4H), 2.74 (d, 3H), 1.30-1.26 (m, 6H); MS (EI) for C$_{23}$H$_{23}$ClF$_2$N$_4$O$_2$: 461 (MH$^+$).

2-bromo-4-(6,9-difluoro-1-methyl-8-{[2-(methyloxy)ethyl]oxy}-3H-pyrazolo[3,4-c]isoquinolin-5-yl)-5-fluorophenol. $^1$H NMR (400 MHz, CD$_3$OD): 7.64 (d, 2H), 7.21 (q, 1H), 6.72 (d, 2H), 4.37 (t, 3H), 3.83 (t, 3H), 3.46 (s, 3H), 2.81 (d, 3H); MS (EI) for C$_{20}$H$_{15}$N$_3$O$_3$BrF$_3$: 483 (MH$^+$).

Example 23

2-chloro-4-(6-fluoro-1-methyl-7-(methyloxy)-8-{[(1-methylpiperidin-4-yl)methyl]oxy}-3H-pyrazolo[3,4-c]isoquinolin-5-yl)phenol hydrochloride: To a suspension of 3-hydroxy-4-(methyloxy)benzoic acid (25 g, 149 mmol.) in methanol (200 mL) was added concentrated sulfuric acid (1 mL) and the mixture was brought to reflux over 18 hours. The resulting homogeneous solution was cooled to room temperature, concentrated in vacuo and the residual oil taken into ethyl acetate (300 mL). The solution was washed once with water, saturated aqueous sodium hydrogencarbonate then brine and dried over anhydrous magnesium sulfate. Filtration and concentration gave methyl 3-hydroxy-4-(methyloxy)benzoate (27 g, 100% yield) as an oil. $^1$H NMR (400 MHz, CDCl$_3$): 7.59 (dd, 1H), 7.57 (d, 1H), 6.85 (d, 1H), 5.72 (s, 1H), 3.93 (s, 3H), 3.87 (s, 3H).

Methyl 3-hydroxy-4-(methyloxy)benzoate (27 g, 149 mmol.) was taken into acetic anhydride (150 mL) followed by addition of sodium acetate (24 g, 298 mmol.) and the resulting mixture was stirred at room temperature over 20 hours. The solid was filtered and washed once with ethyl acetate and the combined organic layers concentrated in vacuo to a slurry. The solid was collected by filtration, washed once with water and dried in vacuo to provide methyl 3-(acetyloxy)-4-(methyloxy)benzoate (25.9 g, 77% yield) as a white solid. $^1$H NMR (400 MHz, CDCl$_3$): 7.92 (dd, 1H), 7.70 (d, 1H), 6.97 (d, 1H), 3.88 (s, 3H), 3.87 (s, 3H), 2.32 (s, 3H).

A mixture of 90% nitric acid (40 mL) and concentrated sulfuric acid (8 mL) were cooled to −5° C. followed by portionwise addition of solid methyl 3-(acetyloxy)-4-(methyloxy)benzoate (25.9 g, 115 mmol.) over 25 minutes. After stirring for 5 minutes the solution was poured onto ice and the aqueous mixture was extracted once with dichloromethane. The organic solution was then washed with dilute aqueous sodium hydrogencarbonate (3×) then once with water and dried over anhydrous magnesium sulfate. Filtration and concentration followed by suspension of the solid residue in hexanes and filtration gave methyl 3-(acetyloxy)-4-(methyloxy)-5-nitrobenzoate (27.2 g, 88% yield) as a white solid on drying. $^1$H NMR (400 MHz, CDCl$_3$): 8.38 (d, 1H), 7.99 (d, 1H), 4.00 (s, 3H), 3.95 (s, 3H), 2.40 (s, 3H).

A solution of methyl 3-(acetyloxy)-4-(methyloxy)-5-nitrobenzoate (27.2 g, 101 mmol.) in ethyl acetate (200 mL) with 10% palladium on carbon (1.0 g) added was hydrogenated at atmospheric pressure until complete reduction to the aniline was observed by TLC (>24 hours). The mixture was then filtered through a bed of celite and the filtrate concentrated to provide methyl 3-(acetyloxy)-5-amino-4-(methyloxy)benzoate (19.8 g, 82% yield) as an oil that slowly crystallized on standing. $^1$H NMR (400 MHz, CDCl$_3$): 7.30 (d, 1H), 7.14 (d, 1H), 3.97 (br d, 2H), 3.85 (s, 3H), 3.82 (s, 3H), 2.34 (s, 3H).

A solution of methyl 3-(acetyloxy)-5-amino-4-(methyloxy)benzoate (1.0 g, 4.18 mmol.) in 1,2-dimethoxyethane (10 mL) was cooled to 0° C. followed by slow addition of boron trifluoride etherate (689 uL, 5.43 mmol.) over 1-2 minutes. Tert-butyl nitrite (550 uL, 4.59 mmol.) was then slowly added and the resulting mixture was allowed to stir an additional 15 minutes at 0° C., during which time a solid formed. The solid was collected by filtration then washed twice with ethyl ether and twice with ethyl acetate. The intermediate diazonium salt (1.02 g) was thus obtained as a pale yellow solid. The diazonium salt was then suspended in 1,2,4-trichlorobenzene (3 mL) and the mixture was heated to 110° C. in an open flask for 17 hours. On cooling to room temperature the reaction mixture was directly loaded onto a silca gel flash column and eluted with a solvent gradient of 100% hexanes to 10% ethyl acetate in hexanes. Fractions containing the desired product were combined, concentrated and dried in vacuo to afford methyl 3-fluoro-5-hydroxy-4-(methyloxy)benzoate (300 mg, 48% yield) as a white solid. $^1$H NMR (400 MHz, CD$_3$OD): 7.30 (tr, 1H), 7.24 (dd, 1H), 3.94 (d, 3H), 3.86 (s, 3H).

To a solution of methyl 3-fluoro-5-hydroxy-4-(methyloxy)benzoate (3.63 g, 18.1 mmol.) in DMF (25 mL) was added cesium carbonate (8.9 g, 27.2 mmol.) followed by benzyl bromide (2.8 mL, 23.6 mmol.) and the mixture was stirred at room temperature over 12 hours. The mixture was then partitioned with ethyl ether and water and the organic phase washed with water (3×) then saturated aqueous sodium chloride and dried over anhydrous magnesium sulfate. Filtration and concentration followed by purification of the residue by silica gel flash chromatography using 50% hexanes in chloroform as eluent afforded methyl 3-fluoro-4-(methyloxy)-5-[(phenylmethyl)oxy]benzoate (3.54 g, 67% yield) as a colorless solid after concentration of the pure fractions and drying in vacuo.

Methyl 3-fluoro-4-(methyloxy)-5-[(phenylmethyl)oxy]benzoate (3.54 g, 12.2 mmol.) was taken into anhydrous THF under a nitrogen atmosphere and the resulting solution was cooled to 0° C. A solution of lithium aluminum hydride (1.0M in THF, 20 mL) was slowly added and the solution was allowed to stir an additional 30 minutes at 0° C. Ethyl acetate (10 mL) was then slowly added followed by slow addition of 50% aqueous sodium hydroxide in portions until a granular precipitate was formed. Addition of anhydrous magnesium sulfate followed by filtration and washing the solid with ethyl ether then concentration of the combined organic layers gave an oily residue. Purification by silica gel flash chromatography using 2:1 hexanes:ethyl acetate as eluent provided {3-fluoro-4-(methyloxy)-5-[(phenylmethyl)oxy]phenyl}methanol (2.69 g, 84% yield) as a colorless oil after concentration of the pure fractions and drying in vacuo. GCMS for C$_{15}$H$_{15}$O$_3$F: 262 (M$^+$).

A solution of {3-fluoro-4-(methyloxy)-5-[(phenylmethyl)oxy]phenyl}methanol (2.69 g, 10.26 mmol.) in dichloromethane (40 mL) was cooled to 0° C. followed by addition of pyridine (913 uL, 11.3 mmol.) then thionyl chloride (750 uL, 10.3 mmol.). The mixture was then allowed to warm to room temperature followed by addition of a second aliquot of pyridine (400 uL). After 5 minutes the organic solution was washed once with 0.1M aqueous hydrochloric acid then dried over anhydrous magnesium sulfate. Filtration and concentration afforded 5-(chloromethyl)-1-fluoro-2-(methyloxy)-3-

[(phenylmethyl)oxy]benzene (2.88 g, 100% yield) as a clear oil that was used without further purification. GCMS for $C_{15}H_{14}O_2FCl$: 280 (M$^+$).

5-(Chloromethyl)-1-fluoro-2-(methyloxy)-3-[(phenylmethyl)oxy]benzene (2.88 g, 10.26 mmol.) was taken into DMF (15 mL) followed by addition of potassium cyanide (1.0 g, 15.4 mmol.) and the resulting mixture was allowed to stir at room temperature over 12 hours. The mixture was then partitioned with ethyl ether and water and the organic phase washed with water (3×) then saturated aqueous sodium chloride and dried over anhydrous magnesium sulfate. Filtration and concentration gave {3-fluoro-4-(methyloxy)-5-[(phenylmethyl)oxy]phenyl}acetonitrile (2.69 g, 97% yield) as a clear oil. GCMS for $C_{16}H_{14}O_2FN$: 271 (M$^+$).

To a solution of {3-fluoro-4-(methyloxy)-5-[(phenylmethyl)oxy]phenyl}acetonitrile (2.69 g, 9.9 mmol.) in THF (25 mL) was added 1-acetylimidazole (2.2 g, 19.8 mmol.) and the resulting solution was cooled to 0° C. Sodium hydride (60% mineral oil dispersion, 800 mg, 19.8 mmol.) was added in portions over 5 minutes and the mixture was then allowed to slowly warm to room temperature over 30 minutes. The solution was then concentrated and the oily residue partitioned with ethyl ether and 0.2M aqueous sodium hydroxide. The organic layer was discarded and the aqueous phase acidified to pH 2 by portionwise addition of concentrated aqueous hydrochloric acid and extracted once with ethyl ether. The organic layer was then washed once with brine then dried over anhydrous sodium sulfate, filtered and concentrated to give the intermediate acetyl derivative (2.74 g) as a pale yellow crystalline solid. The acetyl derivative was then taken into ethanol (30 mL) followed by addition of tert-butyl hydrazine hydrochloride (2.5 g, 19.8 mmol.) and the mixture heated to 75° C. for 12 hours. On cooling to room temperature the resulting solution was transferred to a 250 mL Parr shaker vessel followed by addition of 10% palladium on carbon (500 mg) and the mixture was hydrogenated at 50 psi over 9 hours. The catalyst was then removed by filtration through a bed of celite and the filtrate concentrated. The residue was partitioned with ethyl acetate and water followed by addition of solid sodium hydrogencarbonate in portions until the pH of the aqueous phase was neutral. The organic layer was then washed once with brine and dried over anhydrous magnesium sulfate. Filtration and concentration afforded a white solid residue that was suspended in 50% ethyl ether in hexanes. The mixture was then filtered and the solid washed with additional 50% ethyl ether in hexanes then dried in vacuo to give 5-[5-amino-1-(1,1-diethylethyl)-3-methyl-1H-pyrazol-4-yl]-3-fluoro-2-(methyloxy)phenol (2.43 g, 84% yield) as a white solid. $^1$H NMR (400 MHz, CD$_3$OD): 9.68 (s, 1H), 6.58 (dd, 1H), 6.54 (dd, 1H), 4.58 (s, 2H), 3.78 (s, 3H), 2.02 (s, 3H), 1.53 (s, 9H); MS (EI) for $C_{15}H_{20}N_3O_2F$: 294 (MH$^+$).

5-[5-Amino-1-(1,1-diethylethyl)-3-methyl-1H-pyrazol-4-yl]-3-fluoro-2-(methyloxy)phenol (2.2 g, 7.5 mmol.) and 3-chloro-4-[(phenylmethyl)oxy]benzaldehyde (2.23 g, 8.6 mmol.) were taken into acetic acid (25 mL) and the resulting mixture heated to 90° C. over 12 hours. An additional aliquot of benzaldehyde (250 mg) was then added and heating was continued an additional 7 hours. At this time air was bubbled through the solution at a steady rate while maintaining a temperature of 90° C. then the mixture was allowed to cool to room temperature. The acetic acid was removed and the residue partitioned with saturated aquyeous sodium hydrogencarbonate and ethyl acetate. The organic layer was then washed once with brine then dried over anhydrous sodium sulfate, filtered and concentrated to give a residue containing roughly a 1:1 mixture of two cyclization products. The desired cyclization isomer was purified by silica gel flash chromatography using 2:1 hexanes ethyl acetate as eluent to afford 5-{3-chloro-4-[(phenylmethyl)oxy]phenyl}-3-(1,1-dimethylethyl)-6-fluoro-1-methyl-7-(methyloxy)-3H-pyrazolo[3,4-c]isoquinolin-8-ol (1.73 g, 44% yield) as a yellow solid after concentration and drying of the pure fractions in vacuo. $^1$H NMR (400 MHz, CDCl$_3$): 7.66 (dd, 1H), 7.59 (d, 1H), 7.54 (d, 1H), 7.46-7.34 (m, 5H), 7.07 (d, 1H), 6.54 (s, 1H), 5.25 (S, 2H), 4.03 (d, 3H), 2.80 (s, 3H), 1.83 (s, 9H); MS (EI) for $C_{29}H_{27}N_3O_3FCl$: 520 (MH$^+$).

5-{3-Chloro-4-[(phenylmethyl)oxy]phenyl}-3-(1,1-dimethylethyl)-6-fluoro-1-methyl-7-(methyloxy)-3H-pyrazolo[3,4-c]isoquinolin-8-ol (1.32 g, 2.6 mmol.) and cesium carbonate (1.78 g, 5.4 mmol.) were taken into DMF (15 mL) followed by addition of 1,1-dimethylethyl 4-{[(methylsulfonyl)oxy]methyl}piperidine-1-carboxylate (990 mg, 3.4 mmol.) and the mixture was heated to 90° C. over 12 hours. At this time additional aliquots of both reagent were added and heating was continued an additional 12 hours. The mixture was then partitioned with ethyl acetate and water and the organic phase washed with water (3×) then saturated aqueous sodium chloride and dried over anhydrous magnesium sulfate. Filtration and concentration then purification of the residue by silica gel flash chromatography using 3:1 hexanes: ethyl acetate as eluent gave 1,1-dimethylethyl-4-({[5-{3-chloro-4-[(phenylmethyl)oxy]phenyl}-3-(1,1-dimethylethyl)-6-fluoro-1-methyl-7-(methyloxy)-3H-pyrazolo[3,4-c]isoquiolin-8-yl]oxy}methyl)piperidine-1-carboxylate (1.35 g, 74% yield) as a light yellow solid after concentration and drying of the pure fractions in vacuo. MS (EI) for $C_{40}H_{46}N_4O_5FCl$: 717 (MH$^+$).

1,1-Dimethylethyl-4-({[5-[3-chloro-4-[(phenylmethyl)oxy]phenyl}-3-(1,1-dimethylethyl)-6-fluoro-1-methyl-7-(methyloxy)-3H-pyrazolo[3,4-c]isoquiolin-8-yl]oxy}methyl)piperidine-1-carboxylate (1.35 g, 1.9 mmol.) was taken into dichloromethane (25 mL) then cooled to 0° C. followed by addition of TFA (10 mL). The mixture was allowed to slowly warm to room temperature over one hour followed by addition of chloroform (25 mL) and water (25 mL) and the pH of the aqueous phase adjusted to 10 by portionwise addition of 50% aqueous sodium hydroxide. The layers were separated and the aqueous phase extracted once with chloroform. The combined organic layers were dried over anhydrous sodium sulfate then filtered and concentrated to obtain the intermediate piperidine as an oil that slowly crystallizes. The piperidine was taken into 1,2-dichloroethane (25 mL) followed by addition of 37 W % aqueous formaldehyde (1 mL, 13.3 mmol.) and sodium triacetoxyborohydride (800 mg, 3.8 mmol.). The mixture was allowed to stir at room temperature over one hour then partitioned with 0.5M aqueous potassium carbonate and chloroform. The layers were separated and the aqueous phase extracted once with chloroform then the combined organic layers were dried over anhydrous sodium sulfate. Filtration and concentration then crystallization of the residue from ethyl ether gave a white solid. A second crop was obtained by crystallization of the mother liquor residue and the two crops were combined to provide 5-{3-chloro-4-[(phenylmethyl)oxy]phenyl}-3-(1,1-dimethylethyl)-6-fluoro-1-methyl-7-(methyloxy)-8-{[(1-methylpiperidin-4-yl)methyl]oxy}-3H-pyrazolo[3,4-c]isoquinoline (975 mg, 82% yield) as a white crystalline solid. MS (EI) for $C_{36}H_{40}N_4O_3FCl$: 631 (MH$^+$).

5-{3-Chloro-4-[(phenylmethyl)oxy]phenyl}-3-(1,1-dimethylethyl)-6-fluoro-1-methyl-7-(methyloxy)-8-{[(1-methylpiperidin-4-yl)methyl]oxy}-3H-pyrazolo[3,4-c]isoquinoline (975 mg, 1.54 mmol.) was taken into TFA (25 mL) and the mixture was warmed to 70° C. for 2.5 hours. The solution was then concentrated and the residue taken into aqueous methanol and purified by preparative reverse phase HPLC to give 2-chloro-4-{6-fluoro-1-methyl-7-(methyloxy)-8-{[[(1-methylpiperidin-4-yl)methyl]oxy}-3H-pyrazolo[3,4-c]isoquinolin-5-yl)phenol trifluoroacetate (548 mg, 59% yield) as a light yellow amorphous solid after lyophillization of the combined pure fractions. $^1$H NMR (400 MHz, CD$_3$OD): 7.63-7.61 (m, 2H), 7.22 (ddd, 1H), 7.07 (d, 1H), 4.35 (d, 2H), 3.92 (s, 3H), 3.63 (br d, 2H), 3.13 (br tr, 2H), 2.95 (s, 3H), 2.91 (s, 3H), 2.36-2.28 (m, 1H), 2.23 (br d, 2H), 1.89-1.78 (m, 2H); MS (EI) for C$_{25}$H$_{26}$N$_4$O$_3$FCl: 485 (MH$^+$).

Using the same or analogous synthetic techniques and/or substituting with alternative reagents, the following compounds of the invention were prepared:

3-fluoro-4-(6-fluoro-1-methyl-7-(methyloxy)-8-{[2-(methyloxy)ethyl]oxy}-3H-pyrazolo[3,4-c]isoquinolin-5-yl)phenol. $^1$H NMR (400 MHz, d$_4$-MeOH): 7.59, (s, 1H), 7.35 (t, J=8.6 Hz, 1H), 6.73 (dd, J=2.0, 8.4 Hz, 1H), 6.60 (dd, J=2.0, 11.6 Hz, 1H), 4.67-4.44 (m, 2H), 3.91-3.89 (m, 5H), 3.48 (s, 3H), 2.86 (s, 3H); MS (EI) for C$_{21}$H$_{19}$N$_3$O$_4$F$_2$: 416 (MH$^+$).

2-chloro-4-(6-fluoro-1-methyl-7-(methyloxy)-8-{[2-(methyloxy)ethyl]oxy}-3H-pyrazolo[3,4-c]isoquinolin-5-yl)phenol. $^1$H NMR (400 MHz, DMSO-d$_6$): δ 10.43 (s, 1H), 7.56 (s, 1H), 7.50 (s, 1H), 7.30 (m, 1H), 7.03 (m, 1H), 4.48 (m, 2H), 3.82 (m, 5H), 2.81 (s, 3H); MS (EI) for C$_{21}$H$_{19}$ClFN$_3$O$_4$: 432 (MH$^+$).

2-chloro-4-[8-{[2-(4-ethylpiperazin-1-yl)ethyl]oxy}-6-fluoro-1-methyl-7-(methyloxy)-3H-pyrazolo[3,4-c]isoquinolin-5-yl]phenol. $^1$H NMR (400 MHz, d$_4$-MeOH): 7.73 (tr, 1H), 7.69 (s, 1H), 7.49 (d tr, 1H), 7.13 (d, 1H), 4.96 (tr, 2H), 4.15-4.05 (br, 2H), 3.99 (s, 3H), 3.94 (tr, 2H), 3.85-3.55 (br, 6H), 3.36 (q, 2H), 3.04 (s, 3H), 1.42 (tr, 3H). MS (EI) for C$_{26}$H$_{30}$N$_5$O$_3$ClF: 515 (MH$^+$).

2-chloro-4-[8-{[2-(diethylamino)ethyl]oxy}-6-fluoro-1-methyl-7-(methyloxy)-3H-pyrazolo[3,4-c]isoquinolin-5-yl]phenol. $^1$H NMR (400 MHz, d$_4$-MeOH): 7.73 (s, 1H), 7.70 (s, 1H), 7.49 (d, 1H), 7.13 (d, 1H), 4.88 (br tr, 2H), 3.97 (s, 3H), 3.85 (br tr, 2H), 3.49-3.43 (m, 4H), 3.05 (s, 3H), 1.46 (tr, 6H). MS (EI) for C$_{24}$H$_{27}$N$_4$O$_3$ClF: 474 (MH$^+$).

2-chloro-4-(6-fluoro-1-methyl-7-(methyloxy)-8-{[2-(4-methylpiperazin-1-yl)ethyl]oxy}-3H-pyrazolo[3,4-c]isoquinolin-5-yl)phenol. $^1$H NMR (400 MHz, d$_6$-DMSO): 7.56 (s, 1H), 7.53 (tr, 1H), 7.33 (d tr, 1H), 7.12 (d, 1H), 4.87 (br tr, 2H), 3.98-3.50 (br m, 10H), 3.87 (s, 3H), 2.84 (br s, 6H). MS (EI) for C$_{25}$H$_{28}$N$_5$O$_3$ClF: 501 (MH$^+$).

Example 24

4-(6-fluoro-1-methyl-9-(methyloxy)-8-{[(1-methylpiperidin-4-yl)methyl]oxy}-3H-pyrazolo[3,4-c]isoquinolin-5-yl)-2-methylphenol hydrochloride: D(+)-10-Camphorsulfonic acid (5.1 g, 22 mmol), 4-fluoro-2,6-bis(hydroxymethyl)phenol (74.5 g, 432 mmol), and 2,2-dimethoxypropane (90 mL, 734 mmol) were dissolved in acetone. To the solution was added 45 g of 4 Å molecular sieves. The resulting suspension was heated to 55° C. for 1 h and then cooled to rt. The mixture was neutralized with aqueous NaHCO$_3$ (sat) and diluted with ethyl acetate. Solids were removed by filtration. The solvent volume was reduced in vacuo. Ethyl acetate and aqueous NaHCO$_3$ (sat) were added, and the layers were partitioned. The organic phase was washed with brine, dried over magnesium sulfate, filtered, and concentrated in vacuo. Crude (6-fluoro-2,2-dimethyl-4H-1,3-benzodioxin-8-yl)methanol was isolated as an orange oil (91.7 g, 432 mmol, 100%). (17.2 g, 86.6 mmol, 91% yield). $^1$H NMR (400 MHz, CDCl$_3$): δ 7.01 (dd, 1H), 6.79 (dd, 1H), 5.20 (t, 1H), 4.77 (s, 2H), 4.40 (d, 2H), 1.42 (s, 6H); GCMS for C$_{11}$H$_{13}$FO$_3$: 212 (M$^+$)

The crude (6-fluoro-2,2-dimethyl-4H-1,3-benzodioxin-8-yl)methanol (35.15 g, 166 mmol) was dissolved in biphasic mixture of CH$_2$Cl$_2$ (230 mL) and water (180 mL). The mixture was cooled to 0° C., and TEMPO (519 mg, 3.3 mmol) and KBr (2.0 g, 16.6 mmol) were added. Finally, NaClO (aq) (5%, 500 mL, 332 mmol) saturated with NaHCO$_3$ was added gradually by addition funnel. The mixture was stirred for 15 min after the all the reagents were added. The layers were partitioned, and the aqueous phase was extracted with CH$_2$Cl$_2$. The organic extracts were combined, dried over magnesium sulfate, filtered, and concentrated in vacuo. The resulting solid was triturated sequentially with hexanes and methanol to yield a white crystalline solid. This procedure was repeated two more times on a further 38 g of (6-fluoro-2,2-dimethyl-4H-1,3-benzodioxin-8-yl)methanol (179 mmol). The triturated solids of all three experiments were combined to provide 51.1 g of 6-fluoro-2,2-dimethyl-4H-1,3-benzodioxine-8-carbaldehyde (243 mmol, 70% yield). $^1$H NMR (400 MHz, CDCl$_3$): δ 10.37 (d, 1H), 7.41 (dd, 1H), 6.96-6.94 (m, 1H), 4.88 (s, 2H), 1.61 (s, 6H).

A solution of 6-fluoro-2,2-dimethyl-4H-1,3-benzodioxine-8-carbaldehyde (20 g, 95 mmol) in dichloroethane (100 mL) was treated with m-CPBA (70% pure, 28.1 g, 114 mmol) at 70° C. for 20 min. After cooling to rt, ethyl acetate (300 mL) was added. The organic mixture was then washed with 10% aqueous sodium thiosulfate followed by 1 N KOH (114 mmol) followed by 3 washes with aqueous NaHCO$_3$ (sat). The organic phase was then dried over magnesium sulfate, filtered, and concentrated in vacuo. The residue was dissolved in THF (100 mL), and then 1 M KOH (100 mL) was added. The mixture was stirred for 20 min at rt. The pH was adjusted to 6 by the slow addition of 1 N HCl (aq). Ethyl acetate was then added, and the layers were partitioned. The aqueous phase was extracted with ethyl acetate. The organic extracts were combined, dried over magnesium sulfate, filtered, and concentrated in vacuo. 6-Fluoro-2,2-dimethyl-4H-1,3-benzodioxin-8-ol was isolated as a brown liquid (17.2 g, 86.6 mmol, 91% yield). $^1$H NMR (400 MHz, CDCl$_3$): δ 6.56 (dd, 1H), 6.28-6.25 (m, 1H), 5.57 (br s, 1H), 4.79 (s, 2H), 1.56 (s, 6H); GCMS for C$_{10}$H$_{11}$FO$_3$: 198 (M$^+$).

A solution of 6-fluoro-2,2-dimethyl-4H-1,3-benzodioxin-8-ol (21.4 g, 108 mmol) in DMF (200 mL) was treated with cesium carbonate (70.4 g, 216 mmol) and benzyl bromide (14.1 mL, 119 mmol) for 1 h 45 min at rt. Water was added and the resulting aqueous mixture was extracted twice with ethyl acetate. The organic extracts were combined, washed with brine, dried over magnesium sulfate, filtered, and concentrated in vacuo. The residue was recrystallized from ethanol. The recovered white crystalline product was rinsed with hexanes providing 6-fluoro-2,2-dimethyl-8-[(phenylmethyl)oxy]-4H-1,3-benzodioxine (23.04 g, 80 mmol, 74% yield). $^1$H NMR (400 MHz, CDCl$_3$): δ7.43-7.29 (m, 5H), 6.51 (dd, 1H), 6.31 (dd, 1H), 5.15 (s, 2H), 4.80 (s, 2H), 1.59 (s, 6H); GCMS for C$_{17}$H$_{17}$FO$_3$: 288 (M$^+$).

To 6-fluoro-2,2-dimethyl-8-[(phenylmethyl)oxy]-4H-1,3-benzodioxine (9.9 g, 34.3 mmol) was added ethanol (50 mL) and 4 N HCl (aq) (50 mL). The mixture began as a suspension but became homogeneous while stirring for 20 min at 85° C. After cooling to rt, the ethanol was removed in vacuo, and the resulting aqueous mixture was extracted twice with ethyl acetate. The organic extracts were combined, dried over magnesium sulfate, filtered, and concentrated in vacuo. 4-Fluoro-2-(hydroxymethyl)-6-[(phenylmethyl)oxy]phenol was isolated as an orange oil in quantitative yield. $^1$H NMR (400 MHz, CDCl$_3$): δ 7.42-7.36 (m, 5H), 6.66-6.62 (m, 2H), 5.08 (s, 2H), 4.70 (s, 2H), 4.37 (br s, 2H).

Iodomethane (24 mL, 382 mmol) and cesium carbonate (25 g, 76.4 mmol) were added to a solution of 4-fluoro-2-(hydroxymethyl)-6-[(phenylmethyl)oxy]phenol (9.5 g, 38.2 mmol) in DMF (125 mL). The mixture was stirred for 1 h at rt, and then water was added. The resulting aqueous mixture was extracted twice with ethyl acetate. The organic extracts were combined, dried over magnesium sulfate, filtered, and concentrated in vacuo. The residue was purified by flash chromatography (70% hexanes, 30% ethyl acetate) to provide {5-fluoro-2-(methyloxy)-3-[(phenylmethyl)oxy]phenyl}methanol as a yellow solid (7.9 g, 30.2 mmol, 79% yield). $^1$H NMR (400 MHz, CDCl$_3$): δ 7.44-7.32 (m, 5H), 6.69-6.63 (m, 2H), 5.08 (s, 2H), 4.67 (d, 2H), 3.86 (s, 3H).

A THF (25 mL) solution of {5-fluoro-2-(methyloxy)-3-[(phenylmethyl)oxy]phenyl}methanol (6.94 g, 26 mmol) was cooled to 0° C. and was then treated with thionyl chloride (2.5 mL, 34 mmol) and DMF (5.0 mL, 65 mmol) for 30 min. Ethyl acetate and ice water were then added. The layers were partitioned, and the aqueous phase was extracted with ethyl acetate. The organic extracts were combined, dried over magnesium sulfate, filtered, and concentrated in vacuo. The product, 1-(chloromethyl)-5-fluoro-2-(methyloxy)-3-[(phenylmethyl)oxy]benzene, was obtained as an orange oil (6.82 g, 24.3 mmol, 93% yield), which solidified upon storage in the freezer. $^1$H NMR (400 MHz, CDCl$_3$): δ 7.45-7.26 (m, 5H), 6.72-6.66 (m, 2H), 5.09 (s, 2H), 4.61 (s, 2H), 3.91 (s, 3H).

To a solution of 1-(chloromethyl)-5-fluoro-2-(methyloxy)-3-[(phenylmethyl)oxy]benzene (6.82 g, 24.3 mmol) in DMF (60 mL) was added potassium cyanide (3.2 g, 48.6 mmol), and the resulting mixture was stirred at 50° C. for 2 h 20 min before cooling to rt. Water and brine were added, and the resulting aqueous mixture was extracted with ethyl acetate. The organic phase was washed twice with brine, dried over magnesium sulfate, filtered, and concentrated in vacuo. The residue was purified by flash chromatography (80% hexanes, 20% ethyl acetate) to afford {5-fluoro-2-(methyloxy)-3-[(phenylmethyl)oxy]phenyl}acetonitrile (5.3 g, 19.5 mmol, 80% yield) as a colorless oil which eventually solidified. $^1$H NMR (400 MHz, CDCl$_3$): δ 7.42-7.32 (m, 5H), 6.69-6.67 (m, 2H), 5.08 (s, 2H), 3.89 (s, 3H), 3.70 (s, 2H).

A solution of {5-fluoro-2-(methyloxy)-3-[(phenylmethyl)oxy]phenyl}acetonitrile (5.3 g, 19.5 mmol) in THF (60 mL) was cooled to 0° C. Sodium hydride (60% dispersion in mineral oil, 1.64 g, 41 mmol) was added followed by acetylimidazole (3.2 g, 29.3 mmol). The mixture was heated to 40° C. for 15 min before cooling to rt. Water was added, and this mixture was acidified with 1 N HCl (45 mL). Ethyl acetate was added and the layers were partitioned. The aqueous phase was extracted with ethyl acetate. The organic extracts were combined, dried over magnesium sulfate, filtered, and concentrated in vacuo. The residue was purified by flash chromatography (70% hexanes, 30% ethyl acetate) to provide 2-{5-fluoro-2-(methyloxy)-3-[(phenylmethyl)oxy]phenyl}-3-oxobutanenitrile as a colorless oil (4.9 g, 15.6 mmol, 80% yield). $^1$H NMR (400 MHz, CDCl$_3$): (mixture of tautomers) δ 9.70 (s, 0.2H), 7.42-7.33 (m, 5H), 6.82 (dd, 0.2H), 6.75 (dd, 0.8H) 6.69-6.64 (m, 1H), 5.09 (s, 2H), 4.90 (s, 0.8H), 3.89 (s, 2.1H), 3.83 (s, 0.9H), 2.38 (s, 0.9H), 2.29 (s, 2.11H).

To a solution of 2-{5-fluoro-2-(methyloxy)-3-[(phenylmethyl)oxy]phenyl}-3-oxobutanenitrile (5.7 g, 18.1 mmol) in ethanol (60 mL) was added t-butylhydrazine hydrochloride (6.8 g, 54 mmol). The mixture was stirred for 2 h at 75° C. before cooling to rt and stirring for an additional 14 h. The volatile materials were removed in vacuo. To the residue was added water, and the resulting aqueous mixture was extracted with ethyl acetate 3 times. The organic extracts were combined and washed with 1 N HCl (aq) followed by aqueous NaHCO$_3$ (sat). The organics were then dried over magnesium sulfate, filtered, and concentrated in vacuo to provide 1-(1,1-dimethylethyl)-4-{5-fluoro-2-(methyloxy)-3-[{phenylmethyl)oxy]phenyl}-3-methyl-1H-pyrazol-5-amine as a pale yellow syrup (6.81 g, 17.8 mmol, 98% yield). $^1$H NMR (400 MHz, CDCl$_3$): δ 7.45-7.32 (m, 5H), 6.60 (dd, 1H), 6.53 (dd, 1H), 5.10 (s, 2H), 3.91 (br s, 2H), 3.55 (s, 3H), 2.20 (s, 3H), 1.67 (s, 9H); MS (EI) for C$_{22}$H$_{26}$FN$_3$O$_2$: 384 (MH$^+$).

A solution of 1-(1,1-dimethylethyl)-4-(5-fluoro-2-(methyloxy)-3-[{phenylmethyl)oxy]phenyl}-3-methyl-1H-pyrazol-5-amine (25 g, 0.0652 mol) in a mixture of THF-ethyl acetate (1:1, 300 mL) was hydrogenated over 10% Pd—C (2.5 g) at 40 Psi for 2 h. The catalyst was filtered off, and the filtrate was concentrated. The resulting crude was triturated with diethyl ether; a white solid was precipitated. It was collected by filtration, washed with an additional portion of diethyl ether and dried in vacuo to give 17.8 g of 3-[5-amino-1-(1,1-dimethylethyl)-3-methyl-1H-pyrazol-4-yl]-5-fluoro-2-(methyloxy)phenol (93%). $^1$H NMR (400 MHz, DMSO-d$_6$): δ 9.63 (s, 1H), 6.56 (dd, 1H), 6.38 (dd, 1H), 4.44 (s, 2H), 3.37 (s, 3H), 1.98 (s, 3H), 1.56 (s, 9H); MS (EI) for C$_{15}$H$_{20}$FN$_3$O$_2$: 294 (MH$^+$)

To 3-[5-amino-1-(1,1-dimethylethyl)-3-methyl-1H-pyrazol-4-yl]-5-fluoro-2-(methyloxy)phenol (150 mg, 0.51 mmol) was added 4-benzyloxy-3-methylbenzaldehyde (115 mg, 0.51 mmol) and acetic acid (2 mL). The mixture was heated to 120° C. and stirred overnight. The acetic acid was removed in vacuo. The residue was purified by flash chromatography (70% hexanes, 30% ethyl acetate) to provide 3-(1,1-dimethylethyl)-6-fluoro-1-methyl-9-(methyloxy)-5-{3-methyl-4-[(phenylmethyl)oxy]phenyl}-3H-pyrazolo[3,4-c]isoquinolin-8-ol (207 mg, 0.42 mmol, 81% yield) as an orange foam. $^1$H NMR (400 MHz, CDCl$_3$): δ 7.52-7.35 (m, 7H), 6.99 (br d, 1H), 6.85 (d, 1H), 5.17 (s, 2H), 3.82 (s, 3H), 2.89 (s, 3H), 2.39 (s, 3H), 1.88 (s, 9H); MS (EI) for C$_{30}$H$_{30}$FN$_3$O$_3$: 500 (MH$^+$).

To a solution of 3-(1,1-dimethylethyl)-6-fluoro-1-methyl-9-(methyloxy)-5-{3-methyl-4-[(phenylmethyl)oxy]phenyl}-3H-pyrazolo[3,4-c]isoquinolin-8-ol (207 mg, 0.42 mmol) in DMF (2 mL) was added cesium carbonate (274 mg, 0.84 mmol) and tert-butyl 4-{[(methylsulfonyl)oxy]methyl}piperidine-1-carboxylate (135 mg, 0.46 mmol). The mixture was heated to 90° C. and stirred for 1.5 h. After cooling to rt, water was added and the resulting aqueous mixture was extracted twice with ethyl acetate. The combined organic extracts were dried over magnesium sulfate, filtered, and concentrated in vacuo. The crude residue was purified by flash chromatography (gradient: 25% ethyl acetate in hexanes to 30% ethyl acetate in hexanes) to provide 1,1-dimethylethyl 4-{[(3-(1,1-dimethylethyl)-6-fluoro-1-methyl-9-(methyloxy)-5-{3-methyl-4-[(phenylmethyl)oxy]phenyl}-3H-pyrazolo[3,4-c]isoquinolin-8-yl)oxy]methyl}piperidine-1-carboxylate (214 mg, 0.31 mmol, 73% yield) as a yellow oil. $^1$H NMR (400 MHz, CDCl$_3$): δ 7.51-7.34 (m, 7H), 6.98 (d, 1H), 6.83 (d, 1H), 5.16 (s, 2H), 4.22 (br m, 2H), 3.98 (d, 2H), 3.91 (s, 3H), 2.89 (s, 3H), 2.80 (br m, 2H), 2.37 (s, 3H), 2.12 (m, 1H), 1.93-1.88 (m, 2H), 1.85 (s, 9H), 1.48 (s, 9H), 1.39-1.35 (m, 2H); MS (I) for C$_{41}$H$_{49}$FN$_4$O$_5$: 697 (MH$^+$).

To 1,1-dimethylethyl 4-{[(3-(1,1-dimethylethyl)-6-fluoro-1-methyl-9-(methyloxy)-5-{3-methyl-4-[(phenylmethyl)oxy]phenyl}-3H-pyrazolo[3,4-c]isoquinolin-8-yl)oxy]methyl}piperidine-1-carboxylate (178 mg, 0.26 mmol) was added CH$_2$Cl$_2$ (3 mL). The solution was cooled with an ice bath and TFA (0.5 mL) was added slowly. After 1 h, the reaction mixture was diluted with CHCl$_3$ and water was added. The mixture was then basified with 1 M KOH (aq) and partitioned. The organic layer was dried over magnesium sulfate, filtered and concentrated in vacuo to provide 3-(1,1-dimethylethyl)-6-fluoro-1-methyl-9-(methyloxy)-5-{3-methyl-4-[(phenylmethyl)oxy]phenyl}-8-[(piperidin-4-ylmethyl)oxy]-3H-pyrazolo[3,4-c]isoquinoline (159 mg, 0.26 mmol, 100% yield) as a yellow sticky solid. $^1$H NMR (400 MHz, CDCl$_3$): δ 7.51-7.33 (m, 7H), 6.98 (d, 1H), 6.81 (d, 1H), 5.16 (s, 2H), 4.03 (d, 2H), 3.89 (s, 3H), 3.55 (d, 2H), 3.04-2.95 (m, 2H), 2.88 (s, 3H), 2.37 (s, 3H), 2.26 (m, 1H), 2.16 (d, 2H), 1.85 (s, 9H), 1.88-1.80 (m, 2H); MS (EI) for C$_{36}$H$_{41}$FN$_4$O$_3$: 597 (MH$^+$).

To 3-(1,1-dimethylethyl)-6-fluoro-1-methyl-9-(methyloxy)-5-{3-methyl-4-[(phenylmethyl)oxy]phenyl}-8-[(piperidin-4-ylmethyl)oxy]-3H-pyrazolo[3,4-c]iso-quinoline (159 mg, 0.26 mmol) was added dichloroethane (2 mL), 37% aqueous formaldehyde (40 μL, 0.52 mmol), and sodium triacetoxyborohydride (110 mg, 0.52 mmol). The mixture was stirred for 1 h at rt. Water and CH$_2$Cl$_2$ were added, and the layers were partitioned. The aqueous phase was extracted with CH$_2$Cl$_2$. The organic extracts were combined, dried over magnesium sulfate, filtered, and concentrated in vacuo. The crude residue was purified by flash chromatography (90% CH$_2$Cl$_2$, 10% methanol) to provide 83.1 mg of To 3-(1,1-dimethylethyl)-6-fluoro-1-methyl-9-(methyloxy)-5-{3-methyl-4-[(phenylmethyl)oxy]phenyl}-8-{[(1-methylpiperidin-4-yl)methyl]oxy}-3H-pyrazolo[3,4-c]isoquinoline (0.136 mmol, 52% yield) as a yellow film. $^1$H NMR (400 MHz, CDCl$_3$): δ 7.49-7.32 (m, 7H), 6.96 (d, 1H), 6.81 (d, 1H), 5.15 (s, 2H), 3.98 (d, 2H), 3.89 (s, 3H), 3.10 (d, 2H), 2.87 (s, 3H), 2.40 (s, 3H), 2.36 (s, 3H), 2.17 (br t, 2H), 2.03-1.96 (m, 3H), 1.84 (s, 9H), 1.62 (m, 2H); MS (EI) for C$_{37}$H$_{43}$FN$_4$O$_3$: 611 (MH$^+$).

To 3-(1,1-dimethylethyl)-6-fluoro-1-methyl-9-(methyloxy)-5-{3-methyl-4-[(phenylmethyl)oxy]phenyl}-8-{[(1-methylpiperidin-4-yl)methyl]oxy}-3H-pyrazolo[3,4-c]isoquinoline (83.1 mg, 0.136 mmol) was added TFA (2.5 mL). The resulting solution was stirred at 50° C. for 3 h. After cooling the reaction mixture to rt, TFA was removed in vacuo with methanol added to create an azeotropic mixture. The residue was purified by preparative HPLC. The product-containing fractions were concentrated, treated with 4 N HCl in dioxane, and concentrated again to generate the hydrochloride salt. The final compound, 4-(6-fluoro-1-methyl-9-(methyloxy)-8-{[(1-methylpiperidin-4-yl)methyl]oxy}-3H-pyrazolo[3,4-c]isoquinolin-5-yl)-2-methylphenol hydrochloride, was obtained as a solid (35.3 mg, 0.07 mmol, 52% yield). $^1$H NMR (400 MHz, CD$_3$OD): δ 7.44-7.34 (m, 3H), 6.95 (d, 1H), 4.27 (d, 2H), 4.01 (s, 3H), 3.69-3.58 (m, 2H), 3.66 (s, 3H), 3.16-3.11 (m, 2H), 2.99 (s, 3H), 2.92 (s, 3H), 2.30 (m, 1H), 2.23 (br d, 2H), 1.86-1.75 (m, 2H).

Using the same or analogous synthetic techniques and/or substituting with alternative reagents, the following compounds of the invention were prepared:

2-chloro-4-(6-fluoro-1-methyl-9-(methyloxy)-8-{[(1-methylpiperidin-4-yl)methyl]oxy}-3H-pyrazolo[3,4-c]isoquinolin-5-yl)phenol. $^1$H NMR (400 MHz, d$_4$-MeOH): 7.67 (s, 1H), 7.45 (d, J=8.4 Hz, 1H), 7.39 (d, J=14.0 Hz, 1H), 7.11 (d, J=8.8 Hz, 1H), 4.26 (d, J=5.6 Hz, 2H), 4.00 (s, 3H), 3.63 (d, J=13.2 Hz, 2H), 3.16-3.09 (m, 2H), 2.98 (s, 3H), 2.96 (s, 3H), 2.31 (br s, 1H), 2.22 (d, J=13.2 Hz, 2H), 1.81-1.77 (m, 2H); MS (EI) for C$_{25}$H$_{26}$ClFN$_4$O$_3$: 485 (MH$^+$).

2-chloro-4-{6-fluoro-1-methyl-9-(methyloxy)-8-[(3-pyrrolidin-1-ylpropyl)oxy]-3H-pyrazolo[3,4-c]isoquinolin-5-yl}phenol. $^1$H NMR (400 MHz, d$_4$-MeOH): 7.70 (s, 1H), 7.46 (d, J=8.8 Hz, 1H), 7.39 (d, J=14.4 Hz, 1H), 7.12 (d, J=8.4 Hz, 1H), 4.45 (t, J=5.6 Hz, 2H), 4.01 (s, 3H), 3.78-3.77 (m, 2H), 3.52-3.48 (m, 2H), 3.19-3.16 (m, 2H), 2.98 (s, 3H), 2.44-2.42 (m, 2H), 2.21 (br m, 2H), 2.09-2.07 (m, 2H); MS (EI) for C$_{25}$H$_{26}$ClFN$_4$O$_2$: 485 (MH$^+$).

4-[8-{[(2R)-2-amino-3,3-dimethylbutyl]oxy}-6-fluoro-1-methyl-9-(methyloxy)-3H-pyrazolo[3,4-c]isoquinolin-5-yl]-2-chlorophenol. $^1$H NMR (400 MHz, d$_4$-MeOH): 7.67-7.65 (m, 1H), 7.50 (d, J=13.6 Hz, 1H), 7.46-7.43 (m, 1H), 7.10 (d, J=8.4 Hz, 1H), 4.65 (dd, J=3.4, 10.4 Hz, 1H), 4.48 (dd, J=8.4, 10.4 Hz, 1H), 4.01 (s, 3H), 3.64-3.61 (m, 1H), 3.00 (s, 3H), 1.21 (s, 9H); MS (EI) for C$_{24}$H$_{26}$ClFN$_4$O$_3$: 473 (MH$^+$).

4-[8-{[(2R)-2-amino-3-methylbutyl]oxy}-6-fluoro-1-methyl-9-(methyloxy)-3H-pyrazolo[3,4-c]isoquinolin-5-yl]-2-chlorophenol. $^1$H NMR (400 MHz, d$_4$-MeOH): 7.69-7.68 (m, 1H), 7.50 (s, 1H), 7.47-7.45 (m, 1H), 7.12 (d, J=8.4 Hz, 1H), 4.57-4.55 (m, 2H), 4.01 (s, 3H), 3.49 (br m, 1H), 3.00 (s, 3H), 2.28-2.26 (m, 1H), 1.20-1.15 (m, 6H); MS (EI) for C$_{23}$H$_{24}$ClFN$_4$O$_3$: 459 (MH$^+$).

2-chloro-4-[8-{[3-(4-ethylpiperazin-1-yl)propyl]oxy}-6-fluoro-1-methyl-9-(methyloxy)-3H-pyrazolo[3,4-c]isoquinolin-5-yl]phenol. $^1$H NMR (400 MHz, d$_4$-MeOH): 7.73-7.72 (m, 1H), 7.49-7.47 (m, 1H), 7.43 (d, J=14 Hz, 1H), 7.13 (d, J=8.4 Hz, 1H), 4.50 (t, J=5.8 Hz, 2H), 4.02 (s, 3H), 4.00-3.57 (br m, 10H), 3.39-3.37 (m, 2H), 3.00 (s, 3H), 2.54-2.50 (m, 2H), 1.43 (t, J=7.4 Hz, 3H); MS (EI) for C$_{27}$H$_{31}$ClFN$_5$O$_3$: 528 (MH$^+$).

2-chloro-4-(6-fluoro-1-methyl-9-(methyloxy)-8-{[3-(4-methylpiperazin-1-yl)propyl]oxy}-3H-pyrazolo[3,4-c]isoquinolin-5-yl)phenol. $^1$H NMR (400 MHz, d$_4$-MeOH): 7.70 (m, 1H), 7.47-7.45 (m, 1H), 7.38 (d, J=14.0 Hz, 1H), 7.11 (d, J=8.4 Hz, 1H), 4.47 (t, J=5.8 Hz, 2H), 4.01 (s, 3H), 3.74 (br m, 8H), 3.53-3.50 (m, 2H), 3.03 (s, 3H), 2.98 (s, 3H), 2.50-2.48 (m, 2H); MS (EI) for C$_{26}$H$_{29}$ClFN$_5$O$_3$: 514 (MH$^+$).

5-(3-chlorophenyl)-8-{[2-(4-ethylpiperazin-1-yl)ethyl]oxy}-6-fluoro-1-methyl-9-(methyloxy)-3H-pyrazolo[3,4-c]isoquinoline. $^1$H NMR (400 MHz, d$_6$-DMSO): 7.55 (m, 1H), 7.52 (t, 1H), 7.48 (s, 1H), 7.45 (m, 1H), 7.41 (s, 1H), 7.37 (s, 1H), 4.67 (s, 2H), 3.90 (m, 3H), 3.62-3.77 (m, 6H), 3.56 (s, 3H), 3.45 (m, 2H), 3.20 (m, 2H), 2.82 (s, 2H), 1.28 (t, 3H); MS (EI) for C$_{26}$H$_{29}$N$_5$O$_2$FCl: 498 (MH$^+$).

2-chloro-4-[6-fluoro-1-methyl-9-(methyloxy)-8-({2-[4-(2-methylpropyl)piperazin-1-yl]ethyl}oxy)-3H-pyrazolo[3,4-c]isoquinolin-5-yl]phenol. $^1$H NMR (400 MHz, d$_6$-DMSO): 7.49 (s, 1H), 7.40 (d, 1H), 7.29 (d, 1H), 7.07 (d, 1H), 4.67 (m, 2H), 3.90 (s, 3H), 3.80 (m, 8H), 3.46 (m, 2H), 3.02 (m, 2H), 2.81 (m, 3H), 2.10 (m, 1H), 1.01 (d, 6H); MS (EI) for C$_{28}$H$_{33}$N$_5$O$_3$FCl: 542 (MH$^+$).

2-chloro-4-[8-{[2-(5-ethyl-2,5-diazabicyclo[2.2.1]hept-2-yl)ethyl]oxy}-6-fluoro-1-methyl-9-(methyloxy)-3H-pyrazolo[3,4-c]isoquinolin-5-yl]phenol. $^1$H NMR (400 MHz, d$_6$-DMSO): 7.47 (s, 1H), 7.38 (d, 1H), 7.28 (d, 1H), 7.05 (d, 1H), 4.11-4.69 (m, 10H), 3.88 (s, 3H), 3.70 (m, 1H), 3.47 (m, 1H), 3.34 (m, 1H), 3.20 (m, 1H), 2.81 (s, 3H), 1.30 (m, 3H); MS (EI) for C$_{27}$H$_{29}$N$_5$O$_3$FCl: 526 (MH$^+$).

2-chloro-4-[6-fluoro-1-methyl-8-({2-[4-(1-methylethyl)piperazin-1-yl]ethyl}oxy)-9-(methyloxy)-3H-pyrazolo[3,4-c]isoquinolin-5-yl]phenol. $^1$H NMR (400 MHz, d$_6$-DMSO): 12.00 (broad s, 1H), 7.50 (s, 1H), 7.42 (d, 1H), 7.30 (d, 1H), 7.09 (d, 1H), 4.71 (m, 2H), 3.95 (m, 2H), 3.91 (s, 3H), 3.77 (m, 6H), 3.61 (m, 3H), 2.82 (s, 3H), 1.32 (d, 6H); MS (EI) for C$_{27}$H$_{31}$N$_5$O$_3$FCl: 528 (MH$^+$).

2-chloro-4-[6-fluoro-1-methyl-8-{[(3-exo)-8-methyl-8-azabicyclo[3.2.1]oct-3-yl]oxy}-9-(methyloxy)-3H-pyrazolo[3,4-c]isoquinolin-5-yl]phenol. $^1$H NMR (400 MHz, d$_6$-DMSO): 10.69 (broad s, 1H), 10.52 (broad s, 1H), 7.54 (d, 1H), 7.48 (s, 1H), 7.30 (m, 1H), 7.07 (m, 1H), 5.06 (m, 1H), 4.98 (m, 1H), 3.97 (m, 1H), 3.88 (s, 3H), 3.70 (m, 1H), 3.48

(m, 1H), 2.80 (s, 3H), 2.79 (s, 1H), (2.69 (m, 3H), 2.62 (m, 1H), 2.20-2.36 (m, 4H); MS (EI) for $C_{26}H_{26}N_4O_3FCl$: 497 (MH$^+$).

2-chloro-5-fluoro-4-(6-fluoro-1-methyl-9-(methyloxy)-8-{[(1-methylpiperidin-4-yl)methyl]oxy}-3H-pyrazolo[3,4-c]isoquinolin-5-yl)phenol hydrochloride $^1$H NMR (400 MHz, CD$_3$OD): δ 7.49 (d, 1H), 7.21 (d, 1H), 6.75 (d, 1H), 4.18 (d, 2H), 3.97 (s, 3H), 3.63 (m, 2H), 3.12 (m, 2H), 2.92 (m, 6H), 2.26 (m, 3H), 1.77 (m, 2H); MS (EI) for $C_{25}H_{25}ClFN_4O_3$: 503 (MH$^+$).

2-chloro-4-[8-{[2-(4-ethylpiperazin-1-yl)ethyl]oxy}-6-fluoro-1-methyl-9-(methyloxy)-3H-pyrazolo[3,4-c]isoquinolin-5-yl]phenol. $^1$H-NMR (400 MHz, d$_6$-DMSO): 12.12 (bs, 1H), 10.58 (bs, 1H), 7.50 (t, 1H), 7.42 (d, 1H), 7.32 (2 t, 1H), 7.13 (d, 1H), 4.71 (bs, 2H), 3.94 (m, 2H), 3.91 (s, 3H), 3.82 (m, 4H), 3.72 (m, 2H), 3.50 (bs, 2H), 3.21 (bs, 2H), 2.81 (s, 3H), 1.30 (t, 3H), MS (EI) for $C_{26}H_{29}ClFN_5O_3$: 514.2 (MH$^+$).

2-chloro-4-(6-fluoro-1-methyl-9-(methyloxy)-8-{[2-(4-methylpiperazin-1-yl)ethyl]oxy}-3H-pyrazolo[3,4-c]isoquinolin-5-yl)phenol. $^1$H-NMR (400 MHz, d$_6$-DMSO): 11.94 (bs, 1H), 10.48 (bs, 1H), 7.46 (t, 1H), 7.38 (d, 1H), 7.28 (2 t, 1H), 7.06 (d, 1H), 4.67 (bs, 2H), 3.89 (s, 3H), 3.85 (m, 2H), 3.72 (m, 4H), 3.48 (m, 4H), 2.84 (s, 3H), 2.80 (s, 3H), MS (EI) for $C_{25}H_{27}ClFN_5O_3$: 500.2 (MH$^+$).

2-chloro-4-(6-fluoro-1-methyl-9-(methyloxy)-8-{[2-(1-methylpiperidin-4-yl)ethyl]oxy}-3H-pyrazolo[3,4-c]isoquinolin-5-yl)phenol. $^1$H NMR (400 MHz, d$_4$-MeOH): 7.63 (s, 1H), 7.40 (m, 1H), 7.33 (d, J=14.0 Hz, 1H), 7.07 (d, J=8.4 Hz, 1H), 4.36 (t, J=5.2 Hz, 2H), 3.97 (s, 3H), 3.52 (d, J=12.0 Hz, 2H), 3.01 (t, J=10.8, 2H), 2.95 (s, 3H), 2.85 (s, 3H), 2.13 (d, J=12.8 Hz, 2H), 1.95 (m, 2H), 1.56 (m, 2H) ); MS (EI) for $C_{26}H_{28}ClFN_4O_3$: 499 (MH$^+$).

2-chloro-4-[8-{[(1-ethylpiperidin-4-yl)methyl]oxy}-6-fluoro-1-methyl-9-(methyloxy)-3H-pyrazolo[3,4-c]isoquinolin-5-yl]phenol. $^1$H NMR (400 MHz, d$_4$-MeOH): 7.62 (s, 1H), 7.10 (d, J=8.4, 1H), 7.35 (d, J=14.0 Hz, 1H), 7.07 (d, J=8.8 Hz, 1H), 4.23 (d, J=5.6 Hz, 2H), 3.98 (s, 3H), 3.66 (d, J=12.4 Hz, 2H), 3.20 (q, J=7.2 Hz, 2H), 3.04 (t, J=11.2 Hz, 2H), 2.95 (s, 3H), 2.31 (m, 1H), 2.22 (d, J=13.6 Hz, 2H), 1.79 (m, 2H), 1.37 (t, J=7.2 Hz, 3H); MS (EI) for $C_{26}H_{28}ClFN_4O_3$: 499 (MH$^+$).

4-[8-{[2-(3-amino-8-azabicyclo[3.2.1]oct-8-yl)ethyl]oxy}-6-fluoro-1-methyl-9-(methyloxy)-3H-pyrazolo[3,4-c]isoquinolin-5-yl]-2-chlorophenol. $^1$H NMR (400 MHz, d$_4$-MeOH): 7.69 (s, 1H), 7.45 (m, 1H), 7.43 (d, J=12.4 Hz, 1H), 7.11 (d, J=8.4 Hz, 1H), 4.82 (m, 2H), 4.38 (s, 2H), 4.00 (s, 3H), 3.76 (m, 3H), 3.00 (s, 3H), 2.92 (m, 2H), 2.67 (m, 2H), 2.31 (d, J=10.0 Hz, 2H), 2.23 (d, J=16.8 Hz, 2H); MS (EI) for $C_{26}H_{27}ClFN_5O_3$: 512 (MH$^+$).

2-chloro-4-[8-{[2-(1-ethylpiperidin-4-yl)ethyl]oxy}-6-fluoro-1-methyl-9-(methyloxy)-3H-pyrazolo[3,4-c]isoquinolin-5-yl]phenol. $^1$H NMR (400 MHz, d$_4$-MeOH): 7.68 (s, 1H), 7.36 (d, J=8.0 Hz, 1H), 7.06 (d, J=8.4 Hz, 1H), 6.99 (d, J=13.6 Hz, 1H), 4.16 (m, 2H), 3.90 (s, 2H), 3.58 (d, J=12.4 Hz, 2H), 3.15 (q, J=7.2 Hz, 2H), 2.87 (m, 5H), 2.14 (d, J=14.4 Hz, 2H), 1.90 (m, 3H), 1.55 (m, 2H), 1.34 (t, J=7.6 Hz, 3H); MS (EI) for $C_{27}H_{30}ClFN_4O_3$: 513 (MH$^+$).

2-chloro-4-{6-fluoro-1-methyl-9-(methyloxy)-8-[(3-piperidin-1-ylpropyl)oxy]-3H-pyrazolo[3,4-c]isoquinolin-5-yl}phenol. $^1$H NMR (400 MHz, d$_4$-MeOH): 7.67 (s, 1H), 7.43 (d, J=8.8 Hz, 1H), 7.30 (d, J=14.0 Hz, 1H), 7.09 (d, J=8.4 Hz, 1H), 4.40 (t, J=5.6 Hz, 2H), 3.99 (s, 3H), 3.64 (d, J=11.6 Hz, 2H), 3.40 (m, 2H), 3.02 (t, J=11.2 Hz, 2H), 2.96 (s, 3H), 2.42 (m, 2H), 2.00 (m, 3H), 1.85 (m, 3H); MS (EI) for $C_{27}H_{30}ClFN_4O_3$: 513 (MH$^+$).

2-chloro-4-{6-fluoro-1-methyl-9-(methyloxy)-8-[(3-morpholin-4-ylpropyl)oxy]-3H-pyrazolo[3,4-c]isoquinolin-5-yl}phenol. $^1$H NMR (400 MHz, d$_4$-MeOH): 7.70 (s, 1H), 7.46 (d, J=8.8 Hz, 1H), 7.38 (d, J=14.0 Hz, 1H), 7.12 (d, J=8.8 Hz, 1H), 4.46 (t, J=6.0 Hz, 2H), 4.11 (m, 2H), 4.01 (s, 3H), 3.86 (t, J=12.0 Hz, 2H), 3.62 (d, J=12.4 Hz, 2H), 3.48 (t, J=7.6 Hz, 2H), 3.26 (m, 2H), 2.98 (s, 3H), 2.47 (m, 2H); MS (EI) for $C_{25}H_{26}ClFN_4O_4$: 501 (MH$^+$).

2-chloro-4-{6-fluoro-1-methyl-9-(methyloxy)-8-[(2-morpholin-4-ylethyl)oxy]-3H-pyrazolo[3,4-c]isoquinolin-5-yl}phenol. $^1$H NMR (400 MHz, d$_6$-DMSO): 11.68 (s, 1H), 10.56 (broad s, 1H), 7.48 (dd, 1H), 7.40 (d, 1H), 7.30 (dd, 1H), 7.09 (t, 1H), 4.71 (m, 2H), 4.00-4.14 (m, 2H), 3.852 (m, 5H), 3.28-3.72 (m, 6H), 2.80 (s, 3H); MS (EI) for $C_{24}H_{24}N_4O_4ClF$: 487 (MH$^+$).

4-[8-({2-[butyl(ethyl)amino]ethyl}oxy)-6-fluoro-1-methyl-9-(methyloxy)-3H-pyrazolo[3,4-c]isoquinolin-5-yl]-2-chlorophenol. $^1$H NMR (400 MHz, d$_6$-DMSO): 10.74 (s, 1H), 10.57 (broad s, 1H), 7.49 (t, 1H), 7.39 (d, 1H), 7.30 (dt, 1H), 7.08 (d, 1H), 4.65 (t, 2H), 3.88 (s, 3H), 3.65 (d, 2H), 3.24 (m, 4H), 3.80 (s, 3H), 1.73 (m 2H), 1.35 (m, 5H), 0.94 (t, 3H); MS (EI) for $C_{26}H_{30}N_4O_3ClF$: 501 (MH$^+$).

2-chloro-4-[8-{[2-(diethylamino)ethyl]oxy}-6-fluoro-1-methyl-9-(methyloxy)-3H-pyrazolo[3,4-c]isoquinolin-5-yl]phenol. $^1$H NMR (400 MHz, d$_6$-DMSO): 10.71 (s, 1H), 10.57 (broad s, 1H), 7.49 (t, 1H), 7.39 (d, 1H), 7.30 (dt, 1H), 7.08 (d, 1H), 4.64 (t, 2H), 3.88 (s, 3H), 3.65 (d, 2H), 3.29 (q, 4H), 2.81 (s, 3H), 1.31 (t, 6H); MS (EI) for $C_{24}H_{26}N_4O_3ClF$: 473 (MH$^+$).

2-chloro-5-{6-fluoro-1-methyl-9-(methyloxy)-8-[(2-pyrrolidin-1-ylethyl)oxy]-3H-pyrazolo[3,4-c]isoquinolin-5-yl}phenol. $^1$H NMR (400 MHz, d$_6$-DMSO): 11.19 (s, 1H), 10.58 (broad s, 1H), 7.50 (s, 1H), 7.42 (d, 1H), 7.31 (d, 1H), 7.09 (d, 1H), 4.63 (s, 2H), 3.90 (s, 3H), 3.70 (d, 4H), 3.17 (m, 2H), 2.81 (s, 3H), 1.99 (d, 4H); MS (EI) for $C_{24}H_{24}N_4O_3ClF$: 471 (MH$^+$).

2-chloro-4-[8-({2-[[2-(dimethylamino)ethyl](methyl)amino]ethyl}oxy)-6-fluoro-1-methyl-9-(methyloxy)-3H-pyrazolo[3,4-c]isoquinolin-5-yl]phenol. MS (EI) for $C_{25}H_{29}N_5O_3ClF$: 502 (M$^+$).

2-chloro-4-[8-({2-[[2-(diethylamino)ethyl](methyl)amino]ethyl}oxy)-6-fluoro-1-methyl-9-(methyloxy)-3H-pyrazolo[3,4-c]isoquinolin-5-yl]phenol. MS (EI) for $C_{27}H_{33}ClFN_5O_3$: 530 (MH$^+$).

2-chloro-4-[8-({2-[[2-(dimethylamino)ethyl](ethyl)amino]ethyl}oxy)-6-fluoro-1-methyl-9-(methyloxy)-3H-pyrazolo[3,4-c]isoquinolin-5-yl]phenol. $^1$H NMR (400 MHz, d$_6$-DMSO): 10.51 (s, 1H), 9.01 (s, 1H), 7.46 (m, 1H), 7.33-7.41 (m, 1H), 7.30 (dt, 1H), 7.05 (dd, 1H), 4.72 (m, 1H), 4.51 (m, 3H), 4.03 (m, 1H), 3.89 (d, 3H), 3.76 (m, 1H), 3.55 (m, 3H), 3.31 (s, 3H), 3.06 (m, 1H), 2.86 (s, 3H), 2.80 (d, 3H), 1.23 (t, 3H); MS (EI) for $C_{26}H_{31}N_5O_3ClF$: 587 (MH$^+$).

4-[8-[(2-{bis[3-(dimethylamino)propyl]amino}ethyl)oxy]-6-fluoro-1-methyl-9-(methyloxy)-3H-pyrazolo[3,4-c]isoquinolin-5-yl]-2-chlorophenol. MS (EI) for $C_{30}H_{40}N_6O_3ClF$: 587 (MH$^+$).

2-chloro-4-[6-fluoro-1-methyl-8-({2-[methyl(1-methylpyrrolidin-3-yl)amino]ethyl}oxy)-9-(methyloxy)-3H-pyrazolo[3,4-c]isoquinolin-5-yl]phenol. MS (EI) for $C_{26}H_{29}N_5O_3ClF$: 514 (MH$^+$).

2-chloro-4-{6-fluoro-1-methyl-9-(methyloxy)-8-[(2-{(2S)-2-[(methyloxy)methyl]pyrrolidin-1-yl}ethyl)oxy]-3H-pyrazolo[3,4-c]isoquinolin-5-yl}phenol. MS (EI) for $C_{26}H_{28}N_4O_4ClF$: 515 (MH$^+$).

2-chloro-4-(6-fluoro-1-methyl-9-(methyloxy)-8-{[2-(4-pyrrolidin-1-ylpiperidin-1-yl)ethyl]oxy}-3H-pyrazolo[3,4-c]isoquinolin-5-yl)phenol. MS (EI) for $C_{29}H_{33}N_5O_3ClF$: 554 (MH$^+$).

2-chloro-4-[8-{[2-(4-cyclohexylpiperazin-1-yl)ethyl]oxy}-6-fluoro-1-methyl-9-(methyloxy)-3H-pyrazolo[3,4-c]isoquinolin-5-yl]phenol. MS (EI) for $C_{30}H_{35}N_5O_3ClF$: 568 (MH$^+$).

2-[4-(2-{[5-(3-chloro-4-hydroxyphenyl)-6-fluoro-1-methyl-9-(methyloxy)-3H-pyrazolo[3,4-c]isoquinolin-8-yl]oxy}ethyl)piperazin-1-yl]-N-(1-methylethyl)acetamide. MS (EI) for $C_{29}H_{34}N_6O_4ClF$: 585 (MH$^+$).

4-[8-{[2-(1,4'-bipiperidin-1'-yl)ethyl]oxy}-6-fluoro-1-methyl-9-(methyloxy)-3H-pyrazolo[3,4-c]isoquinolin-5-yl]-2-chlorophenol. MS (EI) for $C_{30}H_{35}N_5O_3ClF$: 568 (MH$^+$).

2-chloro-4-[6-fluoro-1-methyl-8-{[2-(4-methyl-1,4-diazepan-1-yl)ethyl]oxy}-9-(methyloxy)-3H-pyrazolo[3,4-c]isoquinolin-5-yl]phenol. MS (EI) for $C_{26}H_{29}N_5O_3ClF$: 514 (MH$^+$).

2-chloro-4-(6-fluoro-1-methyl-9-(methyloxy)-8-{[2-(4-pyridin-2-ylpiperazin-1-yl)ethyl]oxy}-3H-pyrazolo[3,4-c]isoquinolin-5-yl)phenol. MS (EI) for $C_{29}H_{28}N_6O_3ClF$: 563 (MH$^+$).

2-Chloro-4-[8{[2-(2,6-dimethylmorpholin-4-yl)ethyl]oxy)-6-fluoro-1-methyl-9-(methyloxy)-3H-pyrazolo[3,4c]isoquinolin-5-yl]phenol. MS (EI) for $C_{26}H_{28}N_4O_4ClF$: 515 (MH$^+$).

2-chloro-4-{6-fluoro-1-methyl-9-(methyloxy)-8-[(2-thiomorpholin-4-ylethyl)oxy]-3H-pyrazolo[3,4-c]isoquinolin-5-yl}phenol. MS (EI) for $C_{24}H_{24}SN_4O_3ClF$: 503 (MH$^+$).

2-chloro-4-[8-{[2-(2,6-dimethylpiperidin-1-yl)ethyl]oxy}-6-fluoro-1-methyl-9-(methyloxy)-3H-pyrazolo[3,4-c]isoquinolin-5-yl]phenol. MS (EI) for $C_{27}H_{30}N_4O_3ClF$: 513 (MH$^+$).

2-chloro-4-(6-fluoro-1-methyl-9-(methyloxy)-8-{[2-(octahydroquinolin-1 (2H)-yl)ethyl]oxy}-3H-pyrazolo[3,4-c]isoquinolin-5-yl)phenol. MS (EI) for $C_{29}H_{32}N_4O_3ClF$: 539 (MH$^+$).

4-[8-({2-[bis(1-methylethyl)amino]ethyl}oxy)-6-fluoro-1-methyl-9-(methyloxy)-3H-pyrazolo[3,4-c]isoquinolin-5-yl]-2-chlorophenol. MS (EI) for $C_{26}H_{30}N_4O_3ClF$: 501 (MH$^+$).

4-[8-[(2-{bis[2-(methyloxy)ethyl]amino}ethyl)oxy]-6-fluoro-1-methyl-9-(methyloxy)-3H-pyrazolo[3,4-c]isoquinolin-5-yl]-2-chlorophenol. MS (EI) for $C_{26}H_{30}N_4O_5ClF$: 533 (MH$^+$).

2-chloro-4-{6-fluoro-1-methyl-9-(methyloxy)-8-[(2-piperidin-1-ylethyl)oxy]-3H-pyrazolo[3,4-c]isoquinolin-5-yl}phenol. MS (EI) for $C_{25}H_{26}N_4O_3ClF$: 485 (MH$^+$).

2-bromo-4-(6-fluoro-1-methyl-9-(methyloxy)-8-{[(1-methylpiperidin-4-yl)methyl]oxy}-3H-pyrazolo[3,4-c]isoquinolin-5-yl)phenol. $^1$H NMR (400 MHz, d$_4$-CH$_3$OH) δ 7.84 (br. s, 1H), 7.49 (br. s, 1H), 7.39 (m, 1H), 7.09 (m, 1H), 4.26 (m, 2H), 4.00 (s, 3H), 3.66-3.59 (m, 1H), 3.13 (t, 2H), 2.98 (s, 3H), 2.90 (s, 3H), 2.38-2.16 (m, 4H), 1.79 (m, 2H); MS (EI) for $C_{25}H_{26}BrFN_4O_3$: 529 (MH$^+$).

2-chloro-5-fluoro-4-(6-fluoro-1-methyl-9-(methyloxy)-8-{[2-(methyloxy)ethyl]oxy}-3H-pyrazolo[3,4-c]isoquinolin-5-yl)phenol. $^1$H NMR (400 MHz, CD$_3$OD): 7.42 (d, 1H), 7.08 (q, 1H), 6.65 (d, 1H), 4.38 (t, 2H), 3.98 (s, 3H), 3.82 (t, 2H), 3.45 (s, 3H), 2.85 (d, 3H); MS (EI) for $C_{21}H_{18}N_3O_4F_2Cl$: 450 (MH$^+$).

Example 25

2-Chloro-5-fluoro-4-(6-fluoro-11-methyl-2,3-dihydro-9H-[1,4]dioxino[2,3-f]pyrazolo[3,4-c]isoquinolin-7-yl)phenol: A solution of methyl 2,3-dihydroxybenzoate (27 g, 160 mmol) in dichloromethane (300 mL) was cooled to 0° C. and powdered potassium carbonate (23.3 g, 169 mmol) was added. The reaction mixture was then added benzoyl chloride (19.6 mL, 169 mmol) and the mixture was allowed to warm to room temperature and stirred for 18 h. The reaction mixture was concentrated in vacuo and the residue was partitioned with ethyl acetate and 0.3M aqueous hydrochloric acid. The organic layer was washed with brine, dried over anhydrous magnesium sulfate. Filtration and concentration afforded 42.1 g (97%) of crude methyl 2-hydroxy-3-[(phenylcarbonyl)oxy]benzoate as an orange oil: $^1$H NMR (400 MHz, d$_4$-MeOH): 8.17 (dd, J=1.6, 12.5 Hz, 2H), 7.80 (dd, J=1.6, 8.0 Hz, 1H), 7.71-7.67 (m, 1H), 7.57-7.53 (m, 2H), 7.41 (dd, J=1.8, 8.0 Hz, 1H), 6.97 (t, J=8.6 Hz, 1H), 3.96 (s, 3H).

To a solution of methyl 2-hydroxy-3-[(phenylcarbonyl)oxy]benzoate (42.1 g, 155 mmol) in N,N-dimethylformamide (300 mL) was added 1,2-dibromoethane (135 mL, 1550 mmol) and cesium carbonate (76 g, 232 mmol), and the reaction mixture was stirred at room temperature under nitrogen for 6.5 h. The volume of the reaction mixture was reduced by half in vacuo, and then partitioned between water (500 mL) and ethyl acetate (500 mL). The layers were separated, and the organic layer was washed with brine (200 mL), dried over anhydrous magnesium sulfate and concentrated. The crude precipitate was triturated with 50% diethyl ether/hexanes (200 mL). The solid was washed with 50% diethyl ether/hexanes (2×200 mL) and isolated to give 30.6 g (52% over 2 steps) of methyl 2-[(2-bromoethyl)oxy]-3-[(phenylcarbonyl)oxy]benzoate as an off-white powder: $^1$H NMR (400 MHz, CDCl$_3$): 8.23-8.21 (m, 2H), 7.77 (dd, J=1.6, 7.6 Hz, 1H), 7.68-7.64 (m, 1H), 7.53 (t, J=6.0 Hz, 2H), 7.39 (dd, J=1.8, 8.0 Hz, 1H), 7.25 (t, J=6.4 Hz, 1H), 4.31 (t, J=6.4 Hz, 2H), 3.93 (s, 3H), 3.52 (t, J=6.4 Hz, 2H).

A solution of fuming nitric acid (55 mL) and concentrated sulfuric acid (11 mL) was cooled to −5° C. Powdered methyl 2-[(2-bromoethyl)oxy]-3-[(phenylcarbonyl)oxy]benzoate (30 g, 79.1 mmol) was slowly added over a period of 30 min. After an additional stirring time of 30 min., the reaction mixture was quickly poured over ice, which was then extracted with dichloromethane (2×400 mL). The combined organic layers were washed with water (400 mL) and aqueous saturated sodium bicarbonate (200 mL). The organic solution was washed with brine, dried over anhydrous magnesium sulfate and concentrated. The crude precipitate was triturated with diethyl ether (200 mL) to give 29.1 g (87%) of methyl 2-[(2-bromoethyl)oxy]-5-nitro-3-[(phenylcarbonyl)oxy]benzoate as an off-white powder: $^1$H NMR (400 MHz, CDCl$_3$): 9.06 (t, J=2.2 Hz, 1H), 8.72 (d, J=3.2 Hz, 1H), 8.57-8.53 (m, 3H), 8.32 (d, J=3.2 Hz, 1H), 7.79 (t, J=8.0 H, 1H), 4.43 (t, J=5.8 Hz, 2H), 4.00 (s, 3H), 3.57 (t, J=5.6 Hz, 2H).

To a solution of methyl 2-[(2-bromoethyl)oxy]-5-nitro-3-[(phenylcarbonyl)oxy]benzoate (30 g, 70.7 mmol) in methanol (200 mL) was added potassium carbonate (9.8 g, 70.7 mmol). The reaction mixture was allowed to stir at room temperature for 30 min., at which time it was concentrated in vacuo. The residue was taken up in N,N-dimethylformamide (150 mL) and the resulting suspension was heated to 65° C. and stirred for 12 h. The reaction mixture was then cooled to room temperature and concentrated. The residue was dissolved in water (300 mL) and extracted with ethyl acetate (2×300 mL). The combined organic layers were washed with brine, dried over anhydrous magnesium sulfate and concentrated. The residue was triturated with 10% diethyl ether/hexanes to give 5.6 g (33%) of methyl 7-nitro-2,3-dihydro-1,4-benzodioxine-5-carboxylate as an off-white powder: $^1$H NMR (400 MHz, CDCl$_3$): 8.34 (d, J=2.8 Hz, 1H), 7.90 (d, J=2.8 Hz, 1H), 4.48-4.46 (m, 2H), 4.37-4.35 (m, 2H), 3.93 (s, 3H).

Methyl 7-nitro-2,3-dihydro-1,4-benzodioxine-5-carboxylate (5.6 g, 23.4 mmol) and palladium on carbon (250 mg, 30 wt. %) were suspended in ethyl acetate (200 mL). The reaction vessel was evacuated and then immediately filled with hydrogen gas. This deoxygenation process was repeated three times at atmospheric pressure. The black suspension was stirred under a hydrogen atmosphere for 18 h, at which time it was filtered through a bed of Celite and rinsed with ethyl acetate. The filtrate was concentrated, and the residue was triturated with diethyl ether to give 4.89 g (100%) of methyl 7-amino-2,3-dihydro-1,4-benzodioxine-5-carboxylate as an off-white powder: $^1$H NMR (400 MHz, CDCl$_3$): 6.74 (d, J=2.8 Hz, 1H), 6.40 (d, J=2.8 Hz, 1H), 4.26-4.25 (m, 4H), 3.86 (s, 3H).

A solution of methyl 7-amino-2,3-dihydro-1,4-benzodioxine-5-carboxylate (4.89 g, 23.3 mmol) in ethylene glycol dimethyl ether (15 mL) was cooled to −5° C. and then slowly added boron trifluoride diethyl etherate (3.85 mL, 30.3 mmol) followed by tert-butyl nitrite (3.05 mL, 25.6 mmol). The resulting gray suspension was allowed to warm to 0° C. and stirred for 1 h, at which time it was filtered and rinsed with ethyl acetate to give 6.24 g (93%) of difluoroboranylium {8-[(methyloxy)carbonyl]-2,3-dihydro-1,4-benzodioxin-6-yl}diazenide as a gray powder: $^1$H NMR (400 MHz, d$_6$-DMSO): 8.73 (br s, 1H), 8.32 (br s, 1H), 4.64 (br m, 2H), 4.47 (br m, 2H), 3.88 (s, 3H).

A suspension of difluoroboranylium {8-[(methyloxy)carbonyl]-2,3-dihydro-1,4-benzodioxin-6-yl}diazenide (1.0 g, 3.46 mmol) in 1,2,4-trichlorobenzene (10 mL) was heated to 110° C. and allowed to stir for 3 h. The reaction mixture was then cooled to room temperature and purified immediately by flash column chromatography (SiO$_2$, 100% hexanes, 30% ethyl acetate/hexanes) to yield 400 mg (54%) of methyl 7-fluoro-2,3-dihydro-1,4-benzodioxine-5-carboxylate as a white powder: $^1$H NMR (400 MHz, CDCl$_3$): 7.11 (dd, J=3.2, 8.8 Hz, 1H), 6.78 (dd, J=3.2, 8.8 Hz, 1H), 4.35-4.28 (m, 4H), 3.89 (s, 3H).

A solution of methyl 7-fluoro-2,3-dihydro-1,4-benzodioxine-5-carboxylate (400 mg, 1.88 mmol) in tetrahydrofuran (20 mL) was cooled to 0° C. and then added lithium aluminum hydride (3.78 mL, 1.0 M solution in tetrahydrofuran). The reaction mixture was allowed to warm to room temperature and stirred for 45 min, at which time water (143 μL) was added followed by 15% sodium hydroxide (143 μL) and then water (286 μL) again. The white precipitate was filtered and the filtrate was concentrated to give 345 mg (100%) of (7-fluoro-2,3-dihydro-1,4-benzodioxine-5-yl)methanol as a colorless oil: $^1$H NMR (400 MHz, CDCl$_3$): 6.63 (dd, J=2.8, 8.8 Hz, 1H), 6.56 (dd, J=3.2, 9.2 Hz, 1H), 4.64 (d, J=6.4 Hz, 2H), 4.28-4.25 (m, 4H).

A solution of (7-fluoro-2,3-dihydro-1,4-benzodioxine-5-yl)methanol (436 mg, 2.36 mmol) and triethylamine (400 μL, 2.83 mmol) in dichloromethane (20 mL) was cooled to 0° C. and then slowly added thionyl chloride (260 μL, 3.55 mmol) and stirred for 45 min. The reaction mixture was partitioned with water (100 mL) and ethyl acetate (100 mL). The organic layer was washed with aqueous saturated sodium bicarbonate, brine, and then dried over anhydrous magnesium sulfate and concentrated to give crude 5-(chloromethyl)-7-fluoro-2,3-dihydro-1,4-benzodioxine as a colorless oil. The crude residue was taken up in N,N-dimethylformamide (10 mL) and was added potassium cyanide (460 mg, 7.08 mmol). The reaction mixture was heated to 60° C. and stirred for 5 h, at which time it was cooled to room temperature and partitioned with water (100 mL) and ethyl acetate (150 mL). The organic layer was washed with 10% citric acid (3×100 mL) and then aqueous saturated sodium bicarbonate (2×100 mL). The organic solution was further washed with brine, dried over anhydrous magnesium sulfate and concentrated to give 430 mg (94% over 2 steps) of (7-fluoro-2,3-dihydro-1,4-benzodioxin-5-yl)acetonitrile as an off-white powder. GCMS for C$_{10}$H$_8$FNO$_2$: 193 (M$^+$).

To a solution of (7-fluoro-2,3-dihydro-1,4-benzodioxin-5-yl)acetonitrile (430 mg, 2.23 mmol) and ethyl acetate (2.18 mL, 22.3 mmol) in tetrahydrofuran (30 mL) was added sodium hydride (106 mg, 4.45 mmol, 60% in mineral oil) at 0° C. The reaction mixture was heated to refluxing conditions for 1 h, at which time it was cooled to room temperature and was slowly added 6N HCl until pH <7. The reaction mixture was partitioned with water (100 mL) and ethyl acetate (200 mL). The organic layer was washed with brine, dried over anhydrous magnesium sulfate and concentrated to give 306 mg (59%) of 2-(7-fluoro-2,3-dihydro-1,4-benzodioxin-5-yl)-3-oxobutaneitrile as a yellow oil. GCMS for C$_{12}$H$_{10}$FNO$_3$: 235 (M$^+$).

A solution of 2-(7-fluoro-2,3-dihydro-1,4-benzodioxin-5-yl)-3-oxobutaneitrile (306 mg, 1.30 mmol) and hydrazine dihydrochloride (163 mg, 1.56 mmol) in anhydrous ethyl alcohol (15 mL) was heated to refluxing conditions and stirred for 3.5 h. The reaction mixture was then cooled to room temperature and concentrated. The crude material was triturated with diethyl ether to give 388 mg (93%) of 4-(7-fluoro-2,3-dihydro-1,4-benzodioxin-5-yl)-3-methyl-1H-pyrazol-5-amine as an off-white powder: MS (EI) for C$_{12}$H$_{12}$FN$_3$O$_2$: 250 (MH$^+$).

A solution of 4-(7-fluoro-2,3-dihydro-1,4-benzodioxin-5-yl)-3-methyl-1H-pyrazol-5-amine (109 mg, 0.338 mmol) and 5-chloro-2-fluoro-4-hydroxybenzaldehyde (60 mg, 0.338 mmol) in trifluoroacetic acid (2.0 mL) was heated to 75° C. and allowed to stir for 12 h. The reaction mixture was concentrated in vacuo and the residue was purified by reverse phase HPLC to afford 5.8 mg (4.2%) of 2-Chloro-5-fluoro-4-(6-fluoro-11-methyl-2,3-dihydro-9H-[1,4]dioxino[2,3-f]pyrazolo[3,4-c]isoquinolin-7-yl)phenol as a white powder: $^1$H NMR (400 MHz, d$_4$-MeOH): 7.67 (d, J=7.6 Hz, 1H), 7.07 (d, J=13.2 Hz, 1H), 6.85 (d, J=10.8 Hz, 1H) 4.59-4.56 (m, 4H), 2.99 (s, 3H); MS (EI) for C$_{19}$H$_{12}$ClF$_2$N$_3$O$_3$: 404 (MH$^+$).

Using the same or analogous synthetic techniques and/or substituting with alternative reagents, the following compounds of the invention were prepared:

2-chloro-5-fluoro-4-(6-fluoro-11-methyl-2,3-dihydro-9H-[1,4]dioxino[2,3-f]pyrazolo[3,4-c]isoquinolin-7-yl)phenol. $^1$H NMR (400 MHz, d$_4$-MeOH): 7.67 (d, J=7.6 Hz, 1H), 7.07 (d, J=13.2 Hz, 1H), 6.85 (d, J=10.8 Hz, 1H) 4.59-4.56 (m, 4H), 2.99 (s, 3H); MS (EI) for C$_{19}$H$_{12}$ClF$_2$N$_3$O$_3$: 404 (MH$^+$).

3-fluoro-4-(6-fluoro-11-methyl-2,3-dihydro-9H-[1,4]dioxino[2,3-f]pyrazolo[3,4-c]isoquinolin-7-yl)phenol. $^1$H NMR (400 MHz, d$_4$-MeOH): 7.51 (t, J=8.4 Hz, 1H), 7.09 (d, J=13.2 Hz, 1H), 6.85 (d, J=6.8 Hz, 1H), 6.74 (dd, J=2.0, 12.4 Hz, 1H) 4.61-4.59 (m, 4H), 2.03 (s, 3H); MS (EI) for C$_{19}$H$_{13}$F$_2$N$_3$O$_3$: 370 (MH$^+$).

6-fluoro-7-(2-fluorophenyl)-11-methyl-2,3-dihydro-9H-[1,4]dioxino[2,3-f]pyrazolo[3,4-c]isoquinoline. $^1$H NMR (400 MHz, d$_4$-MeOH): 7.71-7.67 (m, 2H), 7.45 (t, J=7.6 Hz, 1H), 7.37 (t, J=9.2 Hz, 1H), 7.10 (d, J=13.2 Hz, 1H), 4.62-4.60 (m, 4H), 3.02 (s, 3H); MS (EI) for C$_{19}$H$_{13}$F$_2$N$_3$O$_2$: 354 (MH$^+$).

N-[4-(6-fluoro-11-methyl-2,3-dihydro-9H-[1,4]dioxino [2,3-f]pyrazolo[3,4-c]isoquinolin-7-yl)phenyl]acetamide: MS (EI) for C$_{21}$H$_{17}$FN$_4$O$_3$: 393.2 (MH$^+$)

Example 26

2-Chloro-5-fluoro-4-(6-fluoro-1-methyl-8,9-dihydro-3H-[1,4]dioxino[2,3-g]pyrazolo[3,4-c]isoquinolin-5-yl)phenol: Anhydrous aluminum chloride (1.11 g, 8.2 mmol) was added to a solution of 3-fluoro-4-hydroxy-5-methoxy benzaldehyde (1.2 g; 6.8 mmol) in dry dichloromethane (16 ml) under an atmosphere of nitrogen. The reaction mixture was cooled down to 0° C., pyridine (2.5 ml; 31 mmol) was slowly added and the solution was heated to reflux and stirred for 24 h. The solution was cooled to 0° C. and 4M aqueous hydrochloric acid was added to the mixture until the pH was approximately 2. The organic phase was discarded and the water phase was extracted with ethyl ether (3×15 ml). The organic extracts were combined then dried over sodium sulfate and concentrated under vacuum to give 3-fluoro-4,5-dihydroxybenzaldehyde (0.904 g; 85% yield) as a yellow solid. $^1$H NMR (400 MHz, CD$_3$OD) δ 9.68 (d, 1H), 7.17 (dd, 1H), 7.16 (br. s, 1H). MS (EI) for C$_7$H$_5$FO$_3$: 157 (MH$^+$).

3-fluoro-4,5-dihydroxybenzaldehyde (0.9 g; 5.7 mmol) and cesium carbonate (4.6 g; 14.2 mmol) were stirred in DMF (15 ml) at room temperature for 15 min. 1,2 Dibromoethane (638 µl; 7.4 mmol) was added and reaction mixture was stirred at 80° C. for 2.5 h and then diluted with dichloromethane (100 ml). The mixture was washed with water (2×50 ml), 10% aqueous citric acid (50 ml), brine (50 ml), dried over sodium sulfate and evaporated to dryness to yield 8-fluoro-2,3-dihydro-1,4-benzodioxine-6-carbaldehyde (0.9 g; 87% yield). $^1$H NMR (400 MHz, CD$_3$OD) δ 9.74 (d, 1H), 7.25 (m, 2H), 4.37 (m, 4H).

8-fluoro-2,3-dihydro-1,4-benzodioxine-6-carbaldehyde (0.87 g: 4.8 mmol) was dissolved in ethanol (20 ml) and sodium borohydride (0.45 g; 11.95 mmol) was added at 0° C. The reaction mixture was stirred at rt for 2 h and poured into ice-water. The pH was adjusted to 5 by adding glacial acetic acid in portions and the aqueous mixture was extracted with ethyl acetate (80 ml). The organic phase was washed with water (30 ml), brine (30 ml), dried over sodium sulfate and concentrated under vacuum to give (8-fluoro-2,3-dihydro-1,4-benzodioxin-6-yl)methanol (0.84 g; 95% yield) as a yellow oil. $^1$H NMR (400 MHz, CD$_3$OD) δ 6.66 (dd, 1H), 6.64 (br. s, 1H), 4.44 (s, 2H), 4.26 (s, 4H)

To a solution of (8-fluoro-2,3-dihydro-1,4-benzodioxin-6-yl)methanol (0.84 g, 4.55 mmol) and triethylamine (960 µl, 4.84 mmol) in dichloromethane (20 mL) was slowly added thionyl chloride (400 µl, 5.47 mmol) at 0° C. The solution was stirred at 0° C. for 15 min then at rt for 3 h. Dichloromethane (80 mL) was added and the solution was washed with water (40 mL), saturated aqueous sodium bicarbonate (40 mL) then brine (40 mL) and dried over sodium sulfate. Filtration and concentration gave 7-(chloromethyl)-5-fluoro-2,3-dihydro-1,4-benzodioxine (0.92 g, quantitative yield) as a brown oil. The chloride was used in the next step without further purification.

A mixture of 7-(chloromethyl)-5-fluoro-2,3-dihydro-1,4-benzodioxine (0.92 g, 4.55 mmol) and potassium cyanide (1.55 g, 23.8 mmol) in DMF (10 mL) was stirred at 60° C. for 18 h. After cooling to rt ethyl acetate (100 mL) was added and the mixture was washed with water (2×30 mL) then brine (30 mL) and dried over sodium sulfate. Filtration and concentration followed by column chromatography on silica (4:1 hexanes/ethyl acetate) afforded (8-fluoro-2,3-dihydro-1,4-benzodioxin-6-yl)acetonitrile (0.42 g, 46% yield) as a yellow oil. $^1$H NMR (400 MHz, CDCl$_3$) δ 6.61 (m, 2H), 4.30 (s, 4H), 3.62 (s, 2H)

To a solution of (8-fluoro-2,3-dihydro-1,4-benzodioxin-6-yl)acetonitrile (0.40 g, 2.10 mmol) in THF (10 mL) was added sodium hydride (60% dispersion in mineral oil, 0.25 g, 6.3 mmol) and ethyl acetate (2.05 ml, 21.0 mmol) and the mixture was stirred at 60° C. for 2 h. After cooling to 0° C., water was added (25 mL) and the aqueous layer was washed with dichloromethane (3×15 mL), acidified with 1N HCl to pH 3 and extracted with ethyl acetate (3×25 mL). The combined organic extracts were washed with brine (30 mL) then dried with sodium sulfate, filtered and concentrated to give 2-(8-fluoro-2,3-dihydro-1,4-benzodioxin-6-yl)-3-oxobutanenitrile as an orange solid (0.37 g; 75% yield). $^1$H NMR (400 MHz, d$_6$-DMSO) δ 7.05 (dd, 1H), 6.93 (br. s, 1H), 4.30 (m, 5H), 2.30 (s, 3H).

2-(8-fluoro-2,3-dihydro-1,4-benzodioxin-6-yl)-3-oxobutanenitrile (0.37 g; 1.56 mmol) was dissolved in dry ethanol (5 mL) and hydrazine dihydrochloride (0.20 g, 1.87 mmol) then triethylamine (217 µg, 1.56 mmol) were added. The reaction mixture was refluxed for 2 h, cooled to rt and the solvent was evaporated under vacuum. The residue was dissolved in ethyl acetate (50 ml), washed with saturated sodium bicarbonate (2×25 mL), brine (25 ml) then dried over sodium sulfate. Filtration and concentration gave 4-(8-fluoro-2,3-dihydro-1,4-benzodioxin-6-yl)-3-methyl-1H-pyrazol-5-amine (0.36 g, 93% yield) as an orange solid. $^1$H NMR (400 MHz, d$_6$-DMSO) δ 6.75 (dd, 1H), 6.65 (m, 1H), 4.30 (m, 4H), 2.14 (s, 3H). MS (EI) for C$_{12}$H$_{12}$FN$_3$O$_2$: 250 (MH$^+$).

A solution of 4-(8-fluoro-2,3-dihydro-1,4-benzodioxin-6-yl)-3-methyl-1H-pyrazol-5-amine (100 mg, 0.40 mmol) and 5-chloro-2-fluoro-4-hydroxybenzaldehyde (70 mg, 0.40 mmol) in TFA (2 mL) was stirred at 90° C. for 16 h. The reaction mixture was concentrated and purified by preparative reverse phase HPLC to give 2-chloro-5-fluoro-4-(6-fluoro-1-methyl-8,9-dihydro-3H-[1,4]dioxino[2,3-g]pyrazolo[3,4-c]isoquinolin-5-yl)phenol (18 mg, 11% yield) as a yellow solid after lyophillization of the pure fractions. $^1$H NMR (400 MHz, d$_6$-DMSO) δ 10.98 (s, 1H), 7.55 (m, 2H), 6.86 (dd, 1H), 4.44 (m, 4H), 2.74 (s, 3H); MS (EI) for C$_{19}$H$_{12}$ClF$_2$N$_3$O$_3$: 404 (MH$^+$).

Example 27

2-chloro-4-(6-fluoro-1-methyl-8,9-bis{[2-(methyloxy) ethyl]oxy}-3H-pyrazolo[3,4-c]isoquinolin-5-yl)phenol hydrochloric acid salt: To a mixture of methyl 2-hydroxy-3-[(phenylcarbonyl)oxy]benzoate (21.2 g, 78 mmol), potassium carbonate (21.5 g, 156 mmol) and acetonitrile (370 mL) was added 1-bromo-2-(methyloxy)ethane (12.1 mL, 116 mmol). The resulting mixture was heated at reflux 18 hour. After cooling to room temperature, the reaction mixture was diluted with ethyl acetate (400 mL), filtered and concentrated. The residue was then diluted with ethyl acetate (200 mL) and washed with 5% sodium hydroxide solution, water and brine (100 mL each), dried over sodium sulfate, filtered, concentrated, and the residue was chromatographed (silica gel, 30-50% ethyl acetate-hexane) to provide methyl 2-{[2-(methyloxy)ethyl]oxy}-3-[(phenylcarbonyl)oxy]benzoate, (22.5 g, 68 mmol, 87% yield). $^1$H NMR (400 MHz, CDCl$_3$): 8.25-8.23 (d, d, 2H), 7.76-7.74 (d, d, 1H), 7.68-7.64 (d, d, 1H), 7.55-7.51 (d, d, 2H), 7.40-7.38 (d, d, 1H), 7.23-7.19 (d, d, 1H), 4.17-4.15 (m, 2H), 3.92 (s, 3H), 3.58-3.55 (m, 2H), 3.14 (s, 3H).

Methyl 2-{[2-(methyloxy)ethyl]oxy}-3-[(phenylcarbonyl)oxy]benzoate (8.0 g, 24.2 mmol) was added drop wise over 15 minutes to a mixture of 90% nitric acid (15 mL) and concentrated sulfuric acid (3 mL) at −5° C. The resulting mixture was stirred for an additional 15 minutes then it was poured into a mixture of ice (200 g) and dichloromethane (200 mL). The organic portion was separated, washed with saturated sodium bicarbonate solution, brine (100 mL each) dried over sodium sulfate, filtered and concentrated to give methyl 2-{[2-(methyloxy)ethyl]oxy}-5-nitro-3-[(phenylcarbonyl)oxy]benzoate (8.1 g, 21.6 mmol, 89% yield). $^1$H NMR (400 MHz, CDCl$_3$): 8.63-8.62 (d, 1H), 8.27-8.26 (d, 1H), 8.21-8.19 (m, 2H), 7.69-7.67 (d, d, 1H), 7.55-7.51 (d, d, 2H), 4.26-4.24 (m, 2H), 3.96 (s, 3H), 3.58-3.56 (m, 2H), 3.12 (s, 3H).

Methyl 2-{[2-(methyloxy)ethyl]oxy}-5-nitro-3-[(phenylcarbonyl)oxy]benzoate (8.1 g, 21.6 mmol) was dissolved in methanol (150 mL) followed by the addition of potassium carbonate (3.3 g, 24 mmol). The reaction mixture was stirred at room temperature for one hour, filtered and then acidified with 4N hydrogen chloride in dioxane. It was concentrated and then re-dissolved in ethyl acetate (100 mL), washed with water and brine (100 mL each), dried over sodium sulfate, filtered and concentrated to give an oily residue which was purified by flash chromatography (silica gel, 30% ethyl acetate-hexane) to provide methyl 3-hydroxy-2-{[2-(methyloxy)ethyl]oxy}-5-nitrobenzoate (8.1 g, 21.0 mmol, 97% yield). $^1$H NMR (400 MHz, CDCl$_3$): 8.69 (s, 1H), 8.24-8.23 (d, 1H), 7.95-7.94 (d, 1H), 4.31-4.29 (m, 2H), 3.95 (s, 3H), 3.79-3.77 (m, 2H), 3.58 (s, 3H).

To a mixture of methyl 3-hydroxy-2-{[2-(methyloxy)ethyl]oxy}-5-nitrobenzoate (4.4 g, 16.2 mmol), potassium carbonate (4.5 g, 33 mmol) and acetonitrile (100 mL) was added 1-bromo-2-(methyloxy)ethane (2.5 mL, 24 mmol). The resulting mixture was heated at reflux 18 hour. After cooling to room temperature, the reaction mixture was diluted with ethyl acetate (200 mL), filtered and concentrated. The residue was then diluted with ethyl acetate (100 mL) and washed with 5% sodium hydroxide solution, water and brine (100 mL each), dried over sodium sulfate, filtered, concentrated, and the residue was chromatographed (silica gel, 30-50% ethyl acetate-hexane) to provide to give methyl 2,3-bis{[2-(methyloxy)ethyl]oxy}-5-nitrobenzoate, (4.9 g, 14.8 mmol, 91% yield). $^1$H NMR (400 MHz, CDCl$_3$): 8.27-8.26 (d, 1H), 7.92-7.91 (d, 1H), 4.37-4.35 (m, 2H), 4.27-4.25 (m, 2H), 3.94 (s, 3H), 3.83-3.81 (m, 2H), 3.77-3.74 (m, 2H), 3.45 (s, 3H), 3.42 (s, 3H).

Methyl 2,3-bis{[2-(methyloxy)ethyl]oxy}-5-nitrobenzoate (4.9 g, 14.9 mmol). was dissolved in methanol (180 mL), followed by the addition of 2 g of 10% palladium-charcoal. The resulting mixture was hydrogenated in a Parr Apparatus at 30 psi for 3 hours. Filtration and then concentration of the reaction mixture gave methyl 5-amino-2,3-bis{[2-(methyloxy)ethyl]oxy}benzoate (4.2 g, 14.0 mmol, 94% yield). $^1$H NMR (400 MHz, CDCl$_3$): 6.65 (s, 1H), 6.45 (s, 1H), 4.15-4.10 (m, 4H), 3.87 (s, 3H), 3.77-3.70 (m, 4H), 3.44 (s, 3H), 3.43 (s, 3H).

A solution of methyl 5-amino-2,3-bis{[2-(methyloxy)ethyl]oxy}benzoate (2.2 g, 7.4 mmol) in 1,2-dimethoxyethane (5 mL) was cooled at −4° C. and then cooled in solid dry-ice. To this mixture was added first boron trifluoride diethyl etherate (1.3 mL, 10 mmol), and then tert-butylnitrite (1.4 mL, 12 mmol), and the resulting mixture was stirred at −4° C. for 2 hours. It was then diluted with ether (100 mL) and a solid precipitated and was collected and washed with ether. The solid was suspended in 1,2,4-trichlorobenzene (20 mL) and heated at 110° C. for 18 hours. After cooling to room temperature, it was applied directly onto a silica gel column with hexane, and then chromatographed (30% ethyl acetate-hexane) to give methyl 5-fluoro-2,3-bis{[2-(methyloxy)ethyl]oxy}benzoate (0.35 g, 1.2 mmol, 16% yield). $^1$H NMR (400 MHz, CDCl$_3$): 7.05-7.02 (d, d, 1H), 6.83-6.80 (d, d, 1H), 4.20-4.13 (m, 4H), 3.90 (s, 3H), 3.79-3.72 (m, 4H), 3.44 (s, 6H).

To a solution of methyl 5-fluoro-2,3-bis{[2-(methyloxy)ethyl]oxy}benzoate (0.34 g, 1.13 mmol) at 0° C. was added a solution of lithium aluminum hydride in tetrahydrofuran (1M, 1.2 mL, 1.2 mmol) and the resulting mixture was stirred for one hour. It was then quenched with ethyl acetate (1 mL) and 5% sodium hydroxide solution (1 mL), diluted with ether (100 mL), and filtered. The filtrate was washed water and brine (100 mL each), dried over sodium sulfate, filtered and concentrated to give (5-fluoro-2,3-bis{[2-(methyloxy)ethyl]oxy}phenyl)methanol (0.30 g, 1.10 mmol, 97% yield), $^1$H NMR (400 MHz, CDCl$_3$): 6.63-6.59 (m, 2H), 4.58-4.56 (d, 2H), 4.29-4.24 (m, 2H), 4.14-4.10 (m, 2H), 3.77-3.69 (m, 4H), 3.44 (s, 3H), 3.42 (s, 3H).

To a solution of (5-fluoro-2,3-bis{[2-(methyloxy)ethyl]oxy}phenyl)methanol (0.31 g, 1.1 mmol) and pyridine (0.15 mL 1.9 mmol) in tetrahydrofuran (10 mL) at 0° C. was added thionyl chloride (0.093 mL, 1.3 mmol) and the reaction mixture warmed to room temperature and stirred for one hour. Then it was poured into water (20 mL) and extracted with ethyl acetate (3×20 mL). The combined extract was washed with water and brine (20 mL each), dried over sodium sulfate, filtered and concentrated to give 1-(chloromethyl)-5-fluoro-2,3-bis{[2-(methyloxy)ethyl]oxy}benzene (0.33 g, 1.1 mmol, 100% yield), $^1$H NMR (400 MHz, CDCl$_3$): 6.76-6.26 (m, 2H), 4.69 (s, 2H), 4.22-4.13 (m, 4H), 3.86-3.78 (m, 4H), 3.46 (s, 6H).

1-(Chloromethyl)-5-fluoro-2,3-bis{[2-(methyloxy)ethyl]oxy}benzene (0.31 g, 1.06 mmol) was dissolved in N,N-dimethylformamide (2 mL) followed by the addition potassium cyanide (0.10 g, 1.7 mmol), and the resulting mixture was heated at 60° C. for 18 hours. After cooling to room temperature, it was diluted with ethyl acetate (50 mL), washed with water and brine (20 mL each), dried over sodium sulfate, filtered and concentrated to give an oily residue which was purified by flash chromatography (30% ethyl acetate-hexane) to provide (5-fluoro-2,3-bis{[2-(methyloxy)ethyl]oxy}phenyl)acetonitrile (0.25 g, 0.88 mmol, 85% yield). $^1$H NMR (400 MHz, CDCl$_3$): 6.76-6.74 (d, d, 1H), 6.66-6.63 (d, d, 1H), 4.22-4.21 (m, 2H), 4.13-4.11 (m, 2H), 3.84 (s, 2H), 3.78-3.76 (m, 2H), 3.64-3.61 (m, 2H), 3.43 (s, 3H), 3.42 (s, 3H).

A solution of (5-fluoro-2,3-bis{[2-(methyloxy)ethyl]oxy}phenyl)acetonitrile (250 mg, 0.88 mmol) in tetrahydrofuran (2 mL) was added to a suspension of sodium hydride (40% oil dispersion, 70 mg, 1.8 mmol) in tetrahydrofuran (5 mL), followed by the addition of 1-acetylimidazole (145 mg, 1.3 mmol). After five minutes at room temperature, stirring was continued at 60° C. for 20 minutes. After cooling to room temperature, the reaction mixture was quenched with hydrochloric acid (1M, 20 mL) and extracted with ethyl acetate (3×20 mL). The combined extract was washed with water and brine (20 mL each), dried over sodium sulfate, filtered and concentrated to give the crude 2-(5-fluoro-2,3-bis{[2-(methyloxy)ethyl]oxy}phenyl)-3-oxobutanenitrile (0.26 g, 0.80 mmol, 91% yield). $^1$H NMR (400 MHz, CDCl$_3$): 6.73-6.69 (m, 2H), 4.29-4.21 (m, 2H), 4.15-4.13 (m, 2H), 3.79-3.76 (m 2H), 3.62-3.57 (m, 2H), 3.44 (s, 3H), 3.41 (s, 3H), 2.26 (s, 3H); MS (EI) for $C_{16}H_{20}FNO_5$: 326 (MH$^+$).

To a solution of 2-(5-fluoro-2,3-bis{[2-(methyloxy)ethyl]oxy}phenyl)-3-oxobutanenitrile (0.26 mg, 0.80 mmol) in ethanol (5 mL) was added hydrazine dihydrochloride (105 mg, 0.9 mmol). The resulting mixture was heated at reflux for 1 hour. It was cooled to room temperature then poured into a saturated sodium bicarbonate solution (10 mL) and the mixture was extracted with ethyl acetate (3×10 mL). The combined extract was washed with aqueous sodium bicarbonate solution, brine, dried over sodium sulfate, filtered and concentrated to give an oily residue which was purified by flash chromatography (silica gel, 5% methanol-dichloromethane) to provide 4-(5-fluoro-2,3-bis{[2-(methyloxy)ethyl]oxy}phenyl)-3-methyl-1H-pyrazol-5-amine (0.15 g, 0.45 mmol, 56%) yield $^1$H NMR (400 MHz, d$_6$-DMSO): 7.06-7.02 (m, 1H), 6.72-6.69 (m, 1H), 4.18-4.16 (m, 2H), 3.83-3.81 (m, 2H), 3.71-3.69 (m. 2H), 3.36-3.64 (m, 2H), 3.32 (s, 3H), 3.10 (s, 3H), 2.16 (s, 3H); MS (EI) for $C_{16}H_{22}FN_3O_4$: 340 (MH$^+$).

A mixture of 4-(5-fluoro-2,3-bis{[2-(methyloxy)ethyl]oxy}phenyl)-3-methyl-1H-pyrazol-5-amine 0.153 mg, 0.45 mmol), 3-chloro-4-hydroxybenzaldehyde (141 mg, 0.9 mmol) and trifluoroacetic acid (3 mL) was heated at 70° C. for 18 hours. Then the reaction mixture was concentrated, dissolved in 10 mL of N,N-dimethylformamide, and purified by preparatory HPLC (Shimadzu LC-8A HPLC, Waters Xterra C18 30 mm×100 mm column, acetonitrile-water-trifluoroacetic eluent). After concentration then lyophillization of the pure fractions a yellow powder was obtained. It was dissolved in 4 mL of 1:1 methanol: 4M hydrogen chloride in dioxane, and evaporated to dryness (repeated three times) to give 2-chloro-4-(6-fluoro-1-methyl-8,9-bis{[2-(methyloxy)ethyl]oxy}-3H-pyrazolo[3,4-c]isoquinolin-5-yl)phenol hydrochloric acid salt (77 mg, 0.15 mmol, 33% yield), $^1$H NMR (400 MHz, d$_6$-DMSO): 10.48 (b, 1H), 7.48 (s, 1H), 7.32-7.28 (m, 2H), 7.05-7.03 (d, 1H), 4.35-4.33 (m, 2H), 4.25-4.21 (m, 2H), 3.77-3.75 (m, 2H), 3.69-3.66 (m, 2H), 3.35 (s, 3H), 3.22 (s, 3H), 2.80 (s, 3H); MS (EI) for $C_{23}H_{23}ClFN_3O_5$: 476 (MH$^+$).

Example 28

Luciferase-Coupled Chemiluminescent Kinase Assay

ALK biochemical activity was assessed using a Luciferase-Coupled Chemiluminescent Kinase assay (LCCA) format in which kinase activity was measured as the percent ATP remaining following the kinase reaction. ATP remaining after the kinase reaction was detected by luciferase-luciferin-coupled chemiluminescence.

The reaction was initiated by mixing test compounds, 1 µM ATP, 4 µM poly-AEKY and 12 nM ALK (baculovirus expressed human ALK kinase domain F1098-K1410) in a 20 µL assay buffer (20 nM Tris-HCL pH 7.5, 10 mM MgCl$_2$, 0.02% Triton X-100, 100 mM DTT, 2 mM MnCl$_2$). The mixture was incubated at ambient temperature for 2 hours after which 20 µL luciferase-luciferin mix was added and the chemiluminescent signal read using a Wallac Victor$^2$ reader. The luciferase-luciferin mix consists of 50 mM HEPES, pH 7.8, 8.5 µg/mL oxalic acid (pH 7.8), 5 (or 50) mM DTT, 0.4% Triton X-100, 0.25 mg/mL coenzyme A, 63 µM AMP, 28 µg/mL luciferin and 40,000 units of light/mL luciferase. A graph of ATP consumed during the reaction is shown in FIG. 1.

Consumption of ATP by ALK can thus be quantified and utilized as a measure of inhibition of ALK activity by compounds described herein. By employing serial dilutions of compounds to be tested, the ability of test compounds to inhibit ALK activity can be determined. IC$_{50}$ values can also be obtained from these data, as shown in Table 1.

Example 29

The following are examples of representative pharmaceutical dosage forms for the compounds of the invention:

| Injectable Suspension (I.M.) | mg/mL |
|---|---|
| Compound of the invention | 10 |
| methylcellulose | 5.0 |
| Tween 80 | 0.5 |
| benzyl alcohol | 9.0 |
| benzalkonium chloride | 1.0 |

| Tablet | mg/tablet |
|---|---|
| Compound of the invention | 25 |
| microcrystalline cellulose | 415 |
| povidone | 14 |
| Pregelatanized starch | 43.5 |
| magnesium stearate | 2.5 |
| Total | 500 mg |

| Capsule | mg/capsule |
|---|---|
| Compound of the invention | 25 |
| lactose powder | 573.5 |
| magnesium stearate | 1.5 |
| Total | 600 mg |

| Aerosol | mg/Per canister |
|---|---|
| Compound of the invention | 24 |
| lecithin, NF liquid concentration | 1.2 |
| trichlorofluoromethane, NF | 4025 |
| dichlorodifluoromethane, NF | 12150 |

Exemplary Embodiments

Shown in Table 2 are examples of compounds in accordance with the invention. The chemical names are shown along with IC$_{50}$ data for inhibition of ALK where "A" denotes IC$_{50}$ values of less than or equal to 99 nM; "B" denotes IC$_{50}$ values between 100 nM and 999 nM; "C" denotes IC$_{50}$ values between 1000 nM and 1999 nM; "D" denotes IC$_{50}$ values greater than 2000 nM; and "-" denotes lack of data. All reported IC$_{50}$ values are mean values.

TABLE 2

| Entry | Name | IC$_{50}$ ALK |
|---|---|---|
| 3 | 4-[7,8-bis(methyloxy)-1-(phenylmethyl)-3H-pyrazolo[3,4-c]isoquinolin-5-yl]phenol | B |
| 9 | 4-[7,8-bis(methyloxy)-1-(phenylmethyl)-3H-pyrazolo[3,4-c]isoquinolin-5-yl]benzene-1,2-diol | C |
| 10 | 4-{7,8-bis(methyloxy)-1-[(4-methylphenyl)methyl]-3H-pyrazolo[3,4-c]isoquinolin-5-yl}phenol | B |
| 12 | 4-(7,8-bis(methyloxy)-1-{[4-(methyloxy)phenyl]methyl}-3H-pyrazolo[3,4-c]isoquinolin-5-yl)phenol | B |
| 13 | 4-{7,8-bis(methyloxy)-1-[(2-methylphenyl)methyl]-3H-pyrazolo[3,4-c]isoquinolin-5-yl}phenol | B |
| 14 | 4-{7,8-bis(methyloxy)-1-[(3-methylphenyl)methyl]-3H-pyrazolo[3,4-c]isoquinolin-5-yl}phenol | B |
| 15 | 4-[1-methyl-7,8-bis(methyloxy)-3H-pyrazolo[3,4-c]isoquinolin-5-yl]phenol | A |
| 19 | 4-[7,8-bis(methyloxy)-1-(1-phenylethyl)-3H-pyrazolo[3,4-c]isoquinolin-5-yl]phenol | — |
| 20 | 4-[1-{[3,4-bis(methyloxy)phenyl]methyl}-7,8-bis(methyloxy)-3H-pyrazolo[3,4-c]isoquinolin-5-yl]phenol | C |
| 21 | 4-(7,8-bis(methyloxy)-1-{[3-(methyloxy)phenyl]methyl}-3H-pyrazolo[3,4-c]isoquinolin-5-yl)phenol | C |
| 22 | 4-[1-ethyl-7,8-bis(methyloxy)-3H-pyrazolo[3,4-c]isoquinolin-5-yl]phenol | B |
| 24 | 4-[6,7,8-tris(methyloxy)-1-(phenylmethyl)-3H-pyrazolo[3,4-c]isoquinolin-5-yl]phenol | A |
| 25 | 4-[1-methyl-6,7,8-tris(methyloxy)-3H-pyrazolo[3,4-c]isoquinolin-5-yl]phenol | A |
| 26 | 4-[8-(methyloxy)-1-(phenylmethyl)-3H-pyrazolo[3,4-c]isoquinolin-5-yl]phenol | B |
| 27 | 4-[7,8-bis(methyloxy)-1-(trifluoromethyl)-3H-pyrazolo[3,4-c]isoquinolin-5-yl]phenol | B |
| 28 | 4-[1-(1-methylethyl)-7,8-bis(methyloxy)-3H-pyrazolo[3,4-c]isoquinolin-5-yl]phenol | B |
| 29 | 4-[7,8-bis(methyloxy)-3H-pyrazolo[3,4-c]isoquinolin-5-yl]phenol | B |
| 31 | 4-[1-methyl-6,8-bis(methyloxy)-3H-pyrazolo[3,4-c]isoquinolin-5-yl]phenol | A |
| 32 | 4-[6,8-bis(methyloxy)-3H-pyrazolo[3,4-c]isoquinolin-5-yl]phenol | B |
| 34 | 4-[6,7,8-tris(methyloxy)-3H-pyrazolo[3,4-c]isoquinolin-5-yl]phenol | A |
| 35 | 4-[1-methyl-7,8,9-tris(methyloxy)-3H-pyrazolo[3,4-c]isoquinolin-5-yl]phenol | A |
| 36 | 4-[1-methyl-8-(methyloxy)-3H-pyrazolo[3,4-c]isoquinolin-5-yl]phenol | A |
| 37 | 2-methyl-4-[1-methyl-7,8-bis(methyloxy)-3H-pyrazolo[3,4-c]isoquinolin-5-yl]phenol | A |
| 38 | 4-[1-methyl-7,8-bis(methyloxy)-3H-pyrazolo[3,4-c]isoquinolin-5-yl]-2-(methyloxy)phenol | B |
| 39 | 4-{1-methyl-8-(methyloxy)-7-[(2-morpholin-4-ylethyl)oxy]-3H-pyrazolo[3,4-c]isoquinolin-5-yl}phenol | B |
| 40 | 2-(ethyloxy)-4-[1-methyl-7,8-bis(methyloxy)-3H-pyrazolo[3,4-c]isoquinolin-5-yl]phenol | B |
| 41 | 2-chloro-4-[1-methyl-7,8-bis(methyloxy)-3H-pyrazolo[3,4-c]isoquinolin-5-yl]phenol | A |
| 42 | 2-fluoro-4-[1-methyl-7,8-bis(methyloxy)-3H-pyrazolo[3,4-c]isoquinolin-5-yl]phenol | B |
| 44 | 2-bromo-4-[1-methyl-7,8-bis(methyloxy)-3H-pyrazolo[3,4-c]isoquinolin-5-yl]phenol | A |
| 45 | 1-{[5-(4-hydroxyphenyl)-7,8-bis(methyloxy)-3H-pyrazolo[3,4-c]isoquinolin-1-yl]methyl}pyrrolidin-2-one | B |
| 54 | 4-{1-methyl-7-(methyloxy)-8-[(piperidin-4-ylmethyl)oxy]-3H-pyrazolo[3,4-c]isoquinolin-5-yl}phenol | A |
| 55 | 4-{1-methyl-8-(methyloxy)-7-[(piperidin-4-ylmethyl)oxy]-3H-pyrazolo[3,4-c]isoquinolin-5-yl}phenol | B |
| 58 | 4-[8-(ethyloxy)-1-methyl-7-(methyloxy)-3H-pyrazolo[3,4-c]isoquinolin-5-yl]phenol | B |
| 59 | 4-[1-methyl-8,9-bis(methyloxy)-3H-pyrazolo[3,4-c]isoquinolin-5-yl]phenol | A |
| 60 | 4-[7-(ethyloxy)-1-methyl-8-(methyloxy)-3H-pyrazolo[3,4-c]isoquinolin-5-yl]phenol | B |
| 61 | 4-{1-methyl-8-(methyloxy)-9-[(piperidin-4-ylmethyl)oxy]-3H-pyrazolo[3,4-c]isoquinolin-5-yl}phenol | A |
| 63 | 2-ethyl-4-[1-methyl-7,8-bis(methyloxy)-3H-pyrazolo[3,4-c]isoquinolin-5-yl]phenol | B |
| 64 | 4-(1-methyl-8-(methyloxy)-9-{[(1-methylpiperidin-4-yl)methyl]oxy}-3H-pyrazolo[3,4-c]isoquinolin-5-yl)phenol | A |
| 65 | 4-(1-methyl-7-(methyloxy)-8-{[(1-methylpiperidin-4-yl)methyl]oxy}-3H-pyrazolo[3,4-c]isoquinolin-5-yl)phenol | A |
| 66 | 4-[1,7-dimethyl-8-(methyloxy)-3H-pyrazolo[3,4-c]isoquinolin-5-yl]phenol | A |
| 67 | 1,1-dimethylethyl 4-[5-(4-hydroxyphenyl)-7,8-bis(methyloxy)-3H-pyrazolo[3,4-c]isoquinolin-1-yl]piperidine-1-carboxylate | B |
| 69 | 2-chloro-4-[1-methyl-8,9-bis(methyloxy)-3H-pyrazolo[3,4-c]isoquinolin-5-yl]phenol | A |
| 70 | 2-fluoro-4-[1-methyl-8,9-bis(methyloxy)-3H-pyrazolo[3,4-c]isoquinolin-5-yl]phenol | A |
| 71 | 2-methyl-4-[1-methyl-8,9-bis(methyloxy)-3H-pyrazolo[3,4-c]isoquinolin-5-yl]phenol | A |
| 72 | 2-bromo-4-[1-methyl-8,9-bis(methyloxy)-3H-pyrazolo[3,4-c]isoquinolin-5-yl]phenol | A |
| 76 | 2-[(difluoromethyl)oxy]-4-[1-methyl-7,8-bis(methyloxy)-3H-pyrazolo[3,4-c]isoquinolin-5-yl]phenol | C |
| 78 | 4-[1,9-dimethyl-8-(methyloxy)-3H-pyrazolo[3,4-c]isoquinolin-5-yl]phenol | A |
| 79 | 4-[6,9-difluoro-1-methyl-8-(methyloxy)-3H-pyrazolo[3,4-c]isoquinolin-5-yl]phenol | A |
| 80 | 2-bromo-4-{1-methyl-8-(methyloxy)-9-[(2-morpholin-4-ylethyl)oxy]-3H-pyrazolo[3,4-c]isoquinolin-5-yl}phenol | B |
| 81 | 2-chloro-4-{1-methyl-8-(methyloxy)-9-[(2-morpholin-4-ylethyl)oxy]-3H-pyrazolo[3,4-c]isoquinolin-5-yl}phenol | B |
| 82 | 4-(7,8-bis(methyloxy)-1-{[(phenylmethyl)amino]methyl}-3H-pyrazolo[3,4-c]isoquinolin-5-yl)phenol | B |
| 83 | 2,5-dimethyl-4-[1-methyl-7,8-bis(methyloxy)-3H-pyrazolo[3,4-c]isoquinolin-5-yl]phenol | B |
| 85 | 2,5-dichloro-4-[1-methyl-7,8-bis(methyloxy)-3H-pyrazolo[3,4-c]isoquinolin-5-yl]phenol | A |
| 87 | 2-bromo-4-(1-methyl-8-(methyloxy)-9-{[(1-methylpiperidin-4-yl)methyl]oxy}-3H-pyrazolo[3,4-c]isoquinolin-5-yl)phenol | A |
| 88 | 2-chloro-4-(1-methyl-7-(methyloxy)-8-{[(1-methylpiperidin-4-yl)methyl]oxy}-3H-pyrazolo[3,4-c]isoquinolin-5-yl)phenol | A |
| 89 | 4-[9-fluoro-1-methyl-8-(methyloxy)-3H-pyrazolo[3,4-c]isoquinolin-5-yl]phenol | A |
| 90 | 4-(1-methyl-8-(methyloxy)-9-{[2-(methyloxy)ethyl]oxy}-3H-pyrazolo[3,4-c]isoquinolin-5-yl)phenol | A |
| 91 | 2-chloro-4-(1-methyl-8-(methyloxy)-9-{[(1-methylpiperidin-4-yl)methyl]oxy}-3H-pyrazolo[3,4-c]isoquinolin-5-yl)phenol | A |
| 92 | 4-[6-bromo-1,7-dimethyl-8-(methyloxy)-3H-pyrazolo[3,4-c]isoquinolin-5-yl]phenol | A |
| 93 | 4-[6-fluoro-1-methyl-7,8-bis(methyloxy)-3H-pyrazolo[3,4-c]isoquinolin-5-yl]phenol | A |
| 94 | 4-[9-chloro-1,7-dimethyl-8-(methyloxy)-3H-pyrazolo[3,4-c]isoquinolin-5-yl]phenol | A |
| 95 | 2-chloro-4-(8-{[(1-ethylpiperidin-4-yl)methyl]oxy}-1-methyl-7-(methyloxy)-3H-pyrazolo[3,4-c]isoquinolin-5-yl)phenol | A |
| 96 | 3-chloro-4-[1-methyl-7,8-bis(methyloxy)-3H-pyrazolo[3,4-c]isoquinolin-5-yl]phenol | A |
| 97 | 4-(1-methyl-8,9-bis{[2-(methyloxy)ethyl]oxy}-3H-pyrazolo[3,4-c]isoquinolin-5-yl)phenol | A |
| 98 | 4-(1-methyl-3H-pyrazolo[3,4-c]isoquinolin-5-yl)phenol | A |
| 99 | 2-chloro-4-(1-methyl-3H-pyrazolo[3,4-c]isoquinolin-5-yl)phenol | A |
| 100 | 2-bromo-4-(1-methyl-3H-pyrazolo[3,4-c]isoquinolin-5-yl)phenol | A |
| 101 | 2-chloro-4-[1,7-dimethyl-8-(methyloxy)-3H-pyrazolo[3,4-c]isoquinolin-5-yl]phenol | A |
| 102 | 2-bromo-4-[1,7-dimethyl-8-(methyloxy)-3H-pyrazolo[3,4-c]isoquinolin-5-yl]phenol | A |
| 103 | 2-chloro-4-(1-methyl-8-({[1-(1-methylethyl)piperidin-4-yl]methyl}oxy)-7-(methyloxy)-3H-pyrazolo[3,4-c]isoquinolin-5-yl)phenol | A |
| 104 | 4-[9-bromo-1-methyl-8-(methyloxy)-3H-pyrazolo[3,4-c]isoquinolin-5-yl]phenol | A |
| 105 | 4-[7-chloro-9-fluoro-1-methyl-8-(methyloxy)-3H-pyrazolo[3,4-c]isoquinolin-5-yl]phenol | B |

TABLE 2-continued

| Entry | Name | IC$_{50}$ ALK |
|---|---|---|
| 106 | 4-[8-{[(1-acetylpiperidin-4-yl)methyl]oxy}-1-methyl-7-(methyloxy)-3H-pyrazolo[3,4-c]isoquinolin-5-yl]-2-chlorophenol | A |
| 107 | 4-[9-{[(1-acetylpiperidin-4-yl)methyl]oxy}-1-methyl-8-(methyloxy)-3H-pyrazolo[3,4-c]isoquinolin-5-yl]-2-bromophenol | A |
| 108 | 2-chloro-4-(1-methyl-9-(methyloxy)-8-{[2-(methyloxy)ethyl]oxy}-3H-pyrazolo[3,4-c]isoquinolin-5-yl)phenol | A |
| 109 | 4-[7-fluoro-1-methyl-8-(methyloxy)-3H-pyrazolo[3,4-c]isoquinolin-5-yl]phenol | B |
| 110 | 2-chloro-4-(1-methyl-8,9-bis{[2-(methyloxy)ethyl]oxy}-3H-pyrazolo[3,4-c]isoquinolin-5-yl)phenol | A |
| 111 | 2-bromo-4-(1-methyl-8,9-bis{[2-(methyloxy)ethyl]oxy}-3H-pyrazolo[3,4-c]isoquinolin-5-yl)phenol | A |
| 112 | 2-chloro-4-(1-methyl-8-(methyloxy)-9-{[2-(methyloxy)ethyl]oxy}-3H-pyrazolo[3,4-c]isoquinolin-5-yl)phenol | A |
| 113 | 2-bromo-4-(1-methyl-8-(methyloxy)-9-{[2-(methyloxy)ethyl]oxy}-3H-pyrazolo[3,4-c]isoquinolin-5-yl)phenol | A |
| 114 | 3-fluoro-4-[1-methyl-7,8-bis(methyloxy)-3H-pyrazolo[3,4-c]isoquinolin-5-yl]phenol | A |
| 115 | 2-chloro-4-(1-methyl-7-(methyloxy)-8-{[2-(methyloxy)ethyl]oxy}-3H-pyrazolo[3,4-c]isoquinolin-5-yl)phenol | A |
| 116 | 2-bromo-4-(1-methyl-7-(methyloxy)-8-{[2-(methyloxy)ethyl]oxy}-3H-pyrazolo[3,4-c]isoquinolin-5-yl)phenol | A |
| 117 | 2-chloro-4-(1-methyl-7,8-bis{[2-(methyloxy)ethyl]oxy}-3H-pyrazolo[3,4-c]isoquinolin-5-yl)phenol | B |
| 118 | 2-bromo-4-(1-methyl-7,8-bis{[2-(methyloxy)ethyl]oxy}-3H-pyrazolo[3,4-c]isoquinolin-5-yl)phenol | B |
| 120 | 4-(6,9-difluoro-1-methyl-8-{[2-(methyloxy)ethyl]oxy}-3H-pyrazolo[3,4-c]isoquinolin-5-yl)phenol | A |
| 121 | 2-chloro-5-fluoro-4-[1-methyl-7,8-bis(methyloxy)-3H-pyrazolo[3,4-c]isoquinolin-5-yl]phenol | A |
| 122 | 2-bromo-5-fluoro-4-[1-methyl-7,8-bis(methyloxy)-3H-pyrazolo[3,4-c]isoquinolin-5-yl]phenol | A |
| 123 | 4-[9-fluoro-1-methyl-7,8-bis(methyloxy)-3H-benzo[e]indazol-5-yl]phenol | B |
| 125 | 3-fluoro-4-(1-methyl-7-(methyloxy)-8-{[2-(methyloxy)ethyl]oxy}-3H-pyrazolo[3,4-c]isoquinolin-5-yl)phenol | A |
| 126 | 4-(6,9-difluoro-1-methyl-8-{[2-(methyloxy)ethyl]oxy}-3H-pyrazolo[3,4-c]isoquinolin-5-yl)-3-fluorophenol | A |
| 127 | 2-chloro-4-(6,9-difluoro-1-methyl-8-{[2-(methyloxy)ethyl]oxy}-3H-pyrazolo[3,4-c]isoquinolin-5-yl)phenol | A |
| 128 | 2-chloro-4-[8-(ethyloxy)-1-methyl-7-(methyloxy)-3H-pyrazolo[3,4-c]isoquinolin-5-yl]phenol | B |
| 129 | 2-chloro-4-[6-chloro-1-methyl-7,8-bis(methyloxy)-3H-pyrazolo[3,4-c]isoquinolin-5-yl]phenol | B |
| 130 | 3-fluoro-4-(1-methyl-9-(methyloxy)-8-{[2-(methyloxy)ethyl]oxy}-3H-pyrazolo[3,4-c]isoquinolin-5-yl)phenol | A |
| 131 | 2-chloro-4-(1,7-dimethyl-8-{[2-(methyloxy)ethyl]oxy}-3H-pyrazolo[3,4-c]isoquinolin-5-yl)phenol | A |
| 132 | 3-fluoro-4-(6-fluoro-1-methyl-7-(methyloxy)-8-{[2-(methyloxy)ethyl]oxy}-3H-pyrazolo[3,4-c]isoquinolin-5-yl)phenol | A |
| 133 | 2-chloro-4-[1-methyl-8-[(1-methylethyl)oxy]-7-(methyloxy)-3H-pyrazolo[3,4-c]isoquinolin-5-yl]phenol | A |
| 134 | 2-chloro-4-{1-methyl-7-(methyloxy)-8-[(2-methylpropyl)oxy]-3H-pyrazolo[3,4-c]isoquinolin-5-yl}phenol | B |
| 135 | 2-bromo-5-fluoro-4-(1-methyl-7-(methyloxy)-8-{[2-(methyloxy)ethyl]oxy}-3H-pyrazolo[3,4-c]isoquinolin-5-yl)phenol | A |
| 136 | 4-[7,8-bis(methyloxy)-3H-pyrazolo[3,4-c]isoquinolin-5-yl]-2-chlorophenol | B |
| 137 | 4-[7,8-bis(methyloxy)-1-(trifluoromethyl)-3H-pyrazolo[3,4-c]isoquinolin-5-yl]-2-chlorophenol | B |
| 138 | 4-{7,8-bis(methyloxy)-1-[(methyloxy)methyl]-3H-pyrazolo[3,4-c]isoquinolin-5-yl}-2-chlorophenol | B |
| 139 | 2-chloro-4-(1-methyl-3H-[1,3]dioxolo[4,5-g]pyrazolo[3,4-c]isoquinolin-5-yl)phenol | A |
| 140 | 2-chloro-4-(1-methyl-8,9-dihydro-3H-[1,4]dioxino[2,3-g]pyrazolo[3,4-c]isoquinolin-5-yl)phenol | A |
| 141 | 2-chloro-4-(1-methyl-9,10-dihydro-3H,8H-[1,4]dioxepino[2,3-g]pyrazolo[3,4-c]isoquinolin-5-yl)phenol | A |
| 142 | 2-chloro-4-{7-[(difluoromethyl)oxy]-1-methyl-8-(methyloxy)-3H-pyrazolo[3,4-c]isoquinolin-5-yl}phenol | A |
| 143 | 2-chloro-5-fluoro-4-(6-fluoro-1-methyl-9-(methyloxy)-8-{[2-(methyloxy)ethyl]oxy}-3H-pyrazolo[3,4-c]isoquinolin-5-yl)phenol | A |
| 144 | 2-chloro-4-(6,9-difluoro-1-methyl-8-{[2-(methyloxy)ethyl]oxy}-3H-pyrazolo[3,4-c]isoquinolin-5-yl)-5-fluorophenol | A |
| 145 | 2-chloro-4-(11-methyl-2,3-dihydro-9H-[1,4]dioxino[2,3-f]pyrazolo[3,4-c]isoquinolin-7-yl)phenol | A |
| 146 | 2-chloro-5-fluoro-4-(11-methyl-2,3-dihydro-9H-[1,4]dioxino[2,3-f]pyrazolo[3,4-c]isoquinolin-7-yl)phenol | A |
| 147 | 2-chloro-4-[1-methyl-6,7,8-tris(methyloxy)-3H-pyrazolo[3,4-c]isoquinolin-5-yl]phenol | A |
| 148 | 2-bromo-4-(6,9-difluoro-1-methyl-8-{[2-(methyloxy)ethyl]oxy}-3H-pyrazolo[3,4-c]isoquinolin-5-yl)-5-fluorophenol | A |
| 149 | 7-(3-chlorophenyl)-11-methyl-2,3-dihydro-9H-[1,4]dioxino[2,3-f]pyrazolo[3,4-c]isoquinoline | D |
| 150 | 2-chloro-5-fluoro-4-(6-fluoro-1-methyl-8,9-dihydro-3H-[1,4]dioxino[2,3-g]pyrazolo[3,4-c]isoquinolin-5-yl)phenol | A |
| 151 | 2-chloro-4-{1-methyl-7-(methyloxy)-8-[(tetrahydrofuran-2-ylmethyl)oxy]-3H-pyrazolo[3,4-c]isoquinolin-5-yl}phenol | A |
| 152 | 2-chloro-4-{1-methyl-7-(methyloxy)-8-[(tetrahydro-2H-pyran-2-ylmethyl)oxy]-3H-pyrazolo[3,4-c]isoquinolin-5-yl}phenol | A |
| 153 | 2-chloro-4-{1-methyl-7-(methyloxy)-8-[(2,2,2-trifluoroethyl)oxy]-3H-pyrazolo[3,4-c]isoquinolin-5-yl}phenol | B |
| 154 | 2-chloro-5-fluoro-4-[9-fluoro-1-methyl-6,7,8-tris(methyloxy)-3H-pyrazolo[3,4-c]isoquinolin-5-yl]phenol | A |
| 155 | 5-(3-chloro-4-hydroxyphenyl)-6,9-difluoro-1-methyl-3H-pyrazolo[3,4-c]isoquinolin-8-ol | A |
| 156 | 6,9-difluoro-5-(2-fluorophenyl)-1-methyl-8-{[2-(methyloxy)ethyl]oxy}-3H-pyrazolo[3,4-c]isoquinoline | D |
| 157 | 2-chloro-4-{8-[(difluoromethyl)oxy]-6,9-difluoro-1-methyl-3H-pyrazolo[3,4-c]isoquinolin-5-yl}phenol | A |
| 158 | 2-chloro-4-(6,11-difluoro-1-methyl-8,9-dihydro-3H-[1,4]dioxino[2,3-g]pyrazolo[3,4-c]isoquinolin-5-yl)-5-fluorophenol | A |
| 159 | 4-(1-methyl-3H-benzo[e]indazol-5-yl)phenol | B |
| 160 | 6-fluoro-7-(2-fluorophenyl)-11-methyl-2,3-dihydro-9H-[1,4]dioxino[2,3-f]pyrazolo[3,4-c]isoquinoline | B |
| 161 | 2-chloro-4-{1-methyl-7-(methyloxy)-8-[(tetrahydro-2H-pyran-4-ylmethyl)oxy]-3H-pyrazolo[3,4-c]isoquinolin-5-yl}phenol | A |
| 162 | 2-chloro-4-[8-{[2-(ethyloxy)ethyl]oxy}-1-methyl-7-(methyloxy)-3H-pyrazolo[3,4-c]isoquinolin-5-yl]phenol | A |
| 164 | 3-fluoro-4-(6-fluoro-11-methyl-2,3-dihydro-9H-[1,4]dioxino[2,3-f]pyrazolo[3,4-c]isoquinolin-7-yl)phenol | A |
| 165 | 2-chloro-5-fluoro-4-(6-fluoro-11-methyl-2,3-dihydro-9H-[1,4]dioxino[2,3-f]pyrazolo[3,4-c]isoquinolin-7-yl)phenol | A |
| 166 | 2-chloro-4-[8-(cyclopentyloxy)-1-methyl-7-(methyloxy)-3H-pyrazolo[3,4-c]isoquinolin-5-yl]phenol | A |
| 167 | 2-chloro-4-(1-methyl-7-(1-methylethyl)-8-{[2-(methyloxy)ethyl]oxy}-3H-pyrazolo[3,4-c]isoquinolin-5-yl)phenol | A |
| 168 | 2-chloro-4-[9-ethyl-1-methyl-8-(methyloxy)-3H-pyrazolo[3,4-c]isoquinolin-5-yl]phenol | A |
| 169 | 2-chloro-4-(6,9-difluoro-1-methyl-8-{[(1-methylpiperidin-4-yl)methyl]oxy}-3H-pyrazolo[3,4-c]isoquinolin-5-yl)phenol | A |
| 170 | 5-(3-chloro-4-hydroxyphenyl)-8-fluoro-1-methyl-7-(methyloxy)-3H-pyrazolo[3,4-c]isoquinolin-6-ol | A |
| 171 | 2-chloro-4-(6-fluoro-1-methyl-7-(methyloxy)-8-{[(1-methylpiperidin-4-yl)methyl]oxy}-3H-pyrazolo[3,4-c]isoquinolin-5-yl)phenol | A |
| 172 | 2-chloro-4-(6-fluoro-1-methyl-8,9-bis{[2-(methyloxy)ethyl]oxy}-3H-pyrazolo[3,4-c]isoquinolin-5-yl)phenol | A |

TABLE 2-continued

| Entry | Name | IC$_{50}$ ALK |
|---|---|---|
| 173 | 5-[3-chloro-4-(methyloxy)phenyl]-6-fluoro-1-methyl-7-(methyloxy)-8-{[(1-methylpiperidin-4-yl)methyl]oxy}-3H-pyrazolo[3,4-c]isoquinoline | C |
| 174 | 5-[3-chloro-4-(methyloxy)phenyl]-8-fluoro-1-methyl-7-(methyloxy)-3H-pyrazolo[3,4-c]isoquinolin-6-ol | D |
| 176 | 2-chloro-4-{6-fluoro-1-methyl-7-(methyloxy)-8-[(2-piperidin-1-ylethyl)oxy]-3H-pyrazolo[3,4-c]isoquinolin-5-yl}phenol | A |
| 177 | 2-chloro-4-[8-{[2-(4-ethylpiperazin-1-yl)ethyl]oxy}-6-fluoro-1-methyl-7-(methyloxy)-3H-pyrazolo[3,4-c]isoquinolin-5-yl]phenol | A |
| 178 | 2-chloro-4-[8-{[2-(diethylamino)ethyl]oxy}-6-fluoro-1-methyl-7-(methyloxy)-3H-pyrazolo[3,4-c]isoquinolin-5-yl]phenol | A |
| 179 | 2-chloro-4-(6-fluoro-1-methyl-7-(methyloxy)-8-{[2-(methyloxy)ethyl]oxy}-3H-pyrazolo[3,4-c]isoquinolin-5-yl)phenol | A |
| 182 | 2-chloro-4-[6-fluoro-1-methyl-9-(methyloxy)-8-{[(1-methylpiperidin-4-yl)methyl]oxy}-3H-pyrazolo[3,4-c]isoquinolin-5-yl]phenol | A |
| 183 | 2-bromo-4-(6-fluoro-1-methyl-9-(methyloxy)-8-{[(1-methylpiperidin-4-yl)methyl]oxy}-3H-pyrazolo[3,4-c]isoquinolin-5-yl)phenol | A |
| 184 | 2-chloro-5-fluoro-4-(6-fluoro-1-methyl-9-(methyloxy)-8-{[(1-methylpiperidin-4-yl)methyl]oxy}-3H-pyrazolo[3,4-c]isoquinolin-5-yl)phenol | A |
| 185 | 4-(6-fluoro-1-methyl-9-(methyloxy)-8-{[(1-methylpiperidin-4-yl)methyl]oxy}-3H-pyrazolo[3,4-c]isoquinolin-5-yl)-2-methylphenol | A |
| 186 | 2-chloro-4-{6,9-difluoro-1-methyl-8-[(2-piperidin-1-ylethyl)oxy]-3H-pyrazolo[3,4-c]isoquinolin-5-yl}phenol | A |
| 187 | 2-chloro-4-(8-{[2-(4-ethylpiperazin-1-yl)ethyl]oxy}-6,9-difluoro-1-methyl-3H-pyrazolo[3,4-c]isoquinolin-5-yl)phenol | A |
| 188 | 2-chloro-4-(8-{[2-(diethylamino)ethyl]oxy}-6,9-difluoro-1-methyl-3H-pyrazolo[3,4-c]isoquinolin-5-yl)phenol | A |
| 191 | 6,9-difluoro-5-(1H-indol-5-yl)-1-methyl-3H-pyrazolo[3,4-c]isoquinolin-8-ol | B |
| 193 | 5-(4-aminophenyl)-6,9-difluoro-1-methyl-3H-pyrazolo[3,4-c]isoquinolin-8-ol | C |
| 194 | 2-chloro-4-(6-fluoro-1-methyl-7-(methyloxy)-8-{[2-(4-methylpiperazin-1-yl)ethyl]oxy}-3H-pyrazolo[3,4-c]isoquinolin-5-yl)phenol | A |
| 195 | 5-(2-amino-1,3-thiazol-5-yl)-6,9-difluoro-1-methyl-3H-pyrazolo[3,4-c]isoquinolin-8-ol | A |
| 196 | 2-chloro-4-[8-{[2-(4-ethylpiperazin-1-yl)ethyl]oxy}-6-fluoro-1-methyl-9-(methyloxy)-3H-pyrazolo[3,4-c]isoquinolin-5-yl]phenol | A |
| 197 | 2-chloro-4-(6-fluoro-1-methyl-9-(methyloxy)-8-{[2-(4-methylpiperazin-1-yl)ethyl]oxy}-3H-pyrazolo[3,4-c]isoquinolin-5-yl)phenol | A |
| 198 | 5-(6-aminopyridin-3-yl)-6,9-difluoro-1-methyl-3H-pyrazolo[3,4-c]isoquinolin-8-ol | D |
| 199 | 5-(5-amino-2-thienyl)-6,9-difluoro-1-methyl-3H-pyrazolo[3,4-c]isoquinolin-8-ol | B |
| 200 | 2-chloro-4-[8-{[3-(4-ethylpiperazin-1-yl)propyl]oxy}-6-fluoro-1-methyl-9-(methyloxy)-3H-pyrazolo[3,4-c]isoquinolin-5-yl]phenol | A |
| 201 | 2-chloro-4-(6-fluoro-1-methyl-9-(methyloxy)-8-{[3-(4-methylpiperazin-1-yl)propyl]oxy}-3H-pyrazolo[3,4-c]isoquinolin-5-yl)phenol | A |
| 202 | 6,9-difluoro-5-(1H-indol-6-yl)-1-methyl-3H-pyrazolo[3,4-c]isoquinolin-8-ol | D |
| 203 | N-[5-(6,9-difluoro-8-hydroxy-1-methyl-3H-pyrazolo[3,4-c]isoquinolin-5-yl)-1,3-thiazol-2-yl]acetamide | C |
| 206 | 2-chloro-4-{6-fluoro-1-methyl-9-(methyloxy)-8-[(2-morpholin-4-ylethyl)oxy]-3H-pyrazolo[3,4-c]isoquinolin-5-yl}phenol | A |
| 207 | 4-[8-({2-[butyl(ethyl)amino]ethyl}oxy)-6-fluoro-1-methyl-9-(methyloxy)-3H-pyrazolo[3,4-c]isoquinolin-5-yl]-2-chlorophenol | A |
| 208 | 4-[8-{[(2R)-2-amino-3-methylbutyl]oxy}-6-fluoro-1-methyl-9-(methyloxy)-3H-pyrazolo[3,4-c]isoquinolin-5-yl]-2-chlorophenol | A |
| 209 | 2-chloro-4-(6-fluoro-1-methyl-9-(methyloxy)-8-{[2-(1-methylpiperidin-4-yl)ethyl]oxy}-3H-pyrazolo[3,4-c]isoquinolin-5-yl)phenol | A |
| 210 | 2-chloro-4-[8-{[(1-ethylpiperidin-4-yl)methyl]oxy}-6-fluoro-1-methyl-9-(methyloxy)-3H-pyrazolo[3,4-c]isoquinolin-5-yl]phenol | A |
| 212 | 5-(5-amino-1,3,4-thiadiazol-2-yl)-6,9-difluoro-1-methyl-3H-pyrazolo[3,4-c]isoquinolin-8-ol | B |
| 213 | 4-[8-{[(2R)-2-amino-3,3-dimethylbutyl]oxy}-6-fluoro-1-methyl-9-(methyloxy)-3H-pyrazolo[3,4-c]isoquinolin-5-yl]-2-chlorophenol | A |
| 214 | 2-chloro-4-[6-fluoro-1-methyl-9-(methyloxy)-8-({2-[4-(2-methylpropyl)piperazin-1-yl]ethyl}oxy)-3H-pyrazolo[3,4-c]isoquinolin-5-yl]phenol | A |
| 215 | 2-chloro-4-[8-{[2-(5-ethyl-2,5-diazabicyclo[2.2.1]hept-2-yl)ethyl]oxy}-6-fluoro-1-methyl-9-(methyloxy)-3H-pyrazolo[3,4-c]isoquinolin-5-yl]phenol | A |
| 216 | 2-chloro-4-[6-fluoro-1-methyl-8-({2-[4-(1-methylethyl)piperazin-1-yl]ethyl}oxy)-9-(methyloxy)-3H-pyrazolo[3,4-c]isoquinolin-5-yl]phenol | A |
| 217 | 4-[8-{[2-(3-amino-8-azabicyclo[3.2.1]oct-8-yl)ethyl]oxy}-6-fluoro-1-methyl-9-(methyloxy)-3H-pyrazolo[3,4-c]isoquinolin-5-yl]-2-chlorophenol | A |
| 218 | 2-chloro-4-[8-{[2-(1-ethylpiperidin-4-yl)ethyl]oxy}-6-fluoro-1-methyl-9-(methyloxy)-3H-pyrazolo[3,4-c]isoquinolin-5-yl]phenol | A |
| 219 | 2-chloro-4-[8-{[2-(diethylamino)ethyl]oxy}-6-fluoro-1-methyl-9-(methyloxy)-3H-pyrazolo[3,4-c]isoquinolin-5-yl]phenol | A |
| 220 | 2-chloro-5-{6-fluoro-1-methyl-9-(methyloxy)-8-[(2-pyrrolidin-1-ylethyl)oxy]-3H-pyrazolo[3,4-c]isoquinolin-5-yl}phenol | A |
| 221 | 6,9-difluoro-5-(2-imino-3-methyl-2,3-dihydro-1,3-thiazol-5-yl)-1-methyl-3H-pyrazolo[3,4-c]isoquinolin-8-ol | C |
| 223 | 2-chloro-4-[6-fluoro-1-methyl-8-[(8-methyl-8-azabicyclo[3.2.1]oct-3-yl)oxy]-9-(methyloxy)-3H-pyrazolo[3,4-c]isoquinolin-5-yl]phenol | A |
| 224 | 2-chloro-4-{6-fluoro-1-methyl-9-(methyloxy)-8-[(3-pyrrolidin-1-ylpropyl)oxy]-3H-pyrazolo[3,4-c]isoquinolin-5-yl}phenol | A |
| 225 | 2-chloro-4-{6-fluoro-1-methyl-9-(methyloxy)-8-[(3-piperidin-1-ylpropyl)oxy]-3H-pyrazolo[3,4-c]isoquinolin-5-yl}phenol | A |
| 226 | 2-chloro-4-{6-fluoro-1-methyl-9-(methyloxy)-8-[(3-morpholin-4-ylpropyl)oxy]-3H-pyrazolo[3,4-c]isoquinolin-5-yl}phenol | A |
| 227 | 2-chloro-4-[8-({2-[[2-(dimethylamino)ethyl](methyl)amino]ethyl}oxy)-6-fluoro-1-methyl-9-(methyloxy)-3H-pyrazolo[3,4-c]isoquinolin-5-yl]phenol | A |
| 228 | 2-chloro-4-[8-({2-[[2-(diethylamino)ethyl](methyl)amino]ethyl}oxy)-6-fluoro-1-methyl-9-(methyloxy)-3H-pyrazolo[3,4-c]isoquinolin-5-yl]phenol | A |
| 229 | 2-chloro-4-[8-({2-[[2-(dimethylamino)ethyl](ethyl)amino]ethyl}oxy)-6-fluoro-1-methyl-9-(methyloxy)-3H-pyrazolo[3,4-c]isoquinolin-5-yl]phenol | A |
| 230 | 4-[8-({2-{bis[3-(dimethylamino)propyl]amino}ethyl)oxy)-6-fluoro-1-methyl-9-(methyloxy)-3H-pyrazolo[3,4-c]isoquinolin-5-yl]-2-chlorophenol | A |
| 231 | 2-chloro-4-[6-fluoro-1-methyl-8-({2-[methyl(1-methylpyrrolidin-3-yl)amino]ethyl}oxy)-9-(methyloxy)-3H-pyrazolo[3,4-c]isoquinolin-5-yl]phenol | A |
| 232 | 2-chloro-4-{6-fluoro-1-methyl-9-(methyloxy)-8-[(2-{(2S)-2-[(methyloxy)methyl]pyrrolidin-1-yl}ethyl)oxy]-3H-pyrazolo[3,4-c]isoquinolin-5-yl}phenol | A |
| 233 | 2-chloro-4-(6-fluoro-1-methyl-9-(methyloxy)-8-{[2-(4-pyrrolidin-1-ylpiperidin-1-yl)ethyl]oxy}-3H-pyrazolo[3,4-c]isoquinolin-5-yl)phenol | A |
| 234 | 2-chloro-4-{8-{[2-(4-cyclohexylpiperazin-1-yl)ethyl]oxy}-6-fluoro-1-methyl-9-(methyloxy)-3H-pyrazolo[3,4-c]isoquinolin-5-yl)phenol | A |
| 235 | 2-[4-(2-{[5-(3-chloro-4-hydroxyphenyl)-6-fluoro-1-methyl-9-(methyloxy)-3H-pyrazolo[3,4-c]isoquinolin-8-yl]oxy}ethyl)piperazin-1-yl]-N-(1-methylethyl)acetamide | A |

TABLE 2-continued

| Entry | Name | IC$_{50}$ ALK |
|---|---|---|
| 236 | 4-[8-{[2-(1,4'-bipiperidin-1'-yl)ethyl]oxy}-6-fluoro-1-methyl-9-(methyloxy)-3H-pyrazolo[3,4-c]isoquinolin-5-yl]-2-chlorophenol | A |
| 237 | 2-chloro-4-[6-fluoro-1-methyl-8-{[2-(4-methyl-1,4-diazepan-1-yl)ethyl]oxy}-9-(methyloxy)-3H-pyrazolo[3,4-c]isoquinolin-5-yl]phenol | A |
| 238 | 2-chloro-4-(6-fluoro-1-methyl-9-(methyloxy)-8-{[2-(4-pyridin-2-ylpiperazin-1-yl)ethyl]oxy}-3H-pyrazolo[3,4-c]isoquinolin-5-yl)phenol | A |
| 239 | 2-chloro-4-[8-{[2-(2,6-dimethylmorpholin-4-yl)ethyl]oxy}-6-fluoro-1-methyl-9-(methyloxy)-3H-pyrazolo[3,4-c]isoquinolin-5-yl]phenol | A |
| 240 | 2-chloro-4-{6-fluoro-1-methyl-9-(methyloxy)-8-[(2-thiomorpholin-4-ylethyl)oxy]-3H-pyrazolo[3,4-c]isoquinolin-5-yl}phenol | A |
| 241 | 2-chloro-4-[8-{[2-(2,6-dimethylpiperidin-1-yl)ethyl]oxy}-6-fluoro-1-methyl-9-(methyloxy)-3H-pyrazolo[3,4-c]isoquinolin-5-yl]phenol | A |
| 242 | 2-chloro-4-(6-fluoro-1-methyl-9-(methyloxy)-8-{[2-(octahydroquinolin-1(2H)-yl)ethyl]oxy}-3H-pyrazolo[3,4-c]isoquinolin-5-yl)phenol | A |
| 243 | 4-[8-({2-[bis(1-methylethyl)amino]ethyl}oxy)-6-fluoro-1-methyl-9-(methyloxy)-3H-pyrazolo[3,4-c]isoquinolin-5-yl]-2-chlorophenol | A |
| 244 | 4-[8-[(2-{bis[2-(methyloxy)ethyl]amino}ethyl)oxy]-6-fluoro-1-methyl-9-(methyloxy)-3H-pyrazolo[3,4-c]isoquinolin-5-yl]-2-chlorophenol | A |
| 245 | 2-chloro-4-{6-fluoro-1-methyl-9-(methyloxy)-8-[(2-piperidin-1-ylethyl)oxy]-3H-pyrazolo[3,4-c]isoquinolin-5-yl}phenol | A |

What is claimed is:

1. A compound according to formula I,

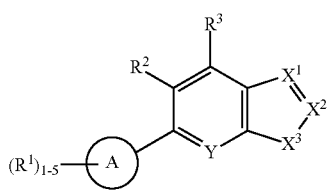

I or a pharmaceutically acceptable salt or a stereoisomer, thereof, wherein,

A is a five- to ten-membered ring containing up to three heteroatoms;

$R^1$ is selected from —H, halo, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(═O)N(R$^4$)R$^4$, —C(═O)R$^4$, —C(═NR$^5$)N(R$^4$)R$^4$, —C(═NR$^5$)R$^4$, —N(R$^4$)SO$_2$R$^4$, —N(R$^4$)C(O)R$^4$, alkoxy, C$_{1-6}$ alkyl, aryl, aryl C$_{1-6}$ alkyl, heterocyclyl, and heterocyclyl C$_{1-6}$ alkyl;

two adjacent of $R^1$, together with the annular atoms to which they are attached, can form a five- to six-membered ring containing up to two heteroatoms and optionally substituted with up to four of $R^{10}$;

$R^2$ and $R^3$, together with the annular atoms to which they are attached, form a five- to six-membered ring containing up to two heteroatoms and optionally substituted with up to five of $R^6$;

each $R^4$ is selected from —H; C$_{1-6}$ alkyl optionally substituted with 1, 2, or 3 halogen; C$_{1-6}$ alkyl optionally substituted with alkoxy; C$_{1-6}$ alkyl substituted with amino where the amino is optionally substituted with one or groups selected from methyl, ethyl, —CH$_2$CH$_2$OCH$_3$, —CH$_2$CH$_2$N(CH$_3$)$_2$, —CH$_2$CH$_2$CH$_2$N(CH$_3$)$_2$, and N-methyl-pyrrolidin3-yl; aryl; aryl C$_{1-6}$ alkyl; heterocyclyl; and heterocyclyl C$_{1-6}$ alkyl where the heterocyclyl is optionally substituted with alkyl, acyl, NH$_2$, alkylamino, dialkylamino, heterocyclyl, cyclohexyl, —CH$_2$OCH$_3$, —CH$_2$C(O)NHCH(CH$_3$)$_2$, or —CH$_2$OCH$_3$;

two of $R^4$, when taken together with a common nitrogen to which they are attached, form an five- to seven-membered heterocyclyl, said optionally substituted five- to seven-membered heterocyclyl optionally containing at least one additional heteroatom selected from N, O, S, and P;

each $R^5$ is selected from —H, —CN, —NO$_2$, —OR$^4$, —S(O)$_{0-2}$R$^4$, —CO$_2$R$^4$, C$_{1-6}$ alkyl, C$_{2-6}$ alkenyl, and C$_{2-6}$ alkynyl;

Y is ═N— or ═C(H);

$X^1$ and $X^2$ are each independently either ═N— or ═C(R$^9$)—;

$X^3$ is —N(R$^7$)—;

$R^7$ is hydrogen;

each of $R^6$ and $R^{10}$ is independently selected from —H, halo, trihalomethyl, —CN, —NO$_2$, —OR$^4$, —N(R$^4$)R$^4$, —S(O)$_{0-2}$R$^4$, —SO$_2$N(R$^4$)R$^4$, —CO$_2$R$^4$, —C(═O)N(R$^4$)R$^4$, —C(═NR$^5$)N(R$^4$)R$^4$, —C(═NR$^5$)R$^4$, —N(R$^4$)SO$_2$R$^4$, —N(R$^4$)C(O)R$^4$, —C(═O)R$^4$, optionally substituted alkoxy, C$_{1-6}$ alkyl, aryl, aryl C$_{1-6}$ alkyl, heterocyclyl, and heterocyclyl C$_{1-6}$ alkyl;

two adjacent of $R^6$, together with the annular atoms to which they are attached, can form a five- to seven-membered ring containing up to two heteroatoms; and each $R^9$ is independently selected from —H; halo; trihalomethyl; —CN; —NO$_2$; —OR$^4$; —N(R$^4$)R$^4$; —S(O)$_{0-2}$R$^4$; —SO$_2$N(R$^4$)R$^4$; —CO$_2$R$^4$; —C(═O)N(R$^4$)R$^4$; —C(═NR$^5$)N(R$^4$)R$^4$; —C(═NR$^5$)R$^4$; —N(R$^4$)SO$_2$R$^4$; —N(R$^4$)C(O)R$^4$; —C(═O)R$^4$; alkoxy; C$_{1-6}$ alkyl optionally substituted with one group selected from alkoxy, benzylamino, and 2-oxo-pyrrolidinyl; aryl C$_{1-6}$ alkyl substituted on the aryl with 1 or 2 groups selected from alkyl and alkoxy; heterocyclyl optionally substituted with —C(O)Ot-Bu; and heterocyclyl C$_{1-6}$ alkyl; provided when $R^9$ is aryl, heteroaryl, —C(H)═C(H)R or —C(H)═NR, where R is an optionally substituted alkyl, cycloalkyl, heteroalicyclic, aryl, or heteroaryl, then Y is not ═C(H)—.

2. The compound according to claim 1, wherein the five- to six-membered ring formed by $R^2$ and $R^3$ is an aryl or a heteroaryl optionally substituted with up to five of $R^6$; or a pharmaceutically acceptable salt or stereoisomer, thereof.

3. The compound according to claim 2, wherein the five- to six-membered ring formed by $R^2$ and $R^3$ is phenyl or pyridyl optionally substituted with up to five of $R^6$; or a pharmaceutically acceptable salt or stereoisomer, thereof.

4. The compound according to claim 3, of formula II,

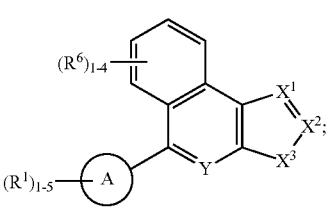

II or a pharmaceutically acceptable salt or stereoisomer, thereof.

5. The compound according to claim 4, wherein $X^1$ is =C($R^9$)—, $X^2$ is =N—, $X^3$ is —N($R^7$)—, and $R^7$ is hydrogen; or a pharmaceutically acceptable salt or stereoisomer, thereof.

6. The compound according to claim 5, wherein Y is =N—; or a pharmaceutically acceptable salt or stereoisomer, thereof.

7. The compound according to claim 6, wherein A is either a six- to ten-membered aryl or a five- to ten-membered heteroaryl containing up to three heteroatoms and where A is substituted with 1-5 $R^1$; or a pharmaceutically acceptable salt or stereoisomer, thereof.

8. The compound according to claim 7, wherein A is either a six-membered aryl or a five- or six-membered heteroaryl containing up to three heteroatoms; and where A is substituted with 1-5 $R^1$; or a pharmaceutically acceptable salt or stereoisomer, thereof.

9. The compound according to claim 8, wherein $R^1$ is selected from —H, halo, trihalomethyl, —CN, —$OR^4$, —N($R^4$)$R^4$, —$SO_2$N($R^4$)$R^4$, —$CO_2R^4$, —C(=O)N($R^4$)$R^4$, —C(=NR)N($R^4$)$R^4$, —C(=N$R^5$)$R^4$, —N($R^4$)$SO_2R^4$, —N($R^4$)C(O)$R^4$, alkoxy, $C_{1-6}$ alkyl, heterocyclyl, and heterocyclyl $C_{1-6}$ alkyl; or a pharmaceutically acceptable salt or stereoisomer, thereof.

10. The compound according to claim 9, of formula III,

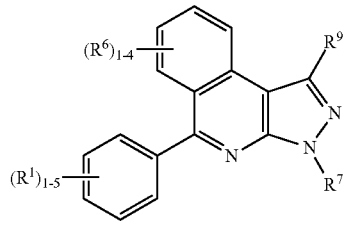

III wherein $R^7$ is hydrogen and at least one of $R^1$ is —OH; or a pharmaceutically acceptable salt or stereoisomer, thereof.

11. The compound according to claim 10, wherein the compound is either of Formula IIa or IIIb:

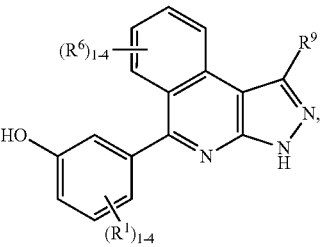

IIIa

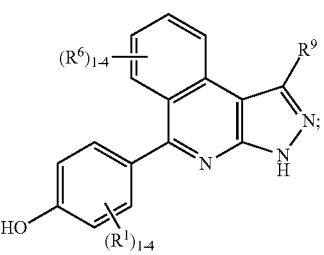

IIIb or a pharmaceutically acceptable salt or stereoisomer, thereof.

12. The compound according to claim 11, wherein $R^9$ is selected from —H; trihalomethyl; $C_{1-6}$ alkyl optionally substituted with one group selected from alkoxy, benzylamino, and 2-oxo-pyrrolidinyl; aryl $C_{1-6}$ alkyl substituted on the aryl with 1 or 2 groups selected from alkyl and alkoxy; heterocyclyl optionally substituted with —C(O)Ot-Bu; and heterocyclyl $C_{1-6}$ alkyl; or a pharmaceutically acceptable salt or stereoisomer, thereof.

13. The compound according to claim 12, wherein $R^6$ is selected from —H, halo, trihalomethyl, —CN, —$OR^4$, —N($R^4$)$R^4$, —$CO_2R^4$, —C(=O)N($R^4$)$R^4$, —N($R^4$)$SO_2R^4$, —N($R^4$)C(O)$R^4$, —C(=O)$R^4$, $C_{1-6}$ alkyl, heterocyclyl, heterocyclyl $C_{1-6}$ alkyl, and a six- or seven-membered heteroalicyclic formed by two adjacent of $R^6$, together with the annular atoms to which they are attached, said six- or seven-membered heteroalicyclic containing up to two heteroatoms; or a pharmaceutically acceptable salt or stereoisomer, thereof.

14. The compound according to claim 13, wherein $R^6$ is selected from —H, halo, —$OR^4$, —N($R^4$)$R^4$, $C_{1-6}$ alkyl, heterocyclyl, heterocyclyl $C_{1-6}$ alkyl, and a six-or seven-membered heteroalicyclic formed by two adjacent of $R^6$, together with the annular atoms to which they are attached, said six- or seven-membered heteroalicyclic containing up to two heteroatoms; or a pharmaceutically acceptable salt or stereoisomer, thereof.

15. The compound according to claim 14, wherein at least one of $R^6$ is —$OR^4$ and $R^4$ is $C_{1-6}$ alkyl optionally substituted with 1, 2, or 3 halogen; $C_{1-6}$ alkyl optionally substituted with alkoxy; $C_{1-6}$ alkyl substituted with amino where the amino is optionally substituted with one or groups selected from methyl, ethyl, —$CH_2CH_2OCH_3$, —$CH_2CH_2N(CH_3)_2$, —$CH_2CH_2CH_2N(CH_3)_2$, and N-methyl-pyrrolidin3-yl; and heterocyclyl where the heterocyclyl is optionally substituted with alkyl, acyl, $NH_2$, alkylamino, dialkylamino, heterocyclyl, cyclohexyl, —$CH_2OCH_3$, —$CH_2C(O)NHCH(CH_3)_2$, or —$CH_2OCH_3$; or a pharmaceutically acceptable salt or stereoisomer, thereof.

16. The compound according to claim 15, wherein at least one of $R^1$ is halo or methyl; or a pharmaceutically acceptable salt or stereoisomer, thereof.

17. The compound according to claim 16, wherein $R^9$ is selected from —H, trihalomethyl, and $C_{1-6}$ alkyl optionally substituted with one group selected from alkoxy, benzylamino, and 2-oxo-pyrrolidinyl; or a pharmaceutically acceptable salt or stereoisomer, thereof.

18. The compound according to claim 14, wherein at least one of $R^6$ is —$OR^4$ and $R^4$ is heterocyclyl $C_{1-6}$ alkyl where the heterocyclyl is a heteroalicyclic; or a pharmaceutically acceptable salt or stereoisomer, thereof.

19. The compound according to claim 18, wherein said heteroalicyclic is selected from the group consisting of dioxolanyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, morpholinyl, quinuclidinyl, tetrahydrofuryl, tetrahydropyranyl, thiamorpholinyl, thiamorpholinyl sulfoxide, 2,5-diaza-bicyclo[2.2.1]heptanyl, and thiamorpholinyl sulfone; or a pharmaceutically acceptable salt or stereoisomer, thereof.

20. A compound according to Formula IIIa or IIIb,

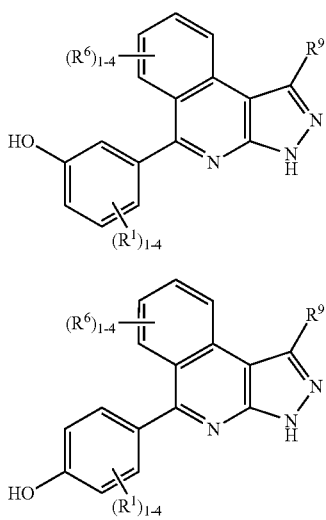

each $R^1$ is independently selected from —H, halo trihalomethyl, —CN, —OR$^4$, —N(R$^4$)R$^4$, —SO$_2$N(R$^4$)R$^4$, —CO$_2$R$^4$, —C(=O)N(R$^4$)R$^4$, —C(=NR$^5$)N(R$^4$)R$^4$, —C(=NR$^5$)R$^4$, —N(R$^4$)SO$_2$R$^4$, —N(R$^4$)C(O)R$^4$, C$_{1-6}$ alkyl, heterocyclyl, and heterocyclyl C$_{1-6}$ alkyl;

$R^9$ is selected from —H, trihalomethyl; C$_{1-6}$ alkyl optionally substituted with one group selected from alkoxy, benzylamino, and 2-oxo-pyrrolidinyl; aryl C$_{1-6}$alkyl substituted on the aryl with 1 or 2 groups selected from alkyl and alkoxy; heterocyclyl optionally substituted with —C(O)Ot-Bu; and heterocyclyl C$_{1-6}$alkyl; and wherein at least one of $R^6$ is —OR$^4$ and R$^4$ is alkyl substituted with at least one additional of alkoxyl, amino, dialkylamino, and monoalkylamino where the amino of the monoalkylamino is further substituted with N-methyl-pyrrolidin-3-yl and where each alkyl of monoalkylamino and dialkylamino are independently optionally substituted with —NH$_2$, —NHCH$_3$, or —N(CH—)$_2$; or a pharmaceutically acceptable salt or stereoisomer, thereof.

21. The compound according to claim 1, selected from Table 3; or a pharmaceutically acceptable salt or stereoisomer, thereof

TABLE 3

| Entry | Name | Structure |
|---|---|---|
| 10 | 4-{7,8-bis(methyloxy)-1-[(4-methylphenyl)methyl]-3H-pyrazolo[3,4-c]isoquinolin-5-yl}phenol | 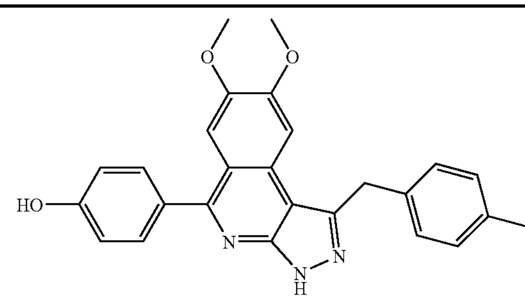 |
| 12 | 4-(7,8-bis(methyloxy)-1-{[4-(methyloxy)phenyl]methyl}-3H-pyrazolo[3,4-c]isoquinolin-5-yl)phenol | 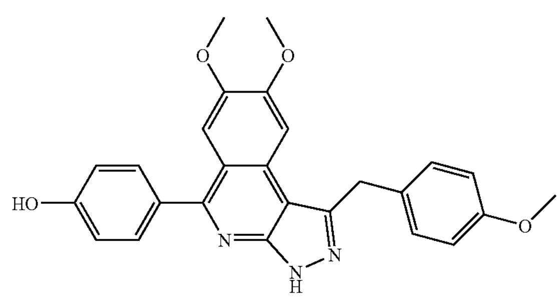 |
| 13 | 4-{7,8-bis(methyloxy)-1-[(2-methylphenyl)methyl]-3H-pyrazolo[3,4-c]isoquinolin-5-yl}phenol | 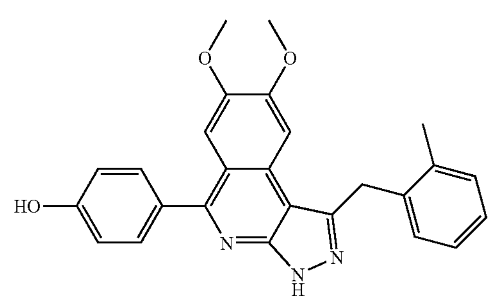 |

TABLE 3-continued

| Entry | Name | Structure |
|---|---|---|
| 14 | 4-{7,8-bis(methyloxy)-1-[(3-methylphenyl)methyl]-3H-pyrazolo[3,4-c]isoquinolin-5-yl}phenol | 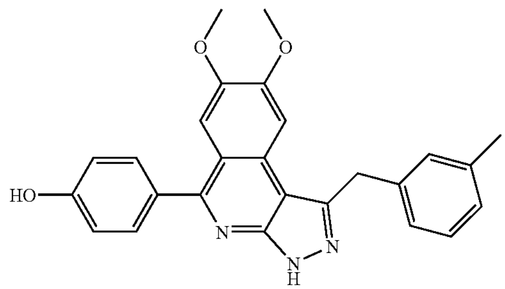 |
| 15 | 4-[1-methyl-7,8-bis(methyloxy)-3H-pyrazolo[3,4-c]isoquinolin-5-yl]phenol | 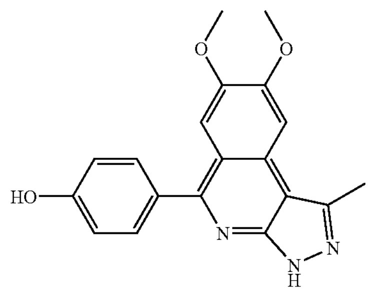 |
| 20 | 4-[1-{[3,4-bis(methyloxy)phenyl]methyl}-7,8-bis(methyloxy)-3H-pyrazolo[3,4-c]isoquinolin-5-yl]phenol | 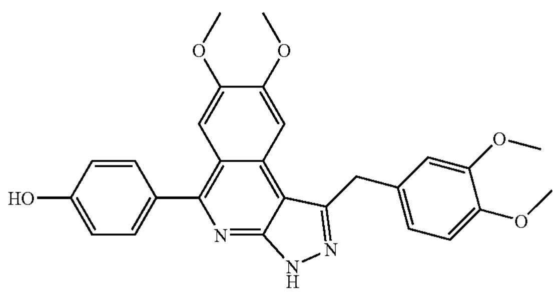 |
| 21 | 4-(7,8-bis(methyloxy)-1-{[3-(methyloxy)phenyl]methyl}-3H-pyrazolo[3,4-c]isoquinolin-5-yl)phenol | 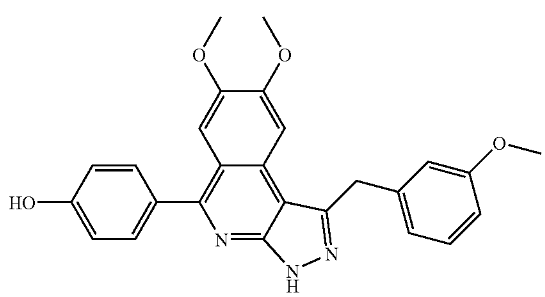 |
| 22 | 4-[1-ethyl-7,8-bis(methyloxy)-3H-pyrazolo[3,4-c]isoquinolin-5-yl]phenol | 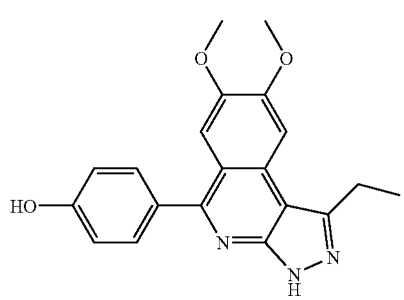 |

TABLE 3-continued

| Entry | Name | Structure |
|---|---|---|
| 25 | 4-[1-methyl-6,7,8-tris(methyloxy)-3H-pyrazolo[3,4-c]isoquinolin-5-yl]phenol | 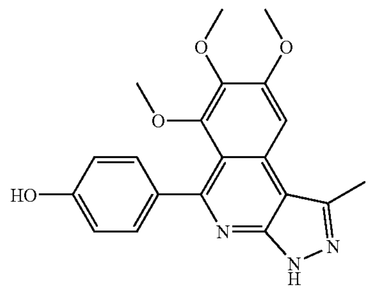 |
| 27 | 4-[7,8-bis(methyloxy)-1-(trifluoromethyl)-3H-pyrazolo[3,4-c]isoquinolin-5-yl]phenol | 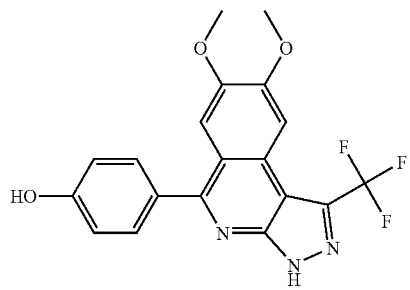 |
| 28 | 4-[1-(1-methylethyl)-7,8-bis(methyloxy)-3H-pyrazolo[3,4-c]isoquinolin-5-yl]phenol | 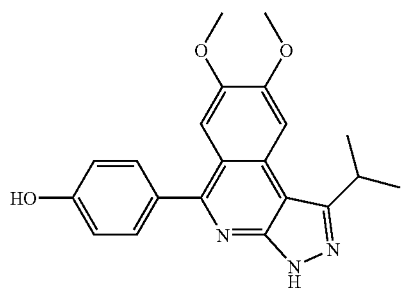 |
| 29 | 4-[7,8-bis(methyloxy)-3H-pyrazolo[3,4-c]isoquinolin-5-yl]phenol | 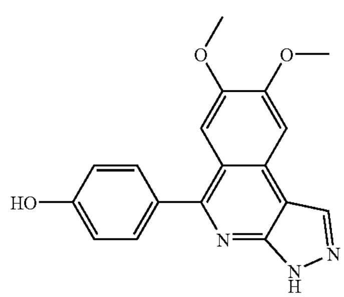 |
| 31 | 4-[1-methyl-6,8-bis(methyloxy)-3H-pyrazolo[3,4-c]isoquinolin-5-yl]phenol | 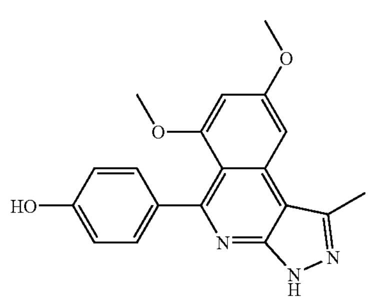 |

TABLE 3-continued

| Entry | Name | Structure |
|---|---|---|
| 32 | 4-[6,8-bis(methyloxy)-3H-pyrazolo[3,4-c]isoquinolin-5-yl]phenol | 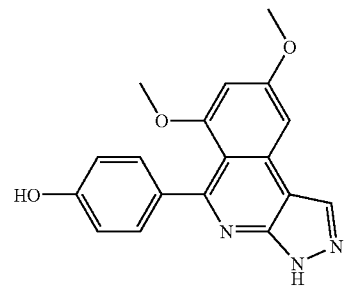 |
| 34 | 4-[6,7,8-tris(methyloxy)-3H-pyrazolo[3,4-c]isoquinolin-5-yl]phenol | 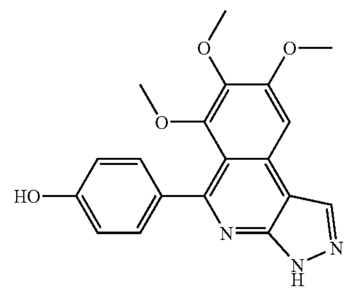 |
| 35 | 4-[1-methyl-7,8,9-tris(methyloxy)-3H-pyrazolo[3,4-c]isoquinolin-5-yl]phenol | 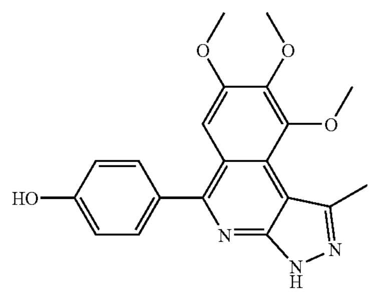 |
| 36 | 4-[1-methyl-8-(methyloxy)-3H-pyrazolo[3,4-c]isoquinolin-5-yl]phenol | 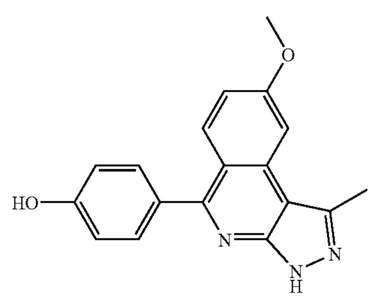 |
| 37 | 2-methyl-4-[1-methyl-7,8-bis(methyloxy)-3H-pyrazolo[3,4-c]isoquinolin-5-yl]phenol | 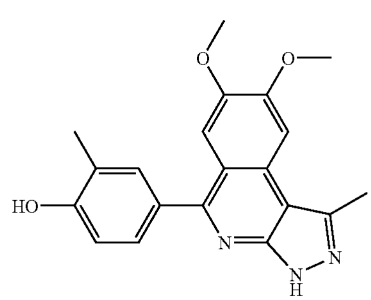 |

TABLE 3-continued

| Entry | Name | Structure |
|---|---|---|
| 38 | 4-[1-methyl-7,8-bis(methyloxy)-3H-pyrazolo[3,4-c]isoquinolin-5-yl]-2-(methyloxy)phenol | 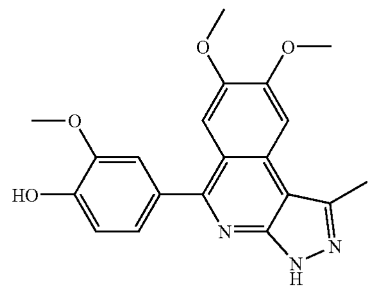 |
| 39 | 4-{1-methyl-8-(methyloxy)-7-[(2-morpholin-4-ylethyl)oxy]-3H-pyrazolo[3,4-c]isoquinolin-5-yl}phenol | 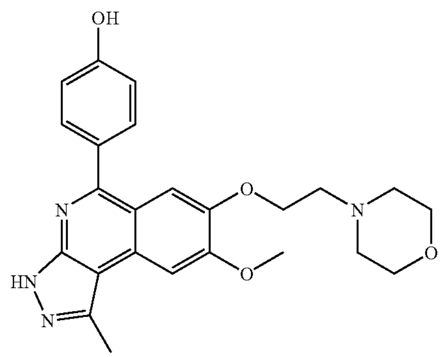 |
| 40 | 2-(ethyloxy)-4-[1-methyl-7,8-bis(methyloxy)-3H-pyrazolo[3,4-c]isoquinolin-5-yl}phenol | 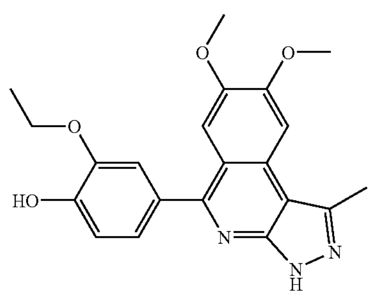 |
| 41 | 2-chloro-4-[1-methyl-7,8-bis(methyloxy)-3H-pyrazolo[3,4-c]isoquinolin-5-yl]phenol | 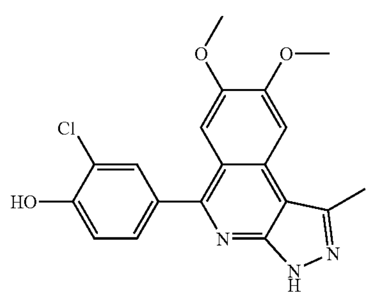 |
| 42 | 2-fluoro-4-[1-methyl-7,8-bis(methyloxy)-3H-pyrazolo[3,4-c]isoquinolin-5-yl]phenol | 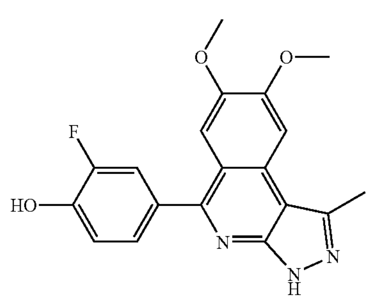 |

TABLE 3-continued

| Entry | Name | Structure |
|---|---|---|
| 44 | 2-bromo-4-[1-methyl-7,8-bis(methyloxy)-3H-pyrazolo[3,4-c]isoquinolin-5-yl]phenol | 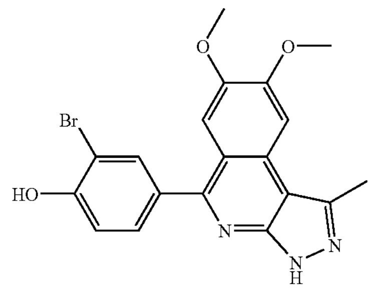 |
| 45 | 1-{[5-(4-hydroxyphenyl)-7,8-bis(methyloxy)-3H-pyrazolo[3,4-c]isoquinolin-1-yl]methyl}pyrrolidin-2-one | 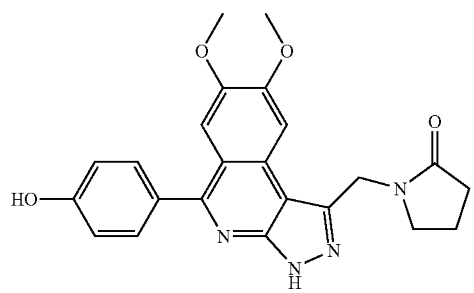 |
| 54 | 4-{1-methyl-7-(methyloxy)-5-[(piperidin-4-ylmethyl)oxy]-3H-pyrazolo[3,4-c]isoquinolin-5-yl}phenol | 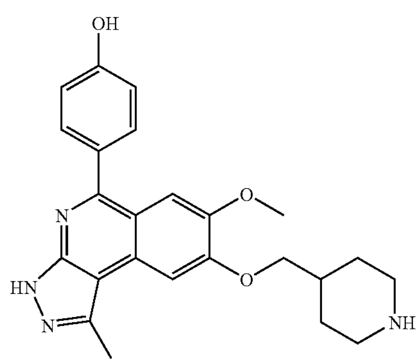 |
| 55 | 4-{1-methyl-8-(methyloxy)-7-[(piperidin-4-ylmethyl)oxy]-3H-pyrazolo[3,4-c]isoquinolin-5-yl}phenol | 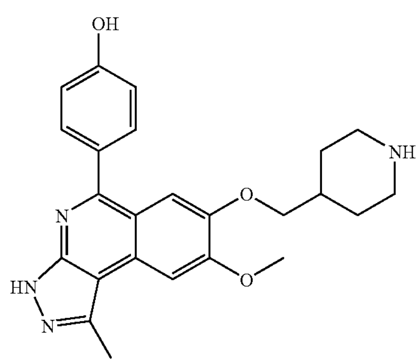 |

TABLE 3-continued

| Entry | Name | Structure |
|---|---|---|
| 58 | 4-[8-(ethyloxy)-1-methyl-7-(methyloxy)-3H-pyrazolo[3,4-c]isoquinolin-5-yl]phenol | 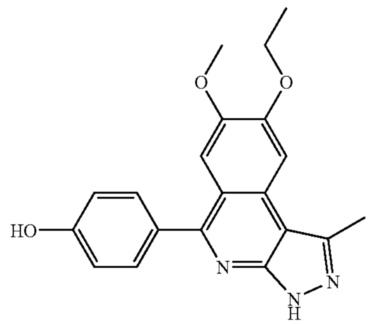 |
| 59 | 4-[1-methyl-8,9-bis(methyloxy)-3H-pyrazolo[3,4-c]isoquinolin-5-yl]phenol | 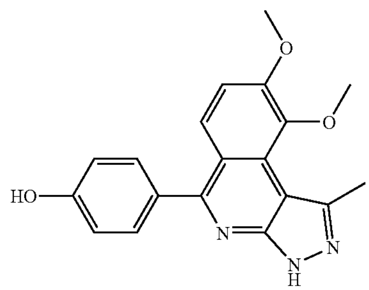 |
| 60 | 4-[7-(ethyloxy)-1-methyl-8-(methyloxy)-3H-pyrazolo[3,4-c]isoquinolin-5-yl]phenol | 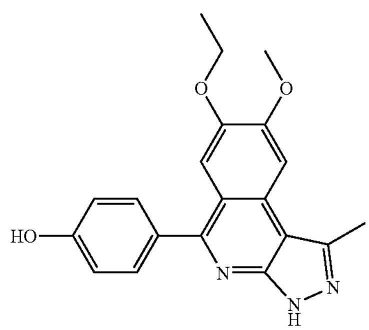 |
| 61 | 4-{1-methyl-8-(methyloxy)-9-[(piperidin-4-ylmethyl)oxy]-3H-pyrazolo[3,4-c]isoquinolin-5-yl}phenol | 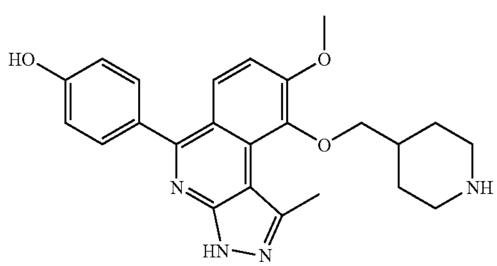 |
| 63 | 2-ethyl-4-[1-methyl-7,8-bis(methyloxy)-3H-pyrazolo[3,4-c]isoquinolin-5-yl]phenol | 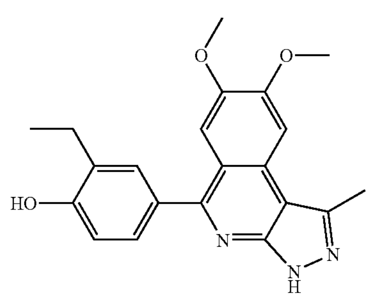 |

TABLE 3-continued

| Entry | Name | Structure |
|---|---|---|
| 64 | 4-(1-methyl-8-(methyloxy)-9-{[(1-methylpiperidin-4-yl)methyl]oxy}-3H-pyrazolo[3,4-c]isoquinolin-5-yl)phenol | 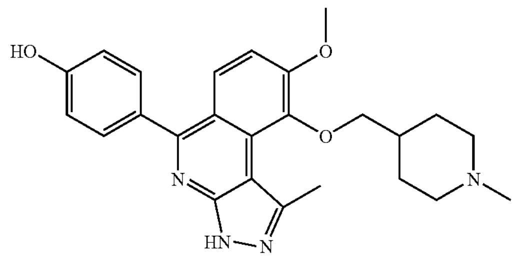 |
| 65 | 4-(1-methyl-7-(methyloxy)-8-{[(1-methylpiperidin-4-yl)methyl]oxy}-3H-pyrazolo[3,4-c]isoquinolin-5-yl)phenol | 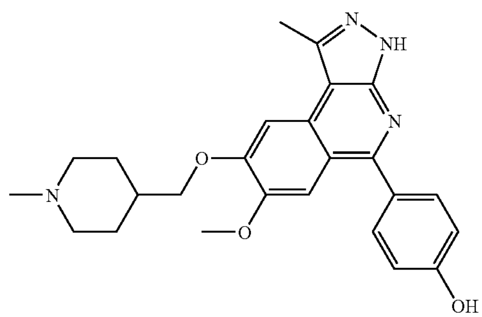 |
| 66 | 4-[1,7-dimethyl-8-(methyloxy)-3H-pyrazolo[3,4-c]isoquinolin-5-yl]phenol | 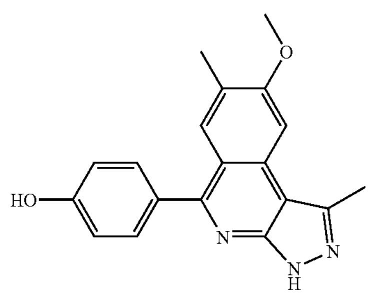 |
| 67 | 1,1-dimethylethyl 4-[5-(4-hydroxyphenyl)-7,8-bis(methyloxy)-3H-pyrazolo[3,4-c]isoquinolin-1-yl]piperidine-1-carboxylate | 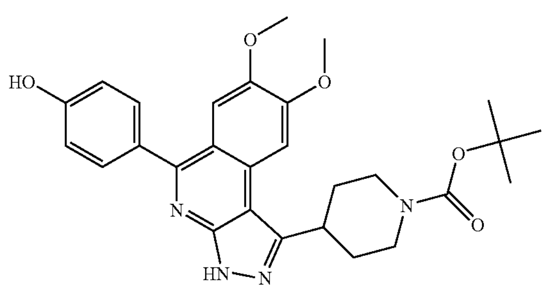 |
| 69 | 2-chloro-4-[1-methyl-8,9-bis(methyloxy)-3H-pyrazolo[3,4-c]isoquinolin-5-yl]phenol | 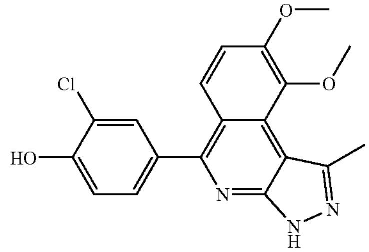 |

TABLE 3-continued

| Entry | Name | Structure |
|---|---|---|
| 70 | 2-fluoro-4-[1-methyl-8,9-bis(methyloxy)-3H-pyrazolo[3,4-c]isoquinolin-5-yl]phenol | 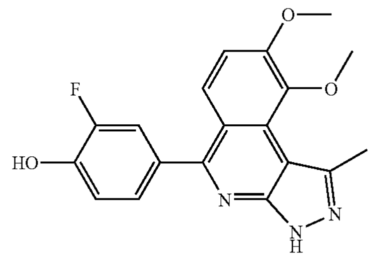 |
| 71 | 2-methyl-4-[1-methyl-8,9-bis(methyloxy)-3H-pyrazolo[3,4-c]isoquinolin-5-yl]phenol | 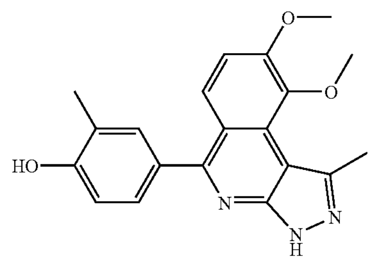 |
| 72 | 2-bromo-4-[1-methyl-8,9-bis(methyloxy)-3H-pyrazolo[3,4-c]isoquinolin-5-yl]phenol | 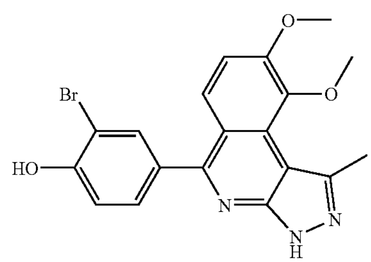 |
| 76 | 2-[(difluoromethyl)oxy]-4-[1-methyl-7,8-bis(methyloxy)-3H-pyrazolo[3,4-c]isoquinolin-5-yl]phenol | 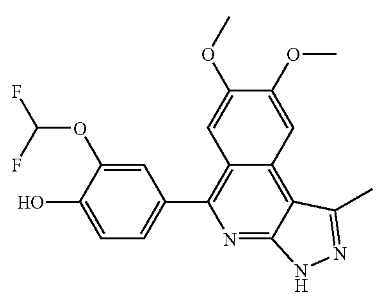 |
| 78 | 4-[1,9-dimethyl-8-(methyloxy)-3H-pyrazolo[3,4-c]isoquinolin-5-yl]phenol | 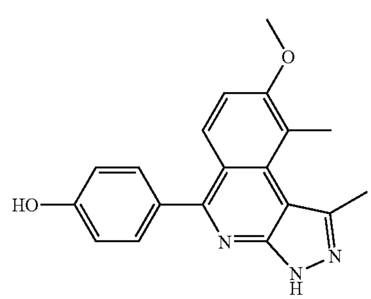 |

TABLE 3-continued

| Entry | Name | Structure |
|---|---|---|
| 79 | 4-[6,9-difluoro-1-methyl-8-(methyloxy)-3H-pyrazolo[3,4-c]isoquinolin-5-yl]phenol | 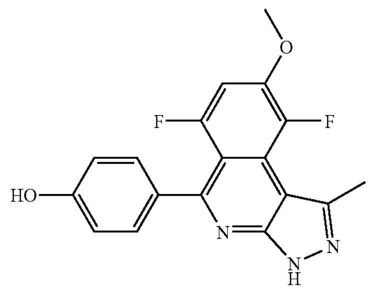 |
| 80 | 2-bromo-4-{1-methyl-8-(methyloxy)-9-[(2-morpholin-pyrazolo[3,4-c]isoquinolin-5-yl}phenol | 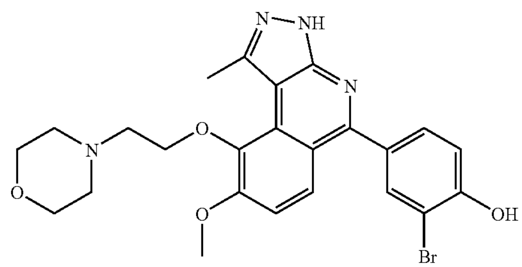 |
| 81 | 2-chloro-4-{1-methyl-8-(methyloxy)-9-[(2-morpholin-4-ylethyl)oxy]-3H-pyrazolo[3,4-c]isoquinolin-5-yl}phenol | 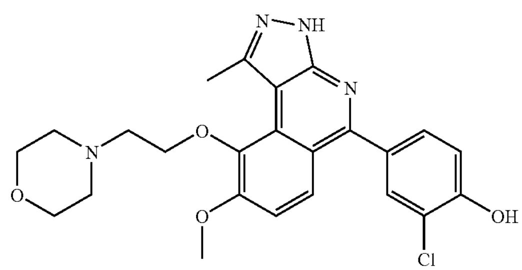 |
| 82 | 4-(7,8-bis(methyloxy)-1-{[(phenylmethyl)amino]methyl}-3H-pyrazolo[3,4-c]isoquinolin-5-yl)phenol | 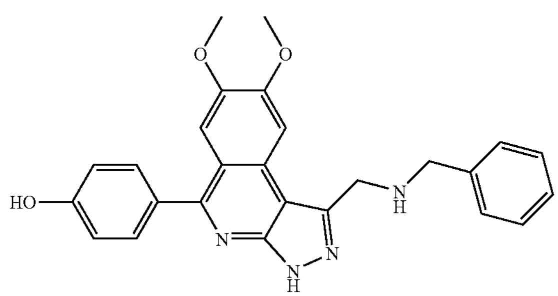 |
| 83 | 2,5-dimethyl-4-[1-methyl-7,8-bis(methyloxy)-3H-pyrazolo[3,4-c]isoquinolin-5-yl]phenol | 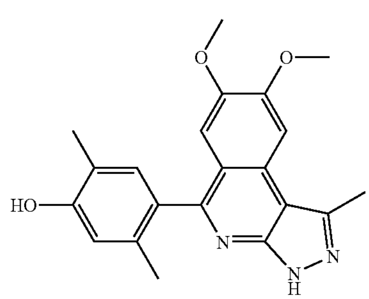 |

TABLE 3-continued

| Entry | Name | Structure |
|---|---|---|
| 85 | 2,5-dichloro-4-[1-methyl-7,8-bis(methyloxy)-3H-pyrazolo[3,4-c]isoquinolin-5-yl]phenol | 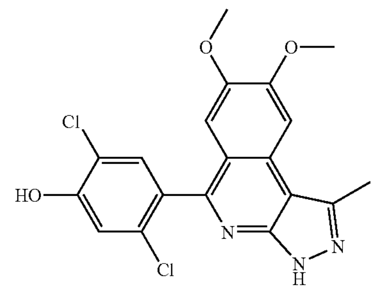 |
| 87 | 2-bromo-4-(1-methyl-8-(methyloxy)-9-{[(1-methylpiperidin-4-yl)methyl]oxy}-3H-pyrazolo[3,4-c]isoquinolin-5-yl)phenol | 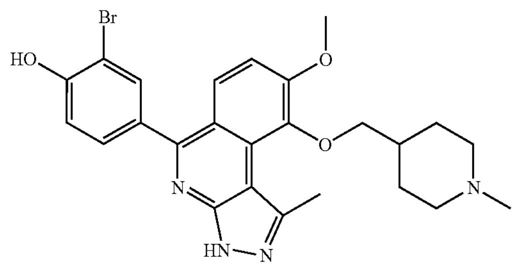 |
| 88 | 2-chloro-4-(1-methyl-7-(methyloxy)-8-{[(1-methylpiperidin-4-yl)methyl]oxy}-3H-pyrazolo[3,4-c]isoquinolin-5-yl)phenol | 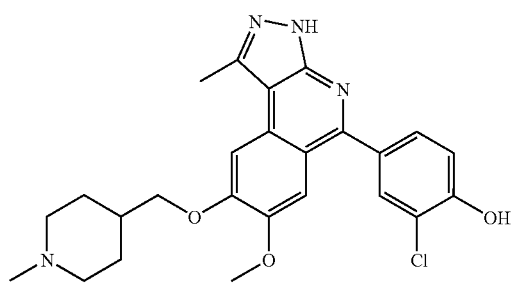 |
| 89 | 4-[9-fluoro-1-methyl-8-(methyloxy)-3H-pyrazolo[3,4-c]isoquinolin-5-yl]phenol | 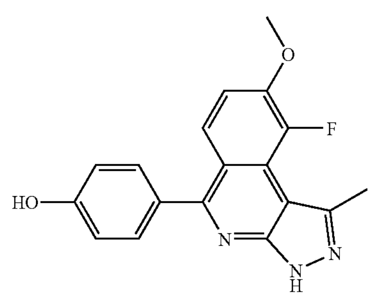 |
| 90 | 4-(1-methyl-8-(methyloxy)-9-{[2-(methyloxy)ethyl]oxy}-3H-pyrazolo[3,4-c]isoquinolin-5-yl)phenol | 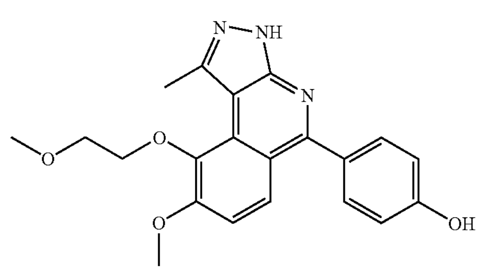 |

TABLE 3-continued

| Entry | Name | Structure |
|---|---|---|
| 91 | 2-chloro-4-(1-methyl-8-(methyloxy)-9-{[(1-methylpiperidin-4-yl)methyl]oxy}-3H-pyrazolo[3,4-c]isoquinolin-5-yl)phenol | 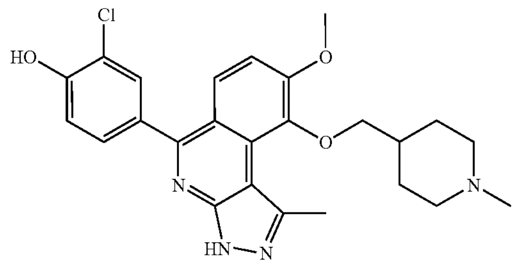 |
| 92 | 4-[6-bromo-1,7-dimethyl-8-(methyloxy)-3H-pyrazolo[3,4-c]isoquinolin-5-yl]phenol | 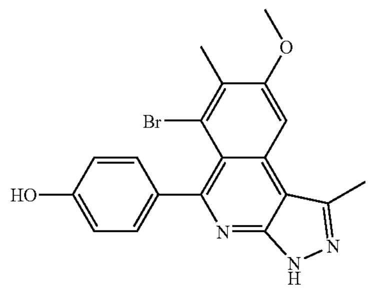 |
| 93 | 4-[6-fluoro-1-methyl-7,8-bis(methyloxy)-3H-pyrazolo[3,4-c]isoquinolin-5-yl]phenol | 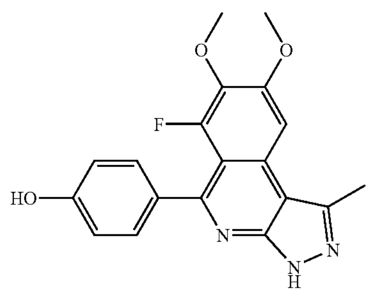 |
| 94 | 4-[9-chloro-1,7-dimethyl-8-(methyloxy)-3H-pyrazolo[3,4-c]isoquinolin-5-yl]phenol | 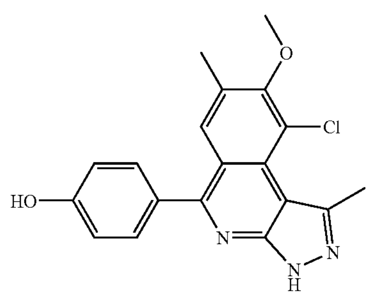 |
| 95 | 2-chloro-4-[8-{[(1-ethylpiperidin-4-yl)methyl]oxy}-1-methyl-7-(methyloxy)-3H-pyrazolo[3,4-c]isoquinolin-5-yl]phenol | 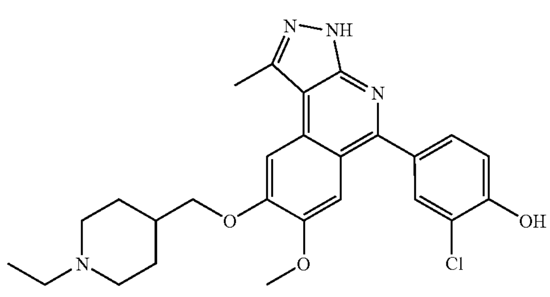 |

TABLE 3-continued

| Entry | Name | Structure |
|---|---|---|
| 96 | 3-chloro-4-[1-methyl-7,8-bis(methyloxy)-3H-pyrazolo[3,4-c]isoquinolin-5-yl]phenol | 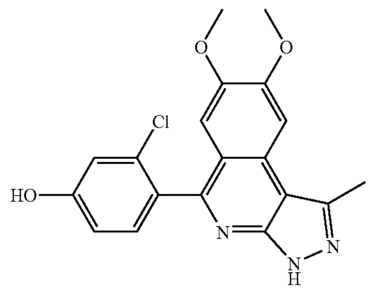 |
| 97 | 4-(1-methyl-8,9-bis{[2-(methyloxy)ethyl]oxy}-3H-pyrazolo[3,4-c]isoquinolin-5-yl)phenol | 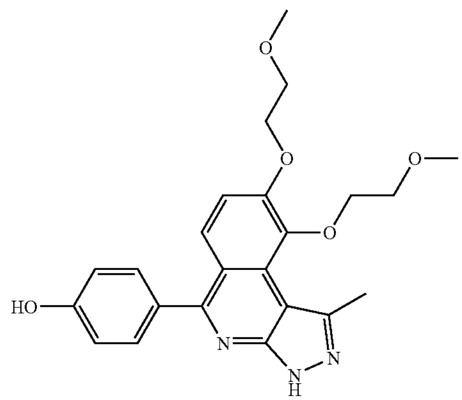 |
| 98 | 4-(1-methyl-3H-pyrazolo[3,4-c]isoquinolin-5-yl)phenol | 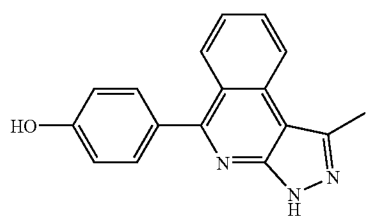 |
| 99 | 2-chloro-4-(1-methyl-3H-pyrazolo[3,4-c]isoquinolin-5-yl)phenol | 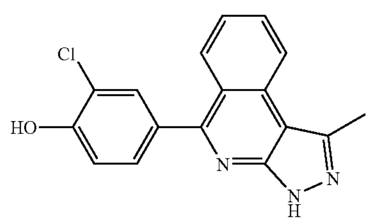 |
| 100 | 2-bromo-4-(1-methyl-3H-pyrazolo[3,4-c]isoquinolin-5-yl)phenol | 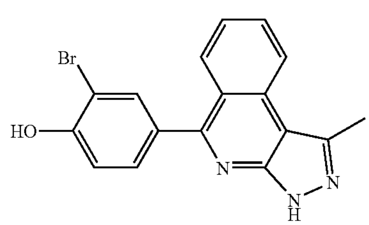 |

TABLE 3-continued

| Entry | Name | Structure |
|---|---|---|
| 101 | 2-chloro-4-[1,7-dimethyl-8-(methyloxy)-3H-pyrazolo[3,4-c]isoquinolin-5-yl]phenol | 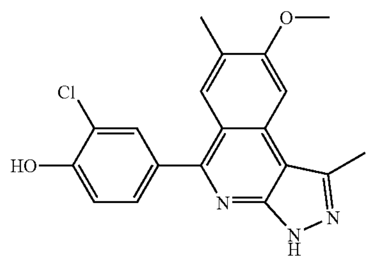 |
| 102 | 2-bromo-4-[1,7-dimethyl-8-(methyloxy)-3H-pyrazolo[3,4-c]isoquinolin-5-yl]phenol | 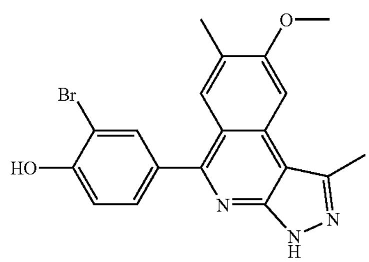 |
| 103 | 2-chloro-4-[1-methyl-8-({[1-(1-methylethyl)piperidin-4-yl]methyl}oxy)-7-(methyloxy)-3H-pyrazolo[3,4-c]isoquinolin-5-yl]phenol | 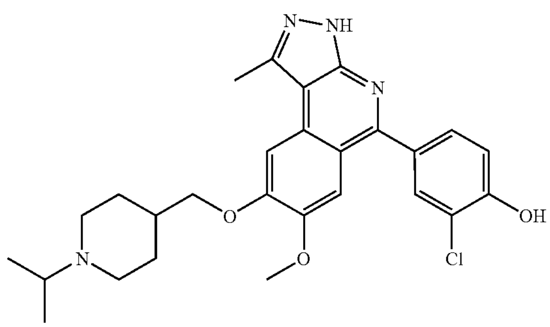 |
| 104 | 4-[9-bromo-1-methyl-8-(methyloxy)-3H-pyrazolo[3,4-c]isoquinolin-5-yl]phenol | 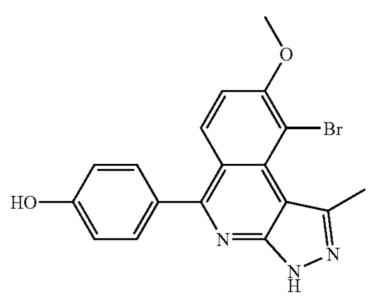 |
| 105 | 4-[7-chloro-9-fluoro-1-methyl-8-(methyloxy)-3H-pyrazolo[3,4-c]isoquinolin-5-yl]phenol | 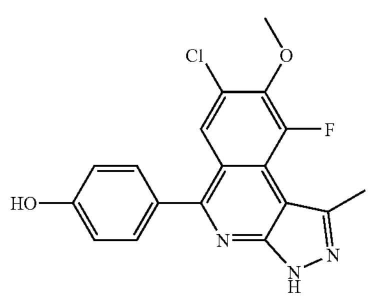 |

TABLE 3-continued

| Entry | Name | Structure |
|---|---|---|
| 106 | 4-[8-{[(1-acetylpiperidin-4-yl)methyl]oxy}-1-methyl-7-(methyloxy)-3H-pyrazolo[3,4-c]isoquinolin-5-yl]-2-chlorophenol | 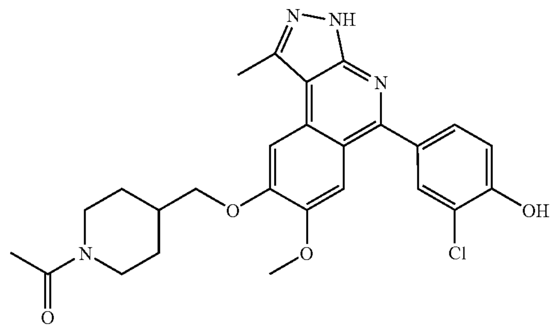 |
| 107 | 4-[9-{[(1-acetylpiperidin-4-yl)methyl]oxy}-1-methyl-8-(methyloxy)-3H-pyrazolo[3,4-c]isoquinolin-5-yl]-2-bromophenol | 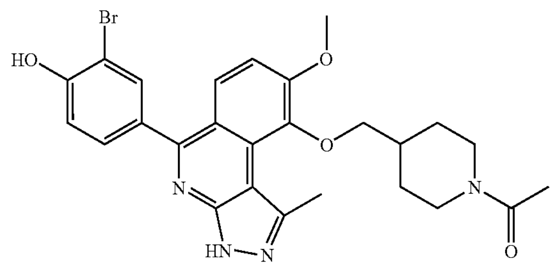 |
| 108 | 2-chloro-4-(1-methyl-9-(methyloxy)-8-{[2-(methyloxy)ethyl]oxy}-3H-pyrazolo[3,4-c]isoquinolin-5-yl)phenol | 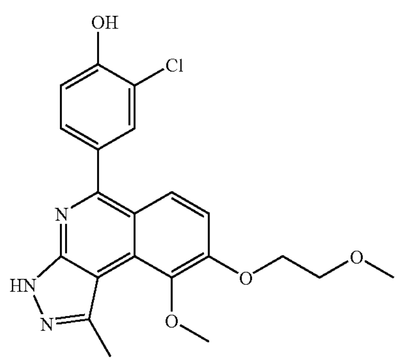 |
| 109 | 4-[7-fluoro-1-methyl-8-(methyloxy)-3H-pyrazolo[3,4-c]isoquinolin-5-yl]phenol | 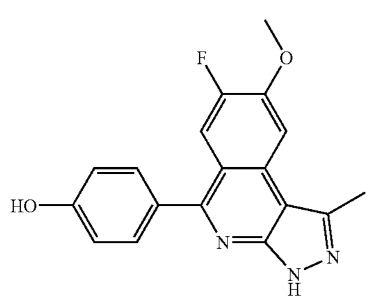 |

TABLE 3-continued

| Entry | Name | Structure |
|---|---|---|
| 110 | 2-chloro-4-(1-methyl-8,9-bis{[2-(methyloxy)ethyl]oxy}-3H-pyrazolo[3,4-c]isoquinolin-5-yl)phenol | 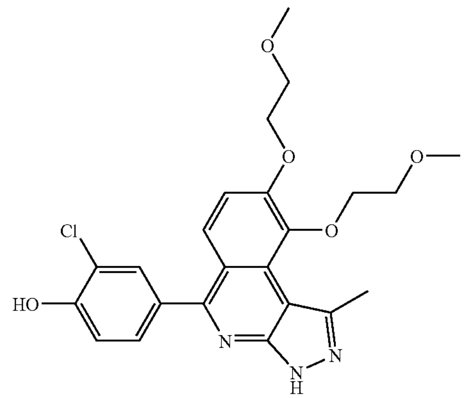 |
| 111 | 2-bromo-4-(1-methyl-8,9-bis{[2-(methyloxy)ethyl]oxy}-3H-pyrazolo[3,4-c]isoquinolin-5-yl)phenol | 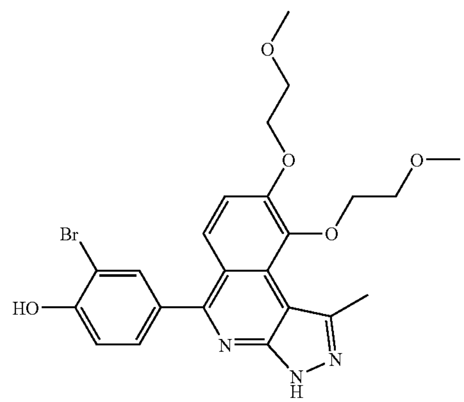 |
| 112 | 2-chloro-4-(1-methyl-8-(methyloxy)-9-{[2-(methyloxy)ethyl]oxy}-3H-pyrazolo[3,4-c)isoquinolin-5-yl)phenol | 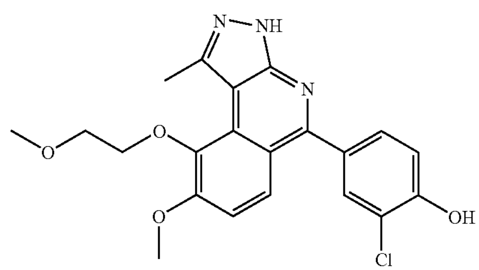 |
| 113 | 2-bromo-4-(1-methyl-8-(methyloxy)-9-{[2-(methyloxy)ethyl]oxy}-3H-pyrazolo[3,4-c]isoquinolin-5-yl)phenol | 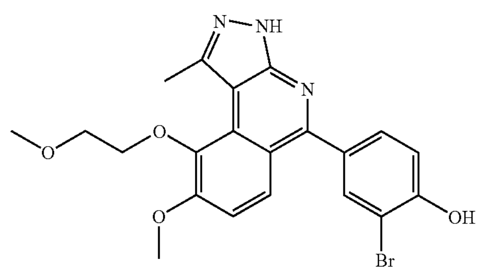 |

TABLE 3-continued

| Entry | Name | Structure |
|---|---|---|
| 114 | 3-fluoro-4-[1-methyl-7,8-bis(methyloxy)-3H-pyrazolo[3,4-c]isoquinolin-5-yl]phenol | 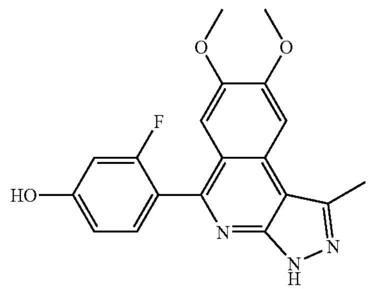 |
| 115 | 2-chloro-4-(1-methyl-7-(methyloxy)-8-{[2-(methyloxy)ethyl]oxy}-3H-pyrazolo[3,4-c]isoquinolin-5-yl)phenol | 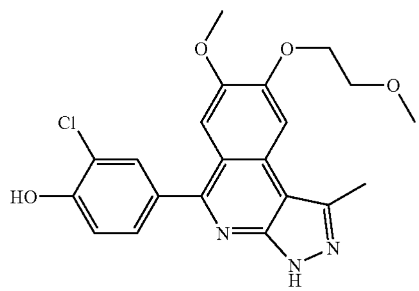 |
| 116 | 2-bromo-4-(1-methyl-7-(methyloxy)-8-{[2-(methyloxy)ethyl]oxy}-3H-pyrazolo[3,4-c]isoquinolin-5-yl)phenol | 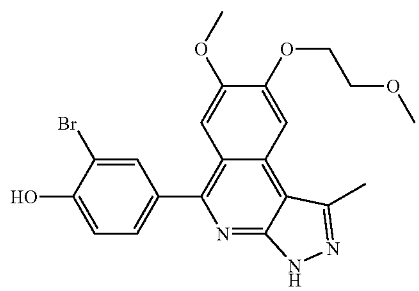 |
| 117 | 2-chloro-4-(1-methyl-7,8-bis{[2-(methyloxy)ethyl]oxy}-3H-pyrazolo[3,4-c]isoquinolin-5-yl)phenol | 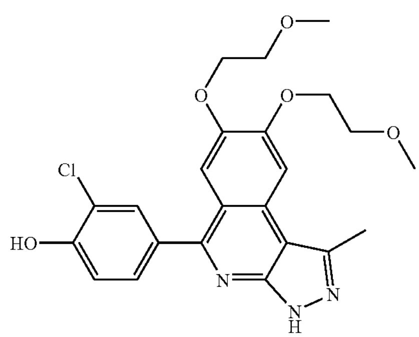 |
| 118 | 2-bromo-4-(1-methyl-7,8-bis{[2-(methyloxy)ethyl]oxy}-3H-pyrazolo[3,4-c]isoquinolin-5-yl)phenol | 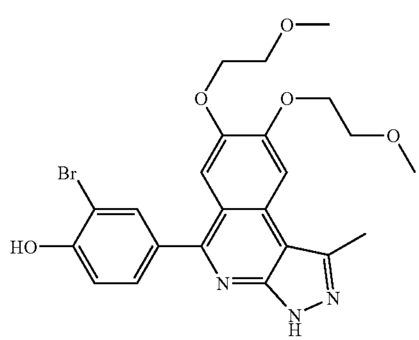 |

TABLE 3-continued

| Entry | Name | Structure |
|---|---|---|
| 120 | 4-(6,9-difluoro-1-methyl-8-{[2-(methyloxy)ethyl]oxy}-3H-pyrazolo[3,4-c]isoquinolin-5-yl)phenol | 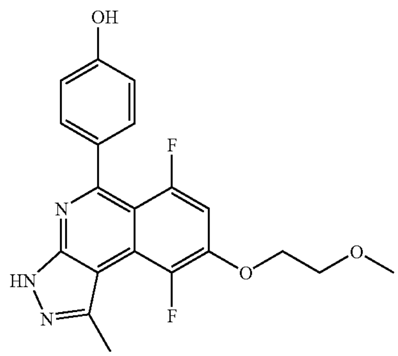 |
| 121 | 2-chloro-5-fluoro-4-[1-methyl-7,8-bis(methyloxy)-3H-pyrazolo[3,4-c]isoquinolin-5-yl]phenol | 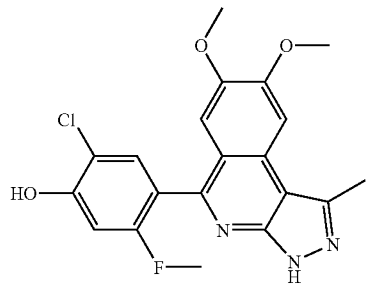 |
| 122 | 2-bromo-5-fluoro-4-[1-methyl-7,8-bis(methyloxy)-3H-pyrazolo[3,4-c]isoquinolin-5-yl]phenol | 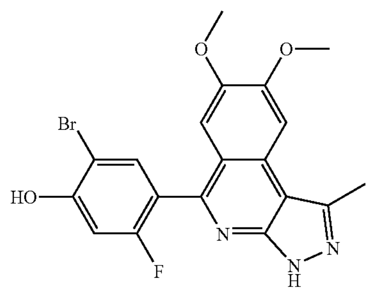 |
| 123 | 4-[9-fluoro-1-methyl-7,8-bis(methyloxy)-3H-benzo[e]indazol-5-yl]phenol | 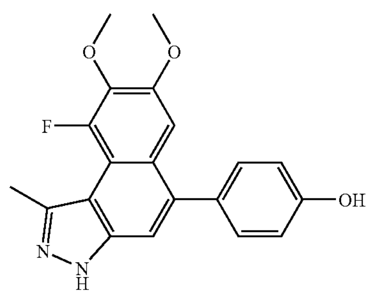 |
| 125 | 3-fluoro-4-(1-methyl-7-(methyloxy)-8-{[2-(methyloxy)ethyl]oxy}-3H-pyrazolo[3,4-c]isoquinolin-5-yl)phenol | 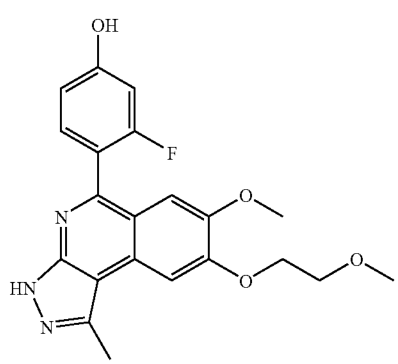 |

TABLE 3-continued

| Entry | Name | Structure |
|---|---|---|
| 126 | 4-(6,9-difluoro-1-methyl-8-{[2-(methyloxy)ethyl]oxy}-3H-pyrazolo[3,4-c]isoquinolin-5-yl)-3-fluorophenol | 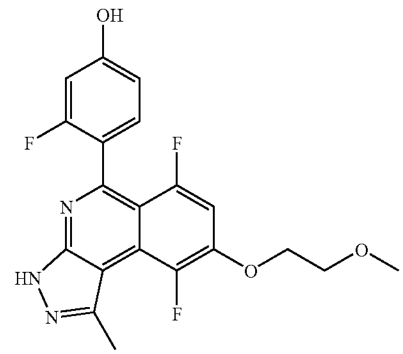 |
| 127 | 2-chloro-4-(6,9-difluoro-1-methyl-8-{[2-(methyloxy)ethyl]oxy}-3H-pyrazolo[3,4-c]isoquinolin-5-yl)phenol | 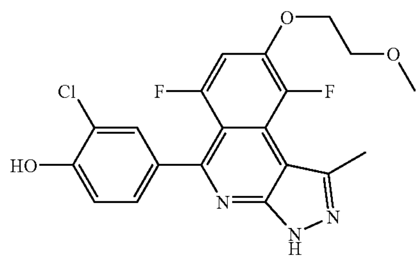 |
| 128 | 2-chloro-4-[8-(ethyloxy)-1-methyl-7-(methyloxy)-3H-pyrazolo[3,4-c]isoquinolin-5-yl]phenol | 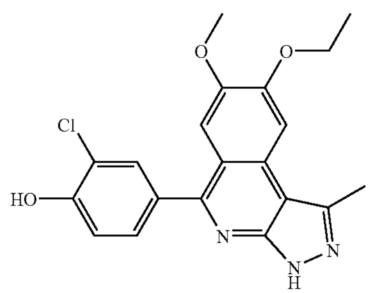 |
| 129 | 2-chloro-4-[6-chloro-1-methyl-7,8-bis(methyloxy)-3H-pyrazolo[3,4-c]isoquinolin-5-yl]phenol | 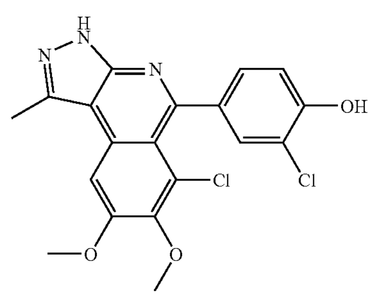 |
| 130 | 3-fluoro-4-(1-methyl-9-(methyloxy)-8-{[2-(methyloxy)ethyl]oxy}-3H-pyrazolo[3,4-c]isoquinolin-5-yl)phenol | 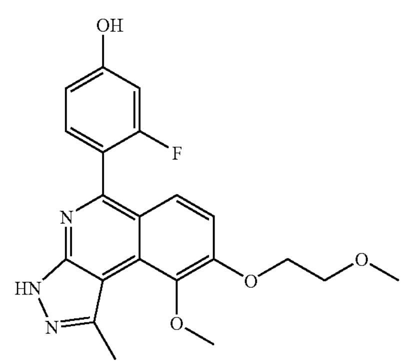 |

TABLE 3-continued

| Entry | Name | Structure |
|---|---|---|
| 131 | 2-chloro-4-(1,7-dimethyl-8-{[2-(methyloxy)ethyl]oxy}-3H-pyrazolo[3,4-c]isoquinolin-5-yl)phenol | 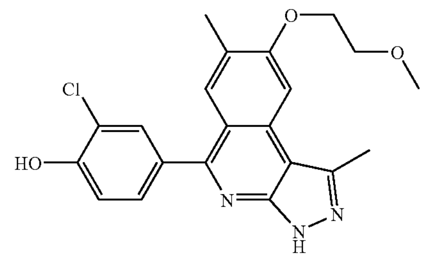 |
| 132 | 3-fluoro-4-(6-fluoro-1-methyl-7-(methyloxy)-8-{[2-(methyloxy)ethyl]oxy}-3H-pyrazolo[3,4-c]isoquinolin-5-yl)phenol | 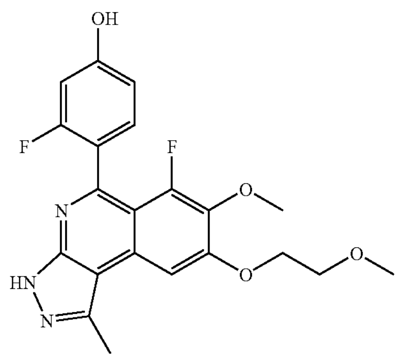 |
| 133 | 2-chloro-4-[1-methyl-8-[(1-methylethyl)oxy]-7-(methyloxy)-3H-pyrazolo[3,4-c]isoquinolin-5-yl]phenol | 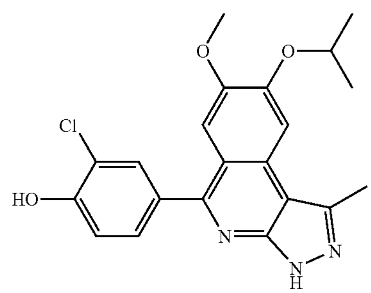 |
| 134 | 2-chloro-4-{1-methyl-7-(methyloxy)-8-[(2-methylpropyl)oxy]-3H-pyrazolo[3,4-c]isoquinolin-5-yl}phenol | 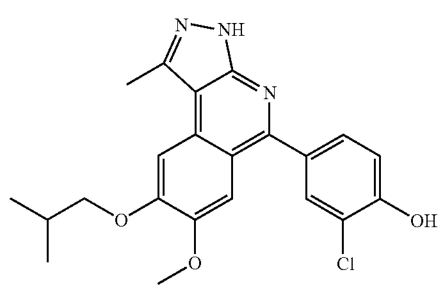 |
| 135 | 2-bromo-5-fluoro-4-(1-methyl-7-(methyloxy)-8-{[2-(methyloxy)ethyl]oxy}-3H-pyrazolo[3,4-c]isoquinolin-5-yl)phenol | 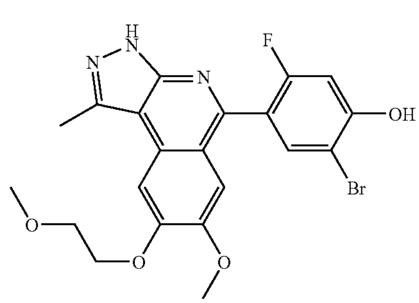 |

TABLE 3-continued

| Entry | Name | Structure |
|---|---|---|
| 136 | 4-[7,8-bis(methyloxy)-3H-pyrazolo[3,4-c]isoquinolin-5-yl]-2-chlorophenol | 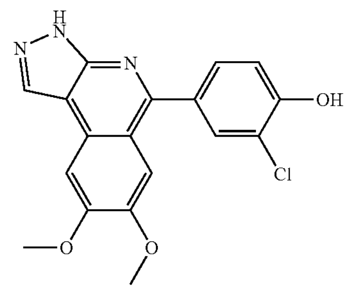 |
| 137 | 4-[7,8-bis(methyloxy)-1-(trifluoromethyl)-3H-pyrazolo[3,4-c]isoquinolin-5-yl]-2-chlorophenol | 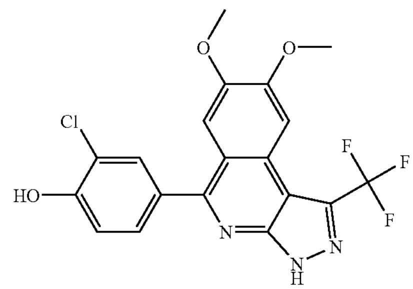 |
| 138 | 4-{7,8-bis(methyloxy)-1-[(methyloxy)methyl]-3H-pyrazolo[3,4-c]isoquinolin-5-yl}-2-chlorophenol | 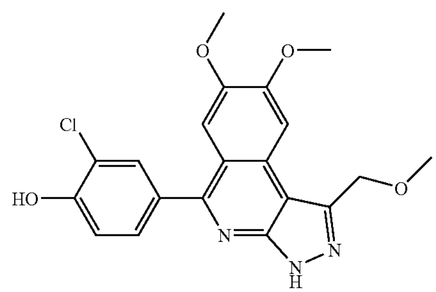 |
| 139 | 2-chloro-4-(1-methyl-3H-[1,3]dioxolo[4,5-g]pyrazolo[3,4-c]isoquinolin-5-yl)phenol | 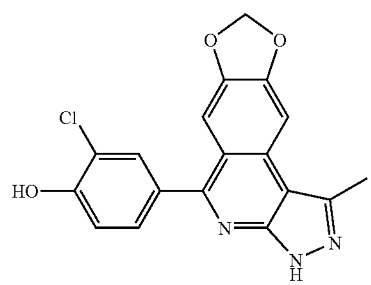 |
| 140 | 2-chloro-4-(1-methyl-8,9-dihydro-3H-[1,4]dioxino[2,3-g]pyrazolo[3,4-c]isoquinolin-5-yl)phenol | 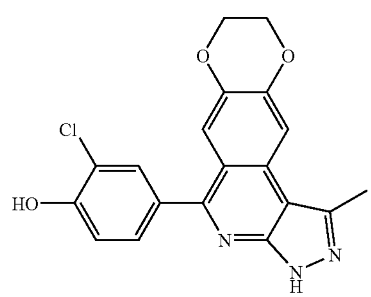 |

TABLE 3-continued

| Entry | Name | Structure |
|---|---|---|
| 141 | 2-chloro-4-(1-methyl-9,10-dihydro-3H, 8H-[1,4]dioxepino[2,3-g]pyrazolo[3,4-c]isoquinolin-5-yl)phenol | 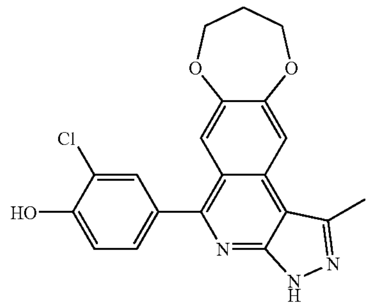 |
| 142 | 2-chloro-4-[7-[(difluoromethyl)oxy]-1-methyl-8-(methyloxy)-3H-pyrazolo[3,4-c]isoquinolin-5-yl]phenol | 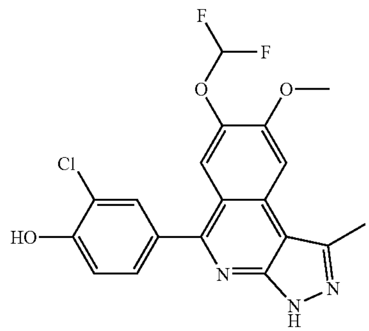 |
| 143 | 2-chloro-5-fluoro-4-(6-fluoro-1-methyl-9-(methyloxy)-8-{[2-(methyloxy)ethyl]oxy}-3H-pyrazolo[3,4-c]isoquinolin-5-yl)phenol | 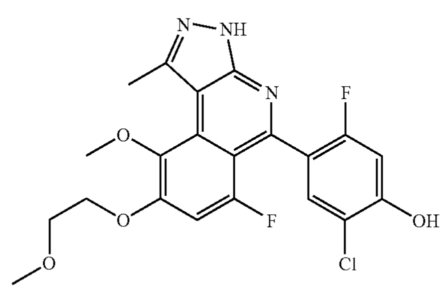 |
| 144 | 2-chloro-4-(6,9-difluoro-1-methyl-8-{[2-(methyloxy)ethyl]oxy}-3H-pyrazolo[3,4-c]isoquinolin-5-yl)-5-fluorophenol | 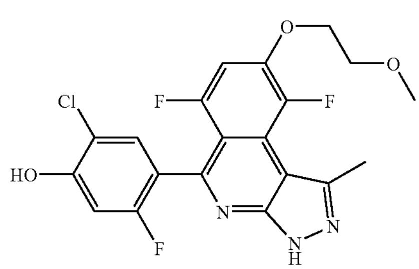 |
| 145 | 2-chloro-4-(11-methyl-2,3-dihydro-9H-[1,4]dioxino[2,3-f]pyrazolo[3,4-c]isoquinolin-7-yl)phenol | 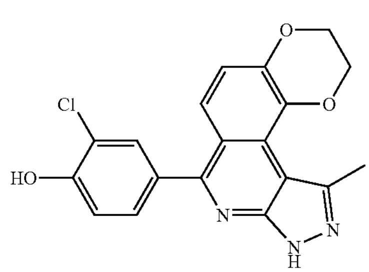 |

TABLE 3-continued

| Entry | Name | Structure |
|---|---|---|
| 146 | 2-chloro-5-fluoro-4-(11-methyl-2,3-dihydro-9H-[1,4]dioxino[2,3-f]pyrazolo[3,4-c]isoquinolin-7-yl)phenol | 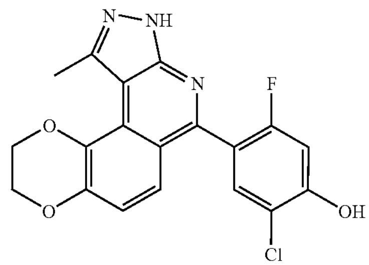 |
| 147 | 2-chloro-4-[1-methyl-6,7,8-tris(methyloxy)-3H-pyrazolo[3,4-c]isoquinolin-5-yl]phenol | 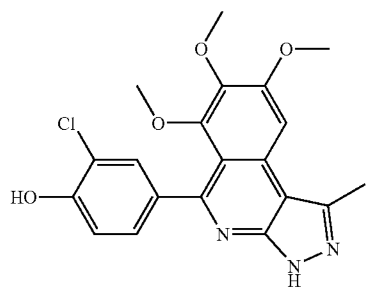 |
| 148 | 2-bromo-4-(6,9-difluoro-1-methyl-8-{[2-(methyloxy)ethyl]oxy}-3H-pyrazolo[3,4-c]isoquinolin-5-yl)-5-fluorophenol | 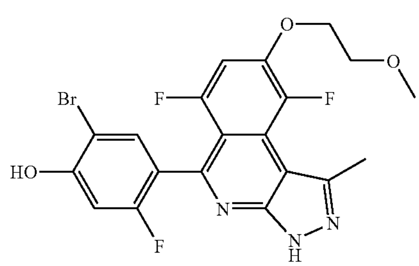 |
| 149 | 7-(3-chlorophenyl)-11-methyl-2,3-dihydro-9H-[1,4]dioxino[2,3-f]pyrazolo[3,4-c]isoquinoline | 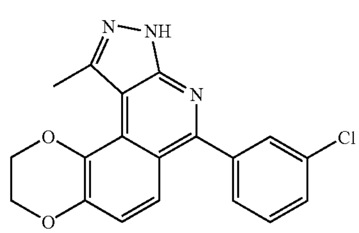 |
| 150 | 2-chloro-5-fluoro-4-(6-fluoro-1-methyl-8,9-dihydro-3H-[1,4]dioxino[2,3-g]pyrazolo[3,4-c]isoquinolin-5-yl)phenol | 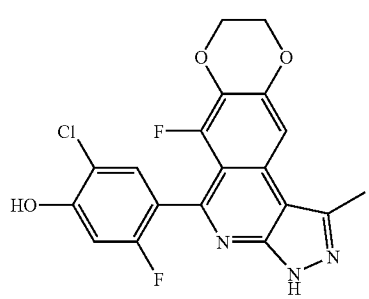 |

TABLE 3-continued

| Entry | Name | Structure |
|---|---|---|
| 151 | 2-chloro-4-{1-methyl-7-(methyloxy)-8-[(tetrahydrofuran-2-ylmethyl)oxy]-3H-pyrazolo[3,4-c]isoquinolin-5-yl}phenol | 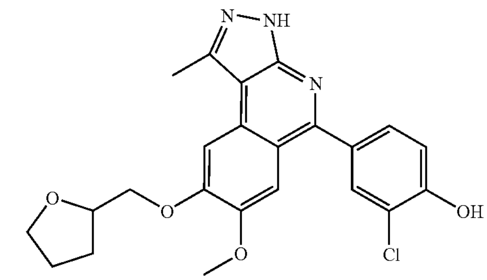 |
| 152 | 2-chloro-4-{1-methyl-7-(methyloxy)-8-[(tetrahydro-2H-pyran-2-ylmethyl)oxy]-3H-pyrazolo[3,4-c]isoquinolin-5-yl}phenol | 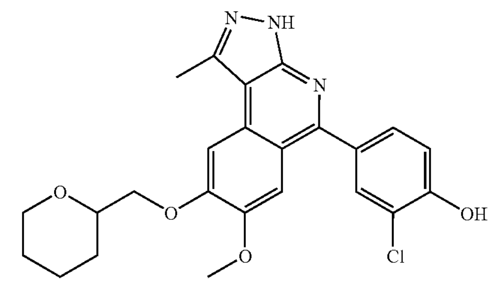 |
| 153 | 2-chloro-4-{1-methyl-7-(methyloxy)-8-[(2,2,2-trifluoroethyl)oxy]-3H-pyrazolo[3,4-c]isoqunolin-5-yl}phenol | 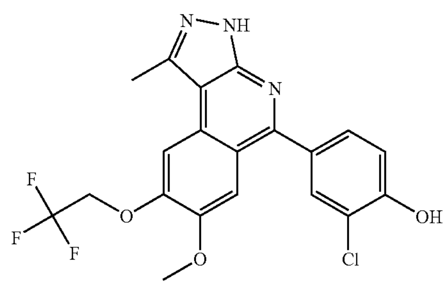 |
| 154 | 2-chloro-5-fluoro-4-[9-fluoro-1-methyl-6,7,8-tris(methyloxy)-3H-pyrazolo[3,4-c]isoquinolin-5-yl]phenol | 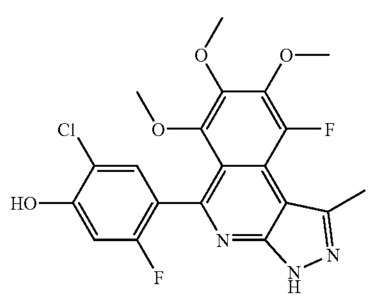 |
| 155 | 5-(3-chloro-4-hydroxyphenyl)-6,9-difluoro-1-methyl-3H-pyrazolo[3,4-c]isoquinolin-8-ol | 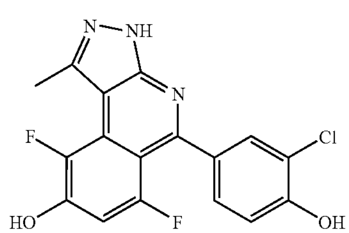 |

TABLE 3-continued

| Entry | Name | Structure |
|---|---|---|
| 156 | 6,9-difluoro-5-(2-fluorophenyl)-1-methyl-8-{[2-(methyloxy)ethyl]oxy}-3H-pyrazolo[3,4-c]isoquinoline | 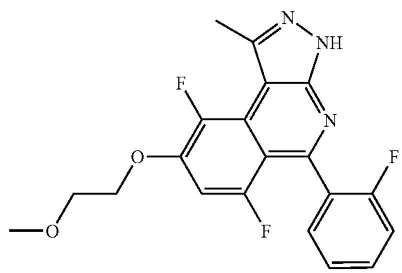 |
| 157 | 2-chloro-4-{8-[(difluoromethyl)oxy]-6,9-difluoro-1-methyl-3H-pyrazolo[3,4-c]isoquinolin-5-yl}phenol | 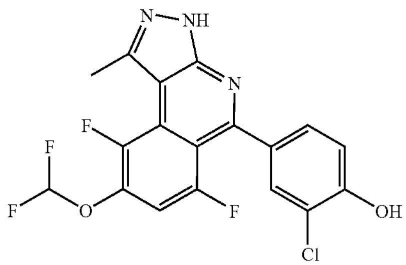 |
| 158 | 2-chloro-4-(6,11-difluoro-1-methyl-8,9-dihydro-3H-[1,4]dioxino[2,3-g]pyrazolo[3,4-c]isoquinolin-5-yl)-5-fluorophenol | 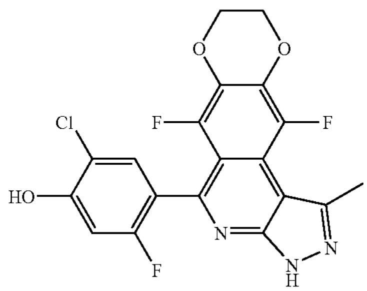 |
| 159 | 4-(1-methyl-3H-benzo[e]indazol-5-yl)phenol | 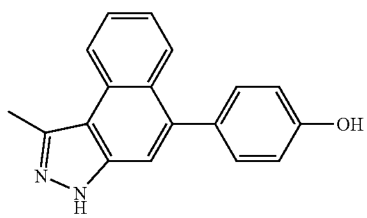 |
| 160 | 6-fluoro-7-(2-fluorophenyl)-11-methyl-2,3-dihydro-9H-[1,4]dioxino[2,3-f]pyrazolo[3,4-c]isoquinoline | 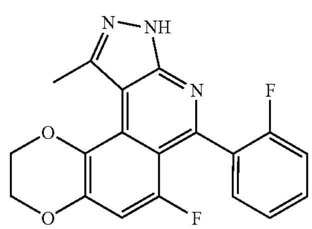 |
| 161 | 2-chloro-4-{1-methyl-7-(methyloxy)-8-[(tetrahydro-2H-pyran-4-ylmethyl)oxy]-3H-pyrazolo[3,4-c]isoquinolin-5-yl}phenol | 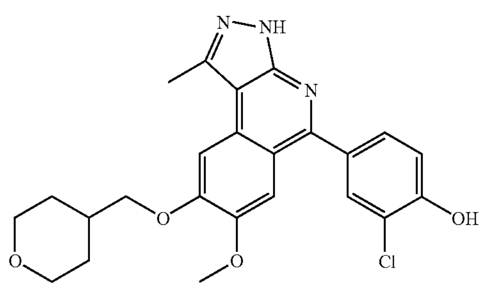 |

TABLE 3-continued

| Entry | Name | Structure |
|---|---|---|
| 162 | 2-chloro-4-[8-{[2-(ethyloxy)ethyl]oxy}-1-methyl-7-(methyloxy)-3H-pyrazolo[3,4-c]isoquinolin-5-yl]phenol | 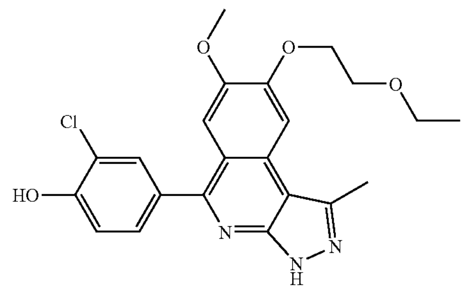 |
| 164 | 3-fluoro-4-(6-fluoro-11-methyl-2,3-dihydro-9H-[1,4]dioxino[2,3-f]pyrazolo[3,4-c]isoquinolin-7-yl)phenol | 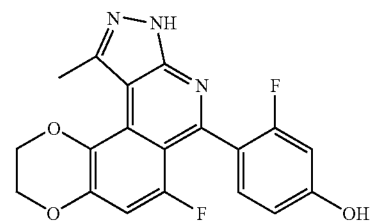 |
| 165 | 2-chloro-5-fluoro-4-(6-fluoro-11-methyl-2,3-dihydro-9H-[1,4]dioxino[2,3-f]pyrazolo[3,4-c]isoquinolin-7-yl)phenol | 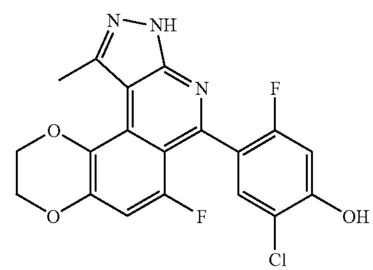 |
| 166 | 2-chloro-4-[8-(cyclopentyloxy)-1-methyl-7-(methyloxy)-3H-pyrazolo[3,4-c]isoquinolin-5-yl]phenol | 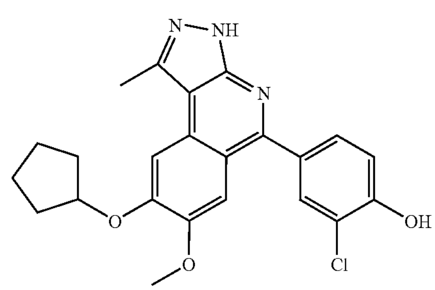 |
| 167 | 2-chloro-4-(1-methyl-7-(1-methylethyl)-8-{[2-(methyloxy)ethyl[oxy}-3H-pyrazolo[3,4-c]isoquinolin-5-yl)phenol | 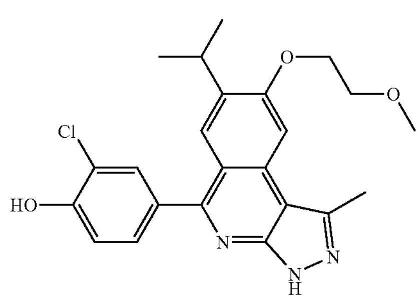 |

TABLE 3-continued

| Entry | Name | Structure |
|---|---|---|
| 168 | 2-chloro-4-[9-ethyl-1-methyl-8-(methyloxy)-3H-pyrazolo[3,4-c]isoquinolin-5-yl]phenol | 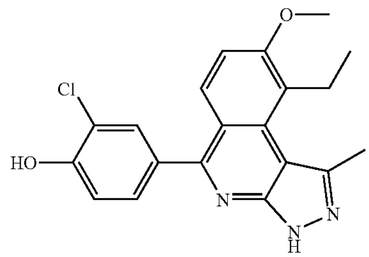 |
| 169 | 2-chloro-4-(6,9-difluoro-1-methyl-8-{[(1-methylpiperidin-4-yl)methyl]oxy}-3H-pyrazolo[3,4-c]isoquinolin-5-yl)phenol | 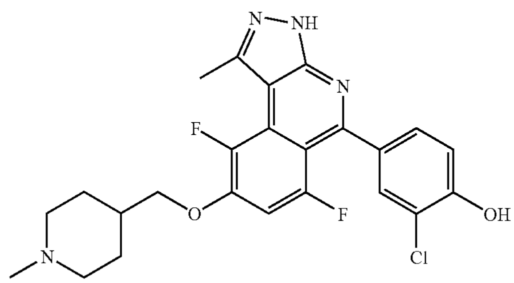 |
| 170 | 5-(3-chloro-4-hydroxyphenyl)-8-fluoro-1-methyl-7-(methyloxy)-3H-pyrazolo[3,4-c]isoquinolin-6-ol | 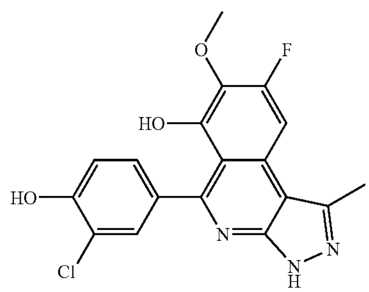 |
| 171 | 2-chloro-4-(6-fluoro-1-methyl-7-(methyloxy)-8-{[(1-methylpiperidin-4-yl)methyl]oxy}-3H-pyrazolo[3,4-c]isoquinolin-5-yl)phenol | 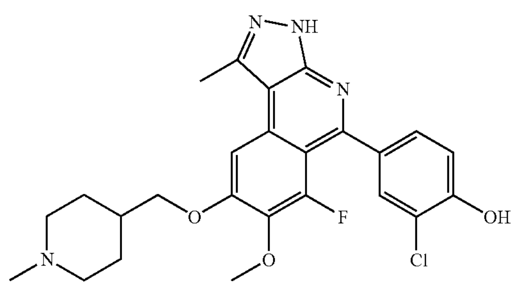 |
| 172 | 2-chloro-4-(6-fluoro-1-methyl-8,9-bis{[2-(methyloxy)ethyl]oxy}-3H-pyrazolo[3,4-c]isoquinolin-5-yl)phenol | 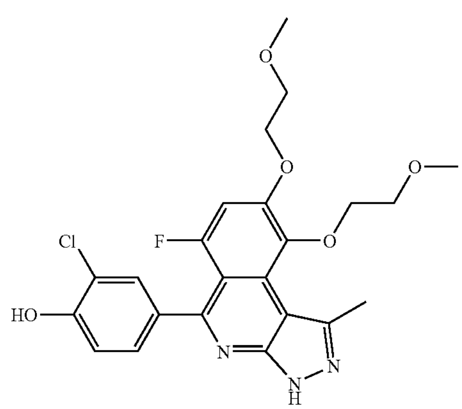 |

TABLE 3-continued

| Entry | Name | Structure |
|---|---|---|
| 173 | 5-[3-chloro-4-(methyloxy)phenyl]-6-fluoro-1-methyl-7-(methyloxy)-8-{[(1-methylpiperidin-4-yl)methyl]oxy}-3H-pyrazolo[3,4-c]isoquinoline | 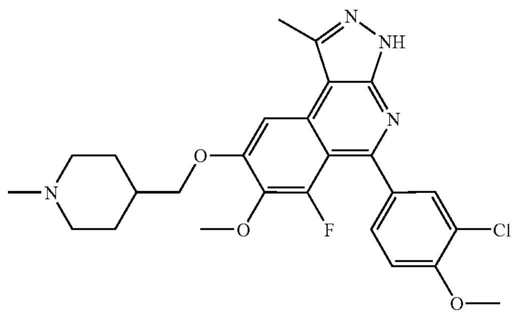 |
| 174 | 5-[3-chloro-4-(methyloxy)phenyl]-8-fluoro-1-methyl-7-(methyloxy)-3H-pyrazolo[3,4-c]isoquinolin-6-ol | 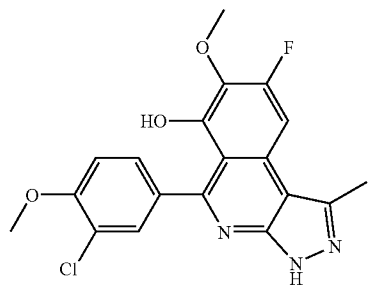 |
| 176 | 2-chloro-4-{6-fluoro-1-methyl-7-(methyloxy)-8-[(2-piperidin-1-ylethyl)oxy]-3H-pyrazolo[3,4-c]isoquinolin-5-yl}phenol | 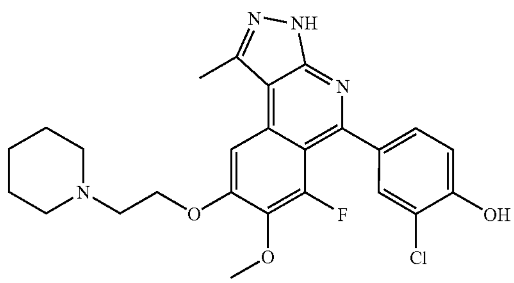 |
| 177 | 2-chloro-4-[8-{[2-(4-ethylpiperazin-1-yl)ethyl]oxy}-6-fluoro-1-methyl-7-(methyloxy)-3H-pyrazolo[3,4-c]isoquinolin-5-yl]phenol | 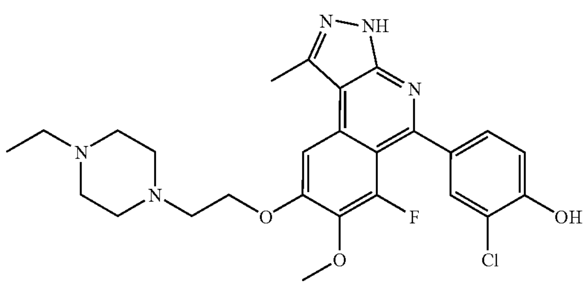 |
| 178 | 2-chloro-4-[8-{[2-(diethylamino)ethyl]oxy}-6-fluoro-1-methyl-7-(methyloxy)-3H-pyrazolo[3,4-c]isoquinolin-5-yl]phenol | 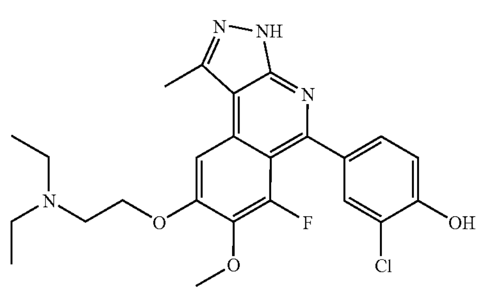 |

TABLE 3-continued

| Entry | Name | Structure |
|---|---|---|
| 179 | 2-chloro-4-(6-fluoro-1-methyl-7-(methyloxy)-8-{[2-(methyloxy)ethyl]oxy}-3H-pyrazolo[3,4-c]isoquinolin-5-yl)phenol | 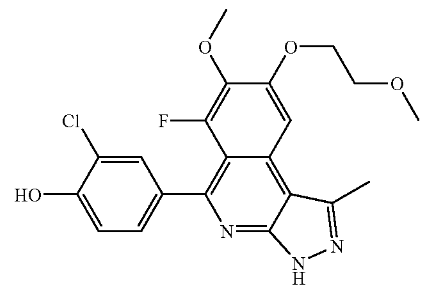 |
| 182 | 2-chloro-4-(6-fluoro-1-methyl-9-(methyloxy)-8-{[(1-methylpiperidin-4-yl)methyl]oxy}-3H-pyrazolo[3,4-c]isoquinolin-5-yl)phenol | 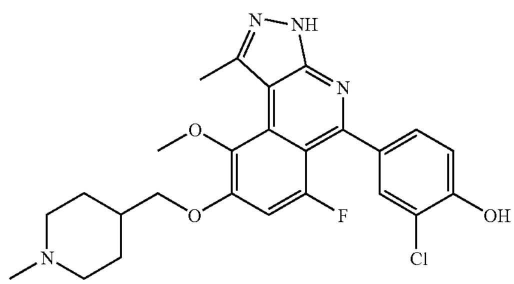 |
| 183 | 2-bromo-4-(6-fluoro-1-methyl-9-(methyloxy)-8-{[(1-methylpiperidin-4-yl)methyl]oxy}-3H-pyrazolo[3,4-c]isoquinolin-5-yl)phenol | 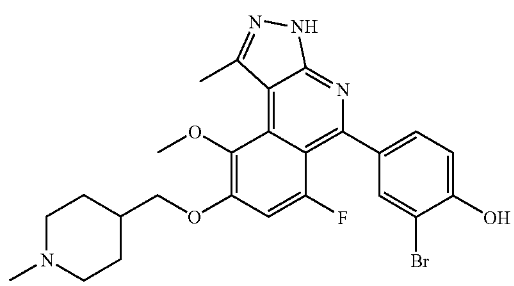 |
| 184 | 2-chloro-5-fluoro-4-(6-fluoro-1-methyl-9-(methyloxy)-8-{[(1-methylpiperidin-4-yl)methyl]oxy}-3H-pyrazolo[3,4-c]isoquinolin-5-yl)phenol | 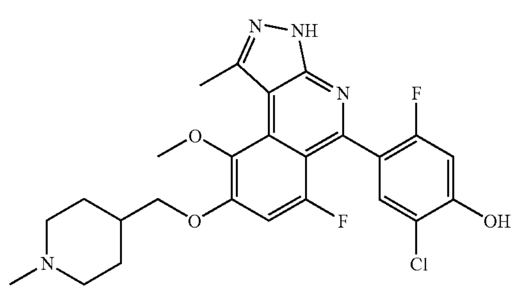 |
| 185 | 4-(6-fluoro-1-methyl-9-(methyloxy)-8-{[(1-methylpiperidin-4-yl)methyl]oxy}-3H-pyrazolo[3,4-c]isoquinolin-5-yl)-2-methylphenol | 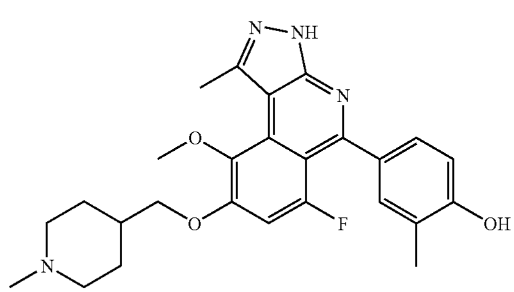 |

TABLE 3-continued

| Entry | Name | Structure |
|---|---|---|
| 186 | 2-chloro-4-{6,9-difluoro-1-methyl-8-[(2-piperidin-1-ylethyl)oxy]-3H-pyrazolo[3,4-c]isoquinolin-5-yl}phenol | 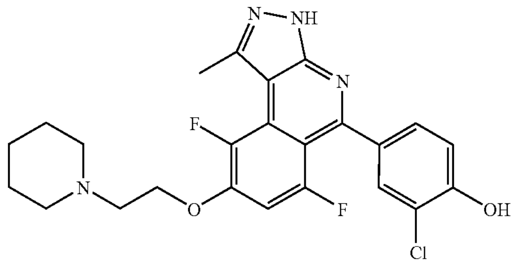 |
| 187 | 2-chloro-4-(8-{[2-(4-ethylpiperazin-1-yl)ethyl]oxy}-6,9-difluoro-1-methyl-3H-pyrazolo[3,4-c]isoquinolin-5-yl)phenol | 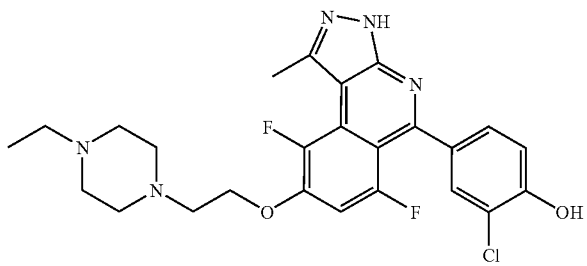 |
| 188 | 2-chloro-4-(8-{[2-(diethylamino)ethyl]oxy}-6,9-difluoro-1-methyl-3H-pyrazolo[3,4-c]isoquinolin-5-yl)phenol | 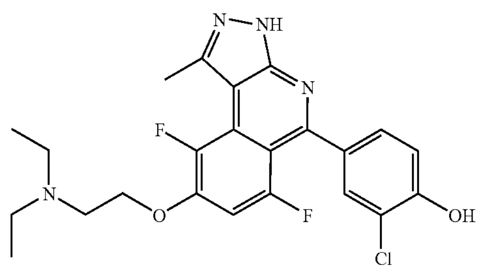 |
| 191 | 6,9-difluoro-5-(1H-indol-5-yl)-1-methyl-3H-pyrazolo[3,4-c]isoquinolin-8-ol | 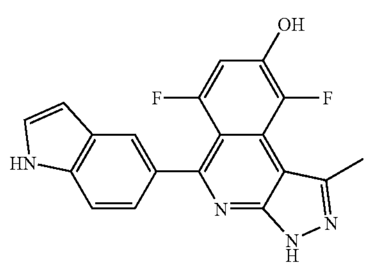 |
| 193 | 5-(4-aminophenyl)-6,9-difluoro-1-methyl-3H-pyrazolo[3,4-c]isoquinolin-8-ol | 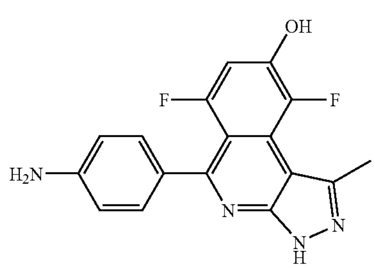 |

TABLE 3-continued

| Entry | Name | Structure |
|---|---|---|
| 194 | 2-chloro-4-(6-fluoro-1-methyl-7-(methyloxy)-8-{[2-(4-methylpiperazin-1-yl)ethyl]oxy}-3H-pyrazolo[3,4-c]isoqunolin-5-yl)phenol | 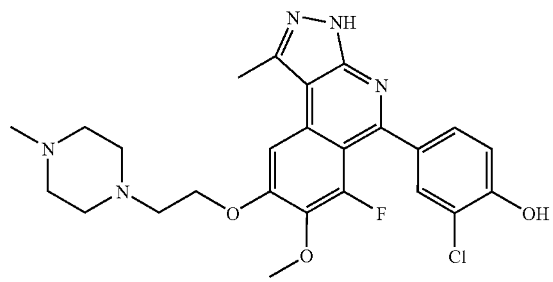 |
| 195 | 5-(2-amino-1,3-thiazol-5-yl)-6,9-difluoro-1-methyl-3H-pyrazolo[3,4-c]isoquinolin-8-ol | 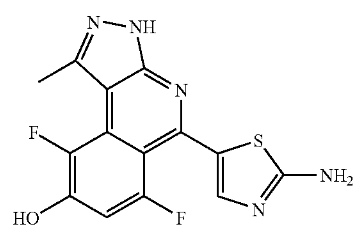 |
| 196 | 2-chloro-4-[8-{[2-(4-ethylpiperazin-1-yl)ethyl]oxy}-6-fluoro-1-methyl-9-(methyloxy)-3H-pyrazolo[3,4-c]isoquinolin-5-yl]phenol | 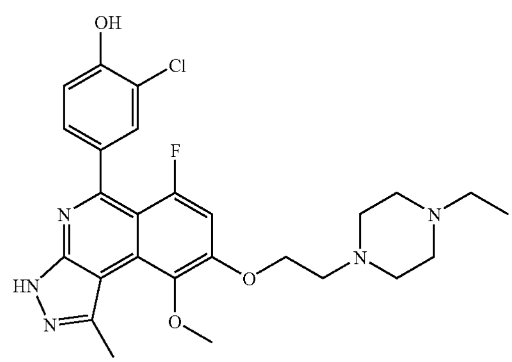 |
| 197 | 2-chloro-4-(6-fluoro-1-methyl-9-(methyloxy)-8-{[2-(4-methylpiperazin-1-yl)ethyl]oxy}-3H-pyrazolo[3,4-c]isoquinolin-5-yl)phenol | 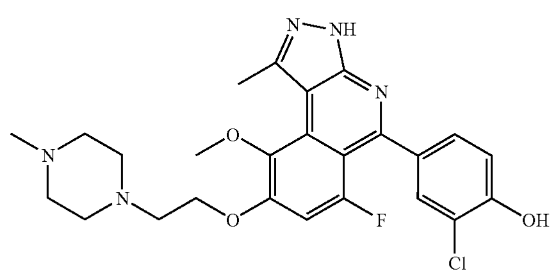 |
| 198 | 5-(6-aminopyridin-3-yl)-6,9-difluoro-1-methyl-3H-pyrazolo[3,4-c]isoquinolin-8-ol | 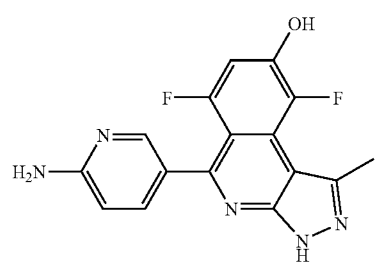 |

TABLE 3-continued

| Entry | Name | Structure |
|---|---|---|
| 199 | 5-(5-amino-2-thienyl)-6,9-difluoro-1-methyl-3H-pyrazolo[3,4-c]isoquinolin-8-ol | 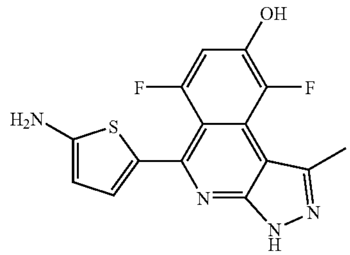 |
| 200 | 2-chloro-4-[8-{[3(4-ethylpiperazin-1-yl)propyl]oxy}-6-fluoro-1-methyl-9-(methyloxy)-3H-pyrazolo[3,4-c]isoquinolin-5-yl]phenol | 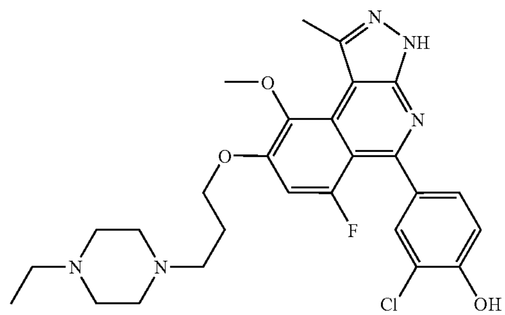 |
| 201 | 2-chloro-4-(6-fluoro-1-methyl-9-(methyloxy)-8-{[3-(4-methylpiperazin-1-yl)propyl]oxy}-3H-pyrazolo[3,4-c]isoquinolin-5-yl)phenol | 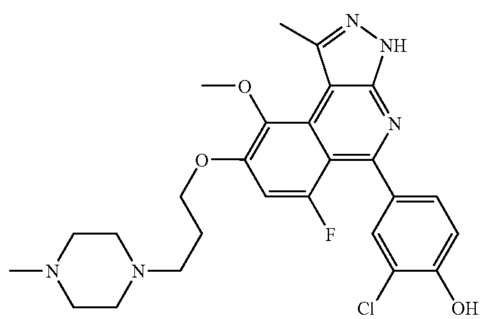 |
| 202 | 6,9-difluoro-5-(1H-indol-6-yl)-1-methyl-3H-pyrazolo[3,4-c]isoquinolin-8-ol | 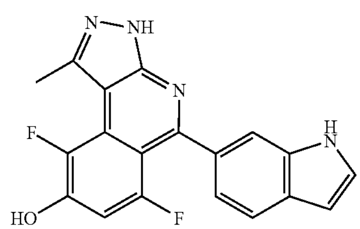 |
| 203 | N-[5-(6,9-difluoro-8-hydroxy-1-methyl-3H-pyrazolo[3,4-c]isoquinolin-5-yl)-1,3-thiazol-2-yl]acetamide | 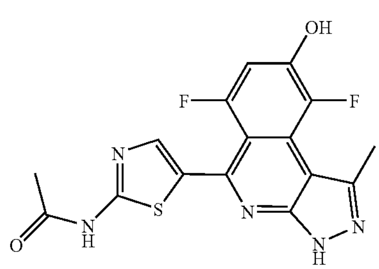 |

TABLE 3-continued

| Entry | Name | Structure |
|---|---|---|
| 206 | 2-chloro-4-{6-fluoro-1-methyl-9-(methyloxy)-8-[(2-morpholin-4-ylethyl)oxy]-3H-pyrazolo[3,4-c]isoquinolin-5-yl}phenol | 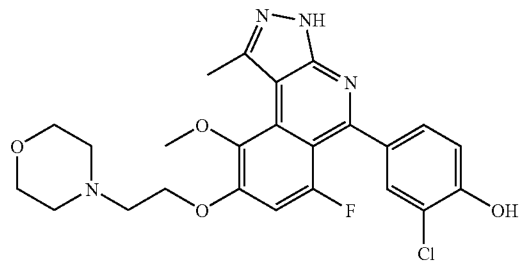 |
| 207 | 4-[8-({2-[butyl(ethyl)amino]ethyl}oxy)-6-fluoro-1-methyl-9-(methyloxy)-3H-pyrazolo[3,4-c]isoquinolin-5-yl]-2-chlorophenol | 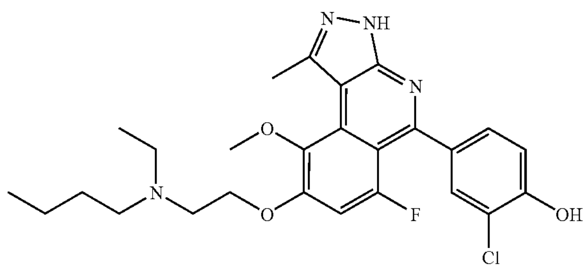 |
| 208 | 4-[8-{[(2R)-2-amino-3-methylbutyl]oxy}-6-fluoro-1-methyl-9-(methyloxy)-3H-pyrazolo[3,4-c]isoquinolin-5-yl]-2-chlorophenol | 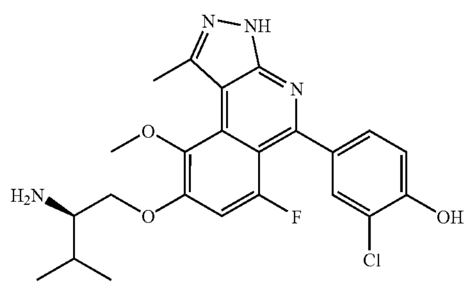 |
| 209 | 2-chloro-4-(6-fluoro-1-methyl-9-(methyloxy)-8-{[2-(1-methylpiperidin-4-yl)ethyl]oxy}-3H-pyrazolo[3,4-c]isoquinolin-5-yl)phenol | 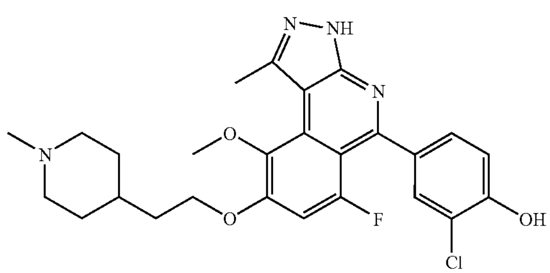 |
| 210 | 2-chloro-4-[8-{[(1-ethylpiperidin-4-yl)methyl]oxy}-6-fluoro-1-pyrazolo[3,4-c]isoquinolin-5-yl]phenol | 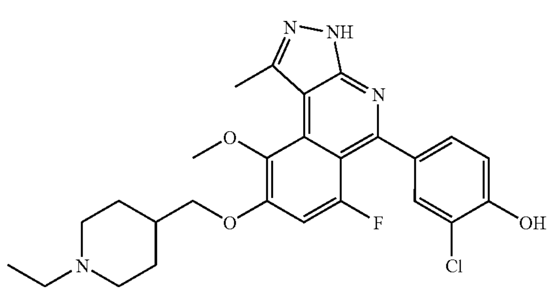 |

TABLE 3-continued

| Entry | Name | Structure |
|---|---|---|
| 212 | 5-(5-amino-1,3,4-thiadiazol-2-yl)-6,9-difluoro-1-methyl-3H-pyrazolo[3,4-c]isoquinolin-8-ol | 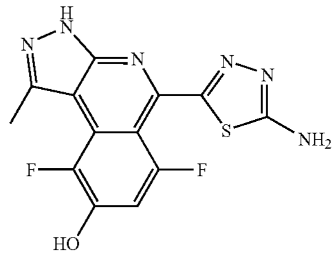 |
| 213 | 4-[8-{[(2R)-2-amino-3,3-dimethylbutyl]oxy}-6-fluoro-1-methyl-9-(methyloxy)-3H-pyrazolo[3,4-c]isoquinolin-5-yl]-2-chlorophenol | 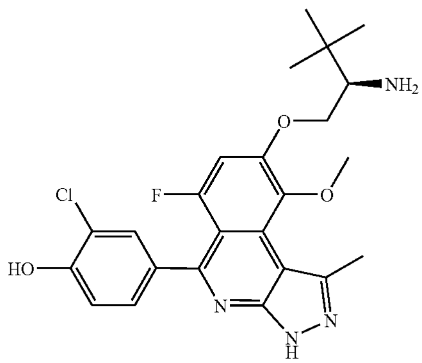 |
| 214 | 2-chloro-4-[6-fluoro-1-methyl-9-(methyloxy)-8-({2-[4-(2-methylpropyl)piperazin-1-yl]ethyl}oxy)-3H-pyrazolo[3,4-c]isoquinolin-5-yl]phenol | 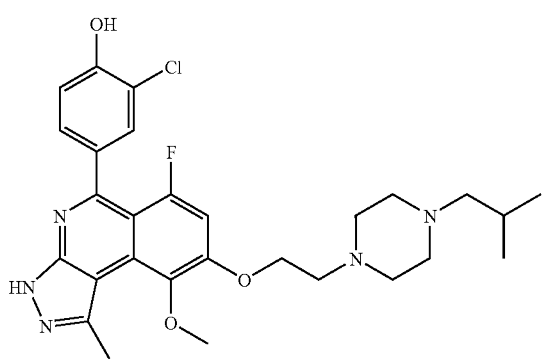 |
| 215 | 2-chloro-4-[8-{[2-(5-ethyl-2,5-diazabicyclo[2.2.1]hept-2-yl)ethyl]oxy}-6-fluoro-1-methyl-9-(methyloxy)-3H-pyrazolo[3,4-c]isoquinolin-5-yl]phenol | 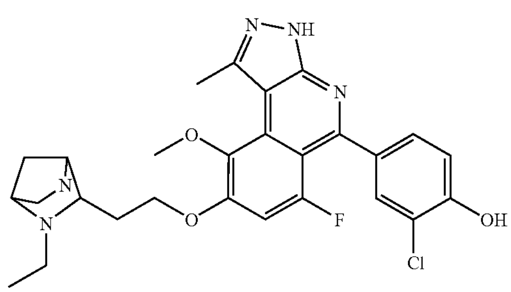 |

TABLE 3-continued

| Entry | Name | Structure |
|---|---|---|
| 216 | 2-chloro-4-[6-fluoro-1-methyl-8-({2-[4-(1-methylethyl)piperazin-1-yl]ethyl}oxy)-9-(methyloxy)-3H-pyrazolo[3,4-c]isoquinolin-5-yl]phenol | 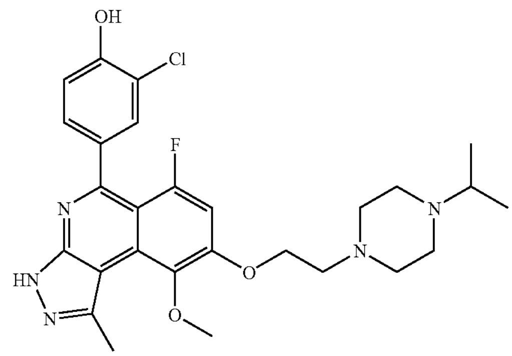 |
| 217 | 4-[8-{[2-(3-amino-8-azabicyclo[3.2.1]oct-8-yl)ethyl]oxy}-6-fluoro-1-methyl-9-(methyloxy)-3H-pyrazolo[3,4-c]isoquinolin-5-yl]-2-chlorophenol | 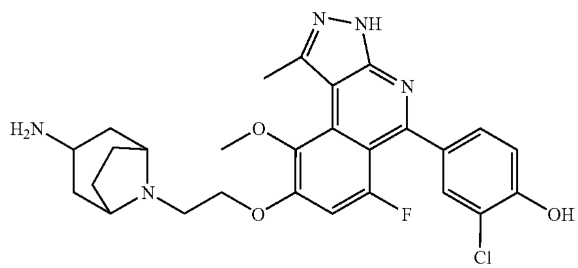 |
| 218 | 2-chloro-4-[8-{[2-(1-ethylpiperidin-4-yl)ethyl]oxy}-6-fluoro-1-methyl-9-(methyloxy)-3H-pyrazolo[3,4-c]isoquinolin-5-yl]phenol | 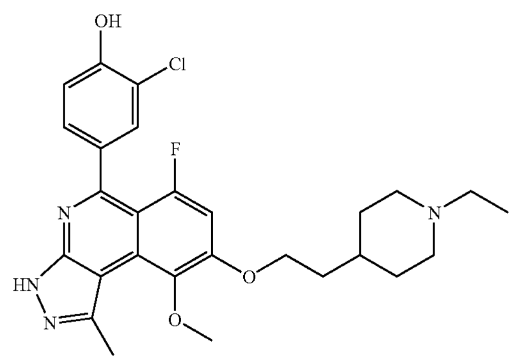 |
| 219 | 2-chloro-4-[8-{[2-(diethylamino)ethyl]oxy}-6-fluoro-1-methyl-9-(methyloxy)-3H-pyrazolo[3,4-c]isoquinolin-5-yl]phenol | 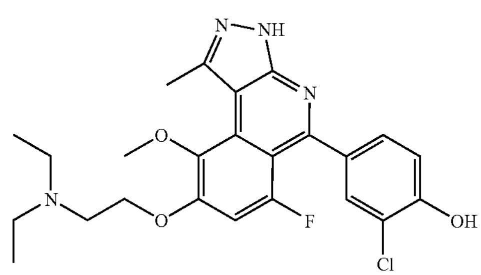 |
| 220 | 2-chloro-5-{6-fluoro-1-methyl-9-(methyloxy)-8-[(2-pyrrolidin-1-ylethyl)oxy]-3H-pyrazolo[3,4-c]isoquinolin-5-yl}phenol | 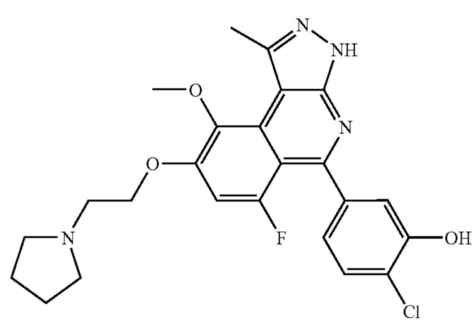 |

TABLE 3-continued

| Entry | Name | Structure |
|---|---|---|
| 223 | 2-chloro-4-[6-fluoro-1-methyl-8-[(8-methyl-8-azabicyclo[3.2.1]oct-3-yl)oxy]-9-(methyloxy)-3H-pyrazolo[3,4-c]isoquinolin-5-yl]phenol | 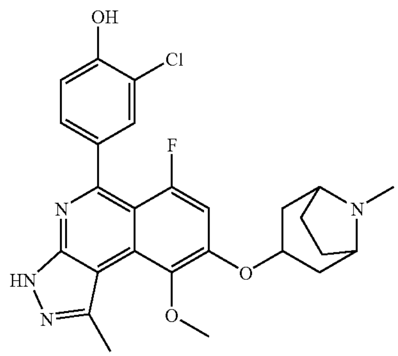 |
| 224 | 2-chloro-4-{6-fluoro-1-methyl-9-(methyloxy)-8-[(3-pyrrolidin-1-ylpropyl)oxy]-3H-pyrazolo[3,4-c]isoquinolin-5-yl}phenol | 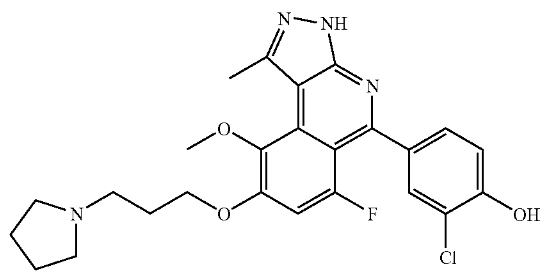 |
| 225 | 2-chloro-4-{6-fluoro-1-methyl-9-(methyloxy)-8-[(3-piperidin-1-ylpropyl)oxy]-3H-pyrazolo[3,4-c]isoquinolin-5-yl}phenol | 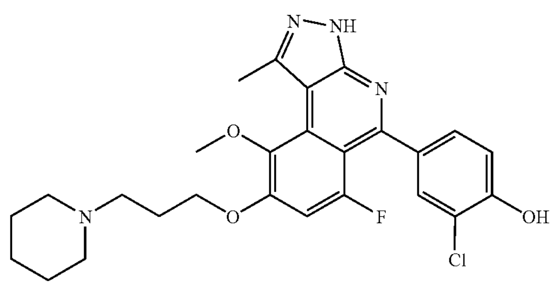 |
| 226 | 2-chloro-4-{6-fluoro-1-methyl-9-(methyloxy)-8-[(3-morpholin-4-ylpropyl)oxy]-3H-pyrazolo[3,4-c]isoquinolin-5-yl}phenol | 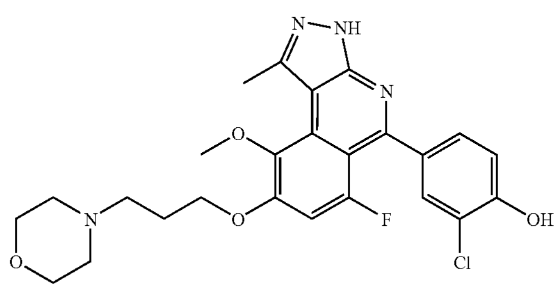 |
| 227 | 2-chloro-4-[8-({2-[[2-(dimethylamino)ethyl](methyl)amino]ethyl}oxy)-6-fluoro-1-methyl-9-(methyloxy)-3H-pyrazolo[3,4-c]isoquinolin-5-yl]phenol | 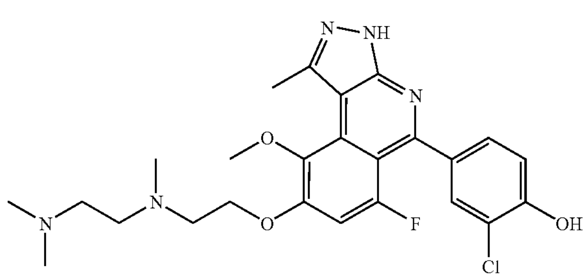 |

TABLE 3-continued

| Entry | Name | Structure |
|---|---|---|
| 228 | 2-chloro-4-[8-({2-[[2-(diethylamino)ethyl](methyl)amino]ethyl}oxy)-6-fluoro-1-methyl-9-(methyloxy)-3H-pyrazolo[3,4-c]isoquinolin-5-yl]phenol | 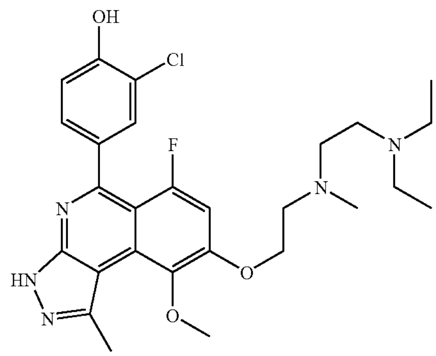 |
| 229 | 2-chloro-4-[8-({2-[[2-(dimethylamino)ethyl](ethyl)amino]ethyl}oxy)-6-fluoro-1-methyl-9-(methyloxy)-3H-pyrazolo[3,4-c]isoquinolin-5-yl]phenol | 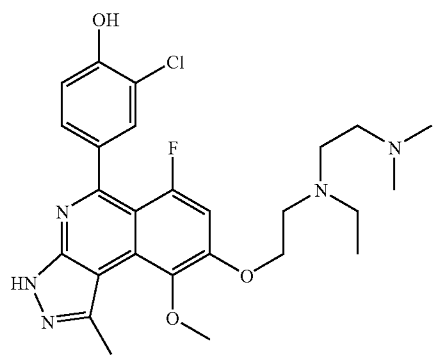 |
| 230 | 4-[8-[(2-{bis[3-(dimethylamino)propyl]amino}ethyl)oxy]-6-fluoro-1-methyl-9-(methyloxy)-3H-pyrazolo[3,4-c]isoquinolin-5-yl]-2-chlorophenol | 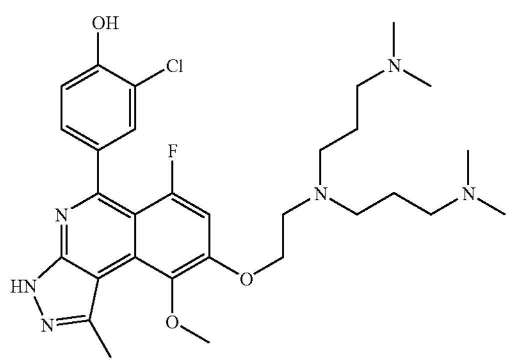 |
| 231 | 2-chloro-4-[6-fluoro-1-methyl-8-({2-[methyl(1-methylpyrrolidin-3-yl)amino]ethyl}oxy)-9-(methyloxy)-3H-pyrazolo[3,4-c]isoquinolin-5-yl]phenol | 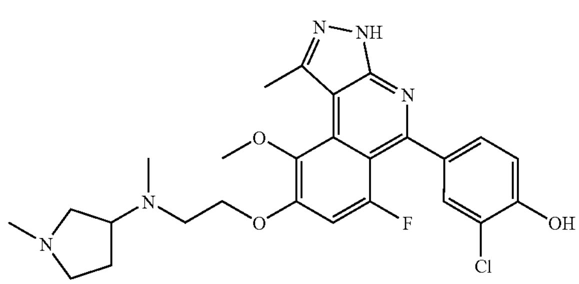 |

TABLE 3-continued

| Entry | Name | Structure |
|---|---|---|
| 232 | 2-chloro-4-{6-fluoro-1-methyl-9-(methyloxy)-8-[(2-{(2S)-2-[(methyloxy)methyl]pyrrolidin-1-yl}ethyl)oxy]-3H-pyrazolo[3,4-c]isoquinolin-5-yl}phenol | 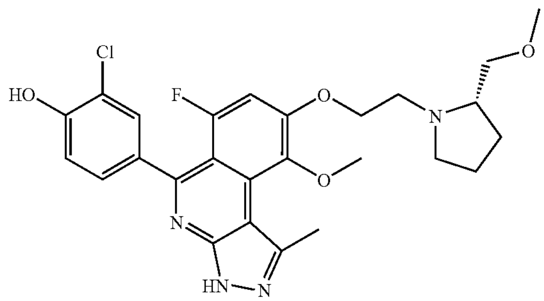 |
| 233 | 2-chloro-4-(6-fluoro-1-methyl-9-(methyloxy)-8-{[2-(4-pyrrolidin-1-ylpiperidin-1-yl)ethyl]oxy}-3H-pyrazolo[3,4-c]isoquinolin-5-yl)phenol | 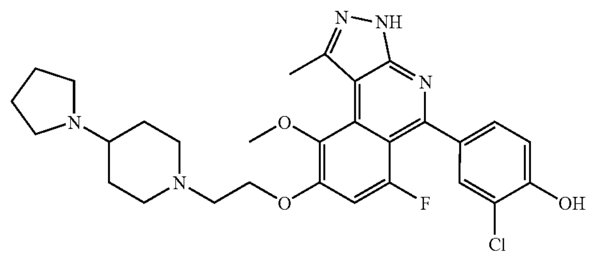 |
| 234 | 2-chloro-4-[8-{[2-(4-cyclohexylpiperazin-1-yl)ethyl]oxy}-6-fluoro-1-methyl-9-(methyloxy)-3H-pyrazolo[3,4-c]isoquinolin-5-yl]phenol | 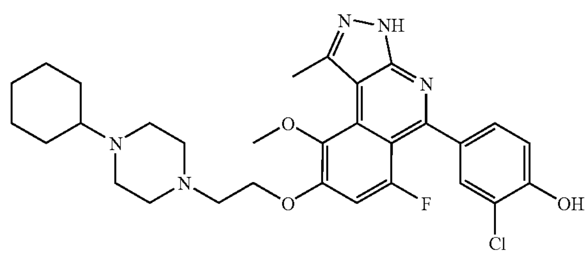 |
| 235 | 2-[4-(2-{5-(3-chloro-4-hydroxyphenyl)-6-fluouo-1-methyl-9-(methyloxy)-3H-pyrazolo[3,4-c]isoquinolin-8-yl]oxy}ethyl)piperazin-1-yl]-N-(1-methylethyl)acetamide | 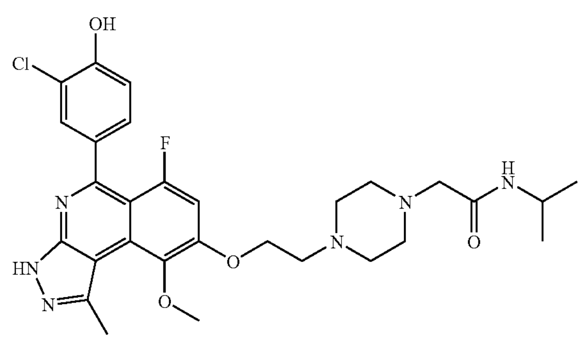 |
| 236 | 4-[8-{[2-(1,4'-bipiperidin-1'-yl)ethyl]oxy}-6-fluoro-1-methyl-9-(methyloxy)-3H-pyrazolo[3,4-c]isoquinolin-5-yl]-2-chlorophenol | 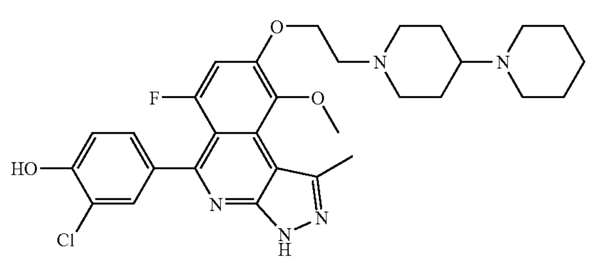 |

TABLE 3-continued

| Entry | Name | Structure |
|---|---|---|
| 237 | 2-chloro-4-[6-fluoro-1-methyl-8-{[2-(4-methyl-1,4-diazepan-1-yl)ethyl]oxy}-9-(methyloxy)-3H-pyrazolo[3,4-c]isoquinolin-5-yl]phenol | 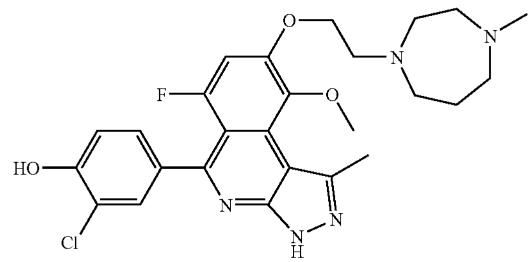 |
| 238 | 2-chloro-4-(6-fluoro-1-methyl-9-(methyloxy)-8-{[2-(4-pyridin-2-ylpiperazin-1-yl)ethyl]oxy}-3H-pyrazolo[3,4-c]isoquinolin-5-yl)phenol | 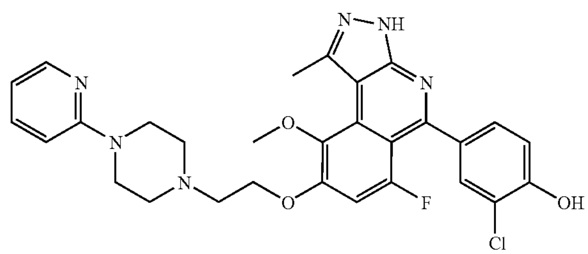 |
| 239 | 2-chloro-4-[8-{[2-(2,6-dimethylmorpholin-4-yl)ethyl]oxy}-6-fluoro-1-methyl-9-(methyloxy)-3H-pyrazolo[3,4-c]isoquinolin-5-yl]phenol | 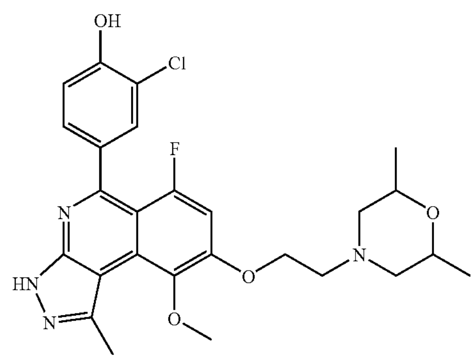 |
| 240 | 2-chloro-4-{6-fluoro-1-methyl-9-(methyloxy)-8-[(2-thiomorpholin-4-ylethyl)oxy]-3H-pyrazolo[3,4-c]isoquinolin-5-yl}phenol | 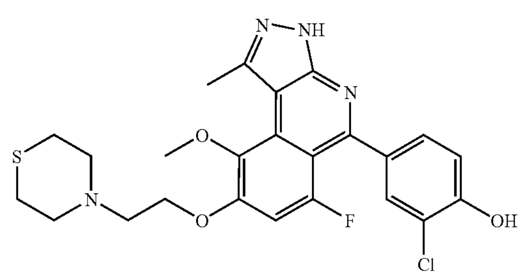 |
| 241 | 2-chloro-4-[8-{[2-(2,6-dimethylpiperidin-1-yl)ethyl]oxy}-6-fluoro-1-methyl-9-(methyloxy)-3H-pyrazolo[3,4-c]isoquinolin-5-yl]phenol | 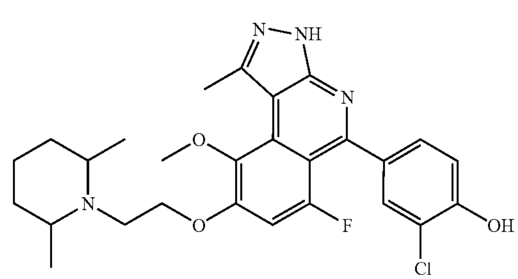 |

TABLE 3-continued

| Entry | Name | Structure |
|---|---|---|
| 242 | 2-chloro-4-(6-fluoro-1-methyl-9-(methyloxy)-8-{[2-(octahydroquinolin-1(2H)-yl)ethyl]oxy}-3H-pyrazolo[3,4-c]isoquinolin-5-yl)phenol | 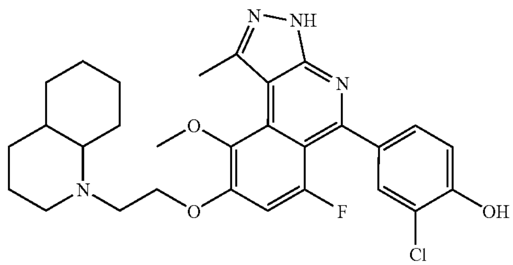 |
| 243 | 4-[8-({2-[bis(1-methylethyl)amino]ethyl}oxy)-6-fluoro-1-methyl-9-(methyloxy)-3H-pyrazolo[3,4-c]isoquinolin-5-yl]-2-chlorophenol | 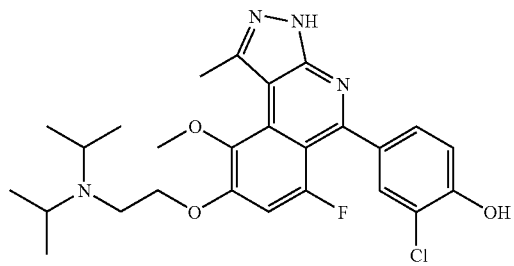 |
| 244 | 4-[8-[(2-{bis[2-(methyloxy)ethyl]amino}ethyl)oxy]-6-fluoro-1-methyl-9-(methyloxy)-3H-pyrazolo[3,4-c]isoquinolin-5-yl]-2-chlorophenol | 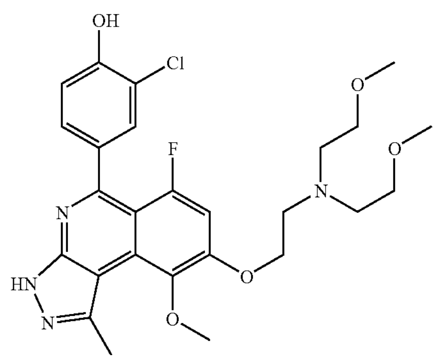 |
| 245 | 2-chloro-4-{6-fluoro-1-methyl-9-(methyloxy)-8-[(2-piperidin-1-ylethyl)oxy]-3H-pyrazolo[3,4-c]isoquinolin-5-yl}phenol | 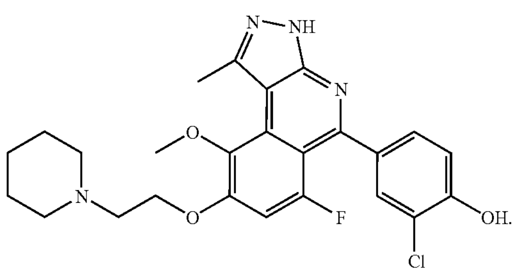 |

22. A Compound selected from

| 9 | 4-[7,8-bis-(methyloxy)-1-(phenyl-methyl)-3H-pyra-zolo[3,4-c]iso-quinolin-5-yl]benzene-1,2-diol | 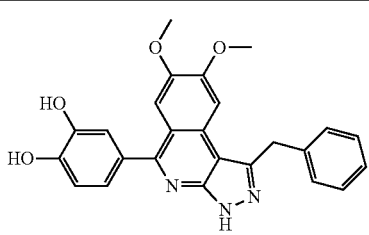 |

-continued

| 19 | 4-[7,8-bis-(methyloxy)-1-(1-phenyl-ethyl)-3H-pyra-zolo[3,4-c]iso-quinolin-5-yl]phenol | 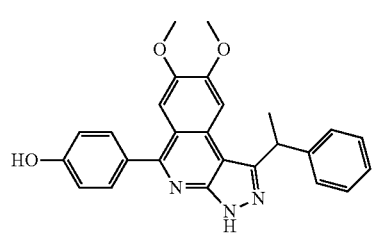 |

| | | |
|---|---|---|
| 24 | 4-[6,7,8-tris(methyl-oxy)-1-(phenyl-methyl)-3H-pyrazolo[3,4-c]iso-quinolin-5-yl]phenol | 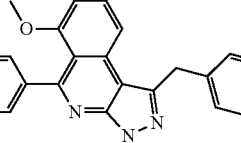 |
| 26 | 4-[8-(methyl-oxy)-1-(phenylmethyl)-3H-pyrazolo-[3,4-c]iso-quinolin-5-yl]phenol | 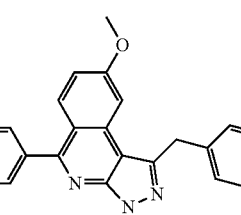 |
| 221 | 6,9-difluoro-5-(2-imino-3-methyl-2,3-dihydro-1,3-thiazol-5-yl)-1-methyl-3H-pyra-zolo[3,4-c]iso-quinolin-8-ol | 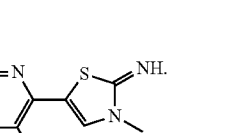 |

23. A pharmaceutical composition comprising the compound according to claim 1 and a pharmaceutically acceptable carrier.

24. A method of treating diseases or disorders associated with uncontrolled, abnormal, and/or unwanted cellular activities, wherein the disease is an ALK-positive lymphoma, B-cell lymphoma, neuroblastoma, or inflammatory myofibroblastic tumor, the method comprising administering, to a mammal in need thereof, a therapeutically effective amount of a compound according to formula I:

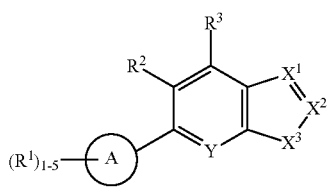

I or a pharmaceutically acceptable salt or a stereoisomer, thereof, wherein,

A is a five- to ten-membered ring containing up to three heteroatoms;

$R^1$ is selected from —H, halo, trihalomethyl, —CN, —$NO_2$, —$OR^4$, —$N(R^4)R^4$, —$S(O)_{0-2}R^4$, —$SO_2N(R^4)R^4$, —$CO_2R^4$, —$C(=O)N(R^4)R^4$, —$C(=O)R^4$, —$C(=NR^5)N(R^4)R^4$, —$C(=NR^5)R^4$, —$N(R^4)SO_2R^4$, —$N(R^4)C(O)R^4$, alkoxy, $C_{1-6}$ alkyl, aryl, aryl $C_{1-6}$ alkyl, heterocyclyl, and heterocyclyl $C_{1-6}$ alkyl;

two adjacent of $R^1$, together with the annular atoms to which they are attached, can form a five- to six-membered ring containing up to two heteroatoms and optionally substituted with up to four of $R^{10}$;

$R^2$ and $R^3$, together with the annular atoms to which they are attached, form a five- to six-membered ring containing up to two heteroatoms and optionally substituted with up to five of $R^6$;

each $R^4$ is selected from —H; $C_{1-6}$ alkyl optionally substituted with 1, 2, or 3 halogen; $C_{1-6}$ alkyl optionally substituted with alkoxy; $C_{1-6}$ alkyl substituted with amino where the amino is optionally substituted with one or groups selected from methyl, ethyl, —$CH_2CH_2OCH_3$, —$CH_2CH_2N(CH_3)_2$, —$CH_2CH_2CH_2N(CH_3)_2$, and N-methyl-pyrrolidin3-yl; aryl; aryl $C_{1-6}$ alkyl; heterocyclyl; and heterocyclyl $C_{1-6}$ alkyl where the heterocyclyl is optionally substituted with alkyl, acyl, $NH_2$, alkylamino, dialkylamino, heterocyclyl, cyclohexyl, —$CH_2OCH_3$, —$CH_2C(O)NHCH(CH_3)_2$, or —$CH_2OCH_3$, two of $R^4$, when taken together with a common nitrogen to which they are attached, form an five- to seven-membered heterocyclyl, said optionally substituted five- to seven-membered heterocyclyl optionally containing at least one additional heteroatom selected from N, O, S, and P;

each $R^5$ is selected from —H, —CN, —$NO_2$, —$OR^4$, —$S(O)_{0-2}R^4$, —$CO_2R^4$, $C_{1-6}$ alkyl, $C_{2-6}$ alkenyl, and $C_{2-6}$ alkynyl;

Y is =N— or =C(H);

$X^1$ and $X^2$ are each independently either =N— or =$C(R^9)$—;

$X^3$ is —$N(R^7)$—;

$R^7$ is hydrogen;

each of $R^6$ and $R^{10}$ is independently selected from —H, halo, trihalomethyl, —CN, —$NO_2$, —$OR^4$, —$N(R^4)R^4$, —$S(O)_{0-2}R^4$, —$SO_2N(R^4)R^4$, —$CO_2R^4$, —$C(=O)N(R^4)R^4$, —$C(=NR^5)N(R^4)R^4$, —$C(=NR^5)R^4$, —$N(R^4)SO_2R^4$, —$N(R^4)C(O)R^4$, —$C(=O)R^4$, optionally substituted alkoxy, $C_{1-6}$ alkyl, aryl, aryl $C_{1-6}$ alkyl, heterocyclyl, and heterocyclyl $C_{1-6}$ alkyl;

two adjacent of $R^6$, together with the annular atoms to which they are attached, can form a five- to seven-membered ring containing up to two heteroatoms; and each $R^9$ is independently selected from —H; halo; trihalomethyl; —CN; —$NO_2$; —$OR^4$; —$N(R^4)R^4$; —$S(O)_{0-2}R^4$; —$SO_2N(R^4)R^4$; —$CO_2R^4$; —$C(=O)N(R^4)R^4$; —$C(=NR^5)N(R^4)R^4$; —$C(=NR^5)R^4$; —$N(R^4)SO_2R^4$; —$N(R^4)C(O)R^4$; —$C(=O)R^4$; alkoxy; $C_{1-6}$ alkyl optionally substituted with one group selected from alkoxy, benzylamino, and 2-oxo-pyrrolidinyl; aryl $C_{1-6}$ alkyl substituted on the aryl with 1 or 2 groups selected from alkyl and alkoxy; heterocyclyl optionally substituted with —C(O)Ot-Bu; and heterocyclyl $C_{1-6}$ alkyl; provided when $R^9$ is aryl, heteroaryl, —C(H)=C(H)R or —C(H)=NR, where R is an optionally substituted alkyl, cycloalkyl, heteroalicyclic, aryl, or heteroaryl, then Y is not =C(H)—.

\* \* \* \* \*